United States Patent
Eckhardt et al.

(10) Patent No.: US 11,766,443 B2
(45) Date of Patent: Sep. 26, 2023

(54) CYCLOPENTATHIOPHENE CARBOXAMIDE DERIVATIVES AS PLATELET ACTIVATING FACTOR RECEPTOR ANTAGONISTS

(71) Applicant: Boehringer Ingelheim International GmbH, Ingelheim am Rhein (DE)

(72) Inventors: Matthias Eckhardt, Biberach an der Riss (DE); Marina Kristina Willwacher, Biberach an der Riss (DE); Juergen Prestle, Biberach an der Riss (DE); Ferenc Kontes, Biberach an der Riss (DE); Leo Thomas, Biberach an der Riss (DE); Christofer Siegfried Tautermann, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/524,759

(22) Filed: Nov. 12, 2021

(65) Prior Publication Data
US 2022/0160725 A1    May 26, 2022

(51) Int. Cl.
*A61K 31/551* (2006.01)
*C07D 495/14* (2006.01)
*C07D 519/00* (2006.01)

(52) U.S. Cl.
CPC .......... *A61K 31/551* (2013.01); *C07D 495/14* (2013.01); *C07D 519/00* (2013.01)

(58) Field of Classification Search
CPC .. A61K 31/551; C07D 495/14; C07D 519/00; A61P 27/02
See application file for complete search history.

(56) References Cited

U.S. PATENT DOCUMENTS

| | | | |
|---|---|---|---|
| 5,104,543 A | 4/1992 | Brandt et al. | |
| 5,155,103 A | 10/1992 | Weber et al. | |
| 5,532,233 A | 7/1996 | Weber et al. | |
| 7,015,213 B1 | 3/2006 | Bigg et al. | |
| 2005/0032713 A1* | 2/2005 | Wurtman | A61K 36/16 514/33 |

FOREIGN PATENT DOCUMENTS

| | | |
|---|---|---|
| CA | 2012411 A1 | 9/1990 |
| DE | 4132763 A1 | 4/1993 |
| EP | 0194416 A1 | 9/1986 |
| EP | 0254245 A1 | 1/1988 |
| EP | 0388789 A1 | 9/1990 |
| EP | 0450504 A1 | 10/1991 |
| WO | 2008063667 A1 | 5/2008 |

OTHER PUBLICATIONS

Weber, K. H.,"Hetrazepines as antagonists of platelet activating factor." Medicinal research reviews 9.2 (1989): 181-218.*
De Sant' Anna, C. M. R., "Toward a platelet-activating factor pseudoreceptor 2. Three-dimensional semiempirical models for agonist and antagonist binding." Journal of Molecular Structure: THEOCHEM 490.1-3 (1999): 167-180.*
Wahlers, T.H., "Future horizons of lung preservation by application of a platelet-activating factor antagonist compared with current clinical standards: Euro-Collins flush perfusion versus donor core cooling." The Journal of Thoracic and Cardiovascular Surgery 103.2 (1992): 200-205.*
Braquet, P., "Recent progress in ginkgolide research." Medicinal research reviews 11.3 (1991): 295-355.*
Zhang, H., "A novel platelet-activating factor receptor antagonist inhibits choroidal neovascularization and subretinal fibrosis." PloS one 8.6 (2013): e68173.*
Database pubchem, [9-2-Chlorophenyl)-3-methyl-16-thia-2,4,5,8-tetrazatetracyclo{8.60.02,6.011 . . . , 2020.
Weber, Hetrazepines as Antagonists of platelet Activating factor, Weber and Heuer, Depts of Medicinal Chem, vol. 9, 1989.
Summers, Platelet activating Factor Antagonists, Curr. Pharm. Design, 1995.

(Continued)

*Primary Examiner* — John M Mauro
(74) *Attorney, Agent, or Firm* — David L. Kershner

(57) ABSTRACT

The invention relates to cyclopentathiophene carboxamides of formula (I.0)

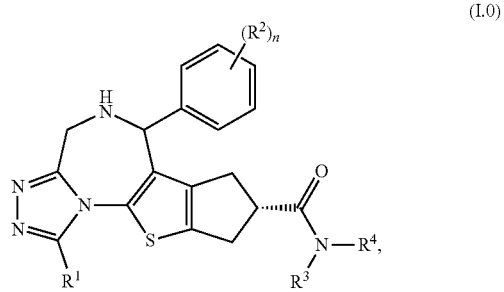

wherein $R^1$, $R^2$, $R^3$, $R^4$, and n are as defined herein, and pharmaceutically acceptable salts thereof. The invention also relates to the use of the cyclopentathiophene carboxamides of formula (I.0) for the treatment of diseases which can be influenced by antagonizing the activity mediated by the platelet activating factor receptor.

34 Claims, No Drawings

(56) References Cited

OTHER PUBLICATIONS

Gallo, Acid Catalyzed Hydrolysis of Brotizolam, J. Heterocyclic Chem, vol. 25, 1988.
Legouin, Isolation and Structural Data of the Opened Ring Derivative, J. Heterocyclic Chem., vol. 37, 2000.
Dupre, Inverse Agonist Activity Of Selected Ligands of Platelet, J. Pharm. Ecp. Ther., vol. 299, 2001.
Cellai, mechanistic Insight into WEB-2170-indiced apoptosis, vol. 37, 2009.
Tahara, Synthesis and Structure activity Relationships of 6-Aryl 4-H, Arzneimittel-forsching, 1978.
Sung, Asymetric Synthesis and Structure-Activity Relationship, Archiv de Pharmzie, vol. 329, 1996.
Fier, An Atom Economical Method to Prepare Enantiopure, Org. Lett., vol. 19, 2017.
Brenna, Biocatalytic Synthesis of chiral cyclic y-oxoesters, Green Chem., vol. 19, 2017.
Abstract in English for DE4132763 cited herein dated Aug. 4, 1993.
International Search Report for PCT/EP2021/081459 dated Dec. 23, 2021.

\* cited by examiner

CYCLOPENTATHIOPHENE CARBOXAMIDE DERIVATIVES AS PLATELET ACTIVATING FACTOR RECEPTOR ANTAGONISTS

FIELD OF THE INVENTION

This invention relates to novel cyclopentathiophene carboxamide derivatives and pharmaceutically acceptable salts thereof, that are platelet activating factor receptor antagonists. In addition, the invention relates to pharmaceutical compositions and combinations comprising said compounds and to their use in methods for the treatment of diseases which can be influenced by antagonizing the platelet activating factor receptor. Particularly, the pharmaceutical compositions of the invention are suitable for the prophylaxis and/or therapy of ocular diseases, allergies, and inflammation-related conditions and diseases, in particular dry and wet age-related macular degeneration, geographic atrophy, urticaria, and NASH.

BACKGROUND OF THE INVENTION

Platelet activating factor (PAF) is an ether-phospholipid and the most potent lipid mediator known. PAF is synthesized constitutively or under specific stimuli by a variety of cells like platelets, macrophages, monocytes, neutrophils, basophils, eosinophils, mast cells and endothelial cells. PAF, PAF-like lipids (PAFLL) and some oxidized phospholipids are structurally defined ligands of the PAF receptor (PAFR), a G protein-coupled receptor. The PAFR has restricted expression on specific target cells of the immune, haemostatic and inflammatory systems. Signalling functions of PAF are mostly associated with acute and chronic inflammation in essentially all organs.

PAF is thought to play a role in a number of inflammatory disorders and may have numerous implications in ocular diseases, cardiovascular diseases, cancer, neurological and neurodegenerative disorders, renal disorders, liver diseases and allergies. The suppression of PAFR activation, e.g. via PAFR antagonists and/or inverse agonists, is thus considered to be useful in the treatment of a wide range of disorders which can be influenced by antagonizing and/or inversely agonizing PAFR, e.g. as mentioned hereinbefore and hereinafter; in particular, PAFR antagonists and/or inverse agonists should be useful for the prevention or treatment of ocular diseases, e.g. dry or wet age-related macular degeneration and geographic atrophy, or allergies and inflammation-related disorders, e.g. urticaria and non-alcoholic steatohepatitis (NASH).

PAFR antagonists and/or inverse agonists suitable for therapeutic use should bind potently and with high selectivity to PAFR. They should be well absorbed from the gastrointestinal tract, be sufficiently metabolically stable and possess favorable pharmacokinetic properties. They should be non-toxic and demonstrate no or few side-effects.

Low molecular weight PAFR antagonists are known in the art, for example, the compounds described in EP0194416A1 and EP0254245A1, by Weber et al. (Med. Res. Rev. 1989, 9, 181-218) and Summers et al. (Curr. Pharm. Des. 1995, 1, 161-190). Compounds of the thienotriazolodiazepine class as disclosed therein have been reported to undergo hydrolytic degradation in acidic solution (e.g. Gallo et al. (J. Heterocyclic Chem. 1988, 25, 867-869), Legouin et al. (J. Heterocyclic Chem. 2000, 37, 127-129)). Some of these compounds have also been identified to act as inverse agonists of PAFR (Dupré et al. (J. Pharm. Exp. Ther. 2001, 299, 1, 358-365), Cellai et al. (Exp. Hematol. 2009, 37, 1176-1185)).

Further methods useful for the syntheses and separation of said and related compounds are disclosed in DE4132763A1, EP0388789A1, EP0450504A1, U.S. Pat. No. 7,015,213B1, WO2008/063667A1, Tahara et al. (Arzneimittelforschung 1978, 28, 1153-1158), Sung et al. (Archiv der Pharmazie 1996, 329, 291-300), Fier et al. (Org. Lett. 2017, 19, 1454-1457), and Brenna et al. (Green Chem. 2017, 19, 5122-5130).

SUMMARY OF THE INVENTION

In a first aspect, the present invention relates to a compound of formula (I.0)

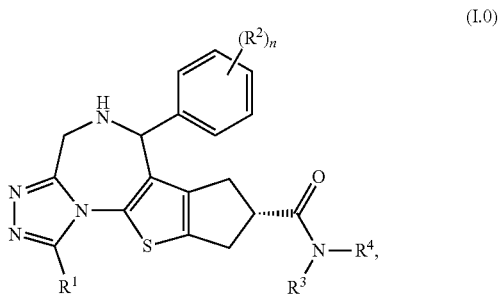

(I.0)

wherein $R^1$ is selected from the group $R^1$-G1 consisting of $C_{1-4}$-alkyl optionally substituted with 1 to 3 F and of $C_{3-4}$-cycloalkyl;

$R^2$ is selected from the group $R^2$-G1 consisting of F, Cl, Br, I, $C_{1-4}$-alkyl optionally substituted with 1 to 3 F or optionally substituted with 1 —CN, with 1 OH, or with 1 —O—$C_{1-4}$-alkyl, further consisting of $C_{3-4}$-cycloalkyl, —CN, —CONH$_2$, —CONH($C_{1-4}$-alkyl), —CON($C_{1-4}$-alkyl)$_2$, —COOH, —COO—$C_{1-4}$-alkyl, OH, —O—$C_{1-4}$-alkyl optionally substituted with 1 to 3 F, and consisting of —S(O)$_r$—$C_{1-4}$-alkyl with r=0, 1, or 2;

n is selected from the group n-G1 consisting of 0, 1, 2, and 3;

$R^3$ is selected from the group $R^3$-G1 consisting of H and $C_{1-4}$-alkyl optionally substituted with 1 to 5 F; and $R^4$ is selected from the group $R^4$-G1a consisting of
  $C_{1-6}$-alkyl
  optionally substituted with 1 to 3 F and
  optionally substituted with 1 to 2 substituents independently selected from —CN, —CONH$_2$, —CONH($C_{1-4}$-alkyl), —CON($C_{1-4}$-alkyl)$_2$, —COOH, —COO—$C_{1-4}$-alkyl, $C_{1-3}$-alkyl-CO—NH—, $C_{1-3}$-alkyl-S(=O)$_2$—NH—, OH, and —O—$C_{1-3}$-alkyl
  optionally substituted with 1 to 3 F;

or $R^4$ is selected from the group $R^4$-G1b consisting of —$C_{0-3}$-alkylene-$C_{3-10}$-cycloalkyl and —$C_{0-3}$-alkylene-$C_{3-10}$-heterocyclyl,
  wherein said alkylene is optionally substituted with 1 to 2 substituents selected from F and CH$_3$,
  wherein the 2H atoms of 1 >CH$_2$ group of said alkylene are optionally replaced by an ethylene (—CH$_2$—CH$_2$—) bridge to form a cyclopropylene moiety >C(—CH$_2$—CH$_2$—), wherein said cycloalkyl and heterocyclyl are saturated mono- or bicyclic ring systems, wherein said heterocyclyl contains 1 to 2 ring members independently selected from N, NH, >N($C_{1-4}$-alkyl), >NCO($C_{1-4}$-alkyl), >NS(=O)$_2$($C_{1-4}$-alkyl), and O, and optionally 1 ring member selected from >C=O and >S(=O)$_r$, with r=0, 1, or 2, provided that said heterocyclyl does not contain any heteroatom-heteroatom bonds other than N—N, N—O, and N—S(=O)$_{r=1,2}$ between ring members, and wherein said cycloalkyl and heterocyclyl are optionally substituted with 1 to 2 F and optionally substituted with 1 to 2 substituents independently selected from Cl, —CN, —CONH$_2$, —CONH($C_{1-4}$-alkyl), —CON($C_{1-4}$-alkyl)$_2$, —OOOH, —COO—$C_{1-4}$-alkyl, OH, —O—$C_{1-3}$-alkyl optionally substituted with 1 to 3 F, and from $C_{1-4}$-alkyl optionally substituted with 1 to 3 F or with 1 substituent selected from —CN, OH, —O—$C_{1-4}$-alkyl;

or $R^4$ is selected from the group $R^4$-G1c consisting of —$C_{0-3}$-alkylene-phenyl and —$C_{0-3}$-alkylene-heteroaryl, wherein said alkylene is optionally substituted with 1 to 2 substituents selected from F and CH$_3$, wherein the 2H atoms of 1 >CH$_2$ group of said alkylene are optionally replaced by an ethylene (—CH$_2$—CH$_2$—) bridge to form a cyclopropylene moiety >C(—CH$_2$—CH$_2$—), wherein said heteroaryl is a 5-membered monocycle containing 1 ring member selected from N, NH, O, and S and optionally further containing 1 to 2 ring members N, or a 6-membered monocycle containing 1 to 2 ring members N, and wherein said phenyl and heteroaryl are optionally substituted with 1 to 3 substituents independently selected from F, Cl, Br, $C_{3-4}$-cycloalkyl, —CN, —CONH$_2$, —CONH($C_{1-4}$-alkyl), —CON($C_{1-4}$-alkyl)$_2$, —OOOH, —COO—$C_{1-4}$-alkyl, —NHCO—$C_{1-4}$-alkyl, —NHS(=O)$_2$—$C_{1-4}$-alkyl, —S(=O)$_r$—$C_{1-4}$-alkyl with r=0, 1, or 2, from —O—$C_{1-4}$-alkyl optionally substituted with 1 to 3 F, and from $C_{1-4}$-alkyl optionally substituted with 1 to 3 F or with 1 substituent selected from —CN, OH, and —O—$C_{1-4}$-alkyl;

or $R^3$ and $R^4$ are selected from the group $R^{3/4}$-G1a in which $R^3$ and $R^4$, together with the amide N atom they are attached to, form a saturated 3- to 8-membered monocyclic heterocyclyl optionally further containing 1 to 2 ring members independently selected from >NH, >N($C_{1-4}$-alkyl), >N(CO—$C_{1-3}$-alkyl), >N(S(=O)$_2$—$C_{1-3}$-alkyl), and O, and optionally containing 1 ring member selected from >C=O and >S(=O)$_r$, with r=0, 1, or 2, provided that said heterocyclyl does not contain any heteroatom-heteroatom bonds other than N—N, N—O, and N—S(=O)$_{r=1,2}$ between ring members, wherein said heterocyclyl is optionally substituted with 1 to 4 F, is optionally substituted with 1 to 4 $C_{1-3}$-alkyl optionally substituted with 1 to 3 F, and is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O— optionally substituted with 1 to 3 F;

or $R^3$ and $R^4$ are selected from the group $R^{3/4}$-G1b in which $R^3$ and $R^4$, together with the amide N atom they are attached to, form a saturated 5- to 12-membered bicyclic heterocyclyl optionally further containing 1 to 3 ring members independently selected from >N—, >NH, >N($C_{1-4}$-alkyl), >N(CO—$C_{1-3}$-alkyl), >N(S(=O)$_2$—$C_{1-3}$-alkyl), and O, and optionally containing 1 ring member selected from >C=O and >S(=O)$_r$, with r=0, 1, or 2, provided that said heterocyclyl does not contain any heteroatom-heteroatom bonds other than N—N, N—O, and N—S(=O)$_{r=1,2}$ between ring members, wherein said heterocyclyl is optionally substituted with 1 to 6 F, is optionally substituted with 1 to 4 $C_{1-3}$-alkyl optionally substituted with 1 to 3 F, and is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O—;

or $R^3$ and $R^4$ are selected from the group $R^{3/4}$-G1c in which $R^3$ and $R^4$, together with the amide N atom they are attached to, form a 7- to 12-membered fused bicyclic ring system, wherein said bicyclic ring system is a heterocyclyl or heteroaryl consisting of one non-aromatic ring containing said amide N atom and optionally further containing 1 to 2 ring members independently selected from =N—, >N—, >NH, >N($C_{1-4}$-alkyl), >N(CO—$C_{1-3}$-alkyl), >N(S(=O)$_2$—$C_{1-3}$-alkyl), and O, and optionally containing 1 ring member selected from >C=O and >S(=O)$_r$, with r=0, 1, or 2, provided that there are no heteroatom-heteroatom bonds other than N—N, N—O, and N—S(=O)$_{r=1,2}$ between members of said non-aromatic ring, and of one aromatic ring selected from 5-membered monocycles containing 1 ring member selected from NH, N, O, and S and optionally further containing 1 to 2 ring members N, and of 6-membered monocycles containing 0, 1, or 2 ring members N, wherein said bicyclic ring system is optionally substituted with 1 to 4 F, is optionally substituted with 1 to 4 $C_{1-3}$-alkyl optionally substituted with 1 to 3 F, and is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O— optionally substituted with 1 to 3 F;

wherein in any definition mentioned hereinbefore and if not specified otherwise, any alkyl or alkylene group may be straight-chained or branched, the isomers, stereoisomers, tautomers, metabolites, prodrugs, solvates, hydrates, cocrystals, and the salts thereof, particularly the pharmaceutically acceptable salts thereof, or the combinations thereof.

In a second aspect, the present invention relates to a pharmaceutical composition comprising one or more compounds of formula (I.0), as defined hereinbefore or hereinafter, or pharmaceutically acceptable salts thereof, optionally together with one or more inert carriers and/or diluents.

In a third aspect, the present invention relates to a pharmaceutical composition comprising one or more compounds of formula (I.0), as defined hereinbefore or hereinafter, or pharmaceutically acceptable salts thereof, and one or more additional therapeutic agents, optionally together with one or more inert carriers and/or diluents.

In a fourth aspect, the present invention relates to a compound of formula (I.0), as defined hereinbefore or hereinafter, or a pharmaceutically acceptable salt thereof for use as a medicament.

In a fifth aspect, the present invention relates to a method for the treatment of diseases or conditions which can be influenced by antagonizing the platelet activating factor receptor in a patient in need thereof, the method comprising administering to the patient one or more compounds of formula (I.0), as defined hereinbefore or hereinafter, or pharmaceutically acceptable salts thereof.

In addition, the present invention relates to the use of one or more compounds of formula (I.0), as defined hereinbefore or hereinafter, or pharmaceutically acceptable salts thereof in the manufacture of a medicament for the treatment of diseases or conditions which can be influenced by antagonizing the platelet activating factor receptor.

Furthermore, the present invention relates to a compound of formula (I.0), as defined hereinbefore or hereinafter, or a pharmaceutically acceptable salt thereof for use in a method for the treatment of diseases or conditions which can be influenced by antagonizing the platelet activating factor receptor, in a patient in need thereof.

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I.0)", "compound(s) of the invention", and the like denote the compounds of formula (I.0) according to the present invention including their tautomers, stereoisomers, and mixtures thereof and the salts thereof, in particular the pharmaceutically acceptable salts thereof, and the solvates, hydrates, and cocrystals of such compounds, including the solvates, hydrates, and cocrystals of such tautomers, stereoisomers, and salts thereof.

Also, unless specifically indicated, throughout the specification and the appended claims, a given chemical formula or name shall encompass tautomers and all stereo, optical, and geometrical isomers (e.g. enantiomers, diastereomers, E/Z isomers, etc. . . . ), and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and solvates thereof, such as for instance hydrates, including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid, and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, EtOAc, EtOH, isopropanol, or MeCN, or a mixture thereof.

Salts of other acids than those mentioned above which for example are useful for purifying or isolating the compounds of the present invention (e.g. trifluoro acetate salts) also comprise a part of the invention.

In case a compound of the present invention is depicted in form of a chemical name and as a formula, in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined. E.g. in the case of more than one attachment point, i.e. more than one asterisk, in a sub-formula, the asterisks may be further specified by a bracketed designation of the connected part of the core molecule.

The numeration of the atoms of a substituent starts with the atom which is closest to the core or to the group to which the substituent is attached.

For example, the term "3-carboxypropyl-group" represents the following substituent:

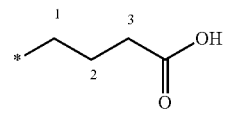

wherein the carboxy group is attached to the third carbon atom of the propyl group. The terms "1-methylpropyl-", "2,2-dimethylpropyl-", or "cyclopropylmethyl-" group represent the following groups:

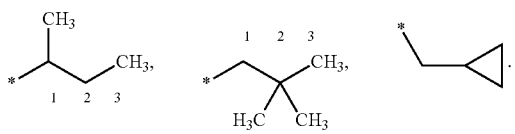

The term "substituted" as used herein, means that any one or more hydrogens on the designated atom, radical, or moiety is replaced with a selection from the indicated group, provided that the atom's normal valence is not exceeded, and that the substitution results in an acceptably stable compound.

In a definition of a group, the term "wherein each X, Y, and Z group is optionally substituted with" and the like denotes that each group X, each group Y, and each group Z either each as a separate group or each as part of a composed group may be substituted as defined. For example a definition "Rex denotes H, $C_{1-3}$-alkyl, $C_{3-6}$-cycloalkyl, $C_{1-3}$-alkyl-$C_{3-6}$-cycloalkylene-, or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{1-3}$-alkyl-$C_{3-6}$-cycloalkylene-, and $C_{1-3}$-alkyl-O—, the alkyl moiety may be substituted with $L^{ex}$ as defined.

The term "$C_{1-n}$-alkyl", wherein n is an integer greater than 1, either alone or in combination with another radical, denotes an acyclic, saturated, linear or branched hydrocarbon radical with 1 to n carbon atoms. For example the term $C_{1-5}$-alkyl includes $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$—, and $H_3C$—$CH_2$—$CH(CH_2CH_3)$—.

The term "$C_{1-n}$-alkylene", wherein n is an integer greater than 1, either alone or in combination with another radical, denotes an acyclic, linear or branched divalent alkyl radical with 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$—, and —$C(CH_3)(CH_2CH_3)$—.

The term "$C_{3-n}$-cycloalkyl", wherein n is an integer greater than 3, either alone or in combination with another radical denotes a cyclic, saturated, unbranched hydrocarbon radical with 3 to n carbon atoms. The cyclic group may be mono-, bi-, tri-, or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term "heterocyclyl" means a saturated or unsaturated mono- or polycyclic ring system, which optionally comprises aromatic rings, that contains one or more heteroatoms selected from N, O, or $S(O)_r$, wherein r=0, 1, or 2, consisting of 3 to 14 ring atoms, wherein none of the heteroatoms is part of an aromatic ring. The term "heterocyclyl" is intended to include all the possible isomeric forms.

Thus, the term "heterocyclyl" includes the following exemplary structures; they are not depicted as radicals as each form is optionally attached through a covalent bond to any atom so long as appropriate valences are maintained:

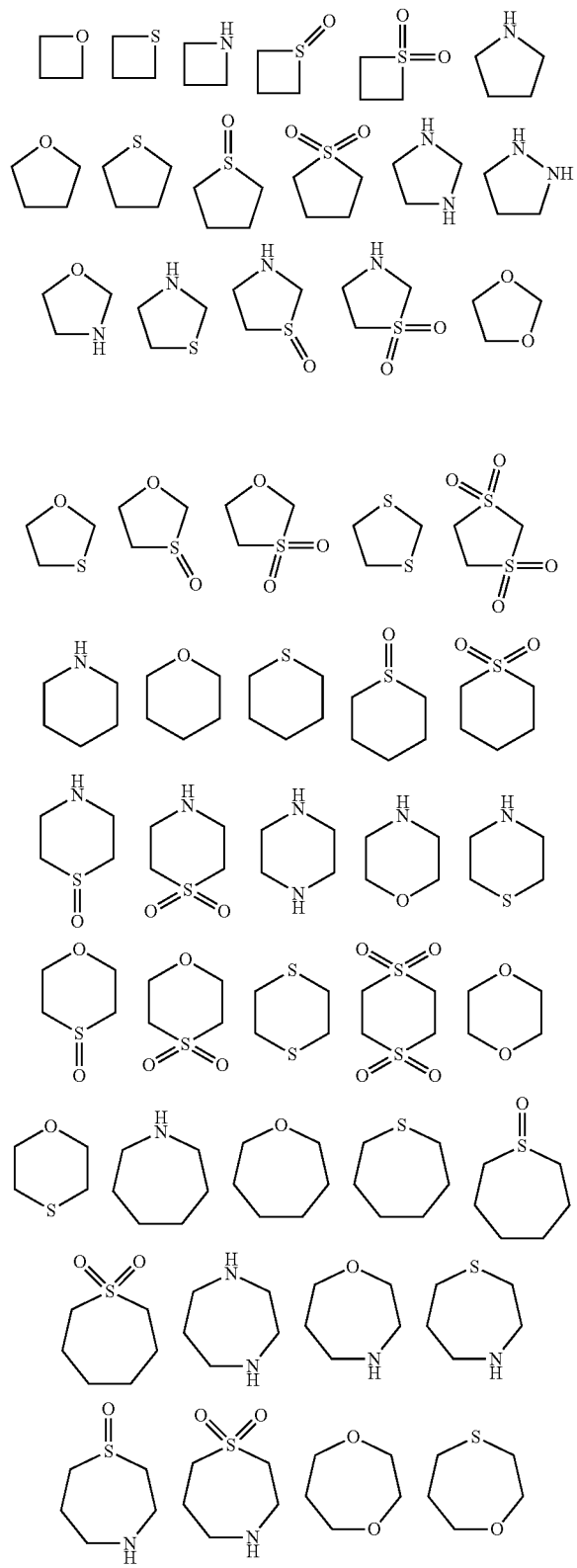

-continued

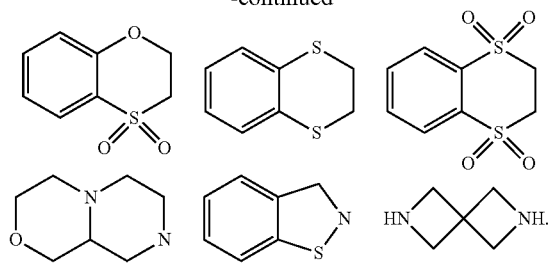

The term "heteroaryl" means a mono- or polycyclic aromatic ring system containing one or more heteroatoms selected from N, O, or $S(O)_r$, wherein r=0, 1, or 2, consisting of 5 to 14 ring atoms, wherein at least one of the heteroatoms is part of an aromatic ring. The term "heteroaryl" is intended to include all the possible isomeric forms.

Thus, the term "heteroaryl" includes the following exemplary structures; they are not depicted as radicals as each form is optionally attached through a covalent bond to any atom so long as appropriate valences are maintained:

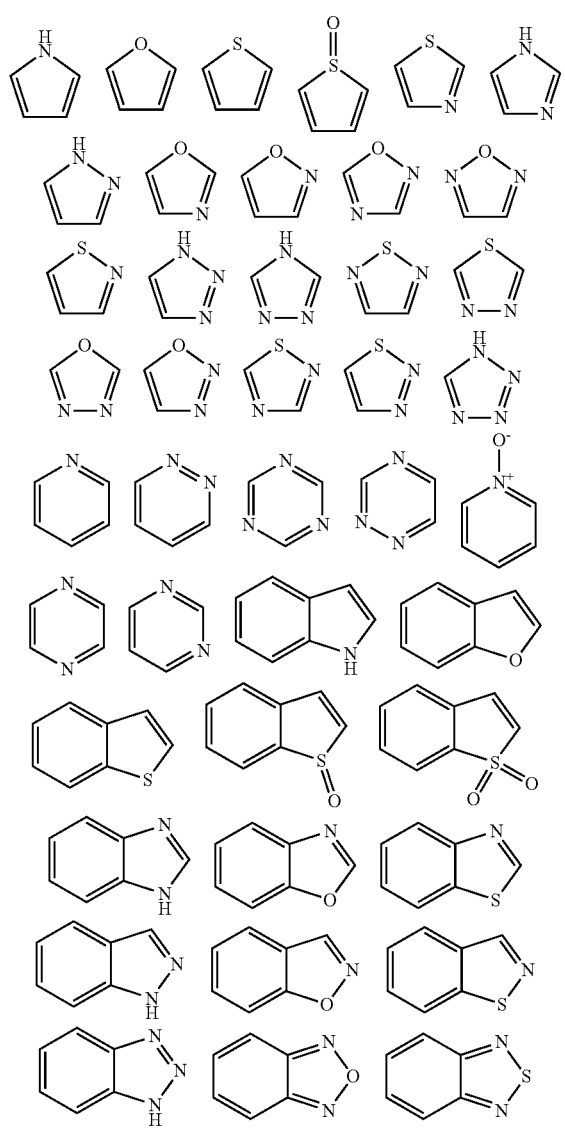

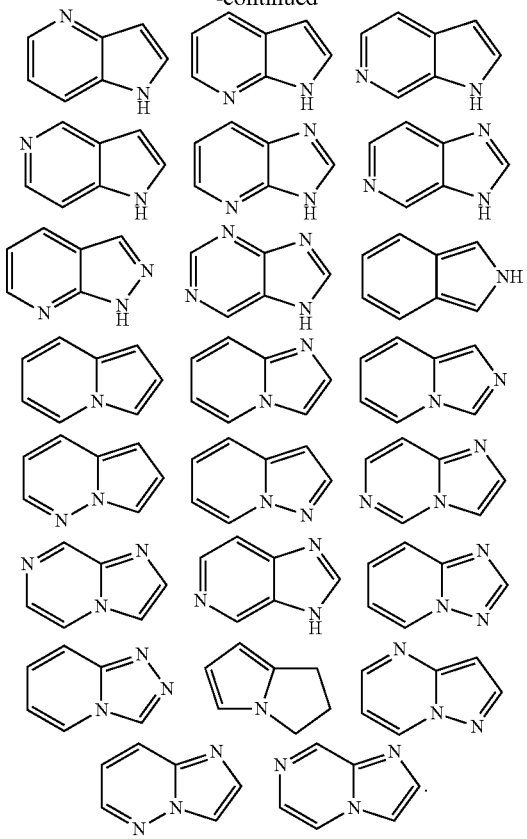

The term "bicyclic ring system" means a group consisting of 2 joined cyclic substructures including spirocyclic, fused, and bridged ring systems.

Many of the terms given above may be used repeatedly in the definition of a formula or group and in each case have one of the meanings given above, independently of one another.

The terms "treatment" and "treating" as used herein encompass both therapeutic, i.e. curative and/or palliative, and preventative, i.e. prophylactic, treatment.

Therapeutic treatment refers to the treatment of patients having already developed one or more of said conditions in manifest, acute, or chronic form. Therapeutic treatment may be symptomatic treatment in order to relieve the symptoms of the specific indication or causal treatment in order to reverse or partially reverse the conditions of the indication or to stop or slow down progression of the disease.

Preventative treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition, or disorder as well as to alleviate the symptoms or complications associated with the disease, condition, or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel cyclopentathiophene carboxamide derivatives, which are effective platelet activating receptor (PAFR) antagonists and possess suitable pharmacological and pharmacokinetic properties to use them as medicaments for the prevention or treatment of diseases and/or conditions that may be influenced by PAFR antagonism, including but not limited to ocular diseases and inflammation-related conditions and diseases, in particular geographic atrophy, wet age-related macular degeneration, and allergies.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

Compounds of the Invention

In a first aspect of the present invention, it is found that compounds of formula (I.0)

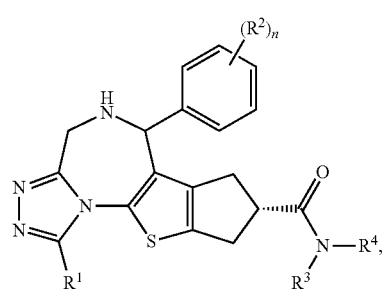

(I-0)

wherein $R^1$, $R^2$, $R^3$, $R^4$, and n are defined as hereinbefore and hereinafter, are potent antagonists of PAFR and may exhibit favorable properties with regard to selectivity, safety and tolerability, metabolic and/or chemical stability, pharmacokinetic and physicochemical characteristics, solubility, permeability, plasma protein binding, bioavailability, and the possibility to form stable salts. In particular, they provide high in vitro potencies as PAFR antagonists and they show good in vivo efficacies in an animal model of choroidal neovascularization. Moreover, they have been found in an in vitro model to also act as PAFR inverse agonists, which might further contribute to a beneficial pharmacological effect. In addition, the compounds according to the invention display advantageous chemical stabilities, particularly even at low pH values, as well as favorable solubilities at various pH values, i.e. also in acidic media; at the same time, their renal clearances remain adequately low.

Therefore, the compounds of formula (I.0), as defined hereinbefore or hereinafter, or pharmaceutically acceptable salts thereof, are expected to be useful in the treatment of diseases and/or conditions that can be influenced by PAFR antagonism.

Surprisingly, it could also be shown that the compounds of formula (I.0) extensively bind to melanin, which impacts their biodistribution and pharmacokinetic properties; in particular, this results in their accumulation and in a prolonged drug retention in the eye. Therefore, the compounds of the invention are expected to be particularly suitable for the treatment of ocular diseases.

Thus, according to one aspect of the present invention, a compound of formula (I.0)

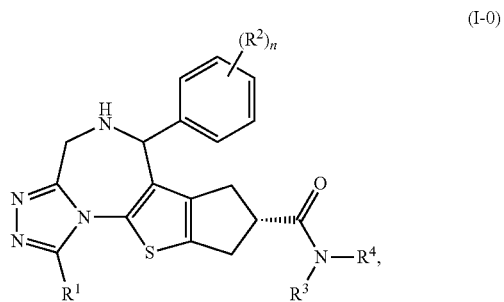

(I-0)

wherein $R^1$, $R^2$, $R^3$, $R^4$, and n are defined as hereinbefore and hereinafter, is provided as well as the isomers, stereoisomers, tautomers, metabolites, prodrugs, solvates, hydrates, cocrystals, and the salts thereof, particularly the pharmaceutically acceptable salts thereof.

Unless otherwise stated, the groups, residues, and substituents, particularly $R^1$, $R^2$, $R^3$, $R^4$, and n are defined as hereinbefore and hereinafter. Some preferred meanings of the substituents $R^1$, $R^2$, $R^3$, $R^4$, and n as well as of the phenyl substitution pattern and the stereochemistry of the compounds of formula (I.0) will be given hereinafter as embodiments of the invention. Any and each of these definitions and embodiments may be combined with one another.

$R^1$:

According to one embodiment, $R^1$ is selected from the group $R^1$-G1 consisting of
$C_{1-4}$-alkyl optionally substituted with 1 to 3 F and of $C_{3-4}$-cycloalkyl.

According to another embodiment, $R^1$ is selected from the group $R^1$-G2 consisting of
$CH_3$, $CH_2CH_3$, $CH_2CH_2CH_3$, $CHF_2$, $CF_3$, and cyclopropyl.

According to another embodiment, $R^1$ is selected from the group $R^1$-G3 consisting of
$CH_3$, $CH_2CH_3$, $CH_2CH_2CH_3$, and cyclopropyl.

According to another embodiment, $R^1$ is selected from the group $R^1$-G4 consisting of $CH_3$.

According to another embodiment, $R^1$ is selected from the group $R^1$-G5 selected from $CH_2CH_3$, $CH_2CH_2CH_3$, and cyclopropyl.

$R^2$:

In cases where more than one substituent $R^2$ is present in a compound of formula (I.0), i.e. n=2 or 3, each $R^2$ is selected independently of one another from the embodiments and groups $R^2$-G1 to $R^2$-G8 defined hereinafter.

According to one embodiment, $R^2$ is selected from the group $R^2$-G1 consisting of
F, Cl, Br, I, $C_{1-4}$-alkyl optionally substituted with 1 to 3 F or optionally substituted with 1 —CN, with 1 OH, or with 1 —O—$C_{1-4}$-alkyl, further consisting of $C_{3-4}$-cycloalkyl, —CN, —CONH$_2$, —CONH($C_{1-4}$-alkyl), —CON($C_{1-4}$-alkyl)$_2$, —OOOH, —COO—$C_{1-4}$-alkyl, OH, —O—$C_{1-4}$-alkyl optionally substituted with 1 to 3 F, and consisting of —S(O)$_r$—$C_{1-4}$-alkyl with r=0, 1, or 2.

According to another embodiment, R$^2$ is selected from the group R$^2$-G2 consisting of F, Cl, Br, $C_{1-3}$-alkyl optionally substituted with 2 or 3 F, further consisting of cyclopropyl, —CN, —$C_{1-3}$-alkylene-OH, —$C_{1-2}$-alkylene-O—$C_{1-2}$-alkyl, OH, —O—$C_{1-3}$-alkyl optionally substituted with 2 or 3 F, and consisting of —S—$C_{1-3}$-alkyl.

According to another embodiment, R$^2$ is selected from the group R$^2$-G3 consisting of F, Cl, Br, CH$_3$, CH$_2$CH$_3$, cyclopropyl, CF$_3$, CH$_2$OH, OH, OCH$_3$, and S—CH$_3$.

According to another embodiment, R$^2$ is selected from the group R$^2$-G4 consisting of F, Cl, and Br, preferably Cl.

According to another embodiment, R$^2$ is selected from the group R$^2$-G5 consisting of CH$_3$ and CH$_2$CH$_3$.

According to another embodiment, R$^2$ is selected from the group R$^2$-G6 consisting of cyclopropyl and CF$_3$.

According to another embodiment, R$^2$ is selected from the group R$^2$-G7 consisting of CH$_2$OH and OH.

According to another embodiment, R$^2$ is selected from the group R$^2$-G8 consisting of OCH$_3$ and S—CH$_3$.

n:

According to one embodiment, n is selected from the group n-G1 consisting of 0, 1, 2, and 3.

According to another embodiment, n is selected from the group n-G2 consisting of 0, 1, and 2.

According to another embodiment, n is the group n-G3 consisting of 0.

According to another embodiment, n is the group n-G4 consisting of 1.

According to another embodiment, n is the group n-G5 consisting of 2.

Phenyl Substitution Pattern:

For describing the substitution pattern of the phenyl ring shown in formula (I.0), the following carbon atom numbering is used:

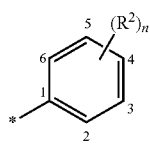

In general, the n substituents R$^2$ may be attached to any of the carbon atoms C-2 to C-6 and to any combinations thereof, respectively.

In case n=1, according to one embodiment, R$^2$ is attached to carbon atom 2; according to another embodiment R$^2$ is attached to carbon atom 4.

In case n=2, according to one embodiment, one R$^2$ is attached to carbon atom 2 and the other R$^2$ is attached to carbon atom 5; according to another embodiment, one R$^2$ is attached to carbon atom 3 and the other R$^2$ is attached to carbon atom 5.

R$^2$, n, and Phenyl Substitution Pattern:

According to one embodiment, R$^2$, n, and the phenyl substitution pattern are selected such that the resulting substituted phenyl ring shown in formula (I.0) is selected from the group Ph-G1 consisting of

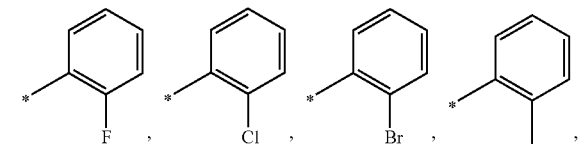

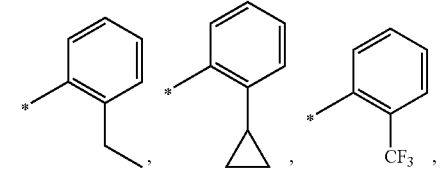

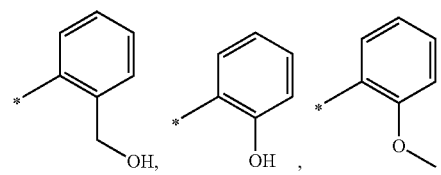

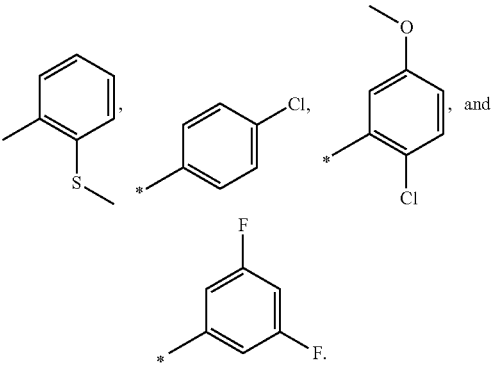

According to another embodiment, R$^2$, n and the phenyl substitution pattern are selected such that the resulting substituted phenyl ring shown in formula (I.0) is selected from the group Ph-G2 consisting of

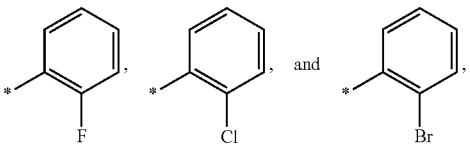

preferably

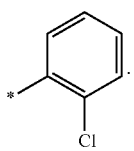

According to another embodiment, R$^2$, n, and the phenyl substitution pattern are selected such that the resulting substituted phenyl ring shown in formula (I.0) is selected from the group Ph-G3 consisting of

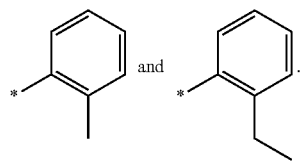

According to another embodiment, R², n, and the phenyl substitution pattern are selected such that the resulting substituted phenyl ring shown in formula (I.0) is selected from the group Ph-G4 consisting of

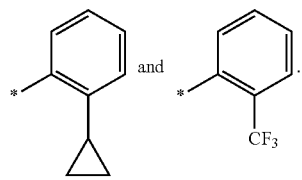

According to another embodiment, R², n, and the phenyl substitution pattern are selected such that the resulting substituted phenyl ring shown in formula (I.0) is selected from the group Ph-G5 consisting of

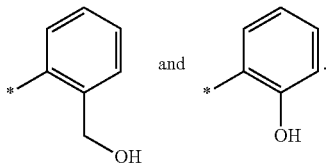 [SMILES: *c1ccccc1CO ; *c1ccccc1O]

According to another embodiment, R², n, and the phenyl substitution pattern are selected such that the resulting substituted phenyl ring shown in formula (I.0) is selected from the group Ph-G6 consisting of

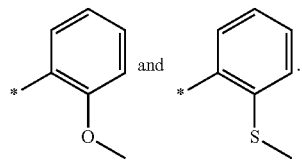

According to another embodiment, R², n, and the phenyl substitution pattern are selected such that the resulting substituted phenyl ring shown in formula (I.0) is selected from the group Ph-G7 consisting of

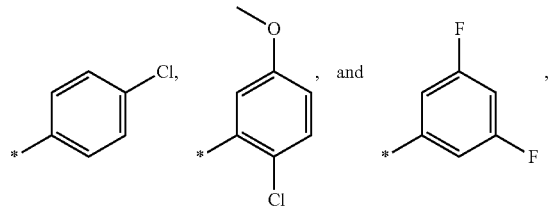

According to another embodiment, R², n, and the phenyl substitution pattern are selected such that the resulting substituted phenyl ring shown in formula (I.0) is selected from the group Ph-G8 consisting of

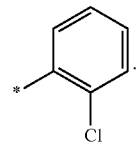

According to one embodiment, $R^3$ is selected from the group $R^3$-G1 consisting of H and $C_{1-4}$-alkyl optionally substituted with 1 to 5 F.

According to another embodiment, $R^3$ is selected from the group $R^3$-G2 consisting of H and $C_{1-3}$-alkyl optionally substituted with 1 to 3 F.

According to another embodiment, $R^3$ is selected from the group $R^3$-G3 consisting of H, $CH_3$, and $CH_2CH_2CH_3$.

According to one embodiment, $R^4$ is selected from the group $R^4$-G1a consisting of $C_{1-6}$-alkyl optionally substituted with 1 to 3 F and optionally substituted with 1 to 2 substituents independently selected from —CN, —$CONH_2$, —CONH($C_{1-4}$-alkyl), —CON($C_{1-4}$-alkyl)$_2$, —OOOH, —COO—$C_{1-4}$-alkyl, $C_{1-3}$-alkyl-CO—NH—, $C_{1-3}$-alkyl-S(=O)$_2$—NH—, OH, and —O—$C_{1-3}$-alkyl optionally substituted with 1 to 3 F.

According to another embodiment, $R^4$ is selected from the group $R^4$-G2a consisting of $C_{1-6}$-alkyl optionally substituted with 1 to 3 F and optionally substituted with 1 substituent selected from —CN, —$CONH_2$, —CONH($C_{1-2}$-alkyl), —CON($C_{1-2}$-alkyl)$_2$, —OOOH, —COO—$C_{1-2}$-alkyl, $C_{1-2}$-alkyl-CO—NH—, $C_{1-2}$-alkyl-S(=O)$_2$—NH—, OH, and —O—$C_{1-2}$-alkyl optionally substituted with 1 to 3 F.

According to another embodiment, $R^4$ is selected from the group $R^4$-G3a consisting of $C_{1-4}$-alkyl optionally substituted with 1 to 3 F and optionally substituted with 1 substituent selected from —CN, —$CONH_2$, —OOOH, OH, and —O—$C_{1-2}$-alkyl optionally substituted with 1 to 3 F.

According to another embodiment, $R^4$ is selected from the group $R^4$-G4a consisting of $C_{1-4}$-alkyl optionally substituted with 1 substituent selected from F, OH, and $OCF_3$.

According to another embodiment, $R^4$ is selected from the group $R^4$-G5a consisting of

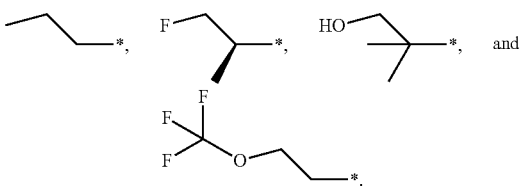

According to one embodiment, $R^4$ is selected from the group $R^4$-G1b consisting of —$C_{0-3}$-alkylene-$C_{3-10}$-cycloalkyl and —$C_{0-3}$-alkylene-$C_{3-10}$-heterocyclyl, wherein said alkylene is optionally substituted with 1 to 2 substituents selected from F and $CH_3$, wherein the 2H atoms of 1 >$CH_2$ group of said alkylene are optionally replaced by an ethylene (—$CH_2$—$CH_2$—) bridge to form a cyclopropylene moiety >C(—$CH_2$—$CH_2$—), wherein said cycloalkyl and heterocyclyl are saturated mono- or bicyclic ring systems, wherein said heterocyclyl contains 1 to 2 ring members independently selected from N, NH, >N($C_{1-4}$-alkyl), >NCO($C_{1-4}$-alkyl), >NS(=O)$_2$($C_{1-4}$-alkyl), and O, and optionally 1 ring member selected from >C=O and >S(=O)$_r$, with r=0, 1, or 2, provided that said heterocyclyl does not contain any heteroatom-heteroatom bonds other than N—N, N—O, and N—S(=O)$_{r=1,2}$ between ring members, and wherein said cycloalkyl and heterocyclyl are optionally substituted with 1 to 2 F and optionally substituted with 1 to 2 substituents independently selected from Cl, —CN, —CONH$_2$, —CONH($C_{1-4}$-alkyl), —CON($C_{1-4}$-alkyl)$_2$, —OOOH, —COO—$C_{1-4}$-alkyl, OH, —O—$C_{1-3}$-alkyl optionally substituted with 1 to 3 F, and from $C_{1-4}$-alkyl optionally substituted with 1 to 3 F or with 1 substituent selected from —CN, OH, —O—$C_{1-4}$-alkyl.

According to another embodiment, $R^4$ is selected from the group $R^4$-G2b consisting of —$C_{0-2}$-alkylene-$C_{3-8}$-cycloalkyl and —$C_{0-2}$-alkylene-$C_{3-8}$-heterocyclyl, wherein said cycloalkyl and heterocyclyl are saturated mono- or bicyclic ring systems, wherein said heterocyclyl contains 1 ring member selected from N, NH, and O, and wherein said cycloalkyl and heterocyclyl are optionally substituted with 1 to 2 F and are optionally substituted with 1 to 2 substituents independently selected from Cl, —CN, OCH$_3$, CH$_3$, and CH$_2$CH$_3$.

According to another embodiment, $R^4$ is selected from the group $R^4$-G3b consisting of —$C_{0-1}$-alkylene-$C_{3-6}$-cycloalkyl, wherein said cycloalkyl is a saturated mono- or bicyclic ring system, and wherein said cycloalkyl is optionally substituted with 1 to 2 F and optionally substituted with 1 CH$_3$ or CH$_2$CH$_3$.

According to another embodiment, $R^4$ is selected from the group $R^4$-G4b consisting of

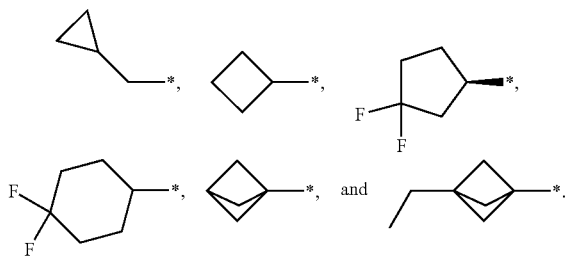

According to another embodiment, $R^4$ is selected from the group $R^4$-G5b consisting of

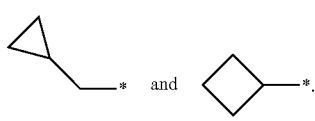

According to another embodiment, $R^4$ is selected from the group $R^4$-G6b consisting of

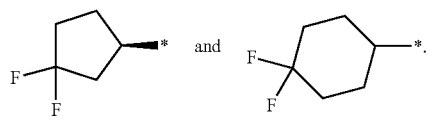

According to another embodiment, $R^4$ is selected from the group $R^4$-G7b consisting of

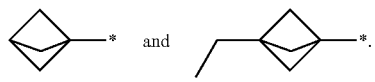

According to one embodiment, $R^4$ is selected from the group $R^4$-G1c consisting of —$C_{0-3}$-alkylene-phenyl and —$C_{0-3}$-alkylene-heteroaryl, wherein said alkylene is optionally substituted with 1 to 2 substituents selected from F and CH$_3$, wherein the 2H atoms of 1 >CH$_2$ group of said alkylene are optionally replaced by an ethylene (—CH$_2$—CH$_2$—) bridge to form a cyclopropylene moiety >C(—CH$_2$—CH$_2$—), wherein said heteroaryl is a 5-membered monocycle containing 1 ring member selected from N, NH, O, and S and optionally further containing 1 to 2 ring members N, or a 6-membered monocycle containing 1 to 2 ring members N, and wherein said phenyl and heteroaryl are optionally substituted with 1 to 3 substituents independently selected from F, Cl, Br, $C_{3-4}$-cycloalkyl, —CN, —CONH$_2$, —CONH($C_{1-4}$-alkyl), —CON($C_{1-4}$-alkyl)$_2$, —OOOH, —COO—$C_{1-4}$-alkyl, —NHCO—$C_{1-4}$-alkyl, —NHS(=O)$_2$—$C_{1-4}$-alkyl, —S(=O)$_r$$C_{1-4}$-alkyl with r=0, 1, or 2, from —O—$C_{1-4}$-alkyl optionally substituted with 1 to 3 F, and from $C_{1-4}$-alkyl optionally substituted with 1 to 3 F or with 1 substituent selected from —CN, OH, and —O—$C_{1-4}$-alkyl.

According to another embodiment, $R^4$ is selected from the group $R^4$-G2c consisting of —$C_{0-2}$-alkylene-phenyl and —$C_{0-2}$-alkylene-heteroaryl, wherein said alkylene is optionally substituted with 1 to 2 CH$_3$, wherein the 2H atoms of 1 >CH$_2$ group of said alkylene are optionally replaced by an ethylene (—CH$_2$—CH$_2$—) bridge to form a cyclopropylene moiety >C(—CH$_2$—CH$_2$—), wherein said heteroaryl is a 5-membered monocycle containing 1 ring member selected from N, NH, O, and S and optionally further containing 1 ring member N, or a 6-membered monocycle containing 1 to 2 ring members N, and wherein said phenyl and heteroaryl are optionally substituted with 1 to 3 substituents independently selected from F, Cl, Br, —CN, —O—$C_{1-3}$-alkyl optionally substituted with 1 to 3 F, and from Cls-alkyl optionally substituted with 1 to 3 F or with 1 substituent selected from —CN and —O—$C_{1-2}$-alkyl.

According to another embodiment, $R^4$ is selected from the group $R^4$-G3c consisting of —$C_{0-1}$-alkylene-phenyl and —$C_{0-1}$-alkylene-heteroaryl, wherein the 2H atoms of 1 >CH$_2$ group of said alkylene are optionally replaced by an ethylene (—CH$_2$—CH$_2$—) bridge to form a cyclopropylene moiety >C(—CH$_2$—CH$_2$—), wherein said heteroaryl is a 5- to 6-membered monocycle containing 1 ring member =N— and optionally containing 1 ring member selected from =N—, >NH, S, and O, and wherein said phenyl and heteroaryl are optionally substituted with 1 to 3 substituents independently selected from F, Cl, —CN, OCH$_3$, OCHF$_2$, OCF$_3$, CH$_3$, CHF$_2$, and CF$_3$.

According to another embodiment, R$^4$ is selected from the group R$^4$-G4c consisting of

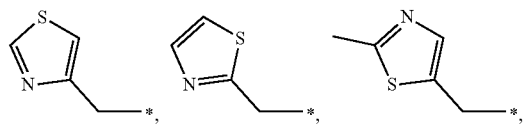

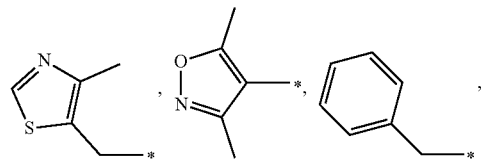

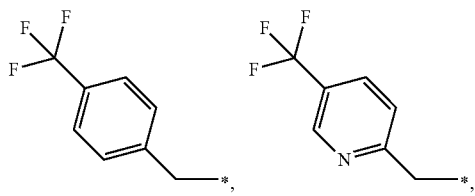

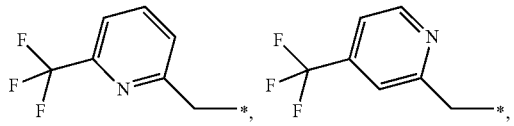

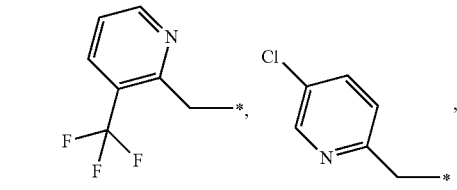

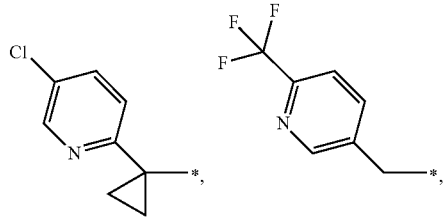

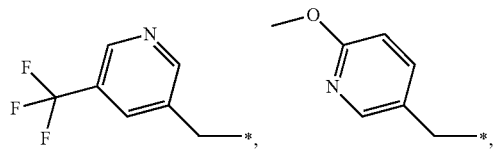

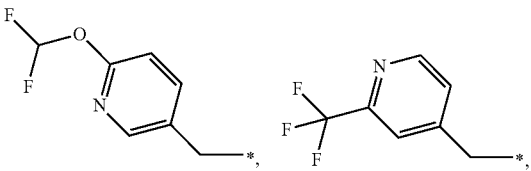

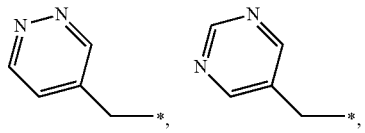

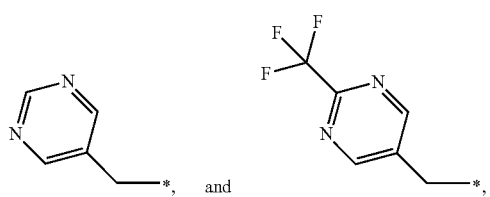

According to another embodiment, R$^4$ is selected from the group R$^4$-G5c consisting of

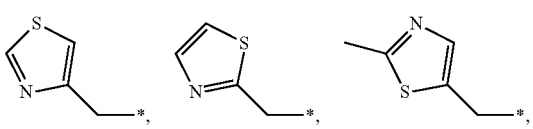

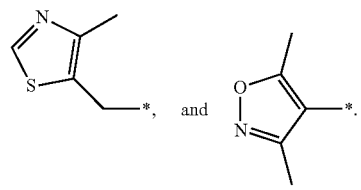

According to another embodiment, R$^4$ is selected from the group R$^4$-G6c consisting of

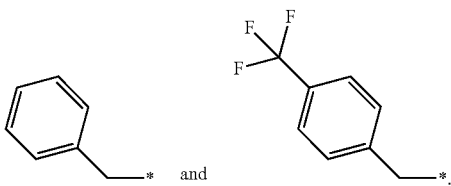

According to another embodiment, R$^4$ is selected from the group R$^4$-G7c consisting of

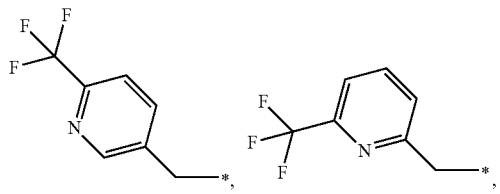

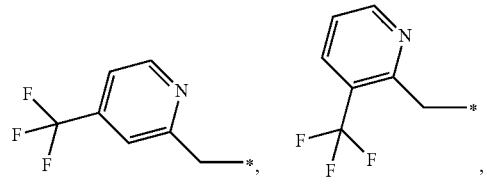

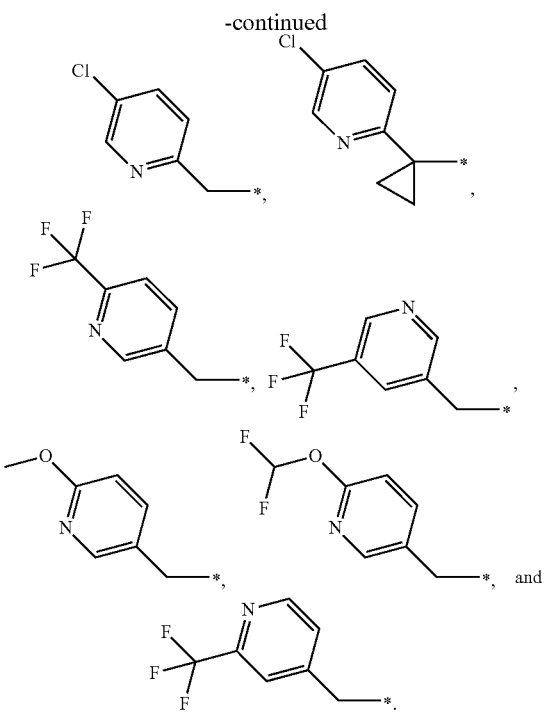

According to another embodiment, $R^4$ is selected from the group $R^4$-G8c consisting of

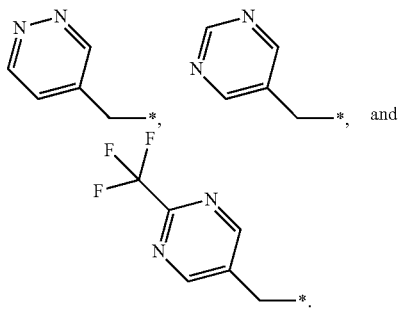

According to one embodiment, $R^3$ and $R^4$ are selected from the group $R^{3/4}$-G1a in which $R^3$ and $R^4$, together with the amide N atom they are attached to, form a saturated 3- to 8-membered monocyclic heterocyclyl optionally further containing 1 to 2 ring members independently selected from >NH, >N($C_{1-4}$-alkyl), >N(CO—$C_{1-3}$-alkyl), >N(S(=O)$_2$—$C_{1-3}$-alkyl), and O, and
  optionally containing 1 ring member selected from >C=O and >S(=O)$_r$, with r=0, 1, or 2,
  provided that said heterocyclyl does not contain any heteroatom-heteroatom bonds other than N—N, N—O, and N—S(=O)$_{r=1,2}$ between ring members,
  wherein said heterocyclyl is optionally substituted with 1 to 4 F,
  is optionally substituted with 1 to 4 $C_{1-3}$-alkyl optionally substituted with 1 to 3 F, and
  is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O— optionally substituted with 1 to 3 F.

According to one embodiment, $R^3$ and $R^4$ are selected from the group $R^{3/4}$-G2a in which $R^3$ and $R^4$, together with the amide N atom they are attached to, form a saturated 3- to 8-membered monocyclic heterocyclyl
  optionally further containing 1 ring member selected from >NH, >N($C_{1-4}$-alkyl), >N(CO—$C_{1-3}$-alkyl), >N(S(=O)$_2$—$C_{1-3}$-alkyl), and O, and optionally containing 1 ring member selected from >C=O, and >S(=O)$_r$, with r=0, 1, or 2,
  provided that said heterocyclyl does not contain any heteroatom-heteroatom bonds other than N—S(=O)$_{r=1,2}$ between ring members,
  wherein said heterocyclyl is optionally substituted with 1 to 2 F,
  is optionally substituted with 1 to 4 $C_{1-3}$-alkyl optionally substituted with 2 to 3 F, and
  is optionally substituted with 1 to 2 substituents selected from Cl, —CN, —CON($C_{1-4}$-alkyl)$_2$, —COO—$C_{1-4}$-alkyl, $C_{1-3}$-alkyl-O—$C_{1-3}$-alkylene-, and $C_{1-3}$-alkyl-O—.

According to one embodiment, $R^3$ and $R^4$ are selected from the group $R^{3/4}$-G3a in which $R^3$ and $R^4$, together with the amide N atom they are attached to, form a saturated 4- to 6-membered monocyclic heterocyclyl
  optionally further containing 1 ring member selected from >N($C_{1-4}$-alkyl) and O that is non-adjacent to the amide N atom,
  wherein said heterocyclyl is optionally substituted with 1 to 2 F,
  is optionally substituted with 1 to 4 $C_{1-3}$-alkyl optionally substituted with 2 to 3 F, and
  is optionally substituted with 1 to 2 substituents selected from Cl, —CN, —CON($C_{1-4}$-alkyl)$_2$, —COO—$C_{1-4}$-alkyl, $C_{1-3}$-alkyl-O—$C_{1-3}$-alkylene-, and $C_{1-3}$-alkyl-O—.

According to one embodiment, $R^3$ and $R^4$ are selected from the group $R^{3/4}$-G4a in which $R^3$ and $R^4$, together with the amide N atom they are attached to, form a saturated 4- to 6-membered monocyclic heterocyclyl
  optionally containing 1 ring member 0 that is non-adjacent to the amide N atom,
  wherein said heterocyclyl is optionally substituted with 2 F and is optionally substituted with 1 to 2 $CH_3$.

According to one embodiment, $R^3$ and $R^4$ are selected from the group $R^{3/4}$-G5a in which $R^3$ and $R^4$, together with the amide N atom they are attached to, form a heterocyclyl selected from the group consisting of

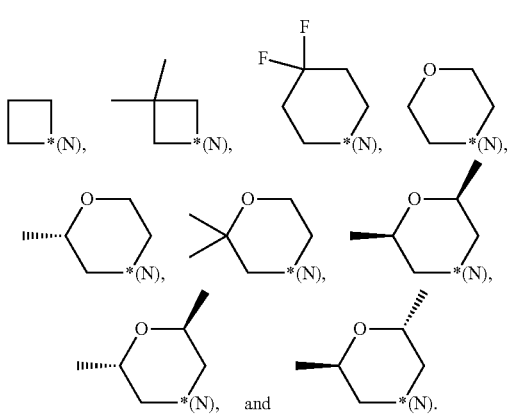

According to one embodiment, R³ and R⁴ are selected from the group R³/⁴-G6a in which R³ and R⁴, together with the amide N atom they are attached to, form a heterocyclyl selected from the group consisting of

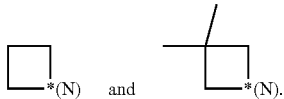

According to one embodiment, R³ and R⁴ are selected from the group R³/⁴-G7a in which R³ and R⁴, together with the amide N atom they are attached to, form the heterocyclyl

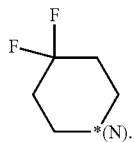

According to one embodiment, R³ and R⁴ are selected from the group R³/⁴-G8a in which R³ and R⁴, together with the amide N atom they are attached to, form a heterocyclyl selected from the group consisting of

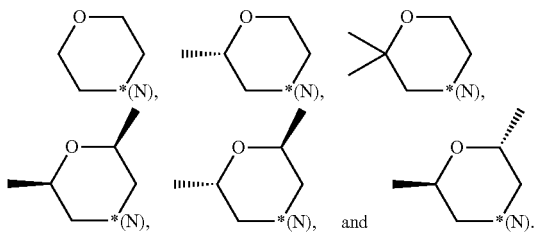

According to one embodiment, R³ and R⁴ are selected from the group R³/⁴-G1b in which R³ and R⁴, together with the amide N atom they are attached to, form a saturated 5- to 12-membered bicyclic heterocyclyl
- optionally further containing 1 to 3 ring members independently selected from >N—, >NH, >N($C_{1-4}$-alkyl), >N(CO—$C_{1-3}$-alkyl), >N(S(=O)₂—$C_{1-3}$-alkyl), and O, and
- optionally containing 1 ring member selected from >C=O and >S(=O)$_r$, with r=0, 1, or 2,
- provided that said heterocyclyl does not contain any heteroatom-heteroatom bonds other than N—N, N—O, and N—S(=O)$_{r=1,2}$ between ring members,
- wherein said heterocyclyl is optionally substituted with 1 to 6 F,
- is optionally substituted with 1 to 4 $C_{1-3}$-alkyl optionally substituted with 1 to 3 F, and
- is optionally substituted with 1 to 2 substituents selected from Cl, —CN, —CONH₂, —CONH($C_{1-4}$-alkyl), —CON($C_{1-4}$-alkyl)₂, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)₂—NH—, OH, and $C_{1-3}$-alkyl-O—.

According to one embodiment, R³ and R⁴ are selected from the group R³/⁴-G2b in which R³ and R⁴, together with the amide N atom they are attached to, form a saturated 6- to 11-membered bicyclic heterocyclyl
- optionally further containing 1 to 2 ring members independently selected from >N—, >NH, >N($C_{1-4}$-alkyl), >N(CO—$C_{1-3}$-alkyl), >N(S(=O)₂—$C_{1-3}$-alkyl), and O, and
- optionally containing 1 ring member selected from >C=O and >S(=O)$_r$, with r=0, 1, or 2,
- provided that said heterocyclyl does not contain any heteroatom-heteroatom bonds other than N—N, N—O, and N—S(=O)$_{r=1,2}$ between ring members,
- wherein said heterocyclyl is optionally substituted with 1 to 6 F,
- is optionally substituted with 1 to 4 $C_{1-3}$-alkyl optionally substituted with 1 to 3 F, and
- is optionally substituted with 1 to 2 substituents selected from Cl, —CN, —CONH₂, —CONH($C_{1-4}$-alkyl), —CON($C_{1-4}$-alkyl)₂, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)₂—NH—, OH, and $C_{1-3}$-alkyl-O—.

According to one embodiment, R³ and R⁴ are selected from the group R³/⁴-G3b in which R³ and R⁴, together with the amide N atom they are attached to, form a saturated 6- to 11-membered bridged or spiro bicyclic heterocyclyl optionally further containing 1 to 2 ring members independently selected from >N—, >NH, >N($C_{1-4}$-alkyl), and O that are non-adjacent to the amide N atom,
- provided that said heterocyclyl does not contain any O—O bonds between ring members,
- wherein said heterocyclyl is optionally substituted with 1 to 4 F,
- is optionally substituted with 1 to 2 $C_{1-3}$-alkyl optionally substituted with 1 to 3 F, and
- is optionally substituted with 1 to 2 substituents selected from Cl, —CN, —CON($C_{1-4}$-alkyl)₂, —COO—$C_{1-4}$-alkyl, $C_{1-3}$-alkyl-O—$C_{1-3}$-alkylene-, and $C_{1-3}$-alkyl-O—.

According to one embodiment, R³ and R⁴ are selected from the group R³/⁴-G4b in which R³ and R⁴, together with the amide N atom they are attached to, form a saturated 6- to 10-membered bridged or spiro bicyclic heterocyclyl optionally containing 1 ring member 0 that is non-adjacent to the amide N atom.

According to one embodiment, R³ and R⁴ are selected from the group R³/⁴-G5b in which R³ and R⁴, together with the amide N atom they are attached to, form a heterocyclyl selected from the group consisting of

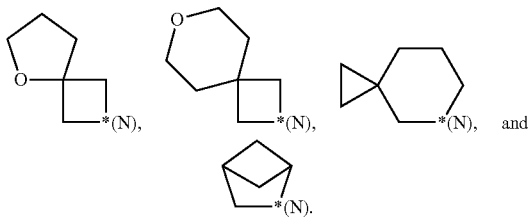

According to one embodiment, R³ and R⁴ are selected from the group R³/⁴-G1c in which R³ and R⁴, together with the amide N atom they are attached to, form a 7- to 12-membered fused bicyclic ring system,
wherein said bicyclic ring system is a heterocyclyl or heteroaryl consisting of
one non-aromatic ring containing said amide N atom and optionally further containing 1 to 2 ring members independently selected from =N—, >N—, >NH, >N($C_{1-4}$-alkyl), >N(CO—$C_{1-3}$-alkyl), >N(S(=O)$_2$—$C_{1-3}$-alkyl), and O, and
optionally containing 1 ring member selected from >C=O and >S(=O)$_r$, with r=0, 1, or 2, provided that there are no heteroatom-heteroatom bonds other than N—N, N—O, and N—S(=O)$_{r=1,2}$ between members of said non-aromatic ring,
and of
one aromatic ring selected from 5-membered monocycles containing 1 ring member selected from NH, N, O, and S and optionally further containing 1 to 2 ring members N, and of 6-membered monocycles containing 0, 1, or 2 ring members N,
wherein said bicyclic ring system is optionally substituted with 1 to 4 F,
is optionally substituted with 1 to 4 $C_{1-3}$-alkyl optionally substituted with 1 to 3 F, and
is optionally substituted with 1 to 2 substituents selected from Cl, —CN, —CONH$_2$, —CONH($C_{1-4}$-alkyl), —CON($C_{1-4}$-alkyl)$_2$, —OOOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O— optionally substituted with 1 to 3 F.

According to another embodiment, $R^3$ and $R^4$ are selected from the group $R^{3/4}$-G2c in which $R^3$ and $R^4$, together with the amide N atom they are attached to, form an 8- to 10-membered fused bicyclic ring system,
wherein said bicyclic ring system is a heterocyclyl or heteroaryl consisting of
one non-aromatic ring containing said amide N atom and optionally containing 1 ring member selected from =N—, >N—, and O,
and of
one aromatic ring selected from 5-membered monocycles containing 1 ring member selected from N, NH, O, and S and optionally further containing 1 ring member N, and of phenyl and pyridine,
wherein said bicyclic ring system is optionally substituted with 1 to 2 F,
is optionally substituted with 1 to 2 $C_{1-2}$-alkyl optionally substituted with 1 to 3 F, and
is optionally substituted with 1 to 2 substituents selected from Cl and $C_{1-2}$-alkyl-O— optionally substituted with 1 to 3 F.

According to another embodiment, $R^3$ and $R^4$ are selected from the group $R^{3/4}$-G3c in which $R^3$ and $R^4$, together with the amide N atom they are attached to, form an 8- to 9-membered fused bicyclic heteroaryl,
wherein said heteroaryl consists of one non-aromatic ring containing said amide N atom and optionally containing 1 ring member >N— that is non-adjacent to the amide N atom,
and of one pyrazolo or imidazolo ring,
wherein said heteroaryl is optionally substituted with 1 to 2 CH$_3$.

According to another embodiment, $R^3$ and $R^4$ are selected from the group $R^{3/4}$-G4c in which $R^3$ and $R^4$, together with the amide N atom they are attached to, form the heteroaryl

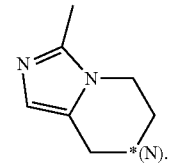

Stereochemistry:

According to one embodiment, the stereochemistry of the compound of formula (I.0) is according to formula (I.1)

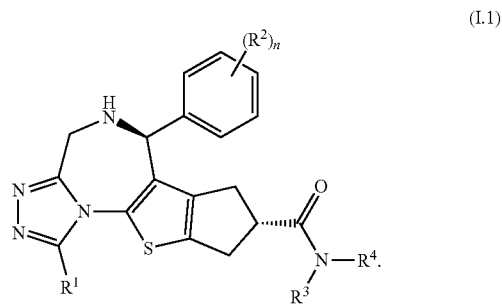

(I.1)

According to another embodiment, the stereochemistry of the compound of formula (I.0) is according to formula (I.2)

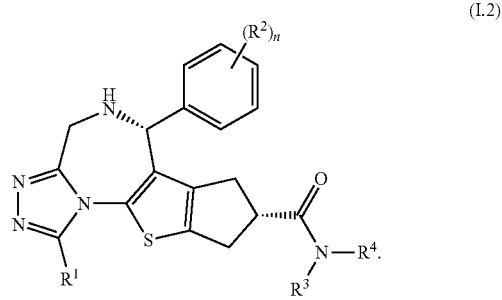

(I.2)

Further preferred subgeneric embodiments of the compounds of formula (I.0) are set forth as embodiments (I-a) to (I-z) in the following Table 1, wherein the above-mentioned substituent definitions are used. For example, the entry $R^1$-G1 in column $R^1$ and row (I-a) means that in embodiment (I-a) substituent $R^1$ is selected from the definition designated $R^1$-G1. The same applies analogously to the other variables incorporated in the general formulas.

TABLE 1

| Embodiment | R$^1$ | R$^2$ | n | R$^3$ | R$^4$ |
|---|---|---|---|---|---|
| (I-a) | R$^1$-G1 | R$^2$-G1 | n-G1 | R$^3$-G1 | R$^4$-G1a or R$^4$-G1b or R$^4$-G1c |
| (I-b) | R$^1$-G1 | R$^2$-G1 | n-G1 | | R$^{3/4}$-G1a or R$^{3/4}$-G1b or R$^{3/4}$-G1c |
| (I-c) | R$^1$-G1 | R$^2$-G1 | n-G1 | R$^3$-G1 | R$^4$-G2a or R$^4$-G1b or R$^4$-G1c |
| (I-d) | R$^1$-G1 | R$^2$-G1 | n-G1 | | R$^{3/4}$-G2a or R$^{3/4}$-G2b or R$^{3/4}$-G1c |
| (I-e) | R$^1$-G1 | R$^2$-G1 | n-G2 | R$^3$-G1 | R$^4$-G2a or R$^4$-G2b or R$^4$-G2c |
| (I-f) | R$^1$-G1 | R$^2$-G1 | n-G2 | | R$^{3/4}$-G2a or R$^{3/4}$-G2b or R$^{3/4}$-G2c |
| (I-g) | R$^1$-G1 | R$^2$-G2 | n-G2 | R$^3$-G1 | R$^4$-G2a or R$^4$-G2b or R$^4$-G2c |
| (I-h) | R$^1$-G1 | R$^2$-G2 | n-G2 | | R$^{3/4}$-G2a or R$^{3/4}$-G2b or R$^{3/4}$-G2c |
| (I-i) | R$^1$-G1 | R$^2$-G2 | n-G2 | R$^3$-G1 | R$^4$-G3a or R$^4$-G2b or R$^4$-G2c |
| (I-j) | R$^1$-G1 | R$^2$-G2 | n-G2 | | R$^{3/4}$-G3a or R$^{3/4}$-G5b or R$^{3/4}$-G2c |
| (I-k) | R$^1$-G2 | R$^2$-G2 | n-G2 | R$^3$-G1 | R$^4$-G3a or R$^4$-G3b or R$^4$-G3c |
| (I-L) | R$^1$-G2 | R$^2$-G2 | n-G2 | | R$^{3/4}$-G3a or R$^{3/4}$-G5b or R$^{3/4}$-G3c |
| (I-m) | R$^1$-G2 | R$^2$-G3 | n-G2 | R$^3$-G2 | R$^4$-G4a or R$^4$-G3b or R$^4$-G3c |
| (I-n) | R$^1$-G2 | R$^2$-G3 | n-G2 | | R$^{3/4}$-G4a or R$^{3/4}$-G4b or R$^{3/4}$-G3c |
| (I-o) | R$^1$-G3 | R$^2$-G3 | n-G2 | R$^3$-G3 | R$^4$-G5a or R$^4$-G4b or R$^4$-G4c |
| (I-p) | R$^1$-G3 | R$^2$-G3 | n-G2 | | R$^{3/4}$-G5a or R$^{3/4}$-G5b or R$^{3/4}$-G4c |
| (I-q) | R$^1$-G3 | Ph-G1* | | R$^3$-G3 | R$^4$-G5a or R$^4$-G4b or R$^4$-G4c |
| (I-r) | R$^1$-G3 | Ph-G1* | | | R$^{3/4}$-G5a or R$^{3/4}$-G5b or R$^{3/4}$-G4c |
| (I-s) | R$^1$-G4 | R$^2$-G4 | n-G4 | R$^3$-G3 | R$^4$-G5a or R$^4$-G4b or R$^4$-G4c |
| (I-t) | R$^1$-G4 | R$^2$-G4 | n-G4 | | R$^{3/4}$-G5a or R$^{3/4}$-G5b or R$^{3/4}$-G4c |
| (I-u) | R$^1$-G4 | Ph-G2* | | R$^3$-G3 | R$^4$-G5a or R$^4$-G4b or R$^4$-G4c |
| (I-v) | R$^1$-G4 | Ph-G2* | | | R$^{3/4}$-G5a or R$^{3/4}$-G5b or R$^{3/4}$-G4c |
| (I-w) | R$^1$-G4 | Ph-G8* | | R$^3$-G3 | R$^4$-G5a or R$^4$-G4b or R$^4$-G4c |
| (I-x) | R$^1$-G4 | Ph-G8* | | R$^3$-G3 | R$^4$-G7c |
| (I-y) | R$^1$-G4 | Ph-G8* | | R$^{3/4}$-G5a or R$^{3/4}$-G4c | |
| (I-z) | R$^1$-G4 | Ph-G8* | | R$^{3/4}$-G8a | |

*including the corresponding substitution pattern as defined in Ph-G1, Ph-G2 and Ph-G8, respectively Particularly preferred are those subgeneric embodiments (I-a) to (I-z) which, in respect of the definitions of R$^1$, R$^2$, R$^3$, R$^4$, and n correspond to the subgeneric embodiments (I-a) to (I-z) of Table 1, in particular (I-w) to (I-z), and wherein the stereochemistry of the compounds is according to formula (I.1), i.e. embodiments (I.1-w), (I.1-x), (I.1-y) and (I.1-z).

Particularly preferred compounds, the salts thereof, or any solvates or hydrates thereof, are those described in the section Examples and Experimental Data.

According to one embodiment, the compound of formula (I.0) is selected from the group consisting of

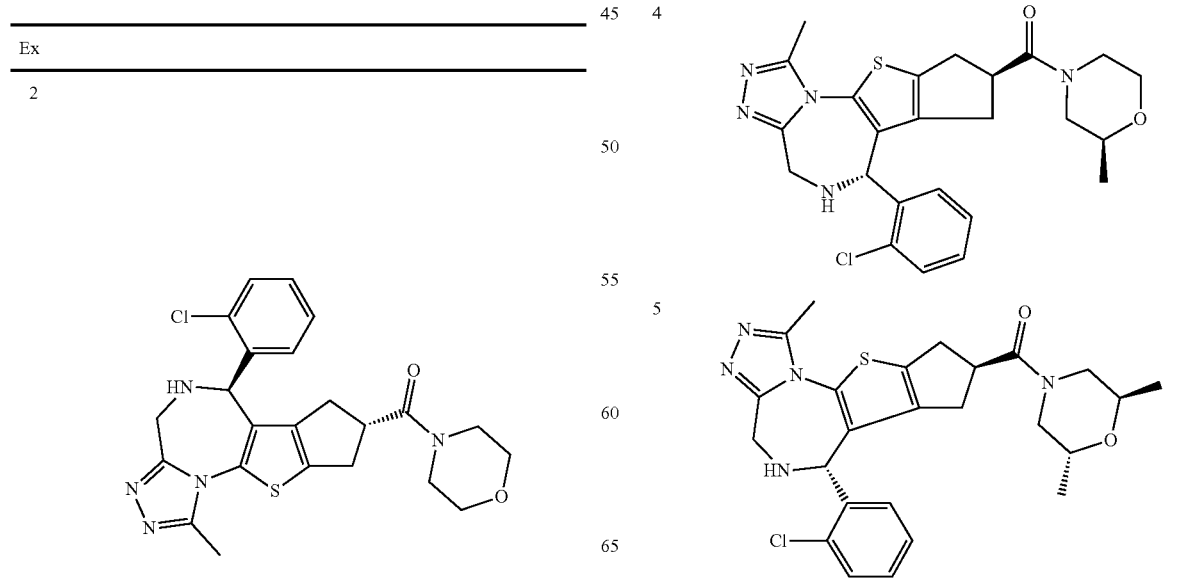

| Ex |
|---|
| 2 |
| 3 |
| 4 |
| 5 |

| Ex | | Ex | |
|---|---|---|---|
| 6 | 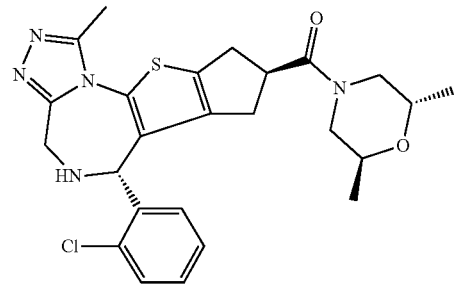 [SMILES: Cc1nnc2n1-c1sc3c(c1[C@H](c1ccccc1Cl)NC2)C[C@H](C(=O)N1C[C@H](C)O[C@@H](C)C1)C3] | 11 | 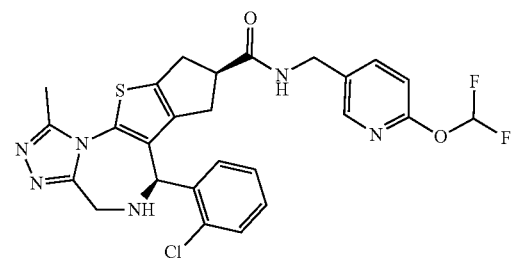 |
| 7 | 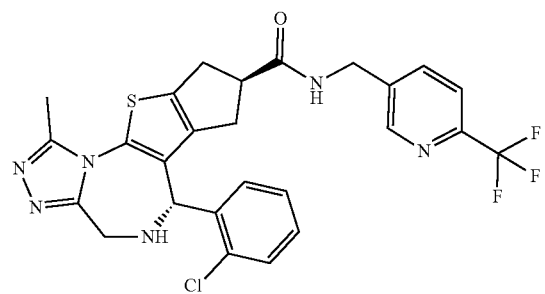 [SMILES: Cc1nnc2n1-c1sc3c(c1[C@H](c1ccccc1Cl)NC2)C[C@H](C(=O)NCc1ccc(C(F)(F)F)nc1)C3] | 12 | 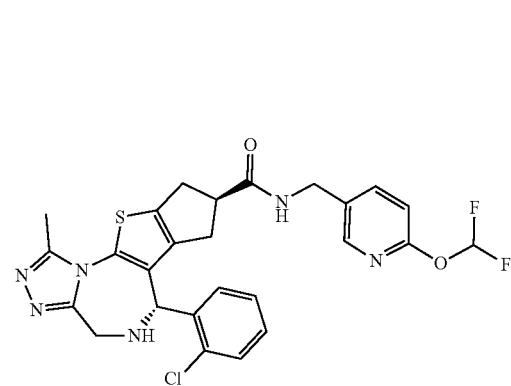 |
| 8 | 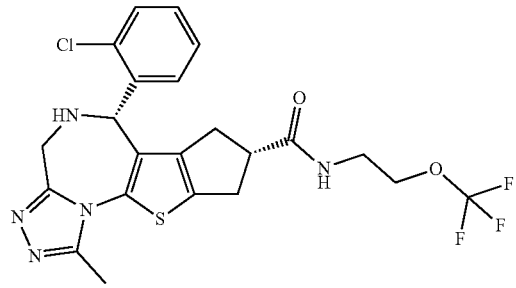 [SMILES: Cc1nnc2n1-c1sc3c(c1[C@@H](c1ccccc1Cl)NC2)C[C@H](C(=O)NCCOC(F)(F)F)C3] | 13 | 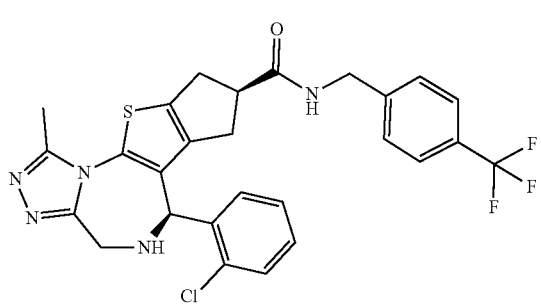 |
| 9 | 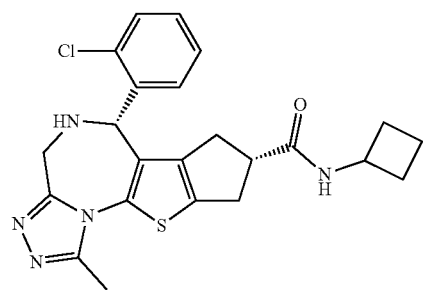 [SMILES: Cc1nnc2n1-c1sc3c(c1[C@@H](c1ccccc1Cl)NC2)C[C@H](C(=O)NC1CCC1)C3] | 14 | 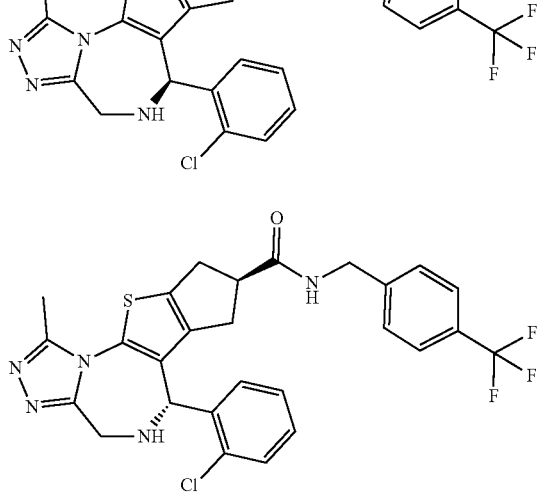 |
| 10 | 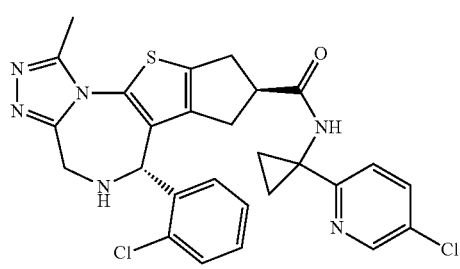 [SMILES: Cc1nnc2n1-c1sc3c(c1[C@H](c1ccccc1Cl)NC2)C[C@H](C(=O)NC1(c2ccc(Cl)cn2)CC1)C3] | 15 | 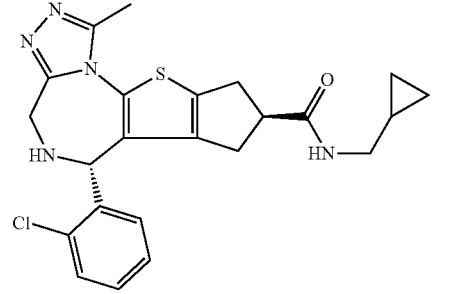 [SMILES: Cc1nnc2n1-c1sc3c(c1[C@H](c1ccccc1Cl)NC2)C[C@H](C(=O)NCC1CC1)C3] |

| Ex | | Ex | |
|---|---|---|---|
| 16 | 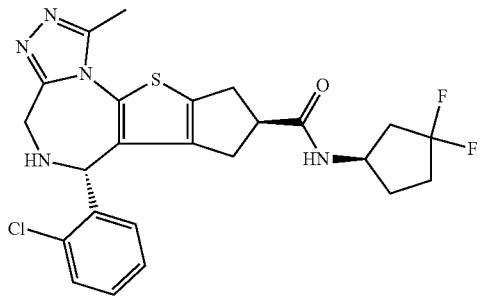 [SMILES: Cc1nnc2n1-c1sc3c(c1[C@H](c1ccccc1Cl)NC2)C[C@H](C(=O)N[C@@H]1CCC(F)(F)C1)C3] | 21 | 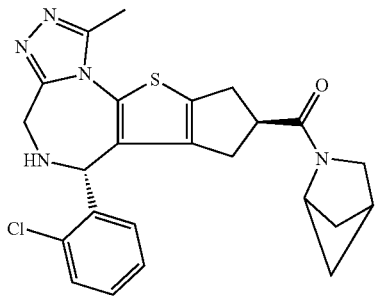 |
| 17 | 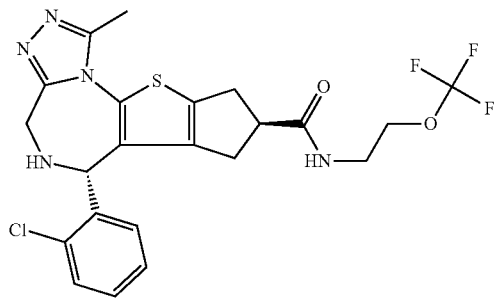 [SMILES: Cc1nnc2n1-c1sc3c(c1[C@H](c1ccccc1Cl)NC2)C[C@H](C(=O)NCCOC(F)(F)F)C3] | 22 | 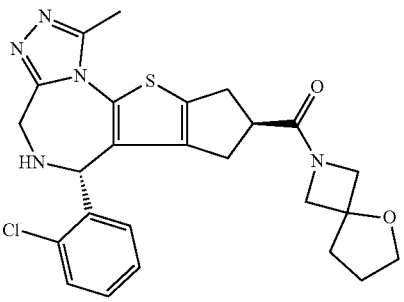 |
| 18 | 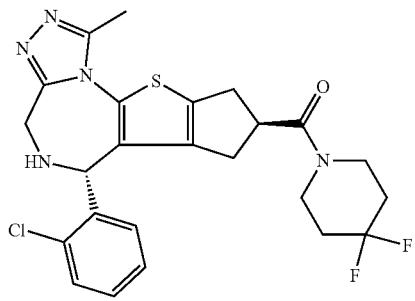 [SMILES: Cc1nnc2n1-c1sc3c(c1[C@H](c1ccccc1Cl)NC2)C[C@H](C(=O)N1CCC(F)(F)CC1)C3] | 23 | 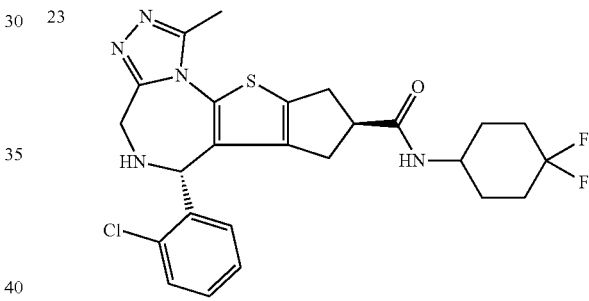 |
| 19 | 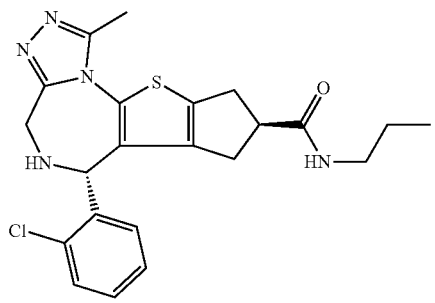 [SMILES: CCCNC(=O)[C@@H]1Cc2sc3c(c2C1)[C@H](c1ccccc1Cl)NCc1nnc(C)n1-3] | 24 | 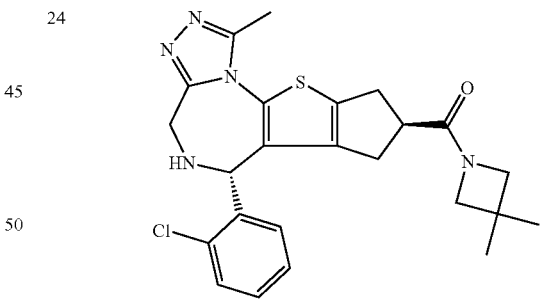 |
| 20 | 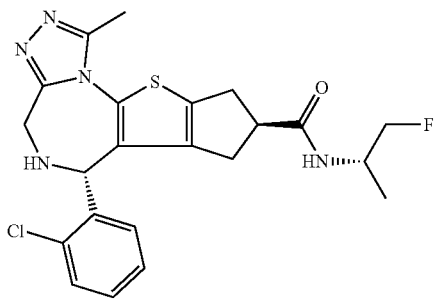 [SMILES: Cc1nnc2n1-c1sc3c(c1[C@H](c1ccccc1Cl)NC2)C[C@H](C(=O)N[C@@H](C)CF)C3] | 25 | 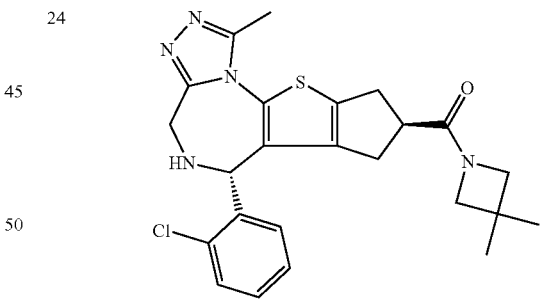 |

| Ex | | Ex | |
|---|---|---|---|
| 26 | 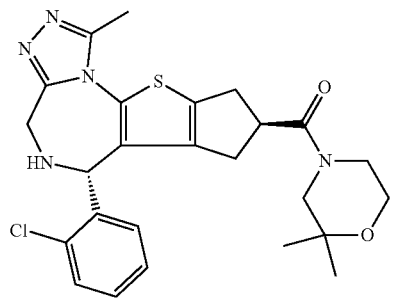 [SMILES: Cc1nnc2n1-c1sc3c(c1[C@H](c1ccccc1Cl)NC2)C[C@H](C(=O)N1CCOC(C)(C)C1)C3] | 31 | 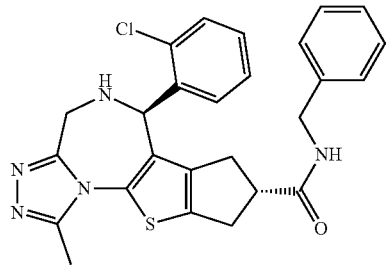 |
| 27 | 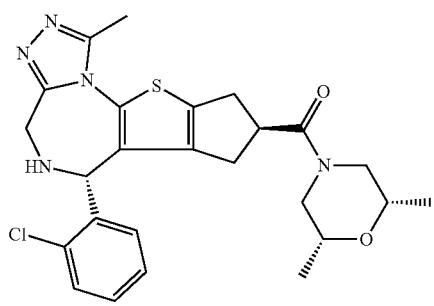 [SMILES: Cc1nnc2n1-c1sc3c(c1[C@H](c1ccccc1Cl)NC2)C[C@H](C(=O)N1C[C@@H](C)O[C@@H](C)C1)C3] | 32 | 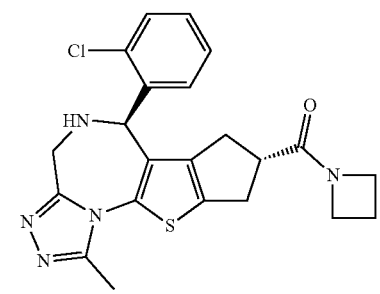 |
| 28 | 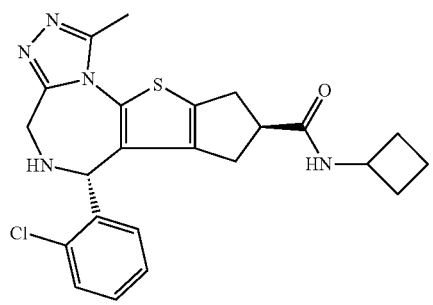 [SMILES: Cc1nnc2n1-c1sc3c(c1[C@H](c1ccccc1Cl)NC2)C[C@H](C(=O)NC1CCC1)C3] | 33 | 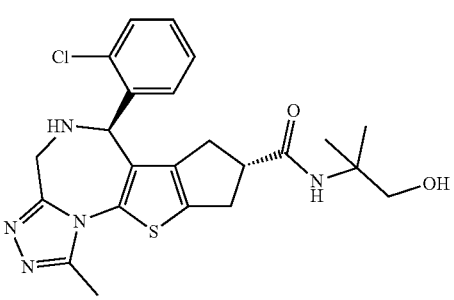 |
| 29 | 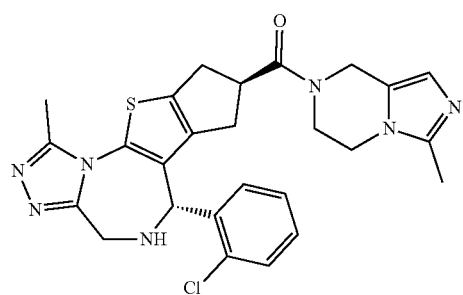 [SMILES: Cc1ncc2n1CCN(C(=O)[C@@H]1Cc3sc4c(c3C1)[C@H](c1ccccc1Cl)NCc1nnc(C)n1-4)C2] | 34 | 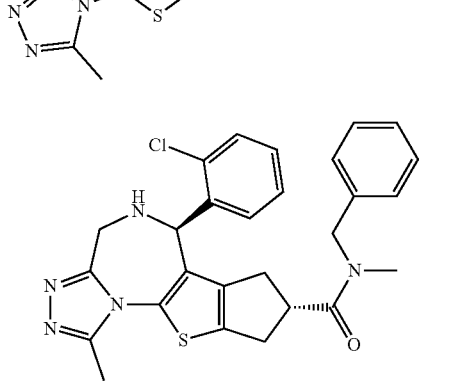 |
| 30 | 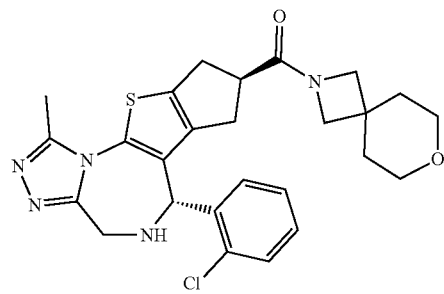 [SMILES: Cc1nnc2n1-c1sc3c(c1[C@H](c1ccccc1Cl)NC2)C[C@H](C(=O)N1CC2(CCOCC2)C1)C3] | 35 | 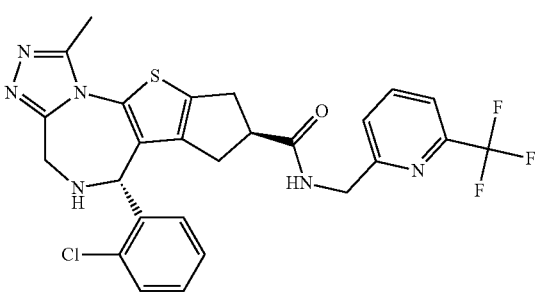 [SMILES: Cc1nnc2n1-c1sc3c(c1[C@H](c1ccccc1Cl)NC2)C[C@H](C(=O)NCc1cccc(C(F)(F)F)n1)C3] |

-continued
| Ex | |
|---|---|
| 36 | 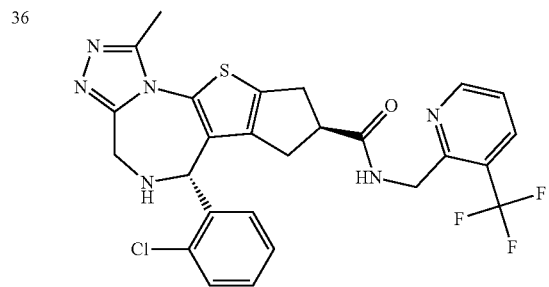 |
| 37 | 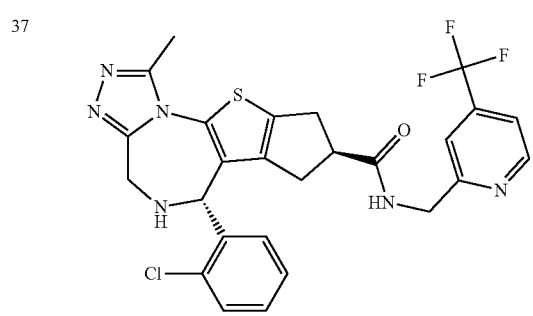 |
| 38 | 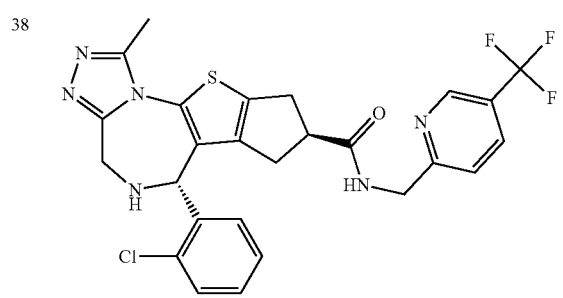 |
| 39 | 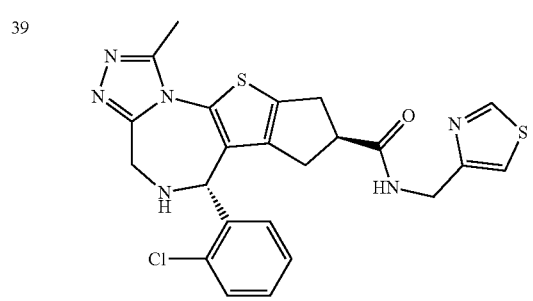 |
| 40 | 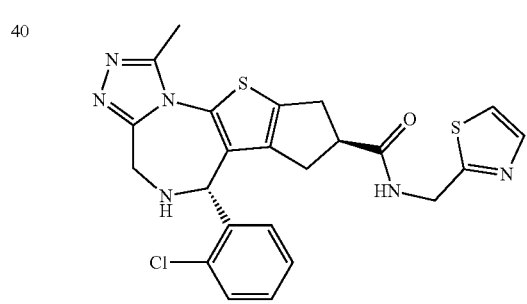 |
-continued
| Ex | |
|---|---|
| 41 | 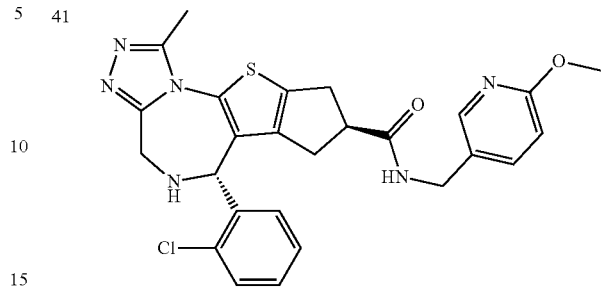 |
| 42 | 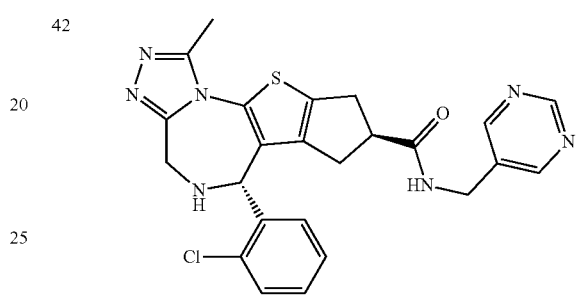 |
| 43 | 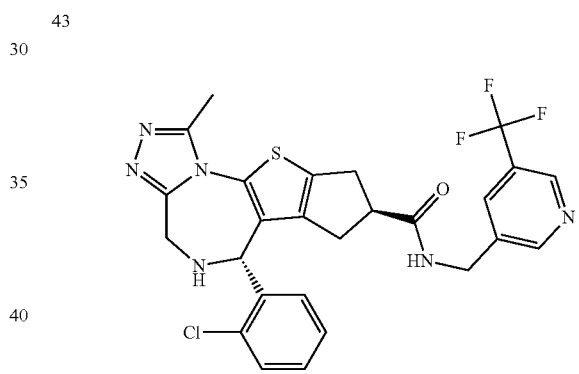 |
| 44 | 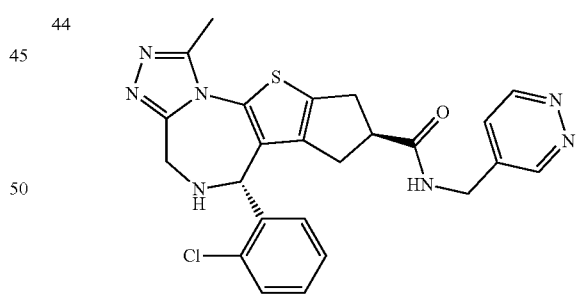 |
| 45 | 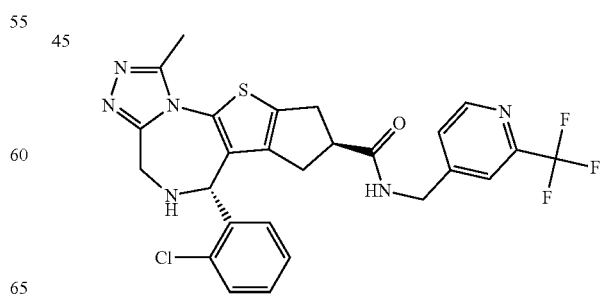 |

| Ex | | Ex | |
|---|---|---|---|
| 46 | 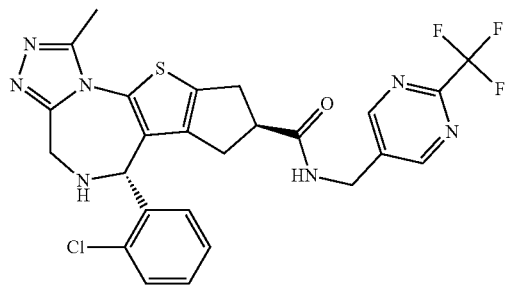 [SMILES: Cc1nnc2n1-c1sc3c(c1[C@H](c1ccccc1Cl)NC2)C[C@H](C(=O)NCc1cnc(C(F)(F)F)nc1)C3] | 51 | 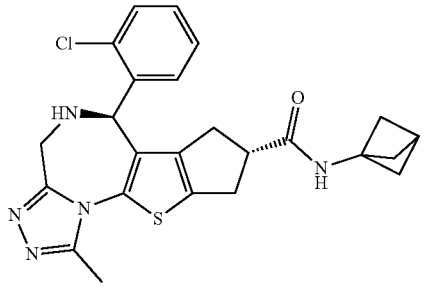 |
| 47 | 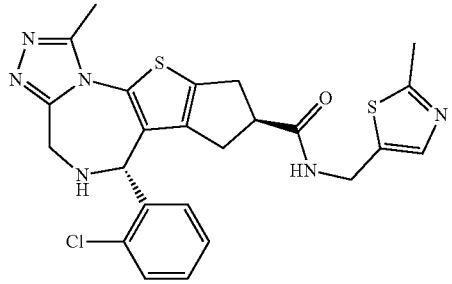 [SMILES: Cc1ncc(CNC(=O)[C@@H]2Cc3sc4c(c3C2)[C@H](c2ccccc2Cl)NCc2nnc(C)n2-4)s1] | 63 | 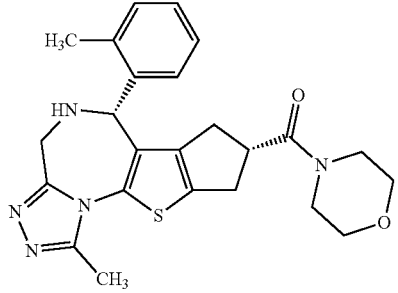 |
| 48 | 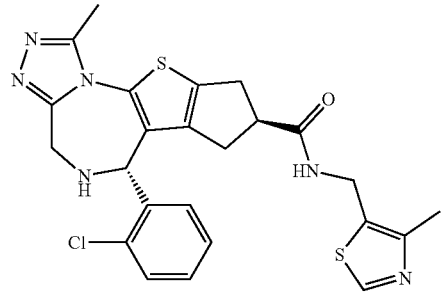 [SMILES: Cc1ncsc1CNC(=O)[C@@H]1Cc2sc3c(c2C1)[C@H](c1ccccc1Cl)NCc1nnc(C)n1-3] | 64 | 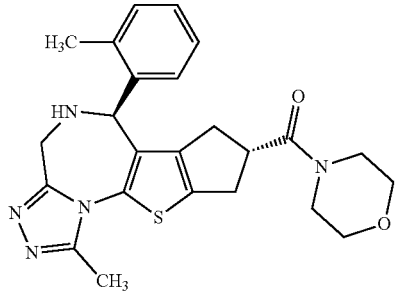 |
| 49 | 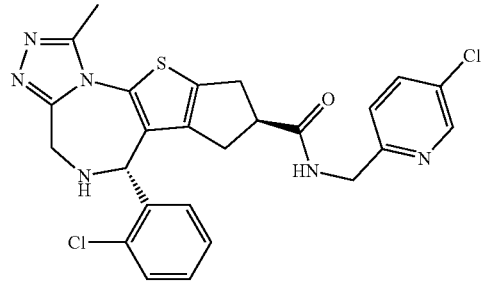 [SMILES: Cc1nnc2n1-c1sc3c(c1[C@H](c1ccccc1Cl)NC2)C[C@H](C(=O)NCc1ccc(Cl)cn1)C3] | 68 | 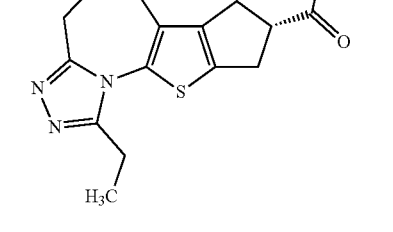 |
| 50 | 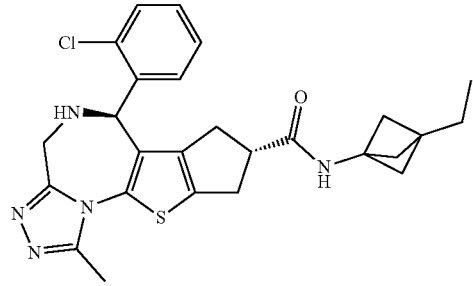 [SMILES: CCC12CC(NC(=O)[C@@H]3Cc4sc5c(c4C3)[C@H](c3ccccc3Cl)NCc3nnc(C)n3-5)(C1)C2] | 69 | 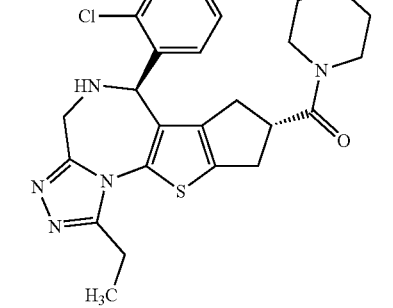 |

| Ex | | Isomer of Ex | |
|---|---|---|---|
| 72 | 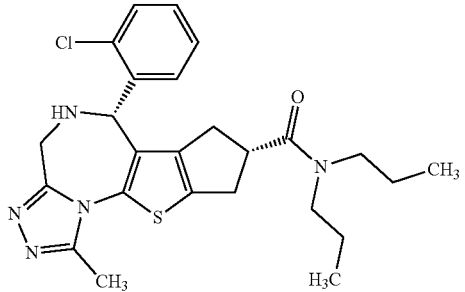 [SMILES: CCCN(CCC)C(=O)[C@@H]1Cc2sc3c(c2C1)[C@@H](c1ccccc1Cl)NCc1nnc(C)n1-3] | 52 | 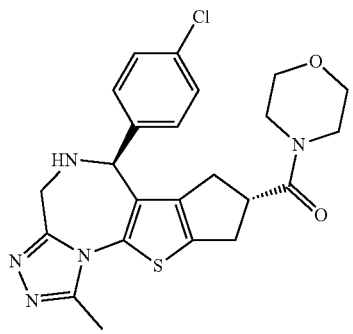 |
| 73 | 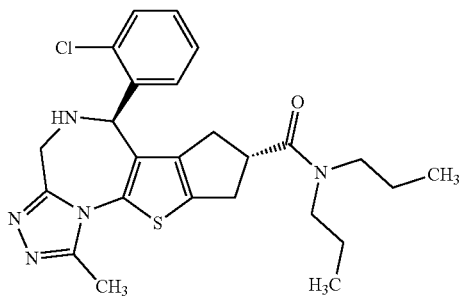 [SMILES: CCCN(CCC)C(=O)[C@@H]1Cc2sc3c(c2C1)[C@H](c1ccccc1Cl)NCc1nnc(C)n1-3] | 53 | 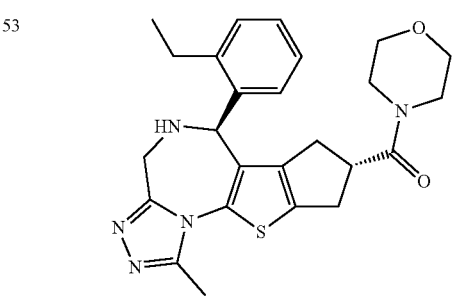 |
| | | 54 | 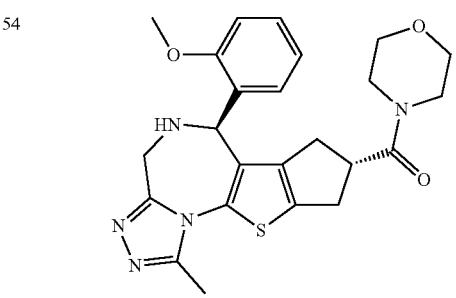 |
| 76 | 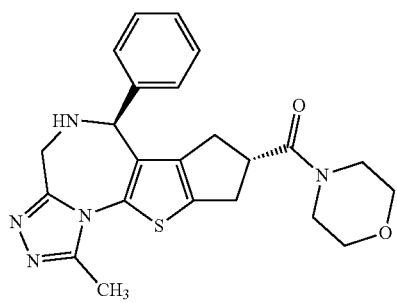 [SMILES: Cc1nnc2n1-c1sc3c(c1[C@H](c1ccccc1)NC2)C[C@H](C(=O)N1CCOCC1)C3] | 55 | 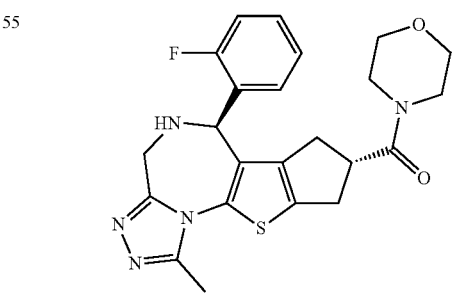 |
| 78 | 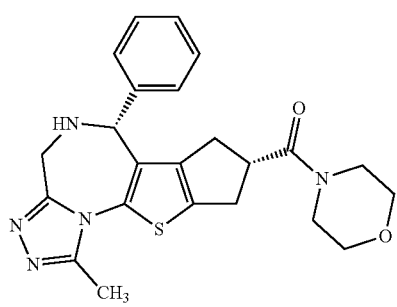 [SMILES: Cc1nnc2n1-c1sc3c(c1[C@@H](c1ccccc1)NC2)C[C@H](C(=O)N1CCOCC1)C3] | 56 | 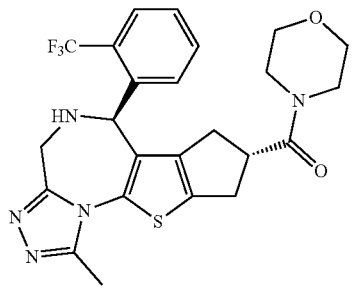 [SMILES: Cc1nnc2n1-c1sc3c(c1[C@H](c1ccccc1C(F)(F)F)NC2)C[C@H](C(=O)N1CCOCC1)C3] |
According to another embodiment, the compound of formula (I.0) and/or (I.1) is selected from the group consisting of

| Isomer of Ex | | Isomer of Ex | |
|---|---|---|---|
| 57 | 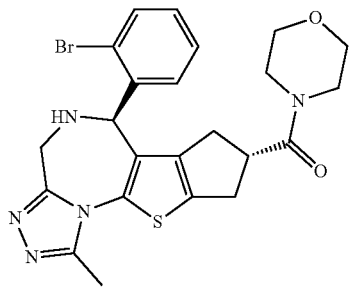 [SMILES: Cc1nnc2n1-c1sc3c(c1[C@H](c1ccccc1Br)NC2)C[C@H](C(=O)N1CCOCC1)C3] | 62 | 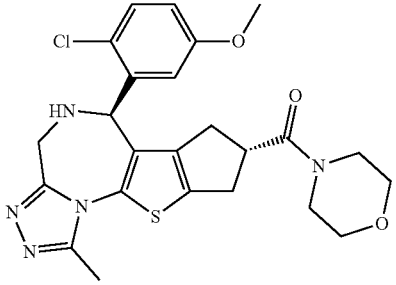 |
| 58 | 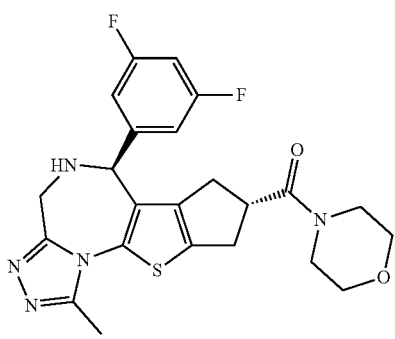 [SMILES: Cc1nnc2n1-c1sc3c(c1[C@H](c1cc(F)cc(F)c1)NC2)C[C@H](C(=O)N1CCOCC1)C3] | 65 | 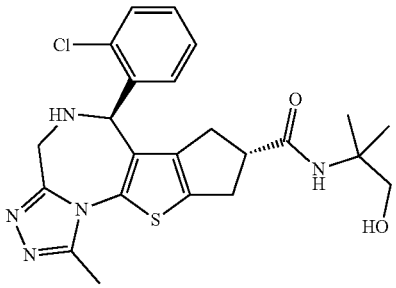 |
| 59 | 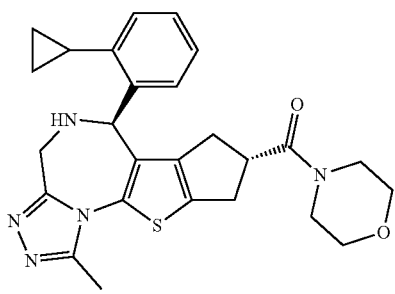 [SMILES: Cc1nnc2n1-c1sc3c(c1[C@H](c1ccccc1C1CC1)NC2)C[C@H](C(=O)N1CCOCC1)C3] | 66 | 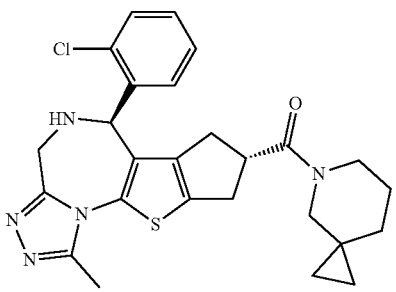 |
| 60 | 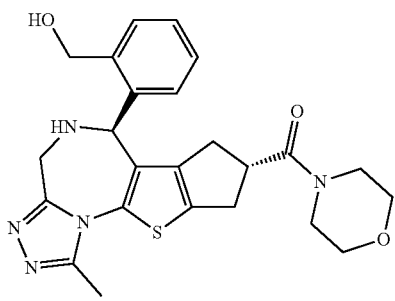 [SMILES: Cc1nnc2n1-c1sc3c(c1[C@H](c1ccccc1CO)NC2)C[C@H](C(=O)N1CCOCC1)C3] | 79 | 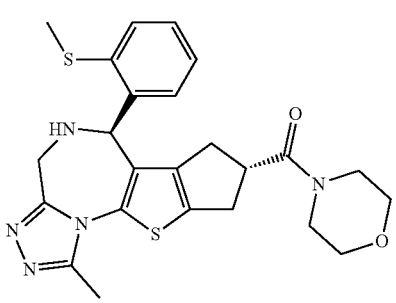 |
| 61 | 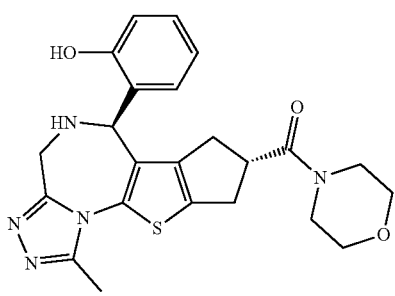 [SMILES: Cc1nnc2n1-c1sc3c(c1[C@H](c1ccccc1O)NC2)C[C@H](C(=O)N1CCOCC1)C3] | 80 | 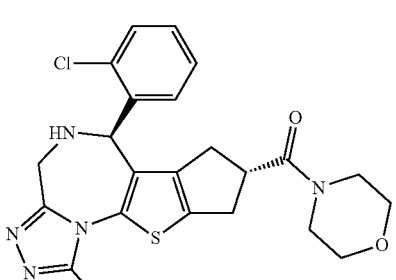 |

| Isomer of Ex | |
|---|---|
| 81 | 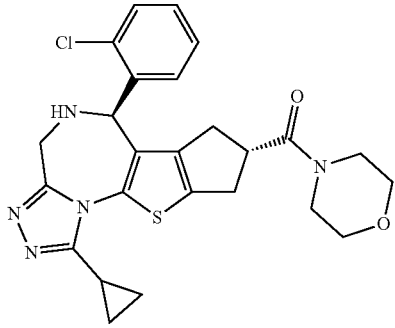 [SMILES: O=C([C@@H]1Cc2sc3c(c2C1)[C@H](c1ccccc1Cl)NCc1nnc(C2CC2)n1-3)N1CCOCC1] |
According to another embodiment, the compound of formula (I.0) and/or (I.1) is selected from the group consisting of
| Ex | |
|---|---|
| 2 | 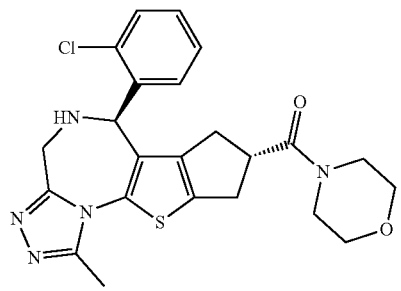 [SMILES: Cc1nnc2n1-c1sc3c(c1[C@H](c1ccccc1Cl)NC2)C[C@H](C(=O)N1CCOCC1)C3] |
| 4 | 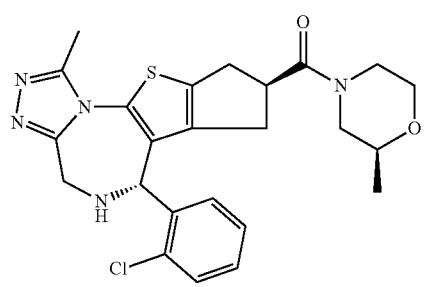 [SMILES: Cc1nnc2n1-c1sc3c(c1[C@H](c1ccccc1Cl)NC2)C[C@H](C(=O)N1CCO[C@@H](C)C1)C3] |
| 5 | 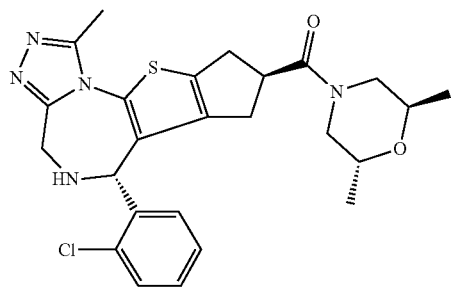 [SMILES: Cc1nnc2n1-c1sc3c(c1[C@H](c1ccccc1Cl)NC2)C[C@H](C(=O)N1C[C@@H](C)O[C@H](C)C1)C3] |
| 6 | 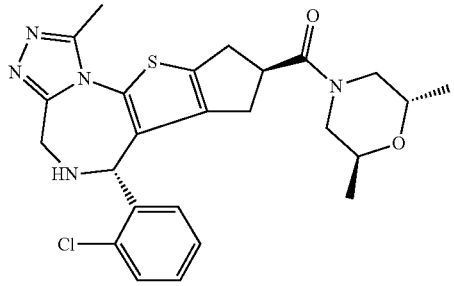 [SMILES: Cc1nnc2n1-c1sc3c(c1[C@H](c1ccccc1Cl)NC2)C[C@H](C(=O)N1C[C@H](C)O[C@@H](C)C1)C3] |
| 15 | 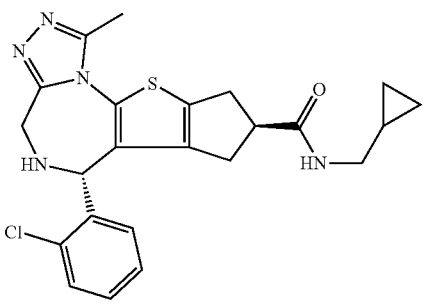 [SMILES: Cc1nnc2n1-c1sc3c(c1[C@H](c1ccccc1Cl)NC2)C[C@H](C(=O)NCC1CC1)C3] |
| 16 | 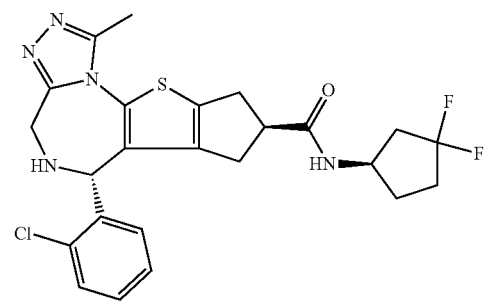 [SMILES: Cc1nnc2n1-c1sc3c(c1[C@H](c1ccccc1Cl)NC2)C[C@H](C(=O)N[C@@H]1CCC(F)(F)C1)C3] |
| 17 | 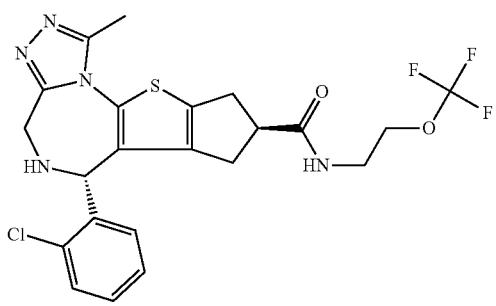 [SMILES: Cc1nnc2n1-c1sc3c(c1[C@H](c1ccccc1Cl)NC2)C[C@H](C(=O)NCCOC(F)(F)F)C3] |
| 18 | 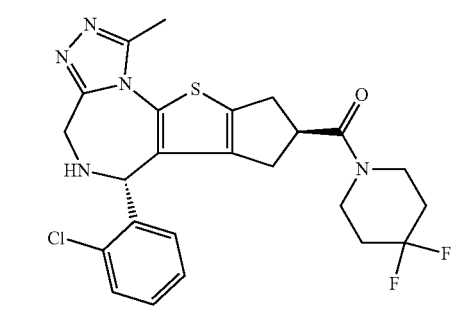 [SMILES: Cc1nnc2n1-c1sc3c(c1[C@H](c1ccccc1Cl)NC2)C[C@H](C(=O)N1CCC(F)(F)CC1)C3] |

| Ex | |
|---|---|
| 19 | 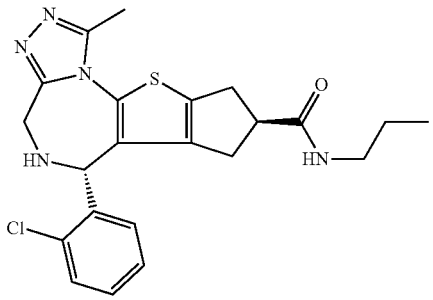 [SMILES: CCCNC(=O)[C@@H]1Cc2sc3c(c2C1)[C@H](c1ccccc1Cl)NCc1nnc(C)n1-3] |
| 21 | 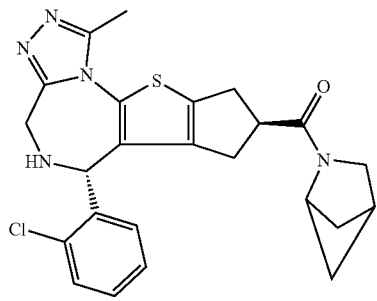 [SMILES: Cc1nnc2n1-c1sc3c(c1[C@H](c1ccccc1Cl)NC2)C[C@H](C(=O)N1CC2CC1C2)C3] |
| 22 | 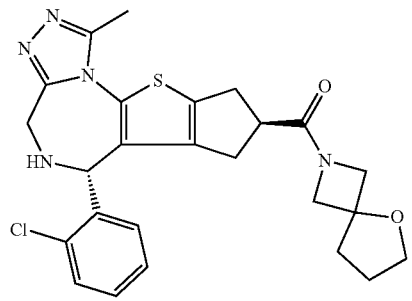 [SMILES: Cc1nnc2n1-c1sc3c(c1[C@H](c1ccccc1Cl)NC2)C[C@H](C(=O)N1CC2(CCCO2)C1)C3] |
| 23 | 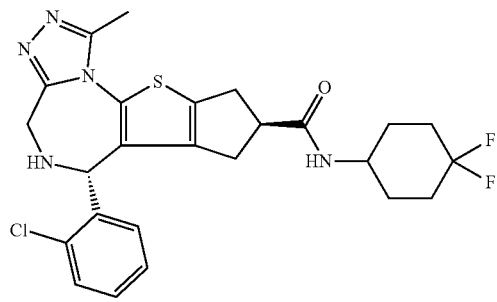 [SMILES: Cc1nnc2n1-c1sc3c(c1[C@H](c1ccccc1Cl)NC2)C[C@H](C(=O)NC1CCC(F)(F)CC1)C3] |
| 24 | 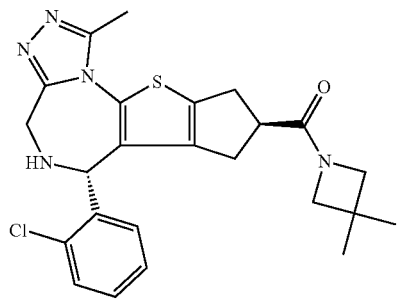 [SMILES: Cc1nnc2n1-c1sc3c(c1[C@H](c1ccccc1Cl)NC2)C[C@H](C(=O)N1CC(C)(C)C1)C3] |
| 25 | 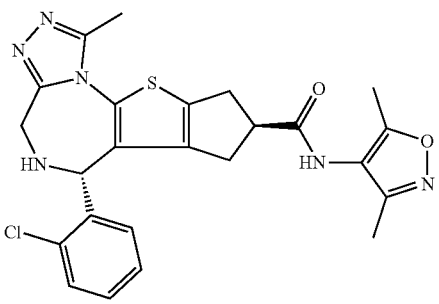 [SMILES: Cc1noc(C)c1NC(=O)[C@@H]1Cc2sc3c(c2C1)[C@H](c1ccccc1Cl)NCc1nnc(C)n1-3] |
| 27 | 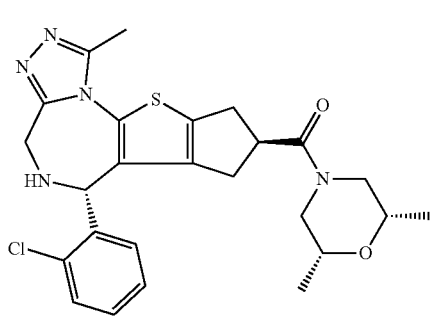 [SMILES: Cc1nnc2n1-c1sc3c(c1[C@H](c1ccccc1Cl)NC2)C[C@H](C(=O)N1C[C@@H](C)O[C@@H](C)C1)C3] |
| 30 | 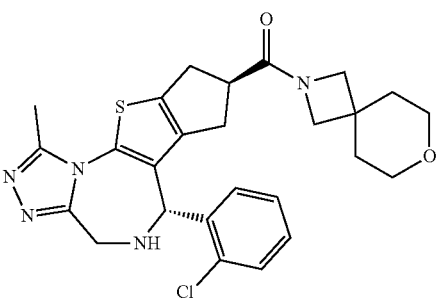 [SMILES: Cc1nnc2n1-c1sc3c(c1[C@H](c1ccccc1Cl)NC2)C[C@H](C(=O)N1CC2(CCOCC2)C1)C3] |
| 31 | 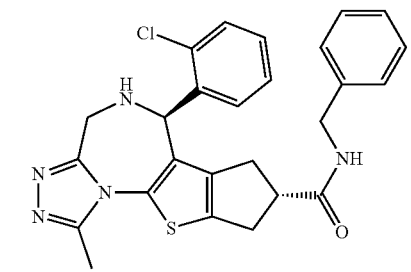 [SMILES: Cc1nnc2n1-c1sc3c(c1[C@H](c1ccccc1Cl)NC2)C[C@H](C(=O)NCc1ccccc1)C3] |
| 32 | 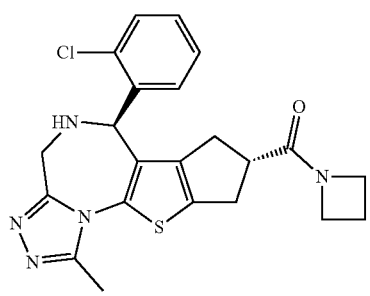 [SMILES: Cc1nnc2n1-c1sc3c(c1[C@H](c1ccccc1Cl)NC2)C[C@H](C(=O)N1CCC1)C3] |

| Ex | | Ex | |
|---|---|---|---|
| 33 | 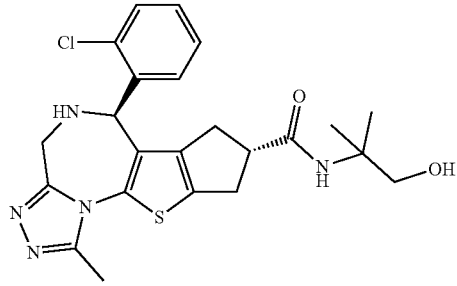 [SMILES: Cc1nnc2n1-c1sc3c(c1[C@H](c1ccccc1Cl)NC2)C[C@H](C(=O)NC(C)(C)CO)C3] | 7 | 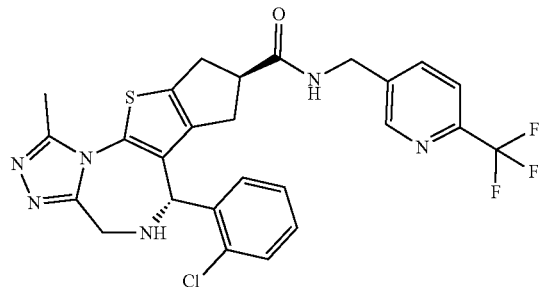 |
| 34 | 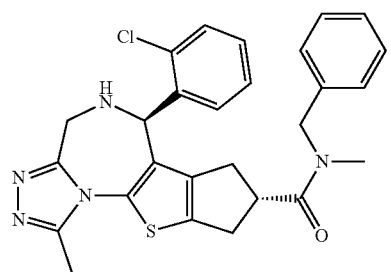 [SMILES: Cc1nnc2n1-c1sc3c(c1[C@H](c1ccccc1Cl)NC2)C[C@H](C(=O)N(C)Cc1ccccc1)C3] | 9 | 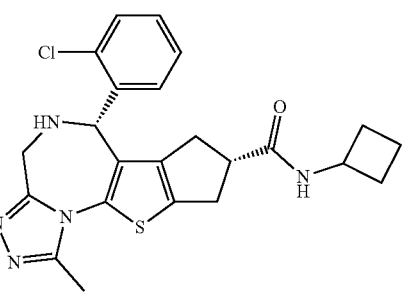 |
| 46 | 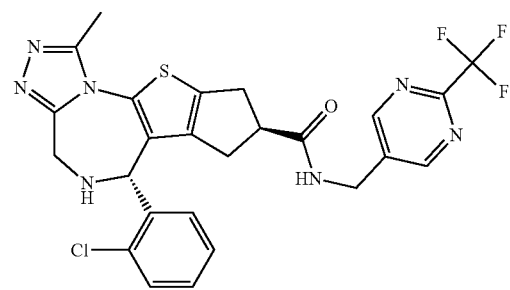 [SMILES: Cc1nnc2n1-c1sc3c(c1[C@H](c1ccccc1Cl)NC2)C[C@H](C(=O)NCc1cnc(C(F)(F)F)nc1)C3] | 10 | 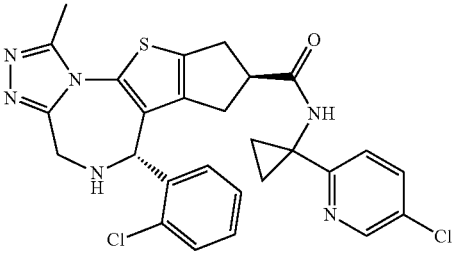 |
| 51 | 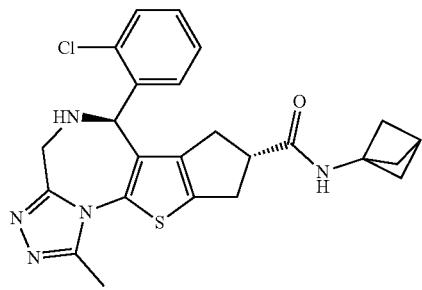 [SMILES: Cc1nnc2n1-c1sc3c(c1[C@H](c1ccccc1Cl)NC2)C[C@H](C(=O)NC12CC(C1)C2)C3] | 12 | 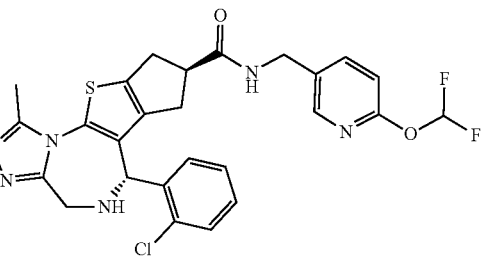 |
| 73 | 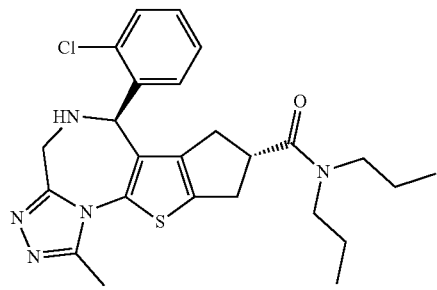 [SMILES: CCCN(CCC)C(=O)[C@@H]1Cc2sc3c(c2C1)[C@H](c1ccccc1Cl)NCc1nnc(C)n1-3] | 14 | 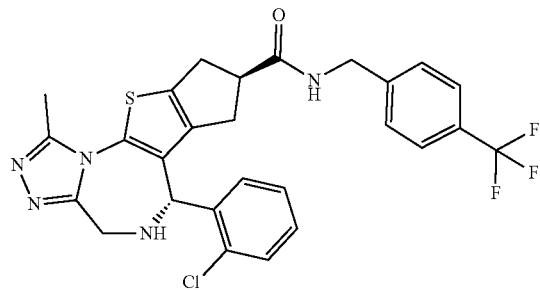 [SMILES: Cc1nnc2n1-c1sc3c(c1[C@H](c1ccccc1Cl)NC2)C[C@H](C(=O)NCc1ccc(C(F)(F)F)cc1)C3] |
According to another embodiment, the compound of formula (I.0) and/or (I.1) is selected from the group consisting of -continued
| Ex | |
|---|---|
| 20 | 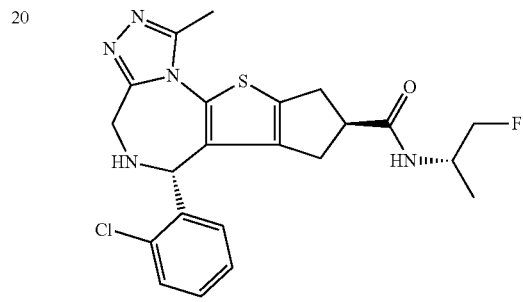 |
| 26 | 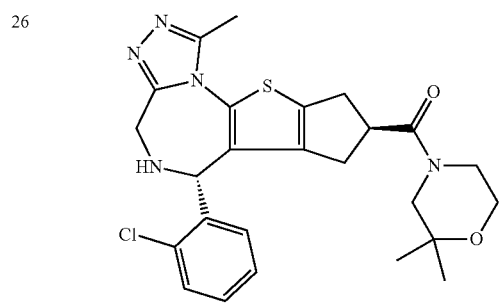 |
| 28 | 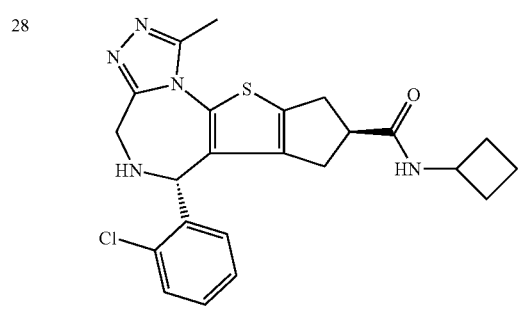 |
| 35 | 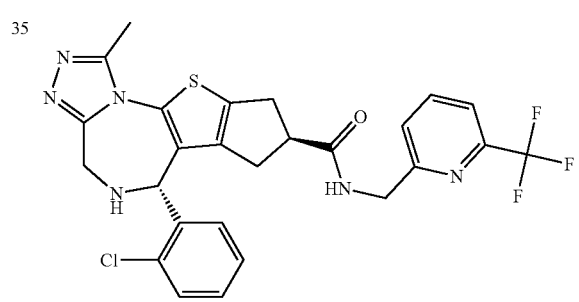 |
| 36 | 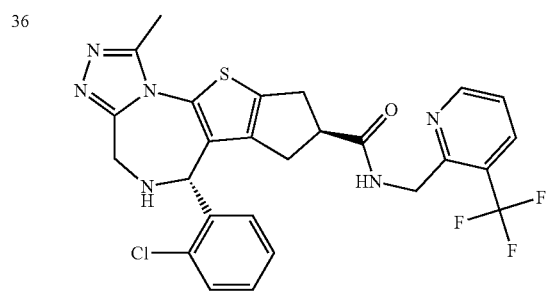 |
-continued
| Ex | |
|---|---|
| 37 | 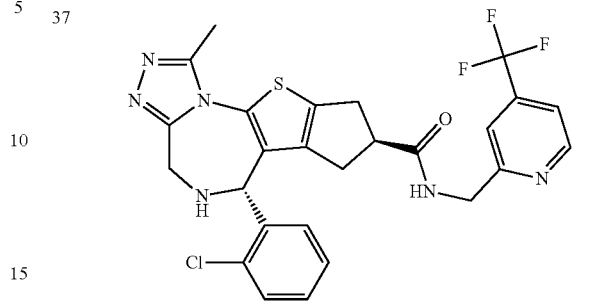 |
| 38 | 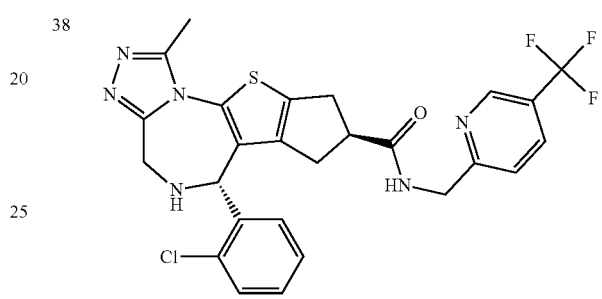 |
| 41 | 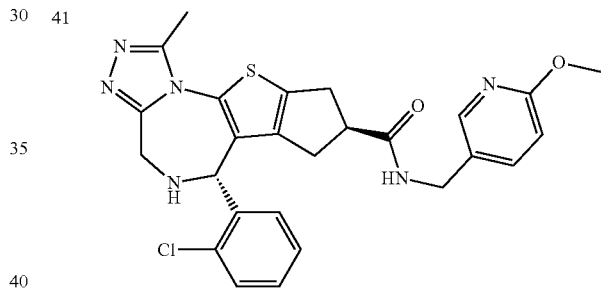 |
| 43 | 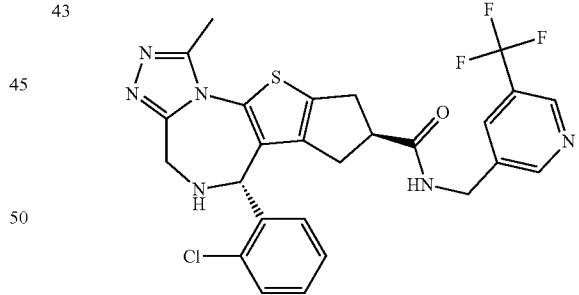 |
| 44 | 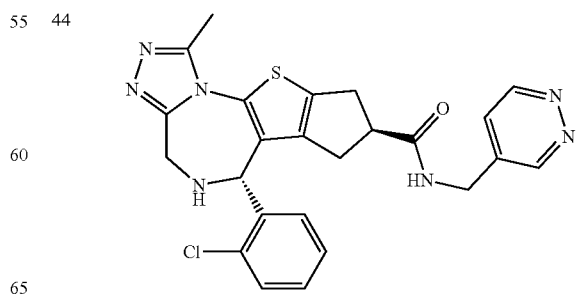 |

| Ex | |
|---|---|
| 45 | 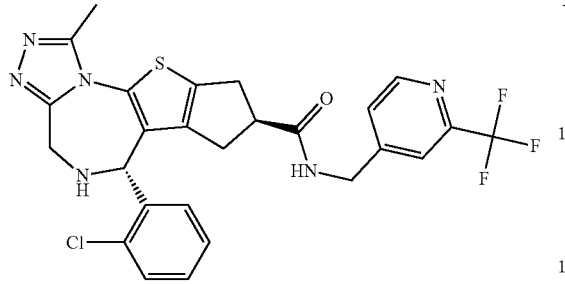 |
| 47 | 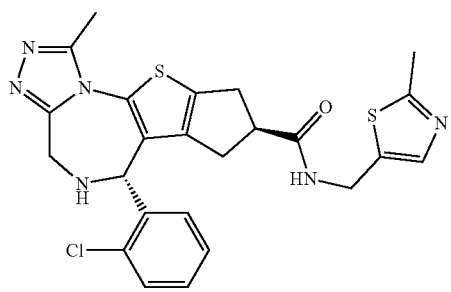 [SMILES: Cc1ncc(CNC(=O)[C@@H]2Cc3sc4c(c3C2)[C@H](c2ccccc2Cl)NCc2nnc(C)n2-4)s1] |
| 48 | 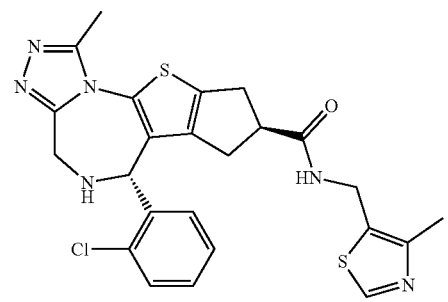 [SMILES: Cc1ncsc1CNC(=O)[C@@H]1Cc2sc3c(c2C1)[C@H](c1ccccc1Cl)NCc1nnc(C)n1-3] |
| 49 | 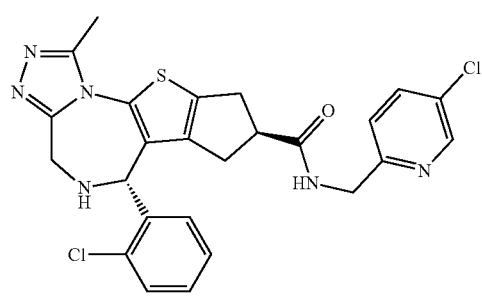 [SMILES: Cc1nnc2n1-c1sc3c(c1[C@H](c1ccccc1Cl)NC2)C[C@H](C(=O)NCc1ccc(Cl)cn1)C3] |
| 50 | 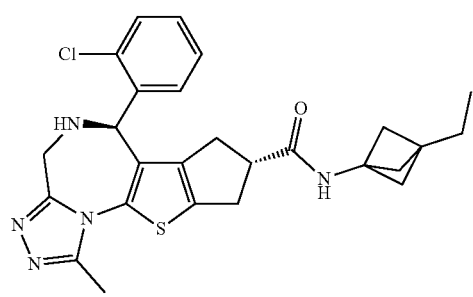 [SMILES: CCC12CC(NC(=O)[C@@H]3Cc4sc5c(c4C3)[C@H](c3ccccc3Cl)NCc3nnc(C)n3-5)(C1)C2] |
According to another embodiment, the compound of formula (I.0) and/or (I.1) is selected from the group consisting of
| Ex | |
|---|---|
| 17 | 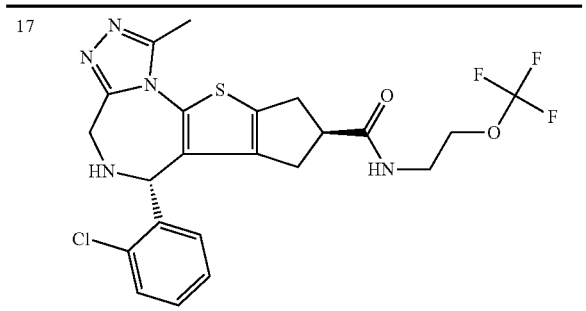 |
| 19 | 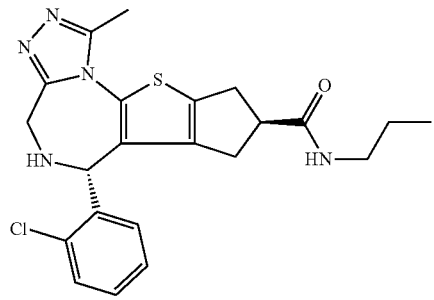 [SMILES: CCCNC(=O)[C@@H]1Cc2sc3c(c2C1)[C@H](c1ccccc1Cl)NCc1nnc(C)n1-3] |
| 20 | 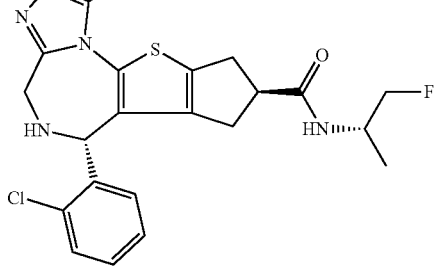 |
| 33 | 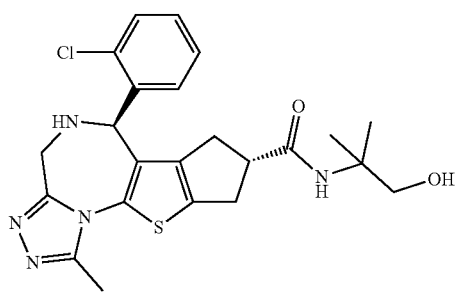 [SMILES: Cc1nnc2n1-c1sc3c(c1[C@H](c1ccccc1Cl)NC2)C[C@H](C(=O)NC(C)(C)CO)C3] |
| 73 | 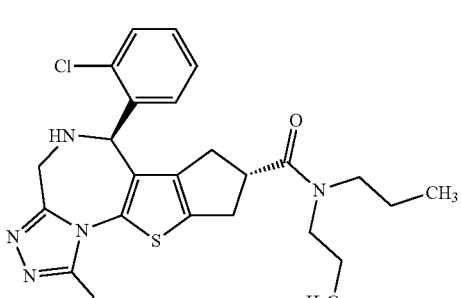 |

According to another embodiment, the compound of formula (I.0) and/or (I.1) is selected from the group consisting of
| Ex | |
|---|---|
| 15 | 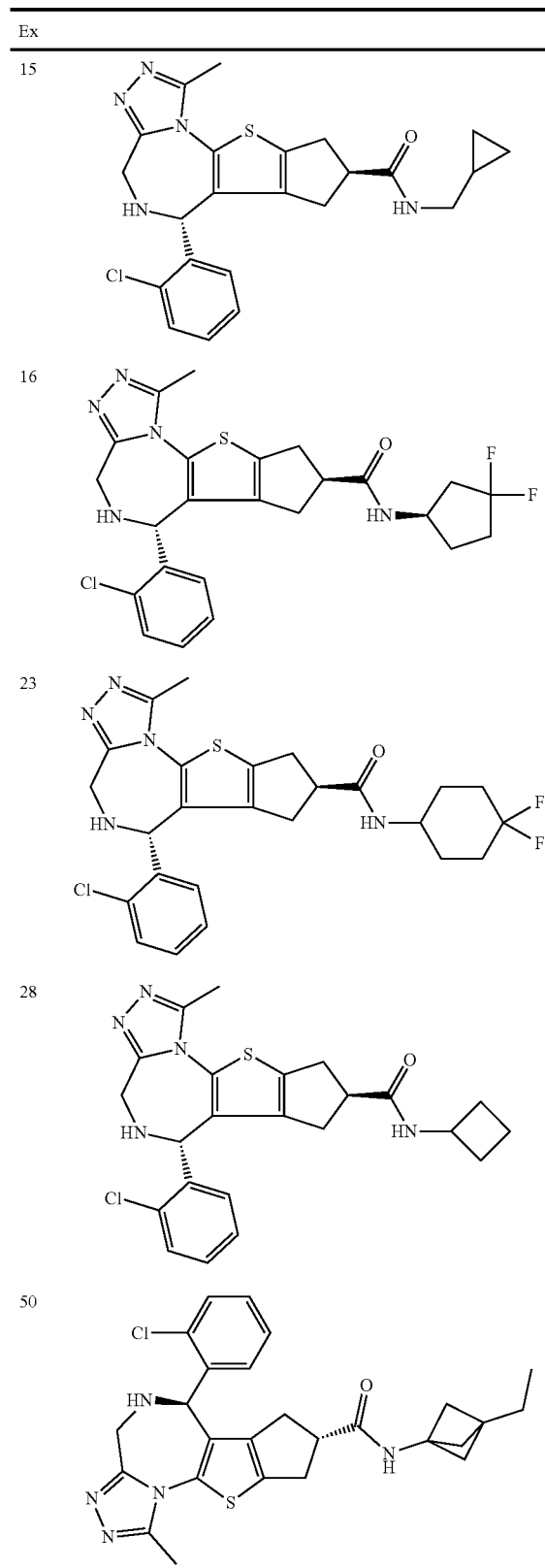 |
| 16 | |
| 23 | |
| 28 | |
| 50 | |
| 51 | 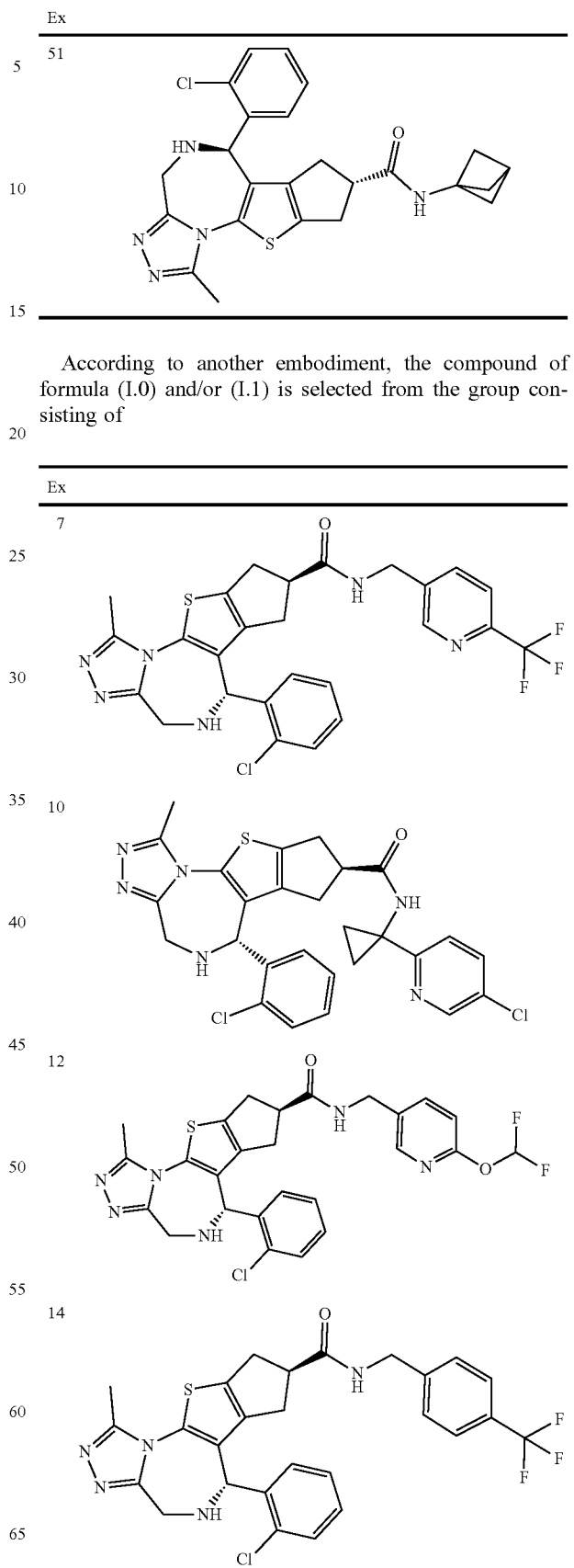 |
According to another embodiment, the compound of formula (I.0) and/or (I.1) is selected from the group consisting of
| Ex | |
|---|---|
| 7 | |
| 10 | |
| 12 | |
| 14 | |

| Ex | |
|---|---|
| 25 | 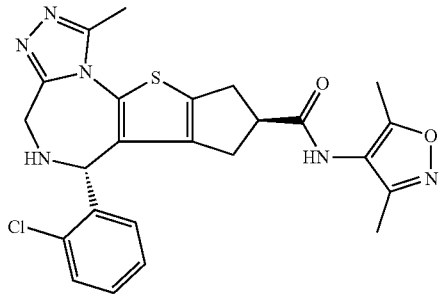 [SMILES: Cc1noc(C)c1NC(=O)[C@@H]1Cc2sc3c(c2C1)[C@H](c1ccccc1Cl)NCc1nnc(C)n1-3] |
| 31 | 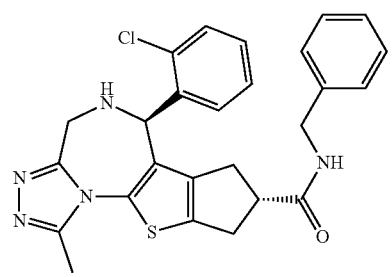 [SMILES: Cc1nnc2n1-c1sc3c(c1[C@H](c1ccccc1Cl)NC2)C[C@H](C(=O)NCc1ccccc1)C3] |
| 34 | 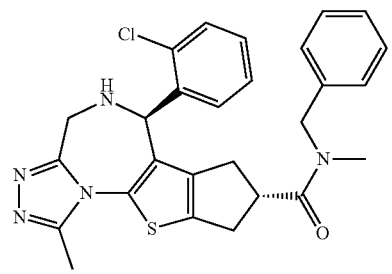 [SMILES: Cc1nnc2n1-c1sc3c(c1[C@H](c1ccccc1Cl)NC2)C[C@H](C(=O)N(C)Cc1ccccc1)C3] |
| 35 | 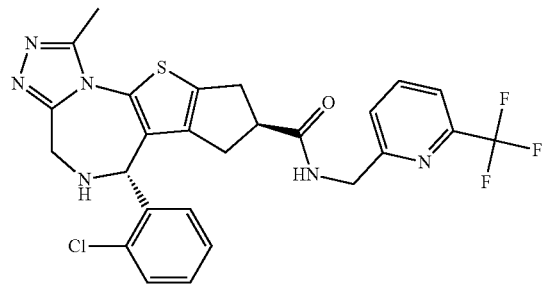 [SMILES: Cc1nnc2n1-c1sc3c(c1[C@H](c1ccccc1Cl)NC2)C[C@H](C(=O)NCc1cccc(C(F)(F)F)n1)C3] |
| 36 | 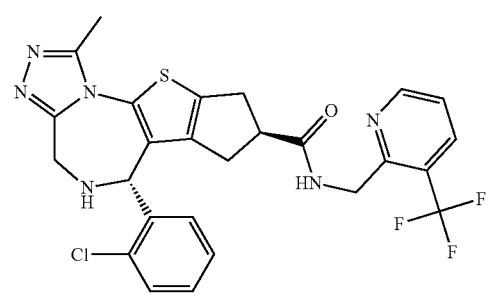 [SMILES: Cc1nnc2n1-c1sc3c(c1[C@H](c1ccccc1Cl)NC2)C[C@H](C(=O)NCc1ncccc1C(F)(F)F)C3] |
| Ex | |
|---|---|
| 37 | 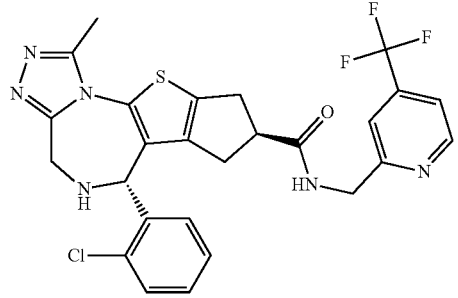 [SMILES: Cc1nnc2n1-c1sc3c(c1[C@H](c1ccccc1Cl)NC2)C[C@H](C(=O)NCc1cc(C(F)(F)F)ccn1)C3] |
| 38 | 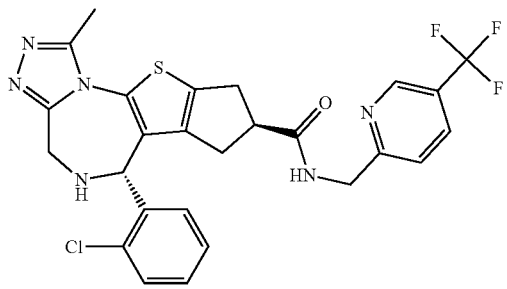 [SMILES: Cc1nnc2n1-c1sc3c(c1[C@H](c1ccccc1Cl)NC2)C[C@H](C(=O)NCc1ccc(C(F)(F)F)cn1)C3] |
| 41 | 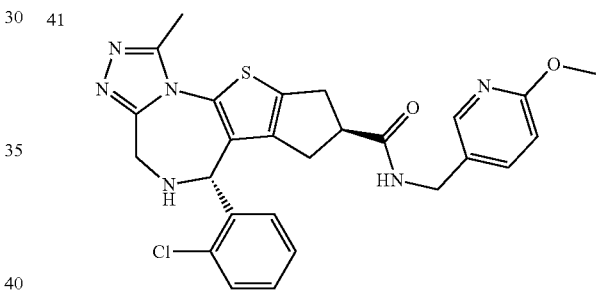 |
| 43 | 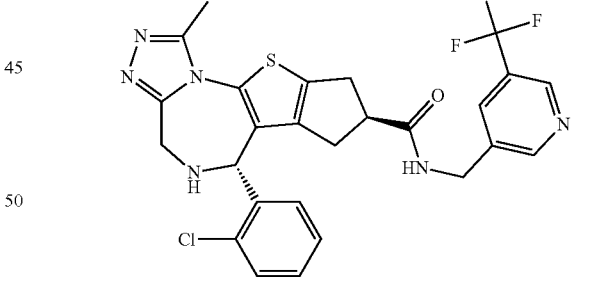 |
| 45 | 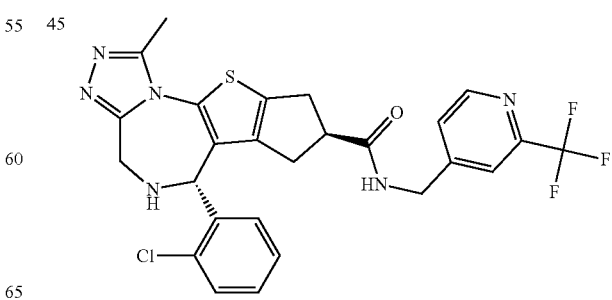 |

| Ex | |
|----|---|
| 46 | 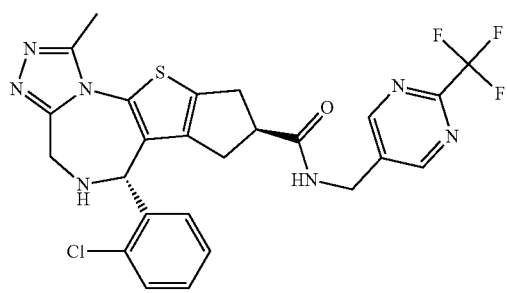 [SMILES: Cc1nnc2n1-c1sc3c(c1[C@H](c1ccccc1Cl)NC2)C[C@H](C(=O)NCc1cnc(C(F)(F)F)nc1)C3] |
| 47 | 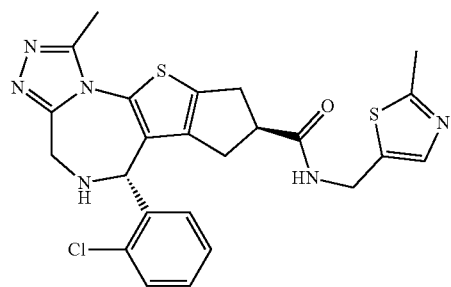 [SMILES: Cc1ncc(CNC(=O)[C@@H]2Cc3sc4c(c3C2)[C@H](c2ccccc2Cl)NCc2nnc(C)n2-4)s1] |
| 48 | 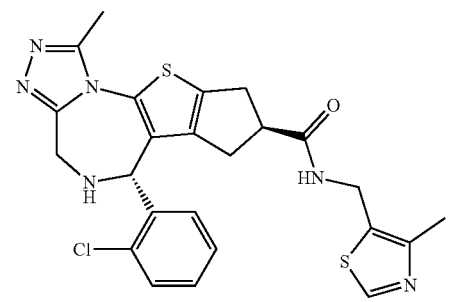 [SMILES: Cc1ncsc1CNC(=O)[C@@H]1Cc2sc3c(c2C1)[C@H](c1ccccc1Cl)NCc1nnc(C)n1-3] |
| 49 | 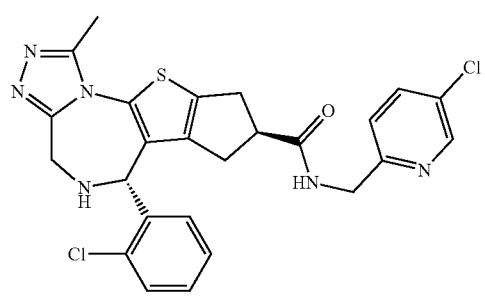 [SMILES: Cc1nnc2n1-c1sc3c(c1[C@H](c1ccccc1Cl)NC2)C[C@H](C(=O)NCc1ccc(Cl)cn1)C3] |
According to another embodiment, the compound of formula (I.0) and/or (I.1) is
| Ex | |
|----|---|
| 2 | 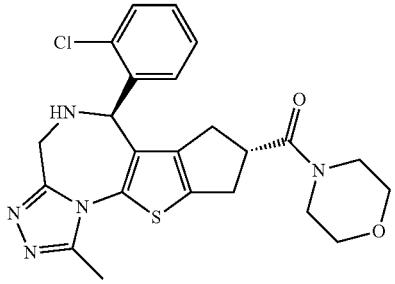 [SMILES: Cc1nnc2n1-c1sc3c(c1[C@H](c1ccccc1Cl)NC2)C[C@H](C(=O)N1CCOCC1)C3] |
According to another embodiment, the compound of formula (I.0) and/or (I.1) is selected from the group consisting of
| Ex | |
|----|---|
| 4 | 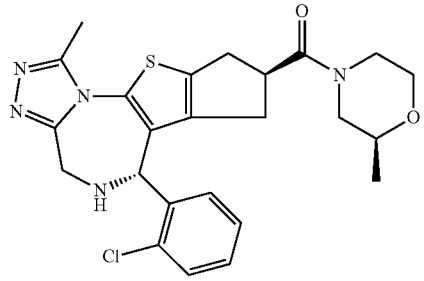 [SMILES: Cc1nnc2n1-c1sc3c(c1[C@H](c1ccccc1Cl)NC2)C[C@H](C(=O)N1CCO[C@@H](C)C1)C3] |
| 5 | 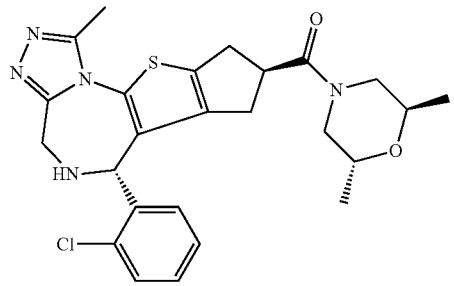 [SMILES: Cc1nnc2n1-c1sc3c(c1[C@H](c1ccccc1Cl)NC2)C[C@H](C(=O)N1C[C@@H](C)O[C@H](C)C1)C3] |
| 6 | 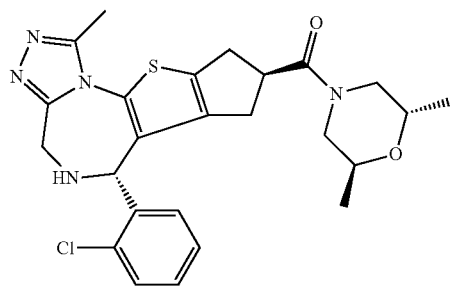 [SMILES: Cc1nnc2n1-c1sc3c(c1[C@H](c1ccccc1Cl)NC2)C[C@H](C(=O)N1C[C@H](C)O[C@@H](C)C1)C3] |

-continued

| Ex | |
|---|---|
| 18 | 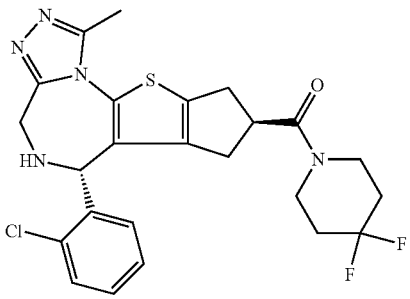 [SMILES: Cc1nnc2n1-c1sc3c(c1[C@H](c1ccccc1Cl)NC2)C[C@H](C(=O)N1CCC(F)(F)CC1)C3] |
| 24 | 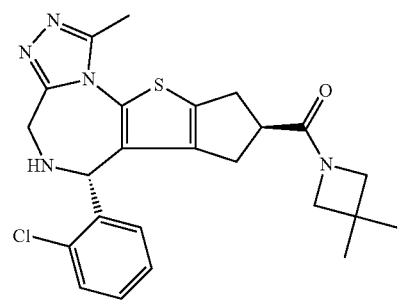 [SMILES: Cc1nnc2n1-c1sc3c(c1[C@H](c1ccccc1Cl)NC2)C[C@H](C(=O)N1CC(C)(C)C1)C3] |
| 26 | 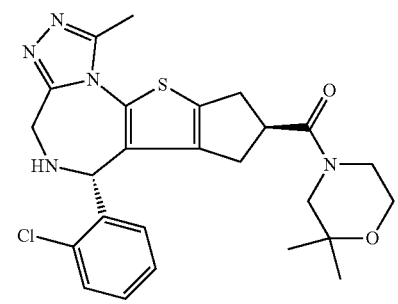 [SMILES: Cc1nnc2n1-c1sc3c(c1[C@H](c1ccccc1Cl)NC2)C[C@H](C(=O)N1CCOC(C)(C)C1)C3] |
| 27 | 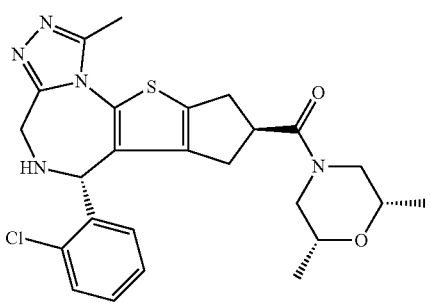 [SMILES: Cc1nnc2n1-c1sc3c(c1[C@H](c1ccccc1Cl)NC2)C[C@H](C(=O)N1C[C@@H](C)O[C@@H](C)C1)C3] |

According to another embodiment, the compound of formula (I.0) and/or (I.1) is selected from the group consisting of

| Ex | |
|---|---|
| 21 | 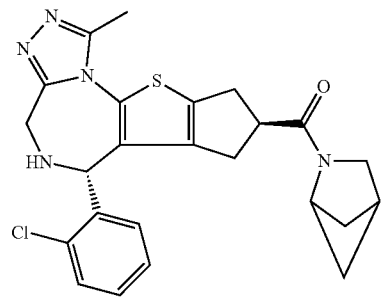 [SMILES: Cc1nnc2n1-c1sc3c(c1[C@H](c1ccccc1Cl)NC2)C[C@H](C(=O)N1CC2CC1C2)C3] |
| 22 | 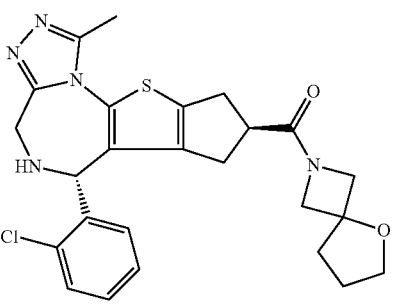 [SMILES: Cc1nnc2n1-c1sc3c(c1[C@H](c1ccccc1Cl)NC2)C[C@H](C(=O)N1CC2(CCCO2)C1)C3] |
| 30 | 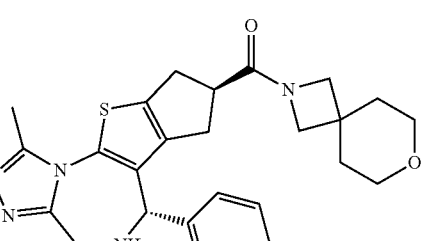 |

Preparation

The compounds according to the invention and their intermediates may be obtained using methods of synthesis which are known to the one skilled in the art and described in the literature of organic chemistry for example in standard textbooks, monographs, and reviews covering basic, advanced, and specialized topics of organic chemistry, in particular organic synthesis. Preferably, the compounds are obtained analogously to the methods of preparation explained more fully hereinafter, in particular as described in the experimental section. In some cases the sequence adopted in carrying out the reaction schemes may be varied. Variants of these reactions that are known to the skilled person, but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled person and described in the literature directed to the use of protecting groups in organic synthesis.

Scheme 1

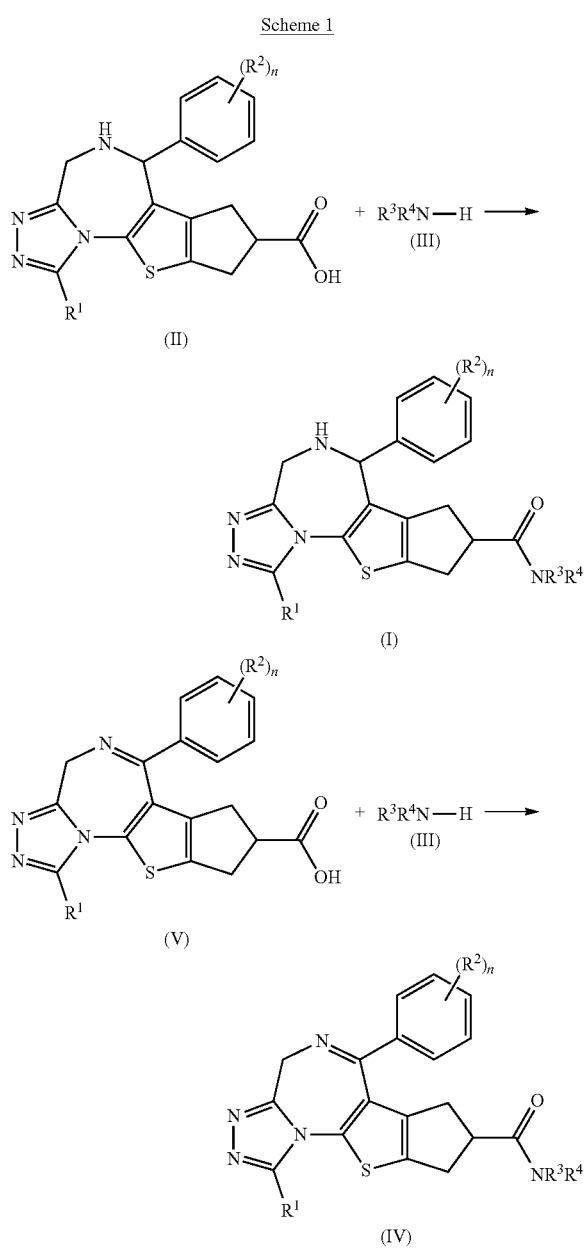

(II)

(I)

(V)

(IV)

ylic acid is transformed into a carboxylic chloride (using, e.g., oxalyl choride or thionyl chloride in DCM) and coupled as such with amine (III) in the presence of a suited base (e.g., triethylamine, N,N-diisopropyl-ethylamine, pyridine, etc.).

Compounds of formula (IV) have been reported in the literature and can also be obtained in enantiomerically enriched or pure form (see, e.g., DE4132763A1, EP0388789A1, EP0254245A1, EP0450504A1, and Med. Res. Rev. 1989, 9, 181-218).

Scheme 2

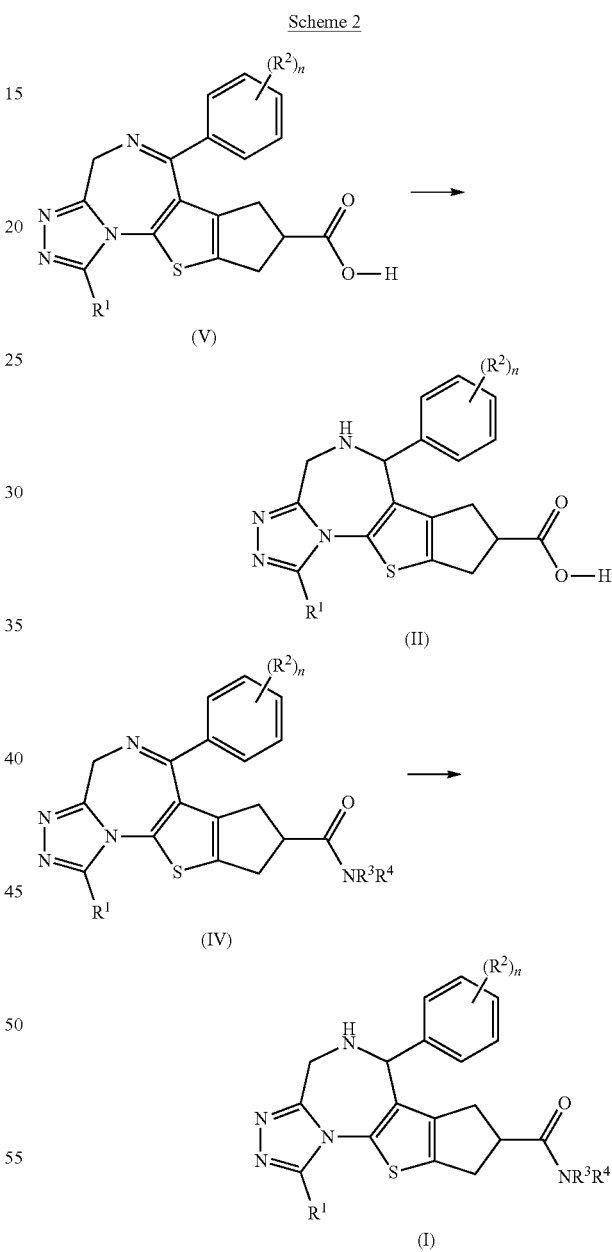

(V)

(II)

(IV)

(I)

Scheme 1: Compounds of formula (I), e.g. (I.0), (I.1) or (I.2), and compounds of formula (IV) can be prepared from the respective acids of formula (II) and formula (V) (either as free acid or carboxylate with a suitable metal cation such as $Li^+$, $Na^+$, $K^+$, etc.), respectively, and a suitable amine of formula (III) (either as free amine or salt such as hydrochloride, hydrobromide, etc.) by employing a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tri-pyrrolidinophosphonium hexafluorophosphate (PyBOP), carbodiimide reagents, etc.) and a base (e.g., triethylamine, N,N-diisopropyl-ethylamine, pyridine, etc.) in a suitable solvent (e.g., DCM, THF, 1,4-dioxane, DMF, N,N-dimethylacetamide, and 1-methyl-2-pyrrolidinone) at −20° C. to 100° C.; $R^1$, $R^2$, $R^3$, $R^4$, and n in Scheme 1 have the meanings as defined hereinbefore. Alternatively, the respective carbox- Scheme 2: Imines of formula (IV) and formula (V), wherein $R^1$, $R^2$, $R^3$, $R^4$, and n have the meanings as defined hereinbefore, may be reduced to the corresponding amines (II) and (I), respectively, by employing hydrogen in the presence of a transition metal catalyst or a suited hydride source. Suited hydride sources may be borohydrides such as $NaBH_4$, $KBH_4$, $Na(NC)BH_3$, $NaHB(OAc)_3$, $Me_4NBH_4$, and $^nBu_4NBH_4$, alanates such as $LiAlH_4$, selectrides such as L-selectride, $HAl^iBu_2$, boranes such as pinacol borane, $H_3B^*THF$, 9-BBN—H, and $Et_2BH$, silanes such as $Et_3SiH$ and $Cl_3SiH$, that, depending on the hydride source, are being used in the presence of a Lewis or Brønsted acid or a transition metal in a suited solvent (e.g., toluene, DCM, THF, MeCN, $H_2O$, etc. or mixtures of them, depending on the hydride and conditions used) at low to elevated temperature (−70° C. to 100° C.). A more specific experimental protocol that may be more generally applicable here encompasses $NaBH_4$ and an acid, e.g., aqueous HCl or acetic acid, in 1,2-dichloroethane at 0° C. to 40° C. Active catalysts that may be used in combination with molecular hydrogen are preferably derived from, e.g., Co, Ni, Pd, Pt, Rh, Ru, and Ir. Reductions of the imine in the presence of one of these transition metal catalysts, optionally in the presence of a ligand coordinating to the transition metal and other additives, may be conducted with hydrogen (1 to 200 bar) in a suited solvent (e.g., DCM, EtOAc, EtOH, THF, etc.) at 0° C. to 150° C. Compounds (I) and (II) obtained according to this proceeding are mixtures of diastereomers or pure diastereomers depending on the reducing agent and conditions applied and may be resolved into the individual stereoisomers by methods known to the skilled person to furnish the pure stereoisomers, e.g. (I.1) or (I.2).

Reduction of imine (IV) or (V) may also be conducted in a stereoselective fashion by using either a chiral hydride or hydrogen in the presence of a chiral catalyst providing compound (I) or (II) as enriched or pure stereoisomer depending on the enantiopurity of the starting imine, (IV) or (V), and the conditions applied. For instance, the chiral hydride formed through the reaction of $^nBu_4NBH_4$ and (S)- or (R)—N-benzyloxycarbonyl(Cbz)-proline (→$^nBu_4NHB$ ((S) or (R)—N-Cbz-proline)$_3$) may be a suited reagent for reducing imines (IV) and (V) with high stereochemical selectivity. The reaction is preferably carried out in DCM at −78° C. to 40° C. with the chiral hydride formed in a separate step or in situ prior to the addition of the imine.

Reduction of the imine may also be carried out using ester (VI) (Scheme 3) under some of the conditions described above to provide the corresponding amine that may be transformed into compound (II) by hydrolysis of the ester group as described below (Scheme 3) and then into compound (I) by coupling with an amine (III) as delineated further above (Scheme 1).

Scheme 3

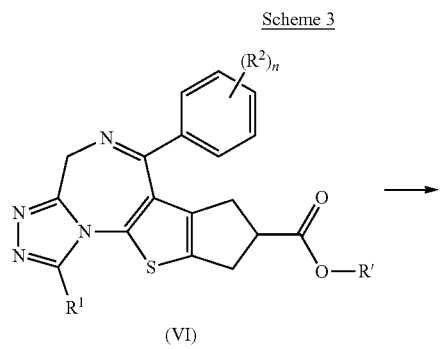

(VI)

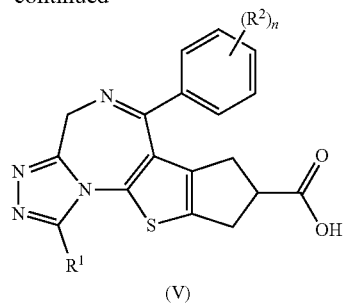

(V)

$R' = C_{1-4}$-alkyl or benzyl

Scheme 3: Acids of formula (V), wherein $R^1$, $R^2$, and n have the meanings as defined hereinbefore, are preferably prepared from the corresponding ester (VI) through hydrolysis or hydrogenolysis depending on the nature of R'. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as a carboxylic acid. A tert-butyl ester is preferably cleaved by treatment with an acid (e.g., hydrochloric acid or TFA) in a suitable solvent (e.g., DCM, 1,4-dioxane, MeOH, EtOH, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAc) under an atmosphere of hydrogen (preferably 1 to 5 bar).

Compounds of formula (V) have been reported in the literature and can also be obtained in enantiomerically enriched or pure form (see, e.g., EP0388789A1, EP0254245A1 and DE4132763A1).

Scheme 4

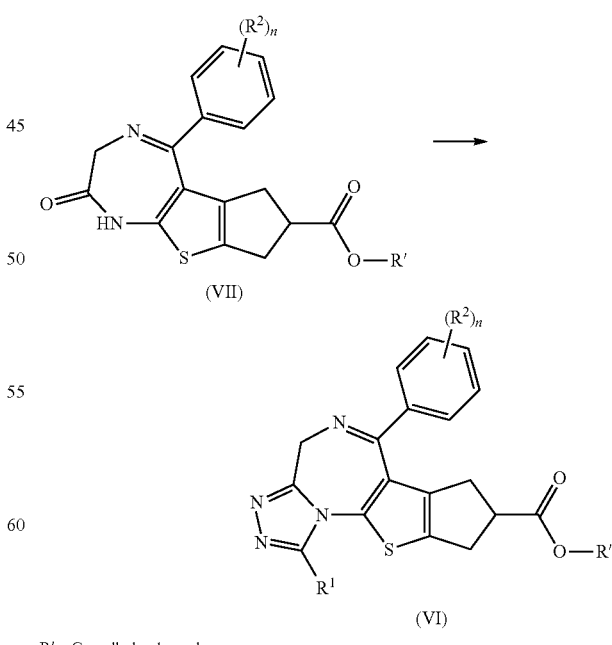

$R' = C_{1-4}$-alkyl or benzyl

Scheme 4: Esters of formula (VI), wherein $R^1$, $R^2$, and n have the meanings as defined hereinbefore, may be prepared from amides (VII) employing different synthesis strategies. A more preferred proceeding comprises the transformation of the amide group in (VII) into the corresponding imidoyl chloride or phosphoric ester anhydride employing diethyl chlorophosphate in the presence of a base (e.g., 1,8-diazabicyclo[5.4.0]undecene (DBU)) in a suited solvent (e.g., THF, 1,4-dioxane, etc.) at medium temperature (preferably between 0° C. and 40° C.). Subsequently, the accordingly decorated acyl hydrazine ($R^1$—CO—$NHNH_2$) is added to the such activated amide to provide the N-acylamino amidine derivative that can be transformed into the triazole by heating (contingently up to 140° C.).

Alternatively, the triazole (VI) may be obtained by applying a 3-step procedure via the thioamide of amide (VII) that is subsequently treated with hydrazine to give the corresponding N-amino amidine that in turn is transformed into the triazole by treatment with the appropriate orthoester ($R^1$—$C(OC_{1-2}$-alkyl$)_3$). This proceeding, variations thereof, and alternative synthesis routes are reported in the literature of organic chemistry and known to the one skilled in the art (see, e.g., EP0388789A1 and EP0254245A1).

Compounds of formula (VI) have been reported in the literature and can also be obtained in enantiomerically enriched or pure form (see, e.g., EP0388789A1).

Scheme 5

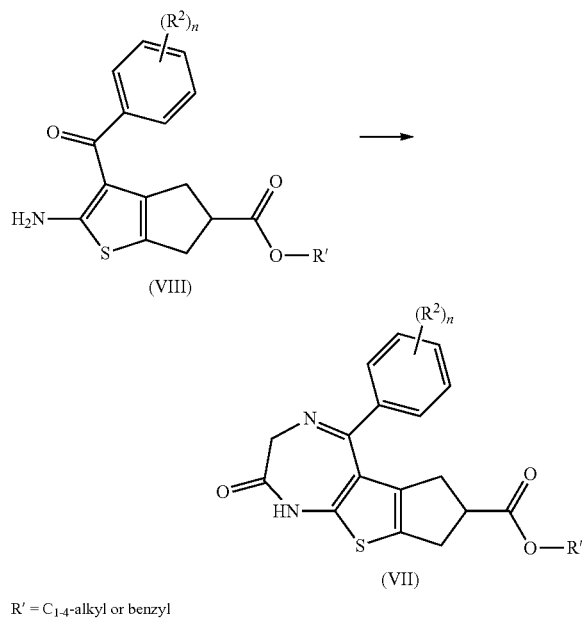

(VIII)

(VII)

R' = $C_{1-4}$-alkyl or benzyl

Scheme 5: Esters of formula (VII), wherein $R^2$ and n have the meanings as defined hereinbefore, may be prepared from ketones (VIII) in one, two, or three separate synthesis steps. A well-established synthesis of compound (VII) runs via the N-bromoacetyl derivative of compound (VIII) that may be obtained by treatment of compound (VIII) with bromoacetyl bromide, in the presence of a base (e.g., $NaHCO_3$), in a suited solvent (e.g., toluene and water) at 0° C. to 80° C. This intermediate is then treated with an ammonia source (e.g., aqueous ammonia or ammonia in THF) to replace the bromine and give the corresponding N-aminoacetyl derivative. The seven-membered ring is then formed by reacting the amino group with the keto group with the help of suited additives in an apt solvent (e.g., silica gel in toluene, pyridine in HOAc, or methanesulfonic acid in 1,4-dioxane) at elevated temperature (preferably between 30° C. and 130° C.) to give compound (VII).

This proceeding has also been reported in the literature and applied to the synthesis of the enantiomerically enriched or pure compound (see, e.g., EP0254245A1 and EP0388789A1).

Compounds (VII) may also be obtained in only one reaction step from compounds (VIII) as reported in Org. Lett. 2017, 19, 1454-1457.

Scheme 6

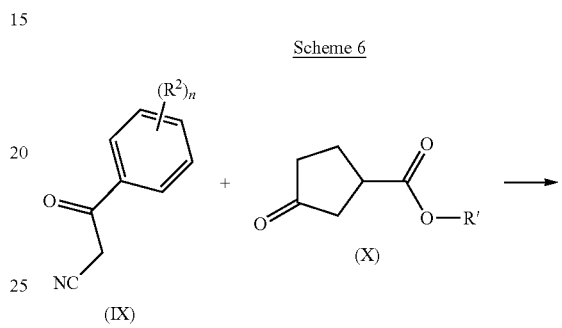

(IX)

(X)

(VIII)

R' = $C_{1-4}$-alkyl or benzyl

Scheme 6: Compounds of formula (VIII) can be prepared from cyanoketones (IX) and ketones (X) following the protocol reported for the so-called Gewald reaction; $R^2$ and n in Scheme 6 have the meanings as defined hereinbefore. Accordingly, compounds (IX) and (X) are combined and treated with a base (e.g., $NEt_3$, $HNEt_2$, morpholine, piperidine, pyridine, etc.) in the presence of elemental sulfur in a solvent (e.g., MeOH, EtOH, DMF, 1,4-dioxane, etc.) at 0° C. to 120° C.

Alternatively, this transformation may be carried out in two separate steps, forming the condensation product from compounds (IX) and (X) in the first step (Knoevenagel reaction) and the product (VIII) in the second upon treatment with elemental sulfur and a base.

Variations of these proceedings have been reported in the literature of organic chemistry.

Compounds (IX) are known compounds or can be prepared in analogy to the former. Principal and specific access to the enantiomerically enriched or pure compounds (X) have also been reported in the literature of organic chemistry (see, e.g., EP0388789A1, Archiv der Pharmazie 1996, 329, 291-300, and Green Chem. 2017, 19, 5122-5130).

Scheme 7

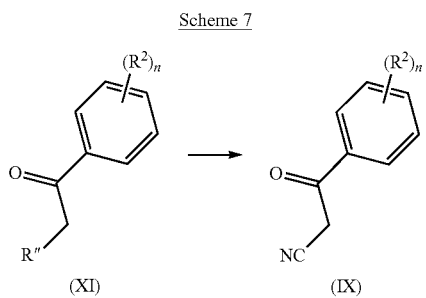

R" = C$_{1-4}$-alkyl or benzyl

Scheme 7: Cyanoketones of formula (IX), wherein R$^2$ and n have the meanings as defined hereinbefore, are preferably prepared from the corresponding ester (XI) and a deprotonated acetonitrile (NCCH$_2^-$) species in a suited solvent (e.g., THF, toluene, MeCN, DMF, DMSO, 1,4-dioxane, etc.) at −78° C. to 100° C. The deprotonated acetonitrile species is prepared from acetonitrile by deprotonation with a suited base (e.g., NaH, LiN$^i$Pr$_2$, LiN(SiMe$_3$)$_2$, KO$^t$Bu, etc.) preferably in one of the solvents used for the subsequent reaction with ester (XI) at −78° C. to 40° C., depending on the base used. Further synthesis routes and procedures to prepare compounds of formula (IX) are reported in the literature of organic chemistry.

Scheme 8

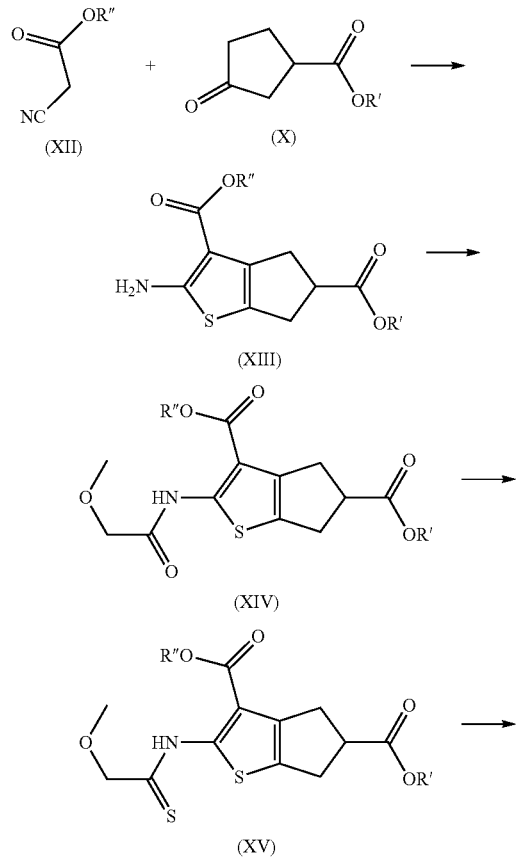

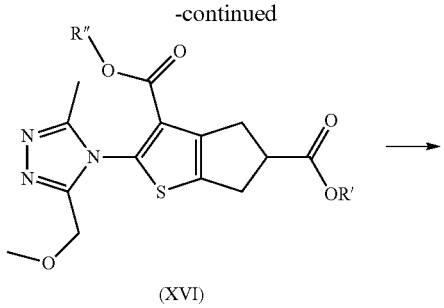
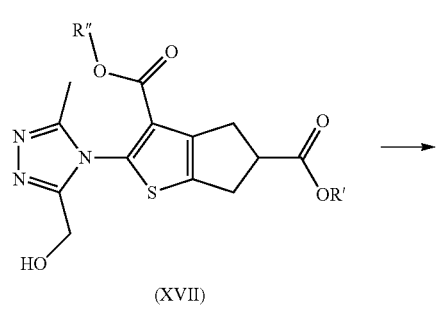
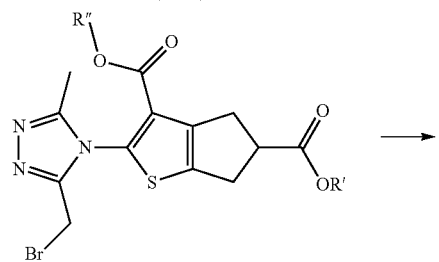
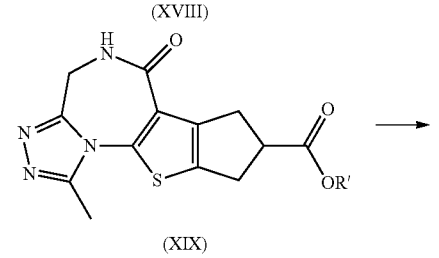
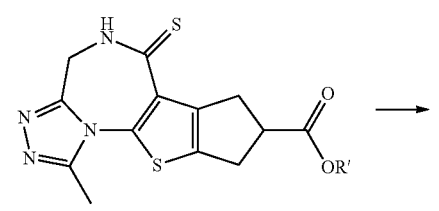
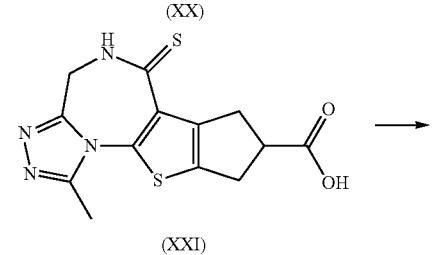

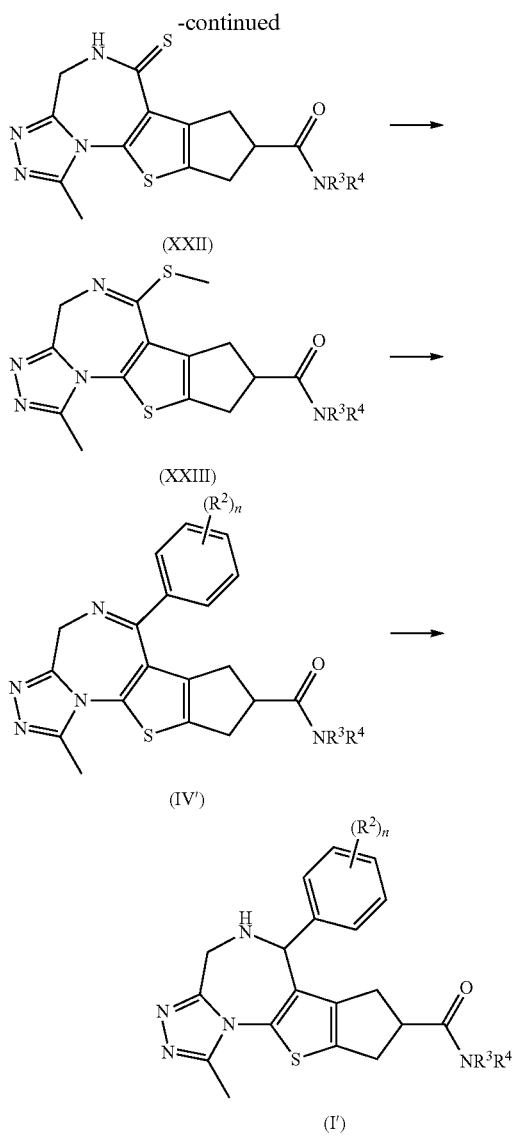

R' = C$_{1-4}$-alkyl or benzyl; R" = C$_{1-4}$-alkyl or benzyl

Scheme 8: Compounds of formula (I) may also be obtained following the route delineated in Scheme 8; R$^2$, R$^3$, R$^4$ and n have the meanings as defined hereinbefore. The synthesis sequence starts out with a Gewald reaction of ketone (X) and cyanoester (XII) to furnish aminothiophene (XIII) (for specific reaction conditions see experimental part and WO2008/063667A1). Aminothiophene (XIII) can be acetylated on the N with methoxyacetyl chloride in the presence of a base (e.g., pyridine) in an inert solvent (e.g., DCM) at ambient temperature to provide compound (XIV). The methoxy group serves as a masked leaving group that is to be replaced with ammonia to introduce amino at a later stage of the synthesis. Thus many other masked or protected amino equivalents can be considered for this purpose such as phenoxy instead of methoxy. Compound (XIV) can then be transformed into triazole (XVI) via thioamide (XV). The latter compound may be obtained by treatment of (XIV) with Lawesson's reagent (or phosphorus pentasulfide) in a solvent (e.g., 1,4-dioxane or toluene) at elevated temperature (60° C. to 120° C.). Triazole (XVI) may be formed by treating thioamide (XV) with hydrazine in a solvent (e.g., THF or 1,4-dioxane) at ambient temperature, providing the N-aminoamidine intermediate, followed by reaction with a trialkyl orthoacetate (e.g., MeC(OMe)$_3$) or an acetamide dialkyl acetal (e.g., MeC(OMe)$_2$(NMe$_2$)), optionally in the presence of an acid (e.g., p-TsOH or MeCOOH), at elevated temperature (ca. 60° C.-120° C.). Alternatively, acetyl hydrazine may be used instead to provide the triazole under similar conditions. Bromide (XVIII) can be produced from compound (XVI) by replacing the methoxy group with bromide directly or via the alcohol derivative (XVII) depending on the conditions applied. The proceeding via the alcohol requires cleavage of the methoxy ether (with, e.g., BBr$_3$ in DCM) and subsequent displacement of the hydroxyl group with Br (with, e.g., MeSO$_2$Br and NEt$_3$ in DCM). Compound (XIX) can then be obtained by treatment of bromide (XVIII) with ammonia (e.g., in methanol at ambient temperature) and heating the substitution product, optionally in the presence of an additional base (e.g., NEt$_3$), to concurrently achieve cyclization and amide formation. The thioamide in (XX) can be installed by treating amide (XIX) with Lawesson's reagent or P$_2$S$_5$ in an inert solvent (e.g., toluene or 1,4-dioxane) at elevated temperature (preferably between 60° C. and 120° C.). The principal proceedings described in Scheme 3, ester hydrolysis, and Scheme 1, amide formation, can be followed to transform the ester function in (XX) into the corresponding amide to afford compound (XXII); ester hydrolysis can be accomplished using NaOH in a mixture of water and methanol at ambient temperature, while amide formation may be conducted with the desired amine (R$^3$R$^4$N—H) and carbonyl diimidazole in DMF at room temperature. Methylation of the sulfur in thioamide (XXII) can be achieved with methyl iodide or methyl triflate, optionally in the presence of a base (e.g., KO$^t$Bu), in a solvent (e.g., acetone or MeCN) at ambient temperature to give compound (XXIII) that entails a functional group (—N=C(SMe)-) amenable to transition metal catalyzed coupling reactions with aromatic nucleophiles such as boronic acids or zinc halides to attach aromatic residues. Coupling of compound (XXIII) with aromatic boronic acids (R—B(OH)$_2$) can be carried out with a transition metal catalyst based on Pd (e.g., Pd(PPh$_3$)$_4$) and a Cu based additive (e.g., copper(I) thiophene-2-carboxylate) in a solvent (e.g., NMP or 1,4-dioxane) at ambient or elevated temperature (preferably between 20° C. and 120° C.) to provide compounds (I'), i.e. compounds (I) wherein R$^1$ is a methyl group. The synthesis scheme delineated in Scheme 8 is not limited to compounds bearing methyl for R$^1$ but can principally be extended to any other residue encompassed by the meanings of R$^1$ as defined hereinbefore.

The compounds of formula (I) may be resolved into their enantiomers and/or diastereomers as mentioned below. Thus, for example, cis/trans mixtures may be resolved into their cis and trans isomers, diastereomeric mixtures may be separated into their diastereomers, and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula (I) may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physicochemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I), e.g. (I.0), may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled person from the literature.

HEK293 cells overexpressing human PAFR (produced in-house) are seeded into a Poly-D-Lysine coated 384 well white cell culture microtiter assay plate with lid (15.000 cells per well). Subsequently, the plates are incubated over night at 37° C./5% $CO_2$. On the next day, cells are being washed and subsequently, various concentrations of the test compounds (compounds in 100% DMSO; final concentration of DMSO in wells is 1%) are added to the assay plate via Echo 555 acoustic liquid handler. Plates are then incubated with lid for 90 minutes at 37° C./5% $CO_2$. Thereafter, PAF ligand (Cayman Chemical Company, Item no.: 60900) is added at a final concentration of 11 nM. Plates are then incubated with lid for 60 minutes at 37° C./5% $CO_2$. Then, 5 µl per well of Anti-IP1-Anti body-Cryptate solution and 5 µL per well of IP1-d2 solution are added to all wells of the plate and the plate is incubated for another 60 minutes light protected at room temperature. The emissions at 620 nm and 665 nm (Excitation wavelength: 320 nm) are measured using an Envision Reader (PerkinElmer).

$IC_{50}$ values for compounds according to the invention are shown in the following table. The number of the compound corresponds to the number of the Example in the experimental section. In cases where a mixture of isomers with regard to the configuration at C-13 was employed for testing, the observed activity can be attributed mainly to the (13S)-isomer which is the isomer according to the invention. This is apparent from the direct comparison of (reference) examples 67-71 and 74-78.

TABLE 2

| Example | $IC_{50}$ (nM) | Example | $IC_{50}$ (nM) | Example | $IC_{50}$ (nM) | Example | $IC_{50}$ (nM) |
|---|---|---|---|---|---|---|---|
| 1 | 102 | 2 | 30 | 3 | 423 | 4 | 6.8 |
| 5 | 8.2 | 6 | 11 | 7 | 3.6 | 8 | 55 |
| 9 | 34 | 10 | 1.3 | 11 | 53 | 12 | 1.9 |
| 13 | 281 | 14 | 0.4 | 15 | 1.7 | 16 | 1.4 |
| 17 | 2.8 | 18 | 3.1 | 19 | 3.0 | 20 | 4.5 |
| 21 | 9.1 | 22 | 5.3 | 23 | 1.3 | 24 | 2.0 |
| 25 | 4.3 | 26 | 4.9 | 27 | 5.5 | 28 | 1.7 |
| 29 | 69 | 30 | 12 | 31 | 1.1 | 32 | 34 |
| 33 | 2.8 | 34 | 2.1 | 35 | 3.8 | 36 | 3.0 |
| 37 | 2.9 | 38 | 1.4 | 39 | 60 | 40 | 83 |
| 41 | 11 | 42 | 138 | 43 | 2.6 | 44 | 41 |
| 45 | 1.9 | 46 | 6.3 | 47 | 12 | 48 | 15 |
| 49 | 1.9 | 50 | 0.5 | 51 | 2.2 | 52 | 283 |
| 53 | 297 | 54 | >322 | 55 | 240 | 56 | >322 |
| 57 | 161 | 58 | >322 | 59 | >322 | 60 | >322 |
| 61 | >322 | 62 | 94 | 63 | >568 | 64 | 210 |
| 65 | 11 | 66 | 2.7 | 67 | 73 | 68 | >999 |
| 69 | 35 | 70* | >1000 | 71* | >999 | 72 | 8.1 |
| 73 | 0.7 | 74 | 252 | 75* | >568 | 76 | 140 |
| 77* | >1000 | 78 | >1000 | 79 | 235 | 80 | 110 |
| 81 | 224 | | | | | | |

*reference example outside the scope of the invention

Pharmacological Activity and Suitability for Pharmaceutical Applications

The activity of the compounds of the invention as well as their suitability for pharmaceutical applications may be demonstrated using the following assays:
Biological Methods The ability of compounds of formula (I.0) to inhibit the activation of the PAF receptor (PAFR) by the PAF C-16 ligand (PAF) is determined using the following cellular HTRF IP1 assay (IP1 Gq assay kit from Cisbio, Cat. no.: 62IP1APEJ) in assay buffer (1×HBSS, 20 mM Hepes, pH 7.4, 50 mM LiCl and containing 0.1% (w/v) BSA):
Evaluation of the Inhibition of PAFR Activation Using an Endpoint Assay Evaluation of the Inverse Agonism Mode Using an Endpoint Assay Due to the constitutive activity of the PAFR, the basal HTRF IP1 signal is higher in HEK293 cells overexpressing human PAFR as compared to non-transfected HEK293 cells. The ability of test compounds to acts as inverse agonists at the PAF receptor can be determined using a modified protocol of the cellular HTRF IP1 assay described above. Various concentrations of the test compounds are added to the assay plate with HEK293 cells overexpressing human PAFR and incubated for 340 minutes at 37° C./5% $CO_2$ without addition of PAF ligand. Inverse agonism of test compounds is demonstrated by the lowering of the HTRF IP1 signal down to the level of non-transfected HEK293 cells.

Evaluation of the In Vivo Efficacy in an Animal Model of Laser-Induced Choroidal Neovascularization in Brown Norway Rats Male Brown Norway rats (BN/Crl) with a body weight between 160 g and 180 g are obtained from Charles River Labs (Sulzfeld, Germany). Animals are kept in group housing with a 12 h/12 h light/dark cycle (lights on at 6 AM) and accustomed for one week before start of the study. They have free access to a standard chow (Provimi Kliba No. 3438) and tap water. Animals are administered test compounds by once daily oral gavage for 2 weeks.

Under anaesthesia, animals are placed on day 1 in front of a fundus camera to position the optic nerve in the center of the image. Laser treatment is performed with a green Argon laser (Merilas) of 532 nm wavelength using a Micron IV system (Phoenix Research Laboratories, Pleasanton, CA). The diameter of the laser beam is matched with the diameter of the optic nerve and laser pulses with an energy of 400 mW and a duration of 150 msec are used to generate 4 lesions per eye. Lesions are placed between the large blood vessels with a distance from the optic nerve of about twice its diameter. A successful disruption of Bruch's membrane is recognized by the formation of bubbles immediately after the laser beam and confirmed by OCT scan.

Animals are sacrificed 14 days after laser treatment by cervical dislocation under anaesthesia. Eyes are enucleated and cut along the Ora serrata. Cornea, iris, lens, vitreous and retina are removed and the remaining eye cup (consisting of RPE, choroidea and sclera) is fixed in PFA (4%) for 1 h at 4° C. and then transferred to PBS containing 0.1% Triton X-100 for 1 h at 4° C. The eye cup is stained overnight in the dark at room temperature with FITC-labelled isolectin B4 (10 µg/ml in saline; obtained from Sigma Aldrich, catalogue no. L9381) and washed 3 times with PBS. The eye cup is transferred to a glass slide and cut four times to achieve a flat cloverleaf-like structure. The tissue is covered with mounting medium (Vectashield H-1200 containing DAPI) and a coverslip is put on top to obtain a RPE/choroidea/sclera flatmount (RPE side up). Flatmounts are stored at 4° C. in the dark until analysis.

The samples are analyzed at a wavelength of 488 nm with a LSM 700 confocal laser scanning-microscope (Carl Zeiss, Jena; gain 650, laser strength 2%) and images of the lesions are obtained. Measurement of the lesion size is done with Zen Blue software. The efficacy read-out is the lesion size as stained by isolectin B4 in RPE-choroidea flatmounts.

Evaluation of Binding of Compounds to Melanin

The ability of the compounds to bind to melanin is determined using an in vitro assay with melanin from *Sepia officinalis* (Sigma-Aldrich, Cat. no.: M2649) in an assay buffer (Phosphate buffer, pH 6.5, 0.9% (w/v) NaCl). To measure the binding, a 1 mg/mL (w/v) melanin suspension and a 0.1% (w/v) BSA solution (control buffer) are prepared in the assay buffer. The compound is incubated on a microtiter plate with the 1 mg/mL melanin suspension (for free compound concentration determination) and without melanin in the control buffer (for total compound concentration determination) at a final compound concentration of 1 µM (compounds are added to the plate in DMSO:assay buffer (40:60); final DMSO concentration is 1%). The plate is incubated for 2 h at 37° C. with 900 rpm orbital shaking. After the incubation, the plate is centrifuged to pellet the melanin and the bound compound. A sample is taken of the supernatants of both melanin and control wells and the concentrations measured with LC-MS. The bound concentration is calculated by subtracting the free compound concentration from the total compound concentration.

Evaluation of Chemical Stability

Degradation studies are used to simulate chemical stability of compounds in the acidic part of the gastro intestinal tract. The compounds of the invention show high chemical stability in acidic aqueous media (pH value ca. 1.2) what makes their application as medical drugs to treat human diseases less restricted and troublesome.

The chemical stability of the compounds of the invention at pH value of ca. 1.2 is determined as follows: Compound is dissolved in an HPLC vial in a mixture of acetonitrile/0.1 M aqueous HCl (ratio: 2:3; pH ca. 1.2) to get a concentration of approximately 0.25 mg/ml. The vial is then transferred into an HPLC autosampler system and maintained at a temperature of 37° C. A first sample is taken and injected immediately into a standard HPLC system with a UV DAD detector. A further samples is injected after 24 hours. Amount of degraded compound is measured by determining the recovery rate of compound [%] for the 24 h injection using an HPLC standard gradient method. Therefore the peak area of the main peak for the first injection ($AU_{t0}$) is determined and set as 100%. Peak area of the main peak is determined also for the 24 h injection ($AU_{24\ h}$) and expressed as fraction of ($AU_{24\ h}$)/($AU_{t0}$)[%].

Exemplary compounds according to the invention were tested for chemical stability as described above. For all of them, the amount of degraded compound was found to be not more than 3%.

The following table shows the extent of degradation of representative compounds of the present invention. The number of the respective compound corresponds to the number of the Example in the experimental section.

TABLE 3

| Example | Amount of degradation after 24 h |
|---|---|
| 2 | 1% |
| 17 | 2% |
| 19 | 3% |
| 21 | 1% |
| 26 | 2.5% |
| 28 | 0.5% |

Evaluation of Permeability

Caco-2 cells (1-2×10$^5$ cells/1 cm$^2$ area) are seeded on filter inserts (Costar transwell polycarbonate or PET filters, 0.4 µm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 μl per time point contains TRIS buffer pH 7.6 at RT (0.1 M), magnesium chloride (5 mM), microsomal protein (1 mg/mL) and the test compound at a final concentration of 1 μM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points. Additionally, the NADPH-independent degradation is monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% species serum.

Following a (typically) 30 min preincubation in an incubator (37° C., 10% $CO_2$) 5 μL of test compound solution (80 μM; from 2 mM in DMSO stock solution diluted 1:25 with medium) are added into 395 μL hepatocyte suspension (cell density in the range 0.25-5 Mio cells/mL, typically 1 Mio cells/mL; final concentration of test compound 1 μM, final DMSO concentration 0.05%).

The cells are incubated for six hours (incubator, orbital shaker) and samples (25 μL) are taken at 0, 0.5, 1, 2, 4 and 6 h. Samples are transferred into ACN and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [μM], CD: cell density of vital cells [10 e6 cells/mL], AUD: area under the data [μM×h], clast: concentration of last data point [μM], k: slope of the regression line for parent decline [h−1].

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 μM. The subsequent dialysis solutions are prepared in pooled human or rat plasma (with NaEDTA) from male and female donors. Aliquots of 200 μL dialysis buffer (100 mM potassium phosphate, pH 7.4) are dispensed into the buffer chamber. Aliquots of 200 μL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 mL ACN/water (80/20). Aliquots of 25 μL of the plasma dialysate are transferred into deep well plates and mixed with 25 μL ACN/water (80/20), 25 μL buffer, 25 μL calibration solution and 25 μL Internal Standard solution. Protein precipitation is done by adding 200 μL ACN.

Aliquots of 50 μL of the buffer dialysate are transferred into deep well plates and mixed with 25 μL blank plasma, 25 μL Internal Standard solution and 200 μL ACN.

Samples are measured on HPLC-MS/MS-Systems and evaluated with Analyst-Software.

Percent bound is calculated with the formula: % bound=(plasma concentration−buffer concentration/plasma concentration)×100

Evaluation of Solubility

The aqueous solubility of the test compound is determined by comparing the amount dissolved in buffer to the amount in an ACN/water (1/1) solution. Starting from a 10 mM DMSO stock solution aliquots are diluted with ACN/water (1/1) or buffer, respectively. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

The compounds of the invention show favorable solubilities also at low pH value (pH 2.2, emulating the acidic part of the gastro intestinal tract) which is a desirable feature for the purposes of drug development and administration. The following table presents the data for selected compounds of this invention.

TABLE 4

| Example | Solubility at pH 2.2 [μg/mL] | Example | Solubility at pH 2.2 [μg/mL] | Example | Solubility at pH 2.2 [μg/mL] | Example | Solubility at pH 2.2 [μg/mL] |
|---|---|---|---|---|---|---|---|
| 1 | >115 | 2 | >117 | 3 | >118 | 4 | >113 |
| 5 | 95 | 6 | >112 | 7 | 130 | 8 | >121 |
| 9 | >105 | 10 | >140 | 11 | 105 | 12 | >129 |
| 13 | 88 | 14 | 109 | 15 | >113 | 16 | >118 |
| 17 | >114 | 18 | >112 | 19 | >111 | 20 | >128 |
| 21 | >105 | 22 | >112 | 23 | >114 | 24 | >105 |
| 25 | >136 | 26 | >136 | 27 | >133 | 28 | >142 |
| 29 | >110 | 30 | 80 | 31 | >132 | 32 | >139 |
| 33 | >139 | 34 | >126 | 35 | 106 | 36 | 95 |
| 37 | 100 | 38 | 108 | 39 | >110 | 40 | >111 |
| 41 | >119 | 42 | >121 | 43 | 104 | 44 | >112 |
| 45 | >140 | 46 | 112 | 47 | >115 | 48 | >128 |
| 49 | 101 | 50 | 98 | 51 | >116 | 53 | 116 |
| 54 | 49 | 55 | >112 | 56 | >126 | 57 | >128 |

TABLE 4-continued

| Example | Solubility at pH 2.2 [µg/mL] | Example | Solubility at pH 2.2 [µg/mL] | Example | Solubility at pH 2.2 [µg/mL] | Example | Solubility at pH 2.2 [µg/mL] |
|---|---|---|---|---|---|---|---|
| 58 | >118 | 59 | >119 | 61 | >113 | 62 | >118 |
| 63 | >110 | 64 | >108 | 65 | >147 | 66 | >124 |
| 67 | >121 | 68 | >116 | 69 | >121 | 72 | >101 |
| 73 | >110 | 74 | >104 | 79 | >119 | 80 | >104 |
| 81 | 68 | | | | | | |

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentrations of analytes—the administered compound and/or metabolites—are quantified in the plasma samples by LC-MS/MS. To determine the renal clearance urine samples are collected over 24 hours after intravenous administration and the urine concentration of the administered compound is quantified by LC-MS/MS.

PK parameters are calculated using non-compartmental PK analysis (NCA). The trapezoidal rule is applied (lin up-log down) to determine the individual area under the curve from time zero to the last measured concentration ($AUC_{0-tz}$).

The $AUC_{0-Inf}$ is calculated by extrapolating the terminal phase and adding the $AUC_{tz-\infty}$ to the $AUC_{1-tz}$. The individual CL value is calculated according to equation 1.

$$CL_{tot}\left[\frac{mL}{min*kg}\right] = \frac{Dose\left[\frac{nmol}{kg}\right]}{AUC_{0-Inf}\left[\frac{nmol}{L}*h\right]} * 1000\left[\frac{mL}{L}\right] \quad \text{(Equation 1)}$$

where $CL_{tot}$ is the total clearance (renal+non-renal), Dose is the administered dose, $AUC_{0-Inf}$ is the calculated area under the curve, and 1000 represents the factor to provide the clearance in mL/min/kg, which is the unit commonly reported in literature.

In a second step, the drug-specific renal clearance for each animal is calculated using equation 2.

$$CL_{ren}\left[\frac{mL}{min*kg}\right] = CL_{tot}\left[\frac{mL}{min*kg}\right] * A_{e,urine} \quad \text{(Equation 2)}$$

where $CL_{ren}$ is the renal clearance and $A_{e,urine}$ is the fraction of the dose excreted into urine over 24 hours after i.v. drug administration.

Methods of Treatment

In another aspect of the present invention, it is described that compounds of formula (I.0) or pharmaceutically acceptable salts thereof possess suitable properties for use in therapy, i.e. for use as medicaments. In particular, compounds of formula (I.0) or pharmaceutically acceptable salts thereof, as well as pharmaceutical compositions containing the same, may be useful for the treatment of diseases or conditions, which can be influenced by antagonizing the platelet activating factor receptor (PAFR), e.g., which are mediated by unwanted activity of PAFR or in which antagonism of PAFR is beneficial, in a patient.

Additional benefit may be provided by inverse agonism of PAFR.

Diseases and conditions which can be influenced by antagonizing and/or inversely agonizing PAFR, e.g., which are mediated by unwanted PAFR activity or in which antagonism and/or inverse agonism of the activity of PAFR are beneficial, encompass ocular diseases, cardiovascular diseases, cancer, neurological and neurodegenerative disorders, renal disorders, liver diseases, and allergies. These disorders include but are not limited to retinopathy or diabetic retinopathy, proliferative and non-proliferative retinopathy, diabetic macular ischemia (DMI), geographic atrophy, Stargardt disease, retinal degeneration in glaucoma, myopic macular degeneration, chronic pan uveitis, retinitis pigmentosa, retinal vein occlusion (such as central, branch or hemiretinal vein occlusion), diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), subretinal fibrosis (e.g. associated with non-exudative or exudative choroidal neovascularization), posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, atherosclerosis, acquired angioedema, hereditary angioedema (HAE), drug-related (ACE-inhibitors) edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, encephalomyelitis, amyotrophic lateral sclerosis, neuropathic pain, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, renal disorders including chronic kidney disease, interstitial cystitis/bladder pain syndrome, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), ulcerative colitis, pancreatitis, lupus, gout, psoriasis, inflammatory bowel, diabetes, diabetic complications, complications arising from metabolic syndrome, non-alcoholic steatohepatitis (NASH), allergies, bacterial and viral infectious diseases including HIV infection, anaphylaxis, sepsis, chronic obstructive pulmonary disease (COPD), asthma, periodontitis, psoriasis, urticaria, UVB-induced dermatitis, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS), cancer (such as breast cancer, colorectal cancer, oesophagal cancer, lung cancer, liver cancer, pancreatic cancer, skin cancer including melanoma, cervical cancer), and other diseases.

Thus, the compounds and pharmaceutical compositions according to the invention are particularly suitable for the treatment of ocular diseases including diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV; e.g. non-exudative choroidal neovascularization).

In addition, the compounds and pharmaceutical compositions according to the invention are particularly suitable for the treatment of allergies and inflammation-related conditions and diseases, such as urticaria and NASH.

The compounds and pharmaceutical compositions according to the invention are most particularly suitable for the treatment of diabetic macular edema (DME), dry and wet age-related macular degeneration (AMD), geographic atrophy, non-exudative choroidal neovascularization (CNV), urticaria, and NASH.

The dose range of the compounds of formula (I.0) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon the patient's unique condition.

The compounds and compositions, including any combinations with one or more additional therapeutic agents, according to the invention may be administered by oral, intravitreal, transdermal, inhalative, parenteral, or sublingual route. Of the possible methods of administration, oral and intravitreal administration are preferred, in particular oral administration. In the case of intravitreal injection the preferred dose should not exceed 5 mg per eye.

The patient to be treated is preferably a mammal, most preferably a human patient.

Thus, in another aspect, the present invention provides a compound of formula (I.0), including pharmaceutically acceptable salts thereof, for use as a medicament.

In another aspect, the present invention provides a method for the treatment of a disease or condition, which is mediated by unwanted platelet activating factor receptor activity or in which antagonism of platelet activating factor receptor is beneficial, in a patient in need thereof.

Likewise, the present invention provides a compound of formula (I.0) or a pharmaceutically acceptable salt thereof for use in a method for the treatment of a disease or condition, which is mediated by unwanted platelet activating factor receptor activity or in which antagonism of platelet activating factor receptor is beneficial, in a patient in need thereof.

Likewise, the present invention provides the use of a compound of formula (I.0) or a pharmaceutically acceptable salt thereof, in the manufacture of a medicament for use in a method for the treatment of a disease or condition, which is mediated by unwanted platelet activating factor receptor activity or in which antagonism of platelet activating factor receptor is beneficial, in a patient in need thereof.

Likewise, the present invention provides the use of a compound of formula (I.0) or a pharmaceutically acceptable salt thereof, in a method for the treatment of a disease or condition, which is mediated by unwanted platelet activating factor receptor activity or in which antagonism of platelet activating factor receptor is beneficial, in a patient in need thereof.

According to one embodiment, the method for the treatment comprises administering to the patient one or more compounds of formula (I.0) or pharmaceutically acceptable salts thereof, preferably administering to the patient a therapeutically effective amount of one or more compounds of formula (I.0) or pharmaceutically acceptable salts thereof.

According to another embodiment, the method for the treatment comprises administering to the patient a pharmaceutical composition according to the present invention.

According to one embodiment, the disease or condition, which is mediated by unwanted platelet activating factor receptor activity or in which antagonism of platelet activating factor receptor is beneficial, is selected from ophthalmic indications such as diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV).

According to another embodiment, the disease or condition, which is mediated by unwanted platelet activating factor receptor activity or in which antagonism of platelet activating factor receptor is beneficial, is selected from allergies and inflammation-related conditions and diseases, such as urticaria and NASH.

According to another embodiment, the disease or condition, which is mediated by unwanted platelet activating factor receptor activity or in which antagonism of platelet activating factor receptor is beneficial, is selected from diabetic complications associated with diabetic retinopathy such as diabetic macular edema, diabetic macular ischemia, and proliferative diabetic retinopathy.

According to one embodiment, the patient is a human patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives, and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I.0) with known excipients, for example inert diluents, carriers, disintegrants, adjuvants, surfactants, binders, and/or lubricants. The tablets may also consist of several layers. The particular excipients, carriers and/or diluents that are suitable for the desired preparations will be familiar to the skilled person on the basis of his specialist knowledge. The preferred ones are those that are suitable for the particular formulation and method of administration that are desired. The preparations or formulations according to the invention may be prepared using methods known per se that are familiar to the skilled person, such as for example by mixing or combining at least one compound of formula (I.0) according to the invention or a pharmaceutically acceptable salt of such a compound, and one or more excipients, carriers, and/or diluents.

Thus, according to another aspect of the present invention, pharmaceutical compositions comprising one or more compounds of formula (I.0), or pharmaceutically acceptable salts thereof, optionally together with one or more inert carriers and/or diluents are provided.

Also, a pharmaceutical composition that comprises one or more of the above-mentioned compounds, or pharmaceutically acceptable salts thereof, optionally together with one or more inert carriers and/or diluents is provided for use in a method for the treatment of diseases or conditions which are mediated by unwanted PAFR activity or in which antagonism of PAFR is beneficial, in a patient in need thereof.

In particular, the invention provides a pharmaceutical composition according to this invention for use in a method for the treatment of ophthalmic indications such as diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV; e.g. non-exudative choroidal neovascularization), and of allergies and inflammation-related conditions and diseases, such as urticaria and NASH.

Furthermore, the present invention relates to the use of a pharmaceutical composition according to this invention for the treatment of diseases or conditions which are mediated by unwanted PAFR activity in a patient, preferably in a human.

Also, the present invention relates to the use of a pharmaceutical composition according to this invention for the treatment of diseases or conditions in which antagonism of PAFR is beneficial in a patient, preferably in a human.

According to one embodiment, a pharmaceutical composition comprising one or more compounds of formula (I.0) or pharmaceutically acceptable salts thereof, and one or more additional therapeutic agents, optionally together with one or more inert carriers and/or diluents is provided.

For instance, this composition comprises one compound of formula (I.0) or a pharmaceutically acceptable salt thereof and one or more additional therapeutic agents.

Combination Therapy

The compounds of the invention may further be combined with one or more, preferably one additional therapeutic agent.

According to one embodiment the additional therapeutic agent is selected from the group of therapeutic agents useful in the treatment of diseases or conditions described hereinbefore, in particular of ocular diseases, allergies, and inflammation-related conditions and diseases, such as diabetic macular edema (DME), dry and wet age-related macular degeneration (AMD), geographic atrophy, non-exudative choroidal neovascularization (CNV), urticaria and NASH, or of metabolic diseases or conditions such as for example diabetes mellitus, obesity, diabetic complications, hypertension, and hyperlipidemia.

Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis, agents for the treatment of ocular diseases and agents for the treatment of allergies and inflammation-related conditions and diseases.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, dual agonists comprising GLP-1 activity together with glucagon or GIP activity, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor, dual agonists of the GLP-1 and glucagon receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte activating inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists, PKK inhibitors.

Additional treatments for ocular diseases may include laser coagulation therapy.

Therapeutic agents for the treatment of urticaria may include for example antihistamines, steroids such as cortisone, epinephrine, antibodies against immunoglobulin E, immunosuppressants such as cyclosporin A, and leukotriene receptor antagonists.

Therapeutic agents for the treatment of NASH may include for example FXR agonists, FXR/TGR5 agonists, THR-β agonists, ACC inhibitors, TGF-b1 antagonists, LTA4 hydrolase inhibitors, SGLT inhibitors, activin type 2 receptor antagonists, NLRP3 inhibitors, avβ1 integrin inhibitors, cGAS/STING inhibitors, GLP-1R agonists, FGF21 agonists, GLP-1/glucagon receptor dual agonists, GLP-1/GIP receptor dual agonists, GLP-1/FGF21 receptor dual agonists, GLP-1/GIP/glucagon receptor triple agonists, AOC3 inhibitors, JNK1 inhibitors, CCR2/5 inhibitors, ACC inhibitors, DGAT inhibitors, KHK inhibitors, PPARα/δ agonists, FGF19 agonists, β-klotho/FGFR1c agonists, PNPLA3 inhibitors, NLRP3 inhibitors, THR-β agonists, HSD17β13 inhibitors, galectin-3 inhibitors, SCD1 inhibitors, ASK1 inhibitors, endothelin receptor A antagonists, FASN inhibitors, calpain inhibitors, autotaxin inhibitors, TREM2 agonists, sGC inhibitors, PKK inhibitors, RORc inhibitors, TLR4 inhibitors, and IL11 inhibitors.

The compounds of the present invention and/or pharmaceutical compositions comprising a compound of the present invention optionally in combination with one or more additional therapeutic agents may be administered in conjunction with exercise and/or a diet.

The dosage for the combination partners mentioned above is usually ⅕ of the lowest dose normally recommended up to 1/1 of the normally recommended dose.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Thus, according to another aspect, this invention relates to a pharmaceutical composition which comprises one or more compounds according to the invention and one or more additional therapeutic agents described hereinbefore and hereinafter, optionally together with one or more inert carriers and/or diluents.

According to another aspect, the present invention provides a method for the treatment of a disease or condition, which is mediated by unwanted platelet activating factor receptor activity or in which antagonism of PAFR is beneficial, in a patient in need thereof, the method comprising administering to the patient one or more compounds of formula (I.0) or pharmaceutically acceptable salts thereof, in combination with one or more additional therapeutic agents described in hereinbefore and hereinafter, preferably administering to the patient a therapeutically effective amount of one or more compounds of formula (I.0) or pharmaceutically acceptable salts thereof, in combination with a therapeutically effective amount of one or more additional therapeutic agents described in hereinbefore and hereinafter.

Likewise, the present invention provides a compound of formula (I.0) or a pharmaceutically acceptable salt thereof in combination with one or more additional therapeutic agents described hereinbefore or hereinafter for use in a method for the treatment of a disease or condition, which is mediated by unwanted PAFR activity or in which antagonism of PAFR is beneficial, in a patient in need thereof.

Likewise, the present invention provides the use of a compound of formula (I.0) or a pharmaceutically acceptable salt thereof, in combination with one or more additional therapeutic agents described hereinbefore or hereinafter, in the manufacture of a medicament for use in a method for the treatment of a disease or condition, which is mediated by unwanted PAFR activity or in which antagonism of PAFR is beneficial, in a patient in need thereof.

Likewise, the present invention provides the use of a compound of formula (I.0) or a pharmaceutically acceptable salt thereof, in combination with one or more additional therapeutic agents described hereinbefore or hereinafter, in a method for the treatment of a disease or condition, which is mediated by unwanted PAFR activity or in which antagonism of PAFR is beneficial, in a patient in need thereof.

According to one embodiment, the method for the treatment comprises administering to the patient one or more compounds of formula (I.0) or pharmaceutically acceptable salts thereof, in combination with one or more additional therapeutic agents described hereinbefore and hereinafter, preferably administering to the patient a therapeutically effective amount of one or more compounds of formula (I.0) or pharmaceutically acceptable salts thereof, in combination with a therapeutically effective amount of one or more additional therapeutic agents described hereinbefore and hereinafter.

According to another embodiment, the method for the treatment comprises administering to the patient a pharmaceutical composition comprising one or more compounds according to the invention and one or more additional therapeutic agents described hereinbefore and hereinafter, optionally together with one or more inert carriers and/or diluents.

According to one embodiment, the one or more additional therapeutic agents are selected from antidiabetic agents, agents for the treatment of overweight and/or obesity, agents for the treatment of high blood pressure, heart failure and/or atherosclerosis, and agents for the treatment of ocular diseases, in particular from those agents specifically mentioned above.

According to one embodiment, the disease or condition, which is mediated by unwanted PAFR activity or in which antagonism of PAFR is beneficial, is selected from ophthalmic indications such as diabetic retinopathy, proliferative and non-proliferative retinopathy, diabetic macular edema (DME), dry and wet age-related macular degeneration (AMD), geographic atrophy, polypoidal choroidal vasculopathy (PCV) and choroidal neovascularization (CNV), from allergies and inflammation-related conditions and diseases such as urticaria or NASH, and from diabetic complications associated with diabetic retinopathy such as diabetic macular edema, diabetic macular ischemia and proliferative diabetic retinopathy.

According to one embodiment, the patient is a human patient.

Other features and advantages of the present invention will become apparent from the following more detailed Examples which illustrate, by way of example, the principles of the invention.

EXAMPLES AND EXPERIMENTAL DATA

The following Examples are for the purpose of illustration of the invention only and are not intended in any way to limit the scope of the present invention.

Abbreviations

Ac acetyl
ACN acetonitrile
BPR backpressure regulator
BSA bovine serum albumin
Cbz benzyloxycarbonyl
d day(s)
DABCO 1,4-diazabicyclo[2.2.2]octane
DAD diode array detector
DBU 1,8-diazabicyclo[5.4.0]undec-7-ene
DCE 1,2-dichloroethane
DCM dichloromethane
DMEM Dulbecco's modified eagle medium
DMF N,N-dimethylformamide
DMSO dimethyl sulfoxide
EDTA ethylenediaminetetraacetate
EtOAc ethyl acetate
EtOH ethanol
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
IPA isopropanol
LC liquid chromatography
LC-MS coupled liquid chromatography-mass spectrometry
M molar (mol/L)
MeTHF 2-methyltetrahydrofuran
MeOH methanol
min minute(s)
MS mass spectrometry
NADPH nicotinamide adenine dinucleotide phosphate
NMP N-methyl-2-pyrrolidone
NMR nuclear magnetic resonance
PET polyethylene terephthalate
pet. petroleum
PyBop (benzotriazol-1-yloxy)tripyrrolidinophosphonium hexafluorophosphate
$R^f$ retention factor
rt/RT room temperature
$t_R$ retention time (in HPLC/LC)
sc supercritical
SFC supercritical fluid chromatography
TBTU O-(benzotriazol-1-yl)-N,N,N',N'-tetramethyluronium tetrafluoroborate
TFA trifluoroacetic acid
THF tetrahydrofuran
UV ultraviolet The terms "ambient temperature" and "room temperature" are used interchangeably and designate a temperature of about 20° C., e.g., 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry, or by biological activity.

Analytical Methods

| Method: | 1 |
| --- | --- |
| Device: | Agilent 1200 with DA- and MS-Detector |
| Column: | XBridge C18, 3 × 30 mm, 2.5 μm |
| Column Supplier: | Waters |

| Gradient/Solvent Time [min] | % Solvent [H$_2$O, 0.1%NH$_3$] | % Solvent [ACN] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 2 |
| --- | --- |
| Device: | Agilent 1200 with DA- and MS-Detector |
| Column: | Sunfire C18, 3 × 30 mm, 2.5 μm |
| Column Supplier: | Waters |

| Gradient/Solvent Time [min] | % Solvent [H$_2$O, 0.1%TFA] | % Solvent [ACN] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 | | | | |
|---|---|---|---|---|---|
| Device: | Agilent 1260 SFC with DA- and MS-Detector | | | | |
| Column: | CHIRAL ART ® Cellulose SC, 4.6 × 250 mm, 5 μm | | | | |
| Column Supplier: | YMC | | | | |

| Gradient/Solvent Time [min] | % Solvent [scCO$_2$] | % Solvent [MeOH, 20 mM NH$_3$] | Flow [mL/min] | Temperature [° C.] | Back pressure [PSI] |
|---|---|---|---|---|---|
| 0.00 | 65.0 | 35.0 | 4.0 | 40.0 | 2175.0 |
| 10.0 | 65.0 | 35.0 | 4.0 | 40.0 | 2175.0 |

| Method: | 4 | | | | |
|---|---|---|---|---|---|
| Device: | Waters Acquity, QDa Detector | | | | |
| Column: | Sunfire C18, 3 × 30 mm, 2.5 μm | | | | |
| Column Supplier: | Waters | | | | |

| Gradient/Solvent Time [min] | % Solvent [H$_2$O, 0.1%TFA] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Method: | 5 | | | | |
|---|---|---|---|---|---|
| Device: | Agilent 1260 SFC with DAD and MS | | | | |
| Column: | Chiralpak ® IG_4.6 × 250 mm_5 μm | | | | |
| Column Supplier: | Daicel | | | | |

| Gradient/Solvent Time [min] | % Solvent [scCO$_2$] | % Solvent [MeOH, 20 mM NH$_3$] | Flow [mL/min] | Temperature [° C.] | Back pressure [PSI] |
|---|---|---|---|---|---|
| 0.00 | 65.0 | 35.0 | 4.0 | 40.0 | 2175 |
| 10.0 | 65.0 | 35.0 | 4.0 | 40.0 | 2175 |

| Method: | 6 | | | | |
|---|---|---|---|---|---|
| Device: | Agilent 1260 SFC with DAD and MS | | | | |
| Column: | CHIRAL ART ® Cellulose SB_4.6 × 250 mm_5 μm | | | | |
| Column Supplier: | YMC | | | | |

| Gradient/Solvent Time [min] | % Solvent [scCO$_2$] | % Solvent [IPA, 20 mM NH$_3$] | Flow [mL/min] | Temperature [° C.] | Back pressure [PSI] |
|---|---|---|---|---|---|
| 0.00 | 65.0 | 35.0 | 4.0 | 40.0 | 2175 |
| 10.0 | 65.0 | 35.0 | 4.0 | 40.0 | 2175 |

| Method: | 7 | | | | |
|---|---|---|---|---|---|
| Device: | Agilent 1260 SFC with DAD and MS | | | | |
| Column: | CHIRAL ART ® Amylose SA_4.6 × 250 mm_5 μm | | | | |
| Column Supplier: | YMC | | | | |

| Gradient/Solvent Time [min] | % Solvent [scCO$_2$] | % Solvent [MeOH, 20 mM NH$_3$] | Flow [mL/min] | Temperature [° C.] | Back pressure [PSI] |
|---|---|---|---|---|---|
| 0.00 | 75.0 | 25.0 | 4.0 | 40.0 | 2175 |
| 10.0 | 75.0 | 25.0 | 4.0 | 40.0 | 2175 |

| Method: | 8 | | | | |
|---|---|---|---|---|---|
| Device: | Agilent 1260 SFC with DAD and MS | | | | |
| Column: | Chiralpak ® IA_4.6 × 250 mm_5 μm | | | | |
| Column Supplier: | Daicel | | | | |

| Gradient/Solvent Time [min] | % Solvent [scCO$_2$] | % Solvent [MeOH, 20 mM NH$_3$] | Flow [mL/min] | Temperature [° C.] | Back pressure [PSI] |
|---|---|---|---|---|---|
| 0.00 | 70.0 | 30.0 | 4.0 | 40.0 | 2175 |
| 10.0 | 70.0 | 30.0 | 4.0 | 40.0 | 2175 |

| Method: | 9 | | | | |
|---|---|---|---|---|---|
| Device: | Agilent 1260 SFC with DAD and MS | | | | |
| Column: | CHIRAL ART ® Amylose SA_4.6 × 250 mm_5 μm | | | | |
| Column Supplier: | YMC | | | | |

| Gradient/Solvent Time [min] | % Solvent [scCO$_2$] | % Solvent [MeOH, 20 mM NH$_3$] | Flow [mL/min] | Temperature [° C.] | Back pressure [PSI] |
|---|---|---|---|---|---|
| 0.00 | 70.0 | 30.0 | 4.0 | 40.0 | 2175 |
| 10.0 | 70.0 | 30.0 | 4.0 | 40.0 | 2175 |

SYNTHESIS OF INTERMEDIATES

Intermediate 1

Methyl 9-(2-chlorophenyl)-3-methyl-16-thia-2,4,5,8-tetraazatetracyclo[8.6.0.0²,⁶.0¹¹,¹⁵]hexadeca-1(10),3,5,8,11-(15)-pentaene-13-carboxylate

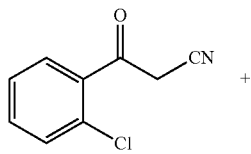
+
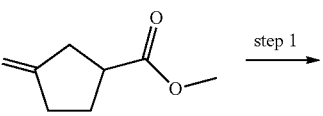
→ step 1

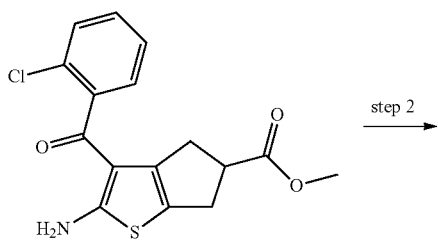
→ step 2

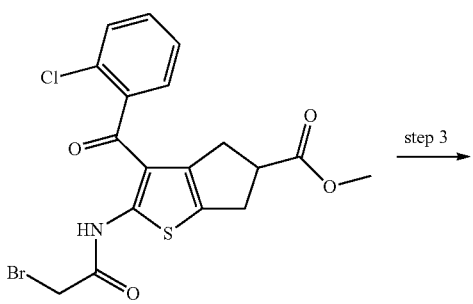
→ step 3

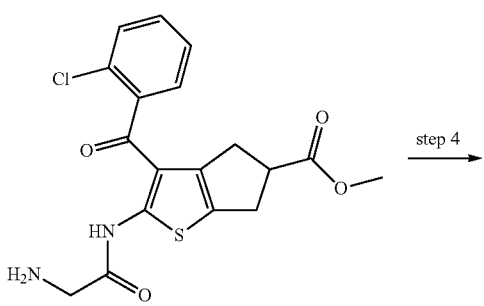
→ step 4

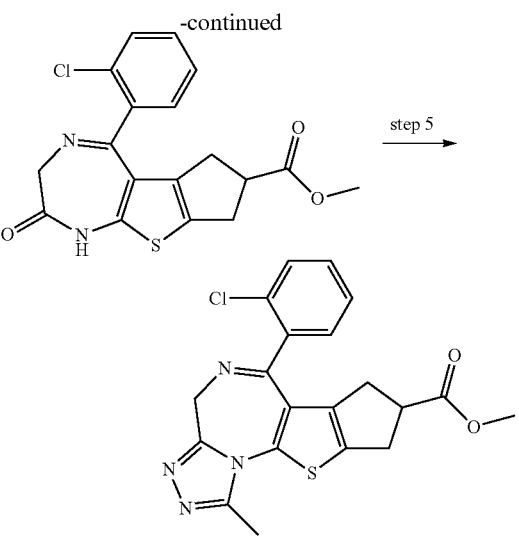
→ step 5

Step 1: methyl 2-amino-3-(2-chlorobenzoyl)-4H,5H,6H-cyclopenta[b]thiophene-5-carboxylate A mixture of 3-(2-chlorophenyl)-3-oxopropanenitrile (126 g), methyl 3-oxocyclopentane-1-carboxylate (100 g), sulfur (22.5 g), morpholine (61.8 mL), and MeOH (800 mL) is stirred at reflux for 4 h. After cooling to room temperature, the reaction mixture is concentrated. The crude product is purified by silica gel column chromatography (pet. ether/DCM 50:50) then recrystallized from MeOH to give the title compound.

Step 2: methyl 3-(2-chlorobenzoyl)-2-(2-bromoacetamido)-4H,5H,6H-cyclopenta[b]thiophene-5-carboxylate Bromoacetyl bromide (41.9 g) is added to a stirred mixture of methyl 2-amino-3-(2-chlorobenzoyl)-4H,5H,6H-cyclopenta[b]thiophene-5-carboxylate (100 g), NaHCO₃ (30.0 g), toluene (1200 mL), and water (100 mL) at 0° C. The cooling bath is removed, and the mixture is stirred at 60° C. for 4 h. After cooling to room temperature, water is added, and the resulting mixture is extracted with EtOAc (2×). The combined extract is dried (Na₂SO₄) and concentrated. The residue is chromatographed on silica gel (pet. ether/EtOAc 70:30) to give the title compound.

Step 3: methyl 2-(2-aminoacetamido)-3-(2-chlorobenzoyl)-4H,5H,6H-cyclopenta[b]thiophene-5-carboxylate Methyl 3-(2-chlorobenzoyl)-2-(2-bromoacetamido)-4H,5H,6H-cyclopenta[b]thiophene-5-carboxylate (10.0 g) and ammonia (0.5 mol/L in THF; 70.0 mL) are added to a flask charged with a stir bar at room temperature. The flask is sealed, and the mixture is stirred overnight. The mixture is concentrated to remove excess of ammonia and most of the THF, and EtOAc is added. The resulting mixture is washed with water, dried (Na₂SO₄) and concentrated to provide the crude title compound that is used in the next reaction step without further purification.

Step 4: methyl 13-(2-chlorophenyl)-10-oxo-7-thia-9,12-diazatricyclo[6.5.0.0²,⁶]trideca-1(8),2(6),12-triene-4-carboxylate Silica gel (3.05 g) is added to a solution of methyl 2-(2-aminoacetamido)-3-(2-chlorobenzoyl)-4H,5H,6H-cyclopenta[b]thiophene-5-carboxylate (8.00 g) in toluene (80.0 mL). To the resulting mixture are added 4 Å molecular sieves (1.00 g). The reaction mixture is stirred at 110° C. for 24 h. After cooling to room temperature, the mixture is filtered and concentrated, and the residue is chromatographed on silica gel (pet. ether/EtOAc 70:30) to give the title compound.

Step 5: methyl 9-(2-chlorophenyl)-3-methyl-16-thia-2,4,5,8-tetraazatetracyclo[8.6.0.0²,⁶.0¹¹,¹⁵]-hexadeca-1(10),3,5,8,11(15)-pentaene-13-carboxylate ClPO(OEt)$_2$ (3.01 mL) and DBU (3.02 mL) are added to a solution of methyl 13-(2-chlorophenyl)-10-oxo-7-thia-9,12-diazatricyclo[6.5.0.0²,⁶]trideca-1(8),2(6),12-triene-4-carboxylate (5.05 g) in THF (50.0 mL) at room temperature. The mixture is stirred for 10 min prior to the addition of acetic hydrazide (1.56 g). After stirring at room temperature for another 30 min, the mixture is stirred at 60° C. for 4 h. After cooling to room temperature, EtOAc is added, and the resulting mixture is washed with water, aqueous NaHCO$_3$ solution, and brine. The organic phase is dried (MgSO$_4$) and concentrated. The residue is chromatographed on silica gel (DCM/MeOH 99:1->95:5) to give the title compound.

Intermediate 2

9-(2-Chlorophenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylic acid

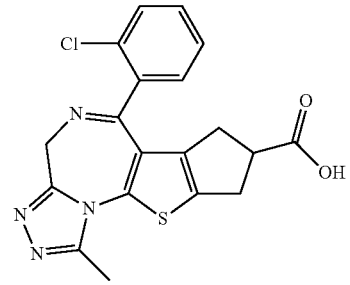 [SMILES: Cc1nnc2n1-c1sc3c(c1C(c1ccccc1Cl)=NC2)CC(C(=O)O)C3]

NaOH (4 mol/L in water; 35.0 mL) is added to a solution of methyl 9-(2-chlorophenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylate (20.0 g) in THF (150 mL) at room temperature. The mixture is stirred at room temperature for 16 h. The mixture is diluted with water, HCl (4 mol/L in water) is added to adjust the pH value of the mixture to ca. 4.5, and then the mixture is extracted with DCM (5×). The combined organic extract is washed with brine, dried (Na$_2$SO$_4$), and concentrated to give the crude title compound that is used as is in the next reaction step.

Intermediate 3 and Reference Intermediate 4

(13S)-9-(2-Chlorophenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylic acid (Intermediate 3) and (13R)-9-(2-chlorophenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylic acid (Reference Intermediate 4)

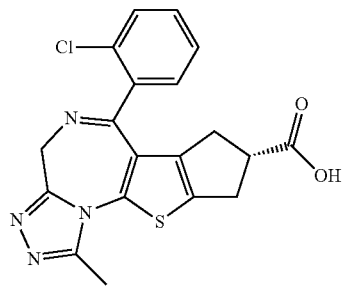

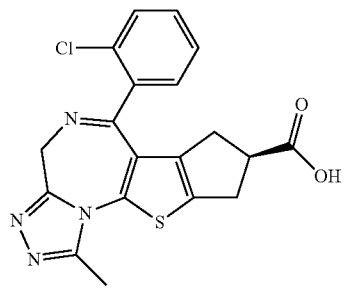

9-(2-Chlorophenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylic acid (racemic mixture, 10.0 g) is dissolved (50 mg/mL in EtOH/DCM 2:1) and then resolved by SFC on chiral phase [column: Lux C4 (30 mm×250 mm, 5 µm); column temperature: 40° C.; flow rate: 50 mL/min; BPR: 100 bar; injection volume: 500 µL (25 mg); isocratic conditions: 50:50 CO$_2$:EtOH (0.2% v/v formic acid)] to give the title compounds separated.

Intermediate 3: LC (Method 3): $t_R$=4.87 min; Mass spectrum (ESI$^+$): m/z=399/401 (Cl) [M+H]$^+$;

Reference Intermediate 4: LC (Method 3): $t_R$=4.26 min; Mass spectrum (ESI$^+$): m/z=399/401 (Cl) [M+H]$^+$.

Intermediate 5

(13S)-9-(2-Chlorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

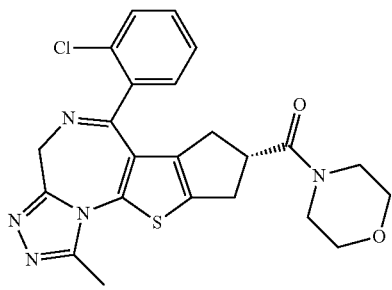 [SMILES: Cc1nnc2n1-c1sc3c(c1C(c1ccccc1Cl)=NC2)C[C@H](C(=O)N1CCOCC1)C3]

HATU (10.0 mg) is added to a mixture of (13S)-9-(2-chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid (10.0 mg), N,N-diisopropyl-ethylamine (0.010 mL), and DMF (1.00 mL) at room temperature. After stirring for 5 min, morpholine (5.00 mg) is added, and the resulting mixture is stirred for 1 h. The reaction mixture is diluted with DMF and purified by reversed phase chromatography (HPLC; ACN/water/aqueous ammonia) to give the title compound.

Intermediate 6

9-(2-Chlorophenyl)-3-methyl-13-(morpholine-4-carbonyl)-16-thia-2,4,5,8-tetraazatetracyclo[8.6.0.0$^{2,6}$.0$^{11,15}$]hexa-deca-1(10),3,5,8,11(15)-pentaene

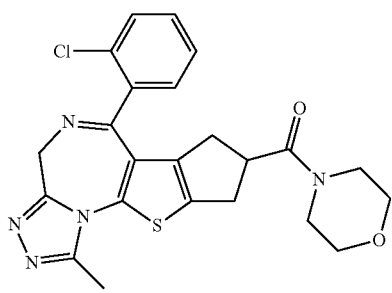 [SMILES: Cc1nnc2n1-c1sc3c(c1C(c1ccccc1Cl)=NC2)CC(C(=O)N1CCOCC1)C3]

The title compound is prepared from 9-(2-chlorophenyl)-3-methyl-16-thia-2,4,5,8-tetraazatetra-cyclo[8.6.0.0$^{2,6}$.0$^{11,15}$]hexadeca-1(10),3,5,8,11(15)-pentaene-13-carboxylic acid and morpholine following a procedure analogous to that described for Intermediate 5.

Reference Intermediate 7

(13R)-9-(2-Chlorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

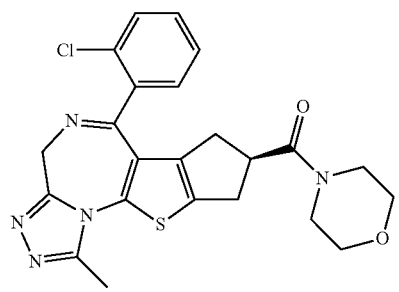 [SMILES: Cc1nnc2n1-c1sc3c(c1C(c1ccccc1Cl)=NC2)C[C@@H](C(=O)N1CCOCC1)C3]

The title compound is prepared from (13R)-9-(2-chlorophenyl)-3-methyl-16-thia-2,4,5,8-tetraazatetra-cyclo[8.6.0.0$^{2,6}$.0$^{11,15}$]hexadeca-1(10),3,5,8,11(15)-pentaene-13-carboxylic acid and morpholine following a procedure analogous to that described for Intermediate 5.

Intermediate 8

(9R,13S)-9-(2-Chlorophenyl)-3-methyl-16-thia-2,4,5,8-tetraazatetracyclo[8.6.0.0$^{2,6}$.0$^{11,15}$]hexadeca-1(10),3,5,11(15)-tetraene-13-carboxylic acid

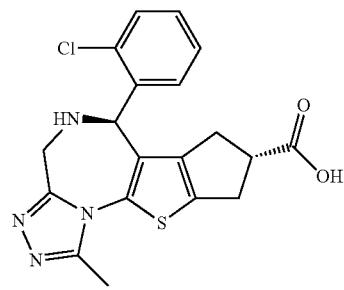 [SMILES: Cc1nnc2n1-c1sc3c(c1[C@H](c1ccccc1Cl)NC2)C[C@H](C(=O)O)C3]

Tetrabutylammonium borohydride (16.6 g) is added in portions to a stirred solution of N-Cbz-L-proline (48.1 g) in DCM (80 ml) at 0° C. After hydrogen evolution stops, the mixture is stirred at room temperature for an additional 1 h. The resulting solution is added dropwise to a solution of (13S)-9-(2-chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid (8.6 g) in DCM (120 mL) cooled to −10° C., and the reaction mixture is stirred at −10° C. for 1 h and at room temperature for an additional 1 h. Aqueous HCl (1 M) is added to adjust the pH value of the mixture to 1, and the mixture is extracted with aqueous HCl (1 M, 3×). The pH of the combined aqueous layers is carefully adjusted with aqueous NaOH (4 M) until pH 4.5 is reached and a white precipitate appears. The mixture is extracted with DCM (3×). The combined organic extracts are dried (MgSO$_4$) and concentrated. The crude product is purified by reversed phase chromatography (HPLC; ACN/ water/TFA) to obtain the title compound. LC (Method 2): $t_R$=0.67 min; Mass spectrum (ESI+): m/z=401 [M+H]+.

Reference Intermediate 9

(9R,13R)-9-(2-Chlorophenyl)-3-methyl-16-thia-2,4,5,8-tetraazatetracyclo[8.6.0.0$^{2,6}$.0$^{11,15}$]hexadeca-1(10),3,5,11(15)-tetraene-13-carboxylic acid

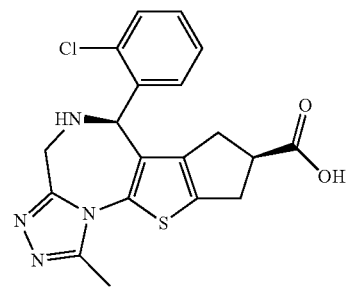 [SMILES: Cc1nnc2n1-c1sc3c(c1[C@H](c1ccccc1Cl)NC2)C[C@@H](C(=O)O)C3]

The title compound is prepared from (13R)-9-(2-chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid following a procedure analogous to that described for Intermediate 8. LC (Method 2): $t_R$=0.70 min; Mass spectrum (ESI+): m/z=401 [M+H]+.

Intermediate 10

(9S,13S)-9-(2-Chlorophenyl)-3-methyl-16-thia-2,4,5,8-tetraazatetracyclo[8.6.0.0$^{2,6}$.0$^{11,15}$]hexadeca-1(10),3,5,11(15)-tetraene-13-carboxylic acid

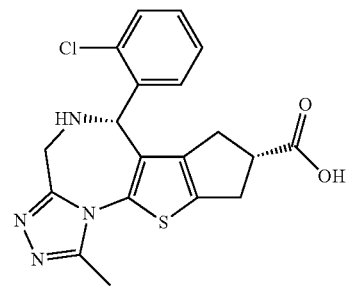 [SMILES: Cc1nnc2n1-c1sc3c(c1[C@@H](c1ccccc1Cl)NC2)C[C@H](C(=O)O)C3]

(13S)-9-(2-Chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid (1.00 g) is dissolved in DCM (35 mL), which is followed by the addition of aqueous HCl (4 M, 1.25 mL) and sodium borohydride (379 mg). The reaction mixture is stirred at room temperature for 1.25 h. Aqueous HCl (4 M) is added and the mixture is stirred until gas evolution stops, then MeOH and THF are added. The resulting precipitate is filtered and the filtrate is concentrated. The residue is taken up in MeTHF and stirred at room temperature for 1 h. The resulting precipitate is filtered and washed with additional MeTHF. The crude product, composed of a diastereomeric mixture of Intermediate 8 and the title compound, is purified by reversed phase chromatography (HPLC; ACN/water/TFA) to obtain the isolated title compound.

LC (Method 2): $t_R$=0.71 min; Mass spectrum (ESI+): m/z=401 [M+H]+.

Intermediate 11

9-(4-Chlorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene

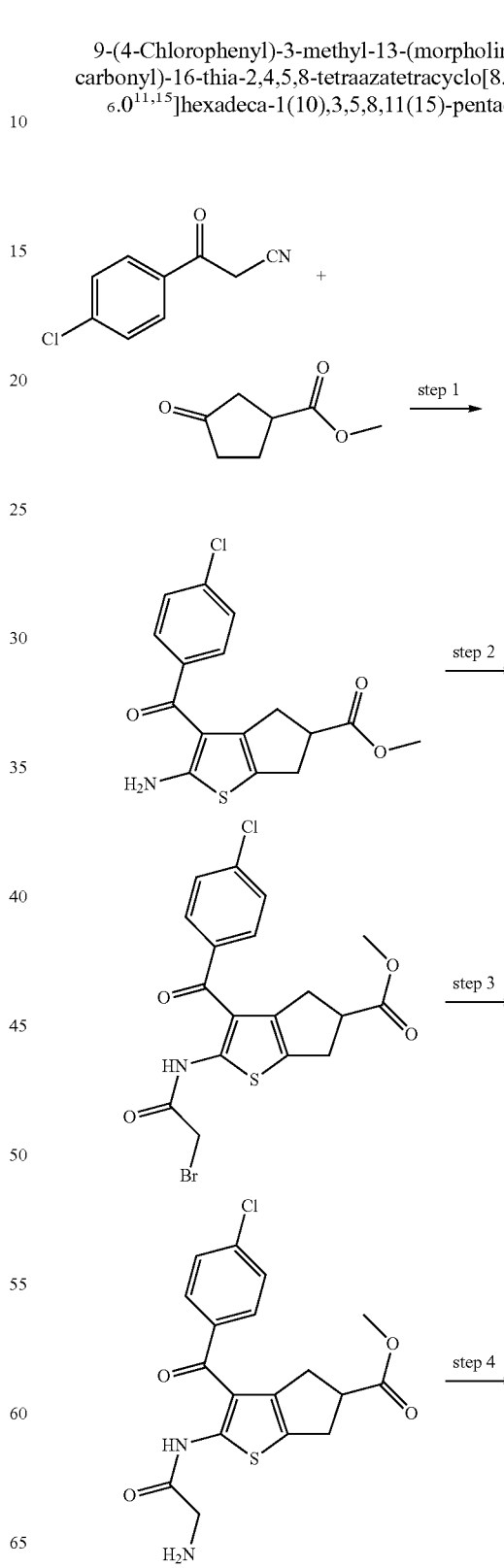

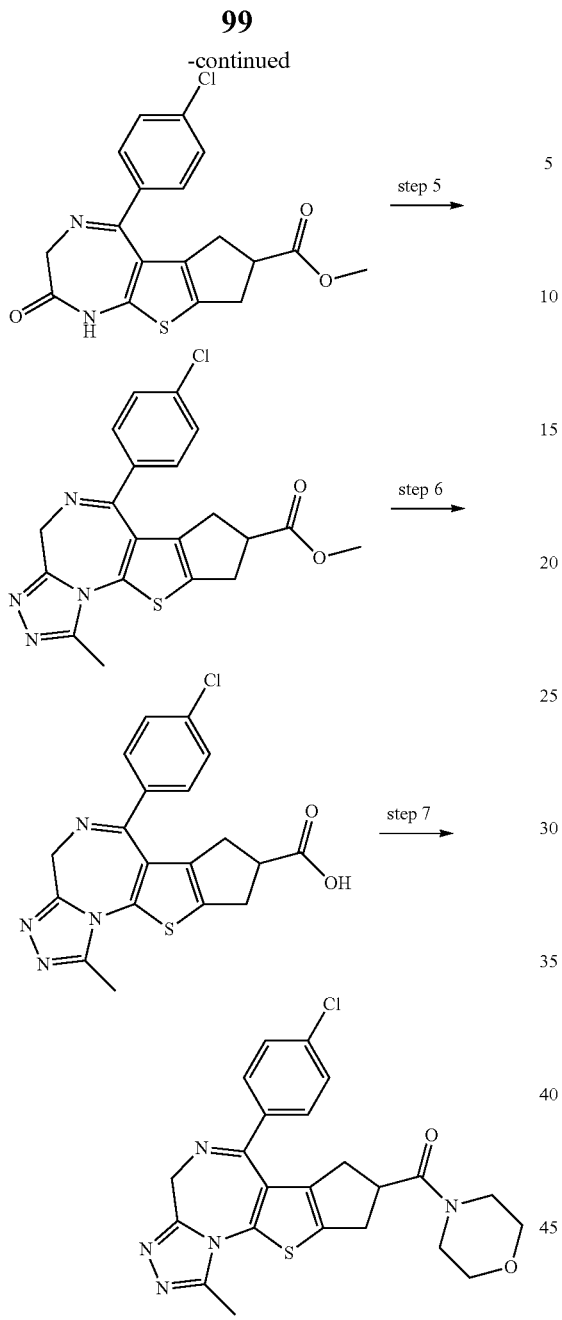

Step 1: methyl 2-amino-3-(4-chlorobenzoyl)-4H,5H, 6H-cyclopenta[b]thiophene-5-carboxylate The title compound is prepared from 3-(4-chlorophenyl)-3-oxopropanenitrile and methyl 3-oxocyclopentane-1-carboxylate following a procedure analogous to that described in Step 1 of Intermediate 1.

LC (Method 2): $t_R$=1.04 min; Mass spectrum (ESI$^+$): m/z=336 [M+H]$^+$.

Step 2: methyl 3-(4-chlorobenzoyl)-2-(2-bromoacetamido)-4H,5H,6H-cyclopenta[b]thiophene-5-carboxylate The title compound is prepared from methyl 2-amino-3-(4-chlorobenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.14 min; Mass spectrum (ESI$^+$): m/z=456/458 (Br) [M+H]$^+$.

Step 3: methyl 2-(2-aminoacetamido)-3-(4-chlorobenzoyl)-4H,5H,6H-cyclopenta[b]thiophene-5-carboxylate The title compound is prepared from methyl 3-(4-chlorobenzoyl)-2-(2-bromoacetamido)-4H,5H,6H-cyclopenta[b]thiophene-5-carboxylate following a procedure analogous to that described in Step 3 of Intermediate 1.

LC (Method 2): $t_R$=0.82 min; Mass spectrum (ESI$^+$): m/z=393 [M+H]$^+$.

Step 4: methyl 13-(4-chlorophenyl)-10-oxo-7-thia-9,12-diazatricyclo[6.5.0.0$^{2,6}$]trideca-1(8),2(6),12-triene-4-carboxylate The title compound is prepared from methyl 2-(2-aminoacetamido)-3-(4-chlorobenzoyl)-4H,5H,6H-cyclopenta[b]thiophene-5-carboxylate following a procedure analogous to that described in Step 4 of Intermediate 1.

LC (Method 2): $t_R$=0.75 min; Mass spectrum (ESI$^+$): m/z=375 [M+H]$^+$.

Step 5: methyl 9-(4-chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylate The title compound is prepared from methyl 13-(4-chlorophenyl)-10-oxo-7-thia-9,12-diazatricyclo[6.5.0.0$^{2,6}$]-trideca-1(8),2(6),12-triene-4-carboxylate following a procedure analogous to that described in Step 5 of Intermediate 1.

LC (Method 2): $t_R$=0.88 min; Mass spectrum (ESI$^+$): m/z=413 [M+H]$^+$.

Step 6: 9-(4-chlorophenyl)-3-methyl-16-thia-2,4,5, 8-tetraazatetracyclo[8.6.0.0$^{2,6}$.0$^{11,15}$]hexadeca-1(10), 3,5,8,11(15)-pentaene-13-carboxylic acid The title compound is prepared from methyl 9-(4-chlorophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylate following a procedure analogous to that described for Intermediate 2. LC (Method 2): $t_R$=0.75 min; Mass spectrum (ESI$^+$): m/z=399 [M+H]$^+$.

Step 7: 9-(4-chlorophenyl)-3-methyl-13-(morpholine-4-carbonyl)-16-thia-2,4,5,8-tetraazatetracyclo [8.6.0.0$^{2,6}$.0$^{11,15}$]-hexadeca-1(10),3,5,8,11(15)-pentaene The title compound is prepared from 9-(4-chlorophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylic acid and morpholine following a procedure analogous to that described for Intermediate 5.

LC (Method 2): $t_R$=0.78 min (diastereomers); Mass spectrum (ESI$^+$): m/z=468 [M+H]$^+$.

Intermediate 12

9-(2-Ethylphenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene

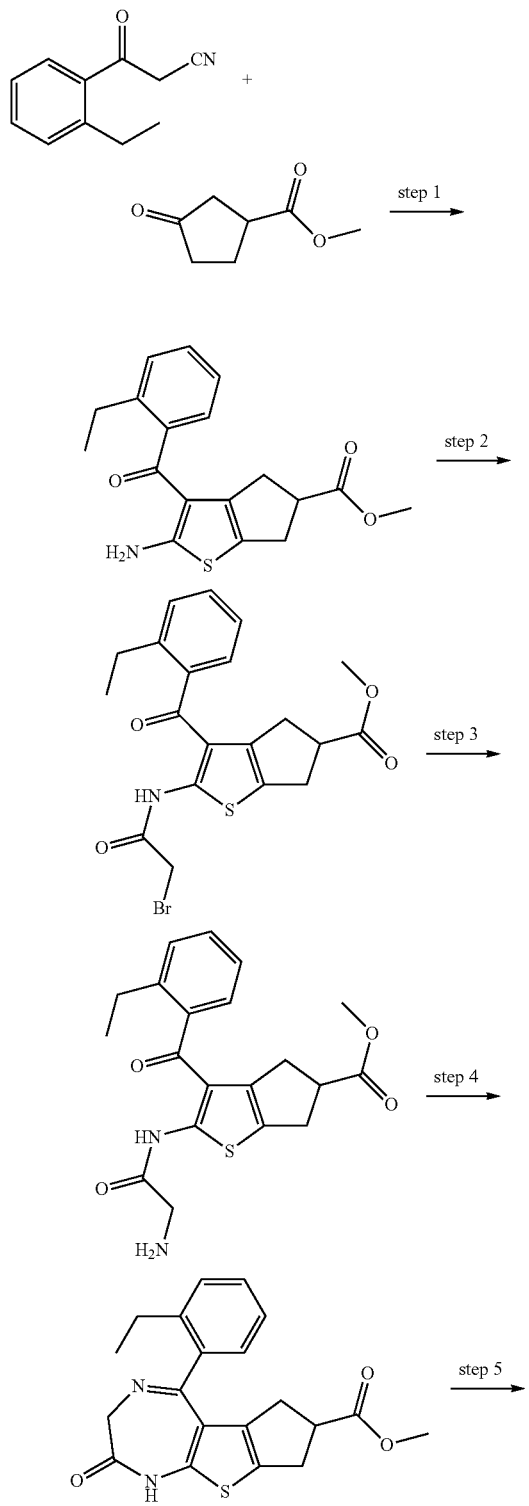

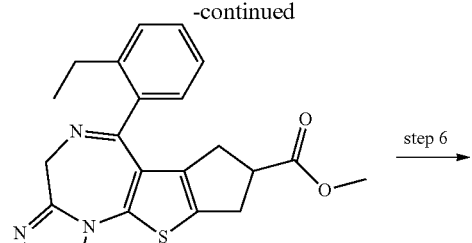

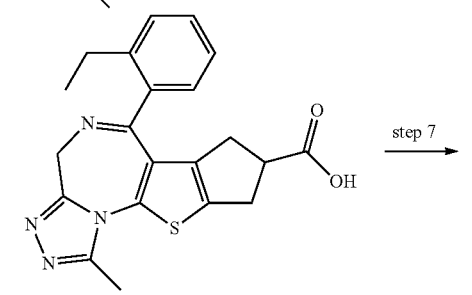

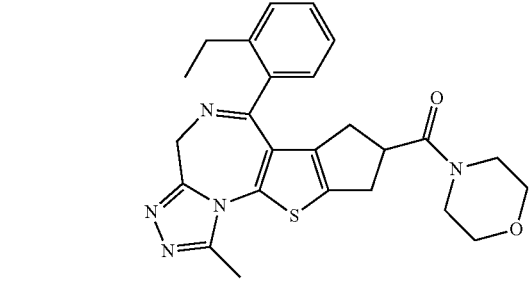

Step 1: methyl 2-amino-3-(2-ethylbenzoyl)-4H,5H,6H-cyclopenta[b]thiophene-5-carboxylate The title compound is prepared from 3-(2-ethylphenyl)-3-oxopropanenitrile and methyl 3-oxocyclopentane-1-carboxylate following a procedure analogous to that described in Step 1 of Intermediate 1.

LC (Method 2): $t_R$=1.05 min; Mass spectrum (ESI$^+$): m/z=330 [M+H]$^+$.

Step 2: methyl 3-(2-ethylbenzoyl)-2-(2-bromoacetamido)-4H,5H,6H-cyclopenta[b]thiophene-5-carboxylate The title compound is prepared from methyl 2-amino-3-(2-ethylbenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.17 min; Mass spectrum (ESI$^+$): m/z=450/452 (Br) [M+H]$^+$.

Step 3: methyl 2-(2-aminoacetamido)-3-(2-ethylbenzoyl)-4H,5H,6H-cyclopenta[b]thiophene-5-carboxylate The title compound is prepared from methyl 3-(2-ethylbenzoyl)-2-(2-bromoacetamido)-4H,5H,6H-cyclopenta[b]thiophene-5-carboxylate following a procedure analogous to that described in Step 3 of Intermediate 1.

LC (Method 2): $t_R$=0.82 min; Mass spectrum (ESI$^+$): m/z=387 [M+H]$^+$.

Step 4: methyl 13-(2-ethylphenyl)-10-oxo-7-thia-9,12-diazatricyclo[6.5.0.0²,⁶]trideca-1(8),2(6),12-triene-4-carboxylate The title compound is prepared from methyl 2-(2-amino-acetamido)-3-(2-ethylbenzoyl)-4H,5H,6H-cyclopenta[b]thiophene-5-carboxylate following a procedure analogous to that described in Step 4 of Intermediate 1.
LC (Method 2): $t_R$=0.75 min; Mass spectrum (ESI⁺): m/z=369 [M+H]⁺.

Step 5: methyl 9-(2-ethylphenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylate The title compound is prepared from methyl 13-(2-ethylphenyl)-10-oxo-7-thia-9,12-diazatricyclo[6.5.0.0²,⁶]-trideca-1(8),2(6),12-triene-4-carboxylate following a procedure analogous to that described in Step 5 of Intermediate 1.
LC (Method 2): $t_R$=0.84 min; Mass spectrum (ESI⁺): m/z=407 [M+H]⁺.

Step 6: 9-(2-ethylphenyl)-3-methyl-16-thia-2,4,5,8-tetraazatetracyclo[8.6.0.0²,⁶.0¹¹,¹⁵]hexadeca-1(10),3,5,8,11(15)-pentaene-13-carboxylic acid The title compound is prepared from methyl 9-(2-ethylphenyl)-3-methyl-16-thia-2,4,5,8-tetraazatetracyclo-[8.6.0.0²,⁶.0¹¹,¹⁵]hexadeca-1(10),3,5,8,11(15)-pentaene-13-carboxylate following a procedure analogous to that described for Intermediate 2. LC (Method 2): $t_R$=0.74 min; Mass spectrum (ESI⁺): m/z=393 [M+H]⁺.

Step 7: 9-(2-ethylphenyl)-3-methyl-13-(morpholine-4-carbonyl)-16-thia-2,4,5,8-tetraazatetracyclo[8.6.0.0²,⁶.0¹¹,¹⁵]-hexadeca-1(10),3,5,8,11(15)-pentaene The title compound is prepared from 9-(2-ethylphenyl)-3-methyl-16-thia-2,4,5,8-tetraazatetracyclo[8.6.0.0²,⁶.0¹¹,¹⁵]-hexadeca-1(10),3,5,8,11(15)-pentaene-13-carboxylic acid and morpholine following a procedure analogous to that described for Intermediate 5. LC (Method 2): $t_R$=0.75 min; Mass spectrum (ESI⁺): m/z=462 [M+H]⁺.

Intermediate 13

9-(2-Methoxyphenyl)-3-methyl-13-(morpholine-4-carbonyl)-16-thia-2,4,5,8-tetraazatetracyclo[8.6.0.0²,⁶.0¹¹,¹⁵]-hexadeca-1(10),3,5,8,11(15)-pentaene

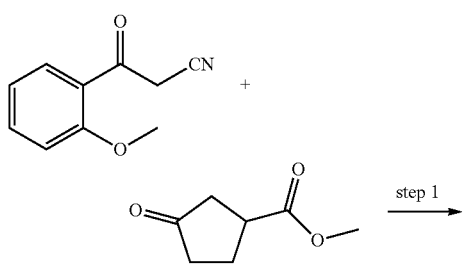

step 1

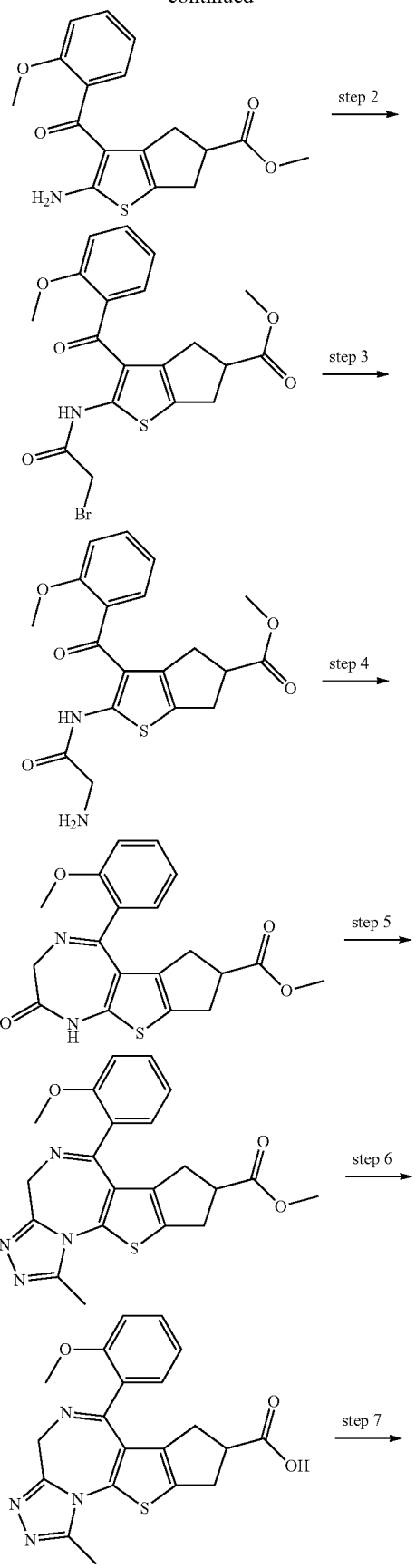

-continued

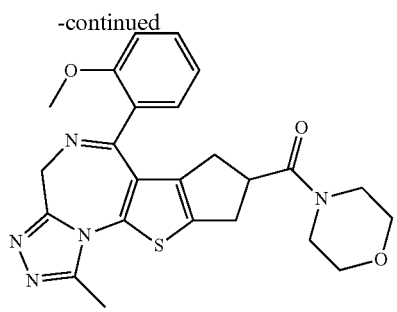

Step 1: methyl 2-amino-3-(2-methoxybenzoyl)-4H,5H,6H-cyclopenta[b]thiophene-5-carboxylate The title compound is prepared from 3-(2-methoxyphenyl)-3-oxopropanenitrile and methyl 3-oxocyclopentane-1-carboxylate following a procedure analogous to that described in Step 1 of Intermediate 1.

LC (Method 2): $t_R$=0.95 min; Mass spectrum (ESI$^+$): m/z=332 [M+H]$^+$.

Step 2: methyl 3-(2-methoxybenzoyl)-2-(2-bromoacetamido)-4H,5H,6H-cyclopenta[b]thiophene-5-carboxylate The title compound is prepared from methyl 2-amino-3-(2-methoxybenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.08 min; Mass spectrum (ESI$^+$): m/z=452/454 (Br) [M+H]$^+$.

Step 3: methyl 2-(2-aminoacetamido)-3-(2-methoxybenzoyl)-4H,5H,6H-cyclopenta[b]thiophene-5-carboxylate The title compound is prepared from methyl 3-(2-methoxybenzoyl)-2-(2-bromoacetamido)-4H,5H,6H-cyclopenta[b]thiophene-5-carboxylate following a procedure analogous to that described in Step 3 of Intermediate 1.

LC (Method 2): $t_R$=0.92 min; Mass spectrum (ESI$^+$): m/z=389 [M+H]$^+$.

Step 4: methyl 13-(2-methoxyphenyl)-10-oxo-7-thia-9,12-diazatricyclo[6.5.0.0$^{2,6}$]trideca-1(8),2(6),12-triene-4-carboxylate The title compound is prepared from methyl 2-(2-aminoacetamido)-3-(2-methoxybenzoyl)-4H,5H,6H-cyclopenta[b]thiophene-5-carboxylate following a procedure analogous to that described in Step 4 of Intermediate 1.

LC (Method 2): $t_R$=0.70 min; Mass spectrum (ESI$^+$): m/z=371 [M+H]$^+$.

Step 5: methyl 9-(2-methoxyphenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylate The title compound is prepared from methyl 13-(2-methoxyphenyl)-10-oxo-7-thia-9,12-diazatricyclo[6.5.0.0$^{2,6}$]-trideca-1(8),2(6),12-triene-4-carboxylate following a procedure analogous to that described in Step 5 of Intermediate 1.

LC (Method 2): $t_R$=0.73 min; Mass spectrum (ESI$^+$): m/z=409 [M+H]$^+$.

Step 6: 9-(2-methoxyphenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid The title compound is prepared from methyl 9-(2-methoxyphenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylate following a procedure analogous to that described for Intermediate 2. LC (Method 2): $t_R$=0.64 min; Mass spectrum (ESI$^+$): m/z=395 [M+H]$^+$.

Step 7: 9-(2-methoxyphenyl)-3-methyl-13-(morpholine-4-carbonyl)-16-thia-2,4,5,8-tetraazatetracyclo-[8.6.0.0$^{2,6}$.0$^{11,15}$]-hexadeca-1(10),3,5,8,11(15)-pentaene The title compound is prepared from 9-(2-methoxyphenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylic acid and morpholine following a procedure analogous to that described for Intermediate 5.

LC (Method 2): $t_R$=0.66 min (diastereomers); Mass spectrum (ESI$^+$): m/z=464 [M+H]$^+$.

Intermediate 14

9-(2-Fluorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

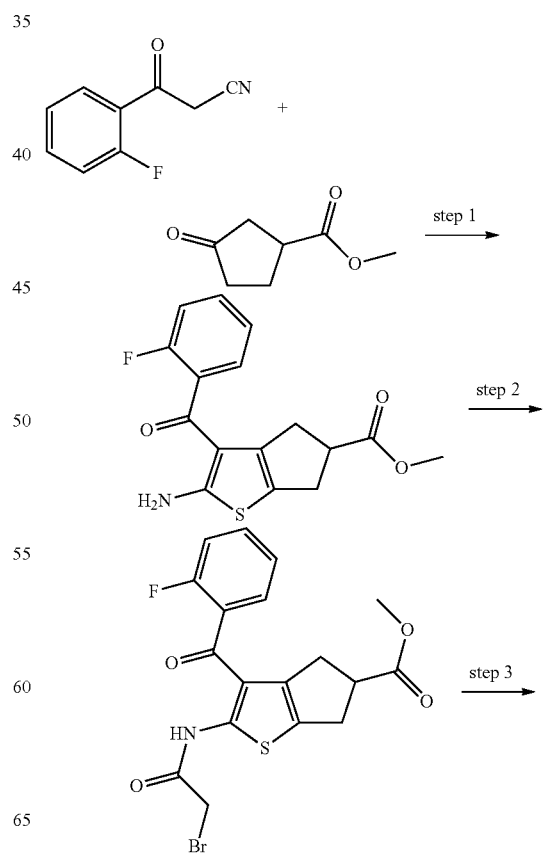

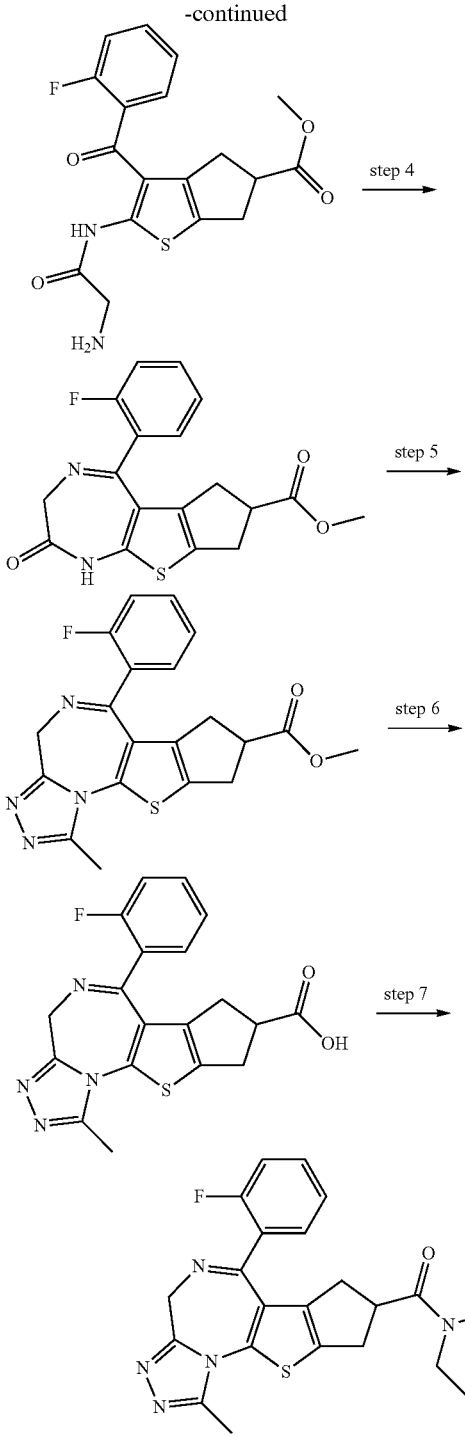

Step 1: methyl 2-amino-3-(2-fluorobenzoyl)-4H,5H, 6H-cyclopenta[b]thiophene-5-carboxylate The title compound is prepared from 3-(2-fluorophenyl)-3-oxopropanenitrile and methyl 3-oxocyclopentane-1-carboxylate following a procedure analogous to that described in Step 1 of Intermediate 1.

LC (Method 2): $t_R$=0.98 min; Mass spectrum (ESI$^+$): m/z=320 [M+H]$^+$.

Step 2: methyl 3-(2-fluorobenzoyl)-2-(2-bromoacetamido)-4H,5H,6H-cyclopenta[b]thiophene-5-carboxylate The title compound is prepared from methyl 2-amino-3-(2-fluorobenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.11 min; Mass spectrum (ESI$^+$): m/z=440/442 (Br) [M+H]$^+$.

Step 3: methyl 2-(2-aminoacetamido)-3-(2-fluorobenzoyl)-4H,5H,6H-cyclopenta[b]thiophene-5-carboxylate The title compound is prepared from methyl 3-(2-fluorobenzoyl)-2-(2-bromoacetamido)-4H,5H,6H-cyclopenta[b]thiophene-5-carboxylate following a procedure analogous to that described in Step 3 of Intermediate 1.

LC (Method 2): $t_R$=0.76 min; Mass spectrum (ESI$^+$): m/z=377 [M+H]$^+$.

Step 4: methyl 13-(2-fluorophenyl)-10-oxo-7-thia-9, 12-diazatricyclo[6.5.0.0$^{2,6}$]trideca-1(8),2(6),12-triene-4-carboxylate The title compound is prepared from methyl 2-(2-aminoacetamido)-3-(2-fluorobenzoyl)-4H,5H,6H-cyclopenta[b] thiophene-5-carboxylate following a procedure analogous to that described in Step 4 of Intermediate 1.

LC (Method 2): $t_R$=0.70 min; Mass spectrum (ESI$^+$): m/z=359 [M+H]$^+$.

Step 5: methyl 9-(2-fluorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylate The title compound is prepared from methyl 13-(2-fluorophenyl)-10-oxo-7-thia-9,12-diazatricyclo[6.5.0.0$^{2,6}$]-trideca-1(8),2(6),12-triene-4-carboxylate following a procedure analogous to that described in Step 5 of Intermediate 1.

LC (Method 2): $t_R$=0.82 min; Mass spectrum (ESI$^+$): m/z=397 [M+H]$^+$.

Step 6: 9-(2-fluorophenyl)-3-methyl-16-thia-2,4,5,8-tetraazatetracyclo[8.6.0.0$^{2,6}$.0$^{11,15}$]hexadeca-1(10),3, 5,8,11(15)-pentaene-13-carboxylic acid The title compound is prepared from methyl 9-(2-fluorophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylate following a procedure analogous to that described for Intermediate 2. LC (Method 2): $t_R$=0.71 min; Mass spectrum (ESI$^+$): m/z=383 [M+H]$^+$.

Step 7: 9-(2-fluorophenyl)-3-methyl-13-(morpholine-4-carbonyl)-16-thia-2,4,5,8-tetraazatetracyclo [8.6.0.0$^{2,6}$.0$^{11,15}$]-hexadeca-1(10),3,5,8,11(15)-pentaene The title compound is prepared from 9-(2-fluorophenyl)-3-methyl-16-thia-2,4,5,8-tetraazatetracyclo-[8.6.0.0$^{2,6}$. 0$^{11,15}$]hexadeca-1(10),3,5,8,11(15)-pentaene-13-carboxylic acid and morpholine following a procedure analogous to that described for Intermediate 5. LC (Method 2): $t_R$=0.73 min; Mass spectrum (ESI$^+$): m/z=452 [M+H]$^+$.

Intermediate 15

3-Methyl-13-(morpholine-4-carbonyl)-9-[2-(trifluoromethyl)phenyl]-16-thia-2,4,5,8-tetraazatetracyclo-[8.6.0.0$^{2,6}$.0$^{11,15}$]hexadeca-1(10),3,5,8,11(15)-pentaene

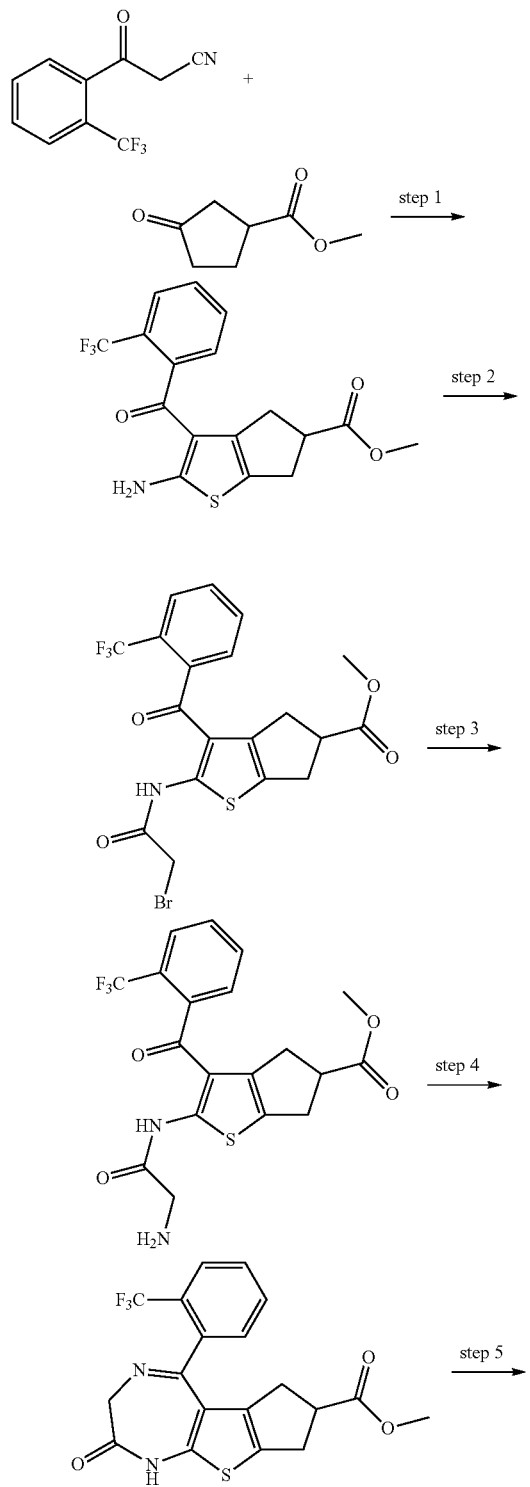

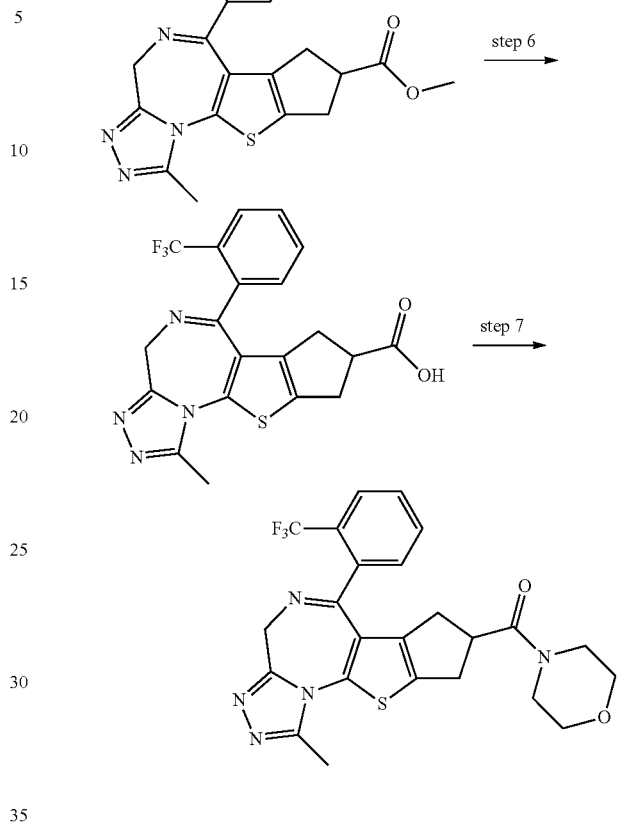

Step 1: methyl 2-amino-3-[2-(trifluoromethyl)benzoyl]-4H,5H,6H-cyclopenta[b]thiophene-5-carboxylate The title compound is prepared from 2-(trifluoromethyl) benzoyl cyanide and methyl 3-oxocyclopentane-1-carboxylate following a procedure analogous to that described in Step 1 of Intermediate 1. Mass spectrum (ESI$^+$): m/z=370 [M+H]$^+$.

Step 2: methyl 2-(2-bromoacetamido)-3-[2-(trifluoromethyl)benzoyl]-4H,5H,6H-cyclopenta[b]thiophene-5-carboxylate The title compound is prepared from methyl 2-amino-3-[2-(trifluoromethyl)benzoyl]-4H,5H,6H-cyclopenta[b]thiophene-5-carboxylate and bromo-acetyl bromide following a procedure analogous to that described in Step 2 of Intermediate 1. LC (Method 2): t$_R$=1.14 min; Mass spectrum (ESI$^+$): m/z=490/492 (Br) [M+H]$^+$.

Step 3: methyl 2-(2-aminoacetamido)-3-[2-(trifluoromethyl)benzoyl]-4H,5H,6H-cyclopenta[b]thiophene-5-carboxylate The title compound is prepared from methyl 2-(2-bromoacetamido)-3-[2-(trifluoromethyl)benzoyl]-4H,5H,6H-cyclopenta[b]thiophene-5-carboxylate following a procedure analogous to that described in Step 3 of Intermediate 1. LC (Method 2): t$_R$=0.80 min; Mass spectrum (ESI$^+$): m/z=427 [M+H]$^+$.

Step 4: methyl 10-oxo-13-[2-(trifluoromethyl)phenyl]-7-thia-9,12-diazatricyclo[6.5.0.0²,⁶]trideca-1(8),2(6),12-triene-4-carboxylate The title compound is prepared from methyl 2-(2-amino-acetamido)-3-[2-(trifluoromethyl)benzoyl]-4H,5H,6H-cyclopenta[b]thiophene-5-carboxylate following a procedure analogous to that described in Step 4 of Intermediate 1. LC (Method 2): $t_R$=0.78 min; Mass spectrum (ESI⁺): m/z=409 [M+H]⁺.

Step 5: methyl 3-methyl-9-[2-(trifluoromethyl)phenyl]-16-thia-2,4,5,8-tetraazatetracyclo[8.6.0.0²,⁶.0¹¹,¹⁵]hexadeca-1(10),3,5,8,11(15)-pentaene-13-carboxylate The title compound is prepared from methyl 10-oxo-13-[2-(trifluoromethyl)phenyl]-7-thia-9,12-diazatricyclo[6.5.0.0²,⁶]trideca-1(8),2(6),12-triene-4-carboxylate following a procedure analogous to that described in Step 5 of Intermediate 1. LC (Method 2): $t_R$=0.91 min; Mass spectrum (ESI⁺): m/z=447 [M+H]⁺.

Step 6: 3-methyl-9-[2-(trifluoromethyl)phenyl]-16-thia-2,4,5,8-tetraazatetracyclo[8.6.0.0²,⁶.0¹¹,¹⁵]hexadeca-1(10),3,5,8,11(15)-pentaene-13-carboxylic acid The title compound is prepared from methyl 3-methyl-9-[2-(trifluoromethyl)phenyl]-16-thia-2,4,5,8-tetraazatetracyclo-[8.6.0.0²,⁶.0¹¹,¹⁵]hexadeca-1(10),3,5,8,11(15)-pentaene-13-carboxylate following a procedure analogous to that described for Intermediate 2. LC (Method 2): $t_R$=0.80 min; Mass spectrum (ESI⁺): m/z=433 [M+H]⁺.

Step 7: 3-methyl-13-(morpholine-4-carbonyl)-9-[2-(trifluoromethyl)phenyl]-16-thia-2,4,5,8-tetraazatetracyclo-[8.6.0.0²,⁶.0¹¹,¹⁵]hexadeca-1(10),3,5,8,11(15)-pentaene The title compound is prepared from 3-methyl-9-[2-(trifluoromethyl)phenyl]-16-thia-2,4,5,8-tetraazatetracyclo-[8.6.0.0²,⁶.0¹¹,¹⁵]hexadeca-1(10),3,5,8,11(15)-pentaene-13-carboxylic acid and morpholine following a procedure analogous to that described for Intermediate 5. LC (Method 2): $t_R$=0.82 min; Mass spectrum (ESI⁺): m/z=502 [M+H]⁺.

Intermediate 16

9-(2-Bromophenyl)-3-methyl-13-(morpholine-4-carbonyl)-16-thia-2,4,5,8-tetraazatetracyclo[8.6.0.0²,⁶.0¹¹,¹⁵]-hexadeca-1(10),3,5,8,11(15)-pentaene

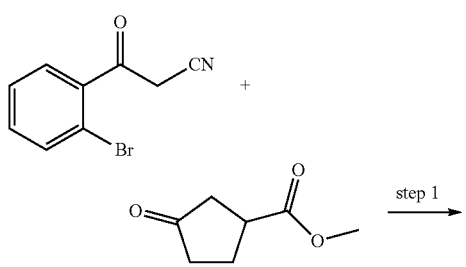

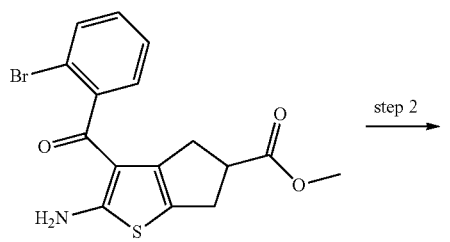

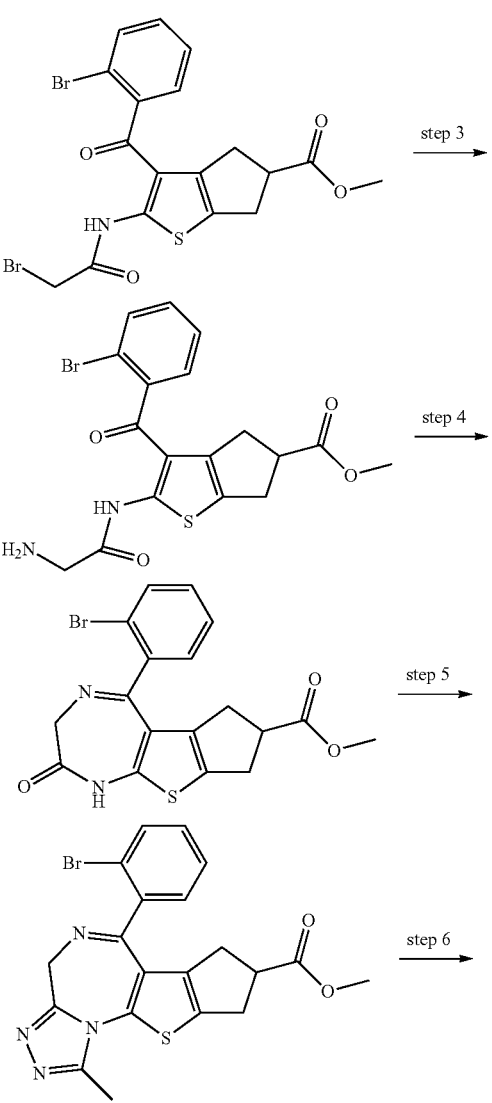

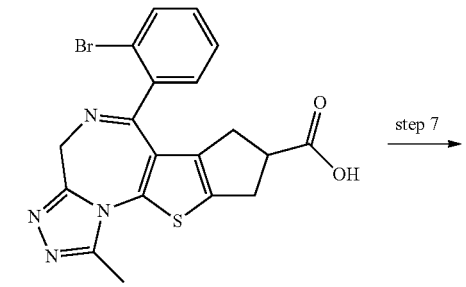

-continued

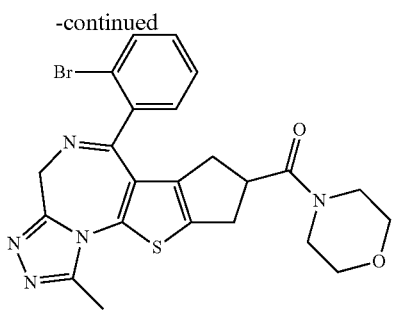

Step 1: methyl 2-amino-3-(2-bromobenzoyl)-4H,5H,6H-cyclopenta[b]thiophene-5-carboxylate The title compound is prepared from 3-(2-bromophenyl)-3-oxopropanenitrile and methyl 3-oxocyclopentane-1-carboxylate following a procedure analogous to that described in Step 1 of Intermediate 1.

LC (Method 2): $t_R$=0.99 min; Mass spectrum (ESI$^+$): m/z=380/382 (Br) [M+H]$^+$.

Step 2: methyl 3-(2-bromobenzoyl)-2-(2-bromoacetamido)-4H,5H,6H-cyclopenta[b]thiophene-5-carboxylate The title compound is prepared from methyl 2-amino-3-(2-bromobenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.14 min; Mass spectrum (ESI$^+$): m/z=500/502/504 (2Br) [M+H]$^+$.

Step 3: methyl 2-(2-aminoacetamido)-3-(2-bromobenzoyl)-4H,5H,6H-cyclopenta[b]thiophene-5-carboxylate The title compound is prepared from methyl 3-(2-bromobenzoyl)-2-(2-bromoacetamido)-4H,5H,6H-cyclopenta[b]thiophene-5-carboxylate following a procedure analogous to that described in Step 3 of Intermediate 1.

LC (Method 2): $t_R$=0.79 min; Mass spectrum (ESI$^+$): m/z=437/439 (Br) [M+H]$^+$.

Step 4: methyl 13-(2-bromophenyl)-10-oxo-7-thia-9,12-diazatricyclo[6.5.0.0$^{2,6}$]trideca-1(8),2(6),12-triene-4-carboxylate The title compound is prepared from methyl 2-(2-aminoacetamido)-3-(2-bromobenzoyl)-4H,5H,6H-cyclopenta[b]thiophene-5-carboxylate following a procedure analogous to that described in Step 4 of Intermediate 1.

LC (Method 2): $t_R$=0.74 min; Mass spectrum (ESI$^+$): m/z=419/421 (Br) [M+H]$^+$.

Step 5: methyl 9-(2-bromophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylate The title compound is prepared from methyl 13-(2-bromophenyl)-10-oxo-7-thia-9,12-diazatricyclo[6.5.0.0$^{2,6}$]-trideca-1(8),2(6),12-triene-4-carboxylate following a procedure analogous to that described in Step 5 of Intermediate 1.

LC (Method 2): $t_R$=0.88 min; Mass spectrum (ESI$^+$): m/z=457/459 (Br) [M+H]$^+$.

Step 6: 9-(2-bromophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid The title compound is prepared from methyl 9-(2-bromophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylate following a procedure analogous to that described for Intermediate 2. LC (Method 2): $t_R$=0.78 min; Mass spectrum (ESI$^+$): m/z=443/445 (Br) [M+H]$^+$.

Step 7: 9-(2-bromophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene The title compound is prepared from 9-(2-bromophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylic acid and morpholine following a procedure analogous to that described for Intermediate 5.

LC (Method 2): $t_R$=0.79 min; Mass spectrum (ESI$^+$): m/z=512/514 (Br) [M+H]$^+$.

Intermediate 17

9-(3,5-Difluorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene

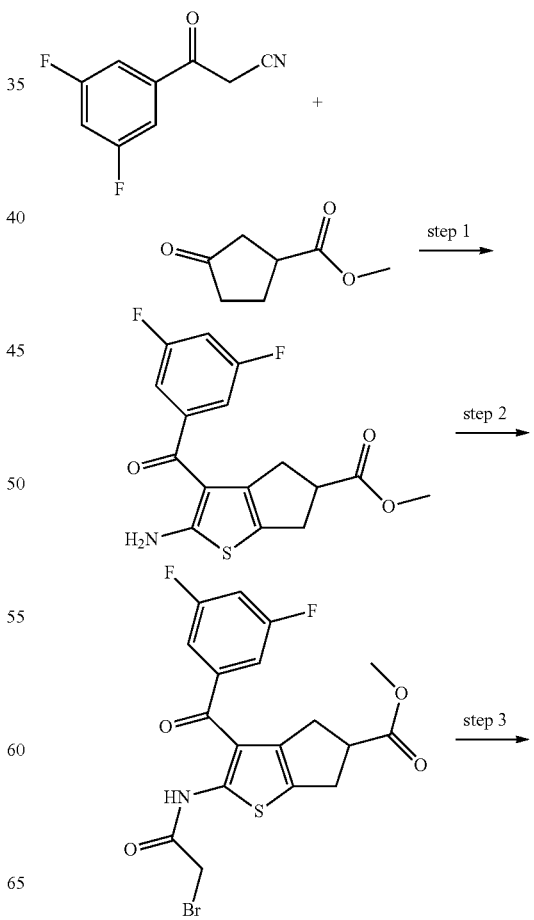

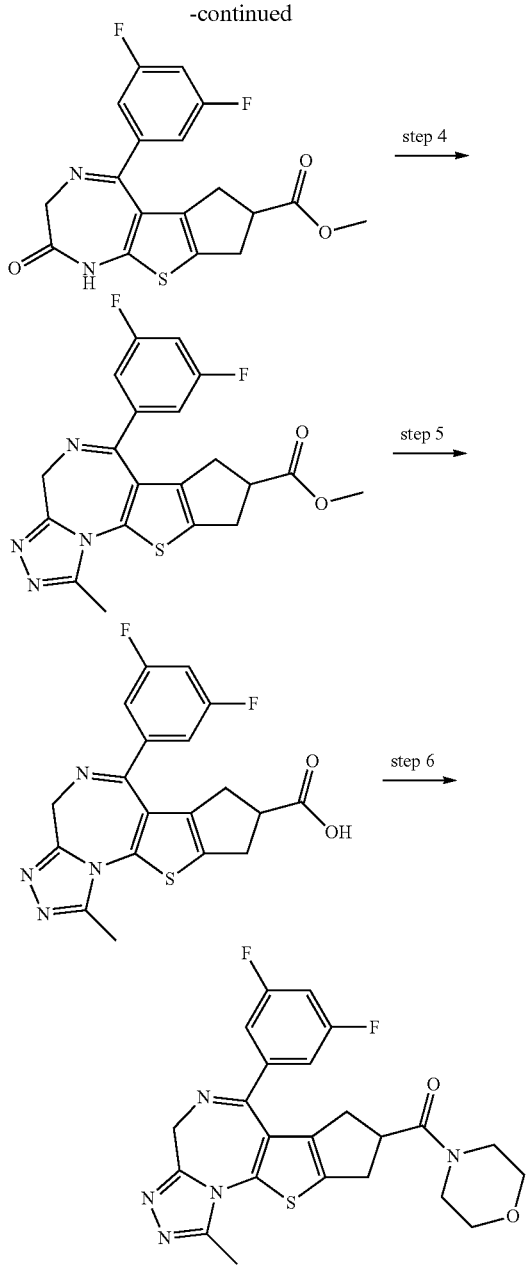

Step 1: methyl 2-amino-3-(3,5-difluorobenzoyl)-4H, 5H,6H-cyclopenta[b]thiophene-5-carboxylate The title compound is prepared from 3-(3,5-difluorophenyl)-3-oxopropanenitrile and methyl 3-oxocyclopentane-1-carboxylate following a procedure analogous to that described in Step 1 of Intermediate 1.

LC (Method 2): $t_R$=1.04 min; Mass spectrum (ESI$^+$): m/z=338 [M+H]$^+$.

Step 2: methyl 2-(2-bromoacetamido)-3-(3,5-difluorobenzoyl)-4H,5H,6H-cyclopenta[b]thiophene-5-carboxylate The title compound is prepared from methyl 2-amino-3-(3,5-difluorobenzoyl)-4H,5H,6H-cyclopenta[b]thiophene-5-carboxylate and bromo-acetyl bromide following a procedure analogous to that described in Step 2 of Intermediate 1.

LC (Method 2): $t_R$=1.14 min; Mass spectrum (ESI$^+$): m/z=460 [M+H]$^+$.

Step 3: methyl 13-(3,5-difluorophenyl)-10-oxo-7-thia-9,12-diazatricyclo[6.5.0.0$^{2,6}$]trideca-1(8),2(6), 12-triene-4-carboxylate The title compound is prepared directly from methyl 2-(2-bromoacetamido)-3-(3,5-difluorobenzoyl)-4H,5H,6H-cyclopenta[b]thiophene-5-carboxylate following a procedure analogous to that described in Step 3 of Intermediate 1.

LC (Method 2): $t_R$=0.77 min; Mass spectrum (ESI$^+$): m/z=377 [M+H]$^+$.

Step 4: methyl 9-(3,5-difluorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylate The title compound is prepared from methyl 13-(3,5-difluorophenyl)-10-oxo-7-thia-9,12-diazatricyclo-[6.5.0.0$^{2,6}$]trideca-1(8),2(6),12-triene-4-carboxylate following a procedure analogous to that described in Step 5 of Intermediate 1. LC (Method 2): $t_R$=0.91 min; Mass spectrum (ESI$^+$): m/z=415 [M+H]$^+$.

Step 5: 9-(3,5-difluorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid The title compound is prepared from methyl 9-(3,5-difluorophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylate following a procedure analogous to that described for Intermediate 2. LC (Method 2): $t_R$=0.79 min; Mass spectrum (ESI$^+$): m/z=401 [M+H]$^+$.

Step 6: 9-(3,5-difluorophenyl)-3-methyl-13-(morpholine-4-carbonyl)-16-thia-2,4,5,8-tetraazatetracyclo-[8.6.0.0$^{2,6}$.0$^{11,15}$]hexadeca-1(10),3,5,8,11(15)-pentaene The title compound is prepared from 9-(3,5-difluorophenyl)-3-methyl-16-thia-2,4,5,8-tetraazatetracyclo-[8.6.0.0$^{2,6}$.0$^{11,15}$]hexadeca-1(10),3,5,8,11(15)-pentaene-13-carboxylic acid and morpholine following a procedure analogous to that described for Intermediate 5. LC (Method 2): $t_R$=0.81 min; Mass spectrum (ESI$^+$): m/z=470 [M+H]$^+$.

Intermediate 18

3-Methyl-9-(methylsulfanyl)-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene

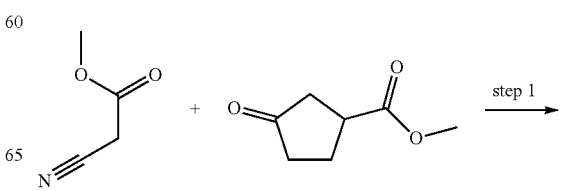

117
-continued

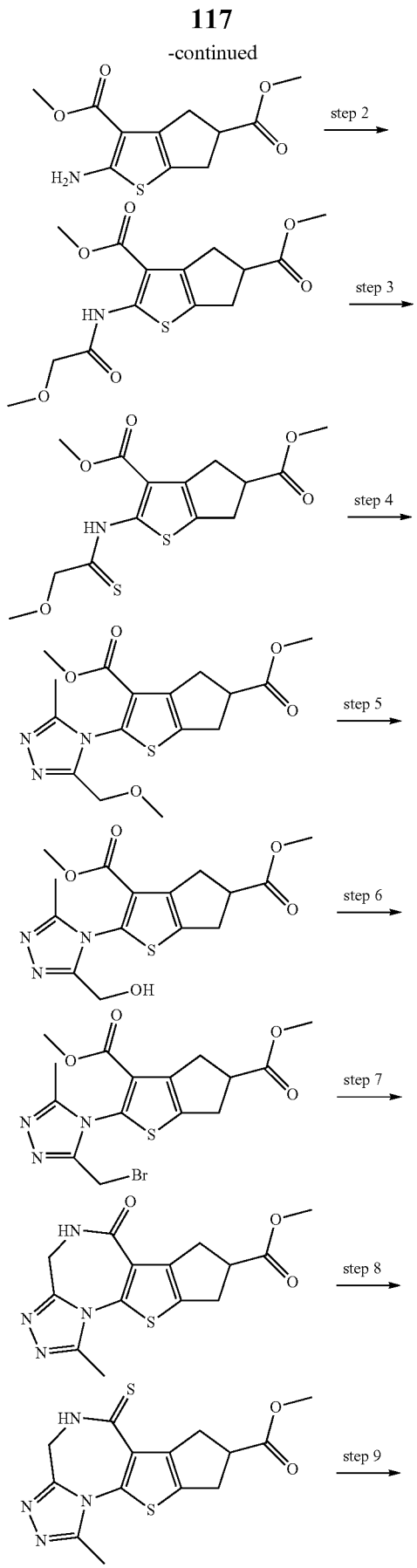

118
-continued

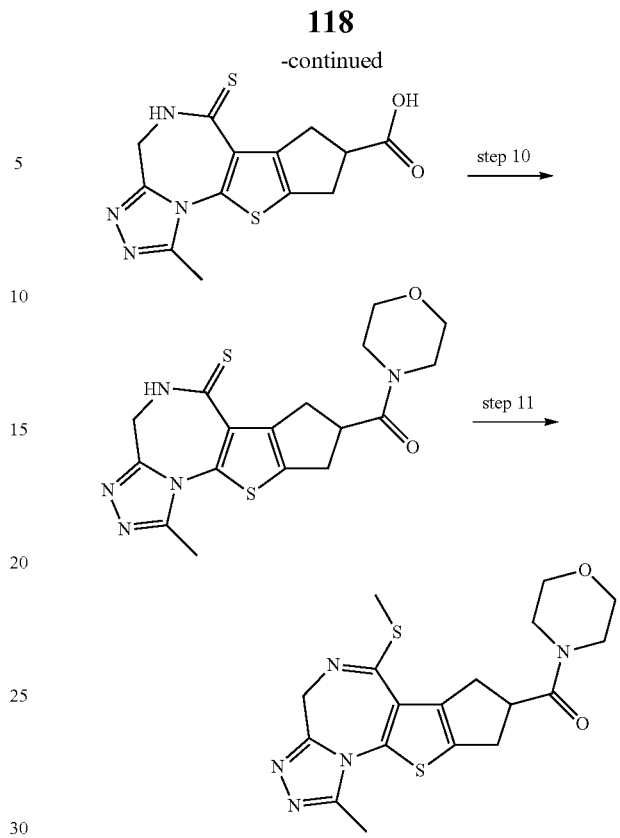

Step 1: 3,5-dimethyl 2-amino-4H,5H,6H-cyclopenta[b]thiophene-3,5-dicarboxylate The title compound is prepared from methyl cyanoacetate and methyl 3-oxocyclopentane-1-carboxylate following a procedure analogous to that described in Step 1 of Intermediate 1.

LC (Method 2): $t_R$=1.93 min; Mass spectrum (ESI$^+$): m/z=256 [M+H]$^+$.

Step 2: 3,5-dimethyl 2-(2-methoxyacetamido)-4H,5H,6H-cyclopenta[b]thiophene-3,5-dicarboxylate 3,5-dimethyl 2-amino-4H,5H,6H-cyclopenta[b]thiophene-3,5-dicarboxylate (26.8 g) and pyridine (12.7 mL) are dissolved in DCM (200 mL). Methoxyacetyl chloride (9.56 mL) is added and the reaction mixture is stirred at room temperature for 1 h. The reaction is quenched by the addition of water, then the organic phase is separated, dried (Na$_2$SO$_4$) and concentrated to dryness to afford the title compound.

LC (Method 2): $t_R$=1.01 min; Mass spectrum (ESI$^+$): m/z=328 [M+H]$^+$.

Step 3: 3,5-dimethyl 2-(2-methoxyethanethioamido)-4H,5H,6H-cyclopenta[b]thiophene-3,5-dicarboxylate 3,5-dimethyl 2-(2-methoxyacetamido)-4H,5H,6H-cyclopenta[b]thiophene-3,5-dicarboxylate (36.0 g) is dissolved in 1,4-dioxane (150 mL) and Lawesson's reagent (48.9 g) is added. The reaction is stirred at 80° C. for 6 h. The reaction mixture is filtered and the filtrate is concentrated to dryness.

The residue is triturated with methanol to give the title compound. LC (Method 2): $t_R$=1.16 min; Mass spectrum (ESI⁺): m/z=344 [M+H]⁺.

Step 4: 3,5-dimethyl 2-[3-(methoxymethyl)-5-methyl-4H-1,2,4-triazol-4-yl]-4H,5H,6H-cyclopenta[b]thiophene-3,5-dicarboxylate 3,5-Dimethyl 2-(2-methoxyethanethioamido)-4H,5H,6H-cyclopenta[b]thiophene-3,5-dicarboxylate (3.00 g) is dissolved in THF (45 mL) and hydrazine hydrate (0.849 mL) is added. The reaction mixture is stirred at room temperature for 0.75 h. N,N-Dimethylacetamide dimethyl acetal (5.1 mL) is added and the reaction is stirred at room temperature for an additional 1.5 h. Acetic acid (15.3 mL) is added and the reaction mixture is stirred at 100° C. for 3.5 days. The reaction mixture is diluted water and EtOAc, basified with NaHCO₃ and extracted with EtOAc (3×). The combined organic extracts are dried (MgSO₄) and concentrated to dryness. The residue is chromatographed on silica gel (pet. ether/EtOAc/methanol 80:16:4->20:64:16) to give the title compound.

LC (Method 1): $t_R$=0.82 min; Mass spectrum (ESI⁺): m/z=366 [M+H]⁺.

Step 5: 3,5-dimethyl 2-[3-(hydroxymethyl)-5-methyl-4H-1,2,4-triazol-4-yl]-4H,5H,6H-cyclopenta[b]thiophene-3,5-dicarboxylate 3,5-Dimethyl 2-[3-(methoxymethyl)-5-methyl-4H-1,2,4-triazol-4-yl]-4H,5H,6H-cyclopenta[b]thiophene-3,5-dicarboxylate (2.79 g) is dissolved in DCM (40 mL) followed by the addition of boron tribromide (1 M in DCM, 15.3 mL). The reaction mixture is stirred at room temperature for 1.75 h. The reaction mixture is diluted with DCM and sat. aqueous NaHCO₃ and stirred for 15 min, followed by extraction with DCM (2×). The combined organic extracts are dried (MgSO₄) and concentrated to afford the title compound.

LC (Method 2): $t_R$=0.75 min; Mass spectrum (ESI⁺): m/z=352 [M+H]⁺.

Step 6: 3,5-dimethyl 2-[3-(bromomethyl)-5-methyl-4H-1,2,4-triazol-4-yl]-4H,5H,6H-cyclopenta[b]thiophene-3,5-dicarboxylate 3,5-Dimethyl 2-[3-(hydroxymethyl)-5-methyl-4H-1,2,4-triazol-4-yl]-4H,5H,6H-cyclopenta[b]thiophene-3,5-dicarboxylate (2.47 g) is dissolved in DCM (30 mL) followed by the addition of Et₃N (2.2 mL) and methanesulfonyl bromide (1.3 mL). The reaction mixture is stirred at room temperature for 3 h. The reaction mixture is diluted with sat. aqueous NaHCO₃ and extracted with DCM (2×). The combined organic extracts are dried (MgSO₄) and concentrated to afford the title compound, which is used immediately in the next step.

LC (Method 2): $t_R$=0.88 min; Mass spectrum (ESI⁺): m/z=414/416 (Br) [M+H]⁺.

Step 7: methyl 3-methyl-9-oxo-16-thia-2,4,5,8-tetraazatetracyclo[8.6.0.0²,⁶.0¹¹,¹⁵]hexadeca-1(10),3,5,11(15)-tetraene-13-carboxylate 3,5-Dimethyl 2-[3-(bromomethyl)-5-methyl-4H-1,2,4-triazol-4-yl]-4H,5H,6H-cyclopenta[b]thiophene-3,5-dicarboxylate (3.20 g) is dissolved in a solution of ammonia in methanol (7 M, 30 mL). The reaction mixture is stirred at room temperature for 3.75 h, after which it is concentrated to dryness. The resulting crude intermediate is dissolved in methanol (40 mL) and Et₃N (1.0 mL) is added. The reaction mixture is stirred at 80° C. for 7 h, after which it is concentrated to dryness. The residue is chromatographed on silica gel (pet. ether/EtOAc/methanol 95:4:1→0:80:20) to give the title compound. LC (Method 2): $t_R$=0.71 min; Mass spectrum (ESI⁺): m/z=319 [M+H]⁺.

Step 8: methyl 3-methyl-9-sulfanylidene-16-thia-2,4,5,8-tetraazatetracyclo[8.6.0.0²,⁶.0¹¹,¹⁵]hexadeca-1(10),3,5,11(15)-tetraene-13-carboxylate Methyl 3-methyl-9-oxo-16-thia-2,4,5,8-tetraazatetracyclo[8.6.0.0²,⁶.0¹¹,¹⁵]hexadeca-1(10),3,5,11(15)-tetraene-13-carboxylate (1.00 g) and Lawesson's reagent (3.00 g) are dissolved in 1,4-dioxane (20 mL). The reaction mixture is stirred at 65° C. for 16 h. An additional batch Lawesson's reagent (1.00 g) is added and stirring is continued at 65° C. for 10 h. The reaction mixture is diluted with aqueous NaHCO₃ and extracted with DCM (2×). The combined organic extracts are washed with brine, dried (MgSO₄) and concentrated to afford the title compound, which is used immediately in the next reaction. LC (Method 2): $t_R$=0.79 min; Mass spectrum (ESI⁺): m/z=335 [M+H]⁺.

Step 9: 3-methyl-9-sulfanylidene-16-thia-2,4,5,8-tetraazatetracyclo[8.6.0.0²,⁶.0¹¹,¹⁵]hexadeca-1(10),3,5,11(15)-tetraene-13-carboxylic acid Methyl 3-methyl-9-sulfanylidene-16-thia-2,4,5,8-tetraazatetracyclo[8.6.0.0²,⁶.0¹¹,¹⁵]hexadeca-1(10),3,5,11(15)-tetraene-13-carboxylate (1.70 g) is suspended in methanol (20 mL) and aqueous NaOH (4 M, 5.00 mL) is added. The reaction mixture is stirred at room temperature for 1 h, after which it is concentrated to near dryness. The reaction mixture is acidified with TFA and the resulting precipitate is collected by filtration to give the title compound.

LC (Method 2): $t_R$=0.68 min; Mass spectrum (ESI+): m/z=321 [M+H]⁺.

Step 10: 3-methyl-13-(morpholine-4-carbonyl)-16-thia-2,4,5,8-tetraazatetracyclo[8.6.0.0²,⁶.0¹¹,¹⁵]hexadeca-1(10),3,5,11(15)-tetraene-9-thione 3-Methyl-9-sulfanylidene-16-thia-2,4,5,8-tetraazatetracyclo[8.6.0.0²,⁶.0¹¹,¹⁵]hexadeca-1(10),3,5,11(15)-tetraene-13-carboxylic acid (1.65 g) and 1,1'-carbonyldiimidazole (0.92 g) are dissolved in DMF (30 mL). The solution is stirred at 50° C. for 1 h. Morpholine (0.68 mL) is added and the solution is stirred at room temperature for 1 h. The reaction mixture is diluted with water/brine (1:1) and extracted with EtOAc (3×) The combined organic extracts are washed with brine, dried (MgSO₄) and concentrated to dryness. The residue is purified by reversed phase chromatography (HPLC; ACN/water/TFA) to obtain the title compound. LC (Method 2): $t_R$=0.71 min; Mass spectrum (ESI⁺): m/z=390 [M+H]⁺.

Step 11: 3-methyl-9-(methylsulfanyl)-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene 3-Methyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene-9-thione (0.60 g) and potassium tert-butoxide (0.175 g) are dissolved in acetone (10 mL), followed by the addition of methyl iodide (0.77 mL). The solution is stirred at room temperature for 1 h. The reaction mixture is diluted with water and extracted with DCM (2×). The combined organic extracts are washed with brine, dried (MgSO$_4$) and concentrated to dryness to afford the title compound.

LC (Method 2): t$_R$=0.70 min; Mass spectrum (ESI$^+$): m/z=404 [M+H]$^+$.

Intermediate 19

9-(2-Cyclopropylphenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

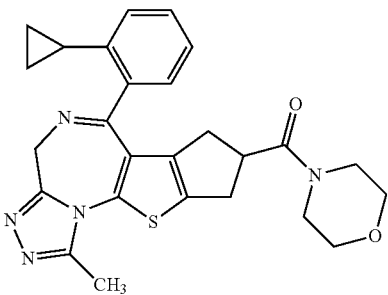 [SMILES: Cc1nnc2n1-c1sc3c(c1C(c1ccccc1C1CC1)=NC2)CC(C(=O)N1CCOCC1)C3]

3-Methyl-9-(methylsulfanyl)-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene (100 mg) and copper(I) 3-methylsalicylate (160 mg) are suspended in NMP (2.00 mL) under an argon atmosphere. (2-Cyclopropylphenyl)boronic acid (100 mg) and tetrakis(triphenylphosphine)palladium(0) (30 mg) are added and the reaction mixture is stirred at 50° C. for 1 h. If the conversion is incomplete, an additional amount of (2-Cyclopropylphenyl)boronic acid (50 mg) and tetrakis(triphenylphosphine)palladium(0) (30 mg) are added, and stirring is continued at 50° C. for 2 h. Upon completion, the reaction mixture is diluted with aqueous NaHCO$_3$ (1 M) and extracted with EtOAc (3×). The combined organic extracts are dried (MgSO$_4$) and concentrated. The crude product is purified by reversed phase chromatography (HPLC; ACN/water/NH$_3$) to obtain the title compound. LC (Method 2): t$_R$=0.75 min; Mass spectrum (ESI$^+$): m/z=474 [M+H]$^+$.

Intermediate 20

{2-[3-Methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaen-9-yl]phenyl}methanol

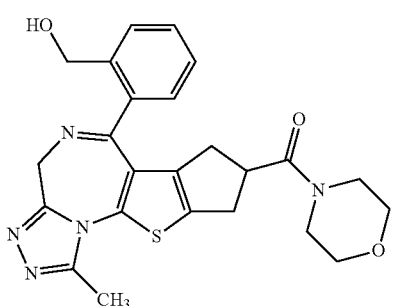

The title compound is prepared from 3-methyl-9-(methylsulfanyl)-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene and 2-(hydroxymethyl)phenylboronic acid following a procedure analogous to that described for Intermediate 19.

LC (Method 2): t$_R$=0.66 min; Mass spectrum (ESI$^+$): m/z=464 [M+H]$^+$.

Intermediate 21

2-[3-Methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaen-9-yl]phenol

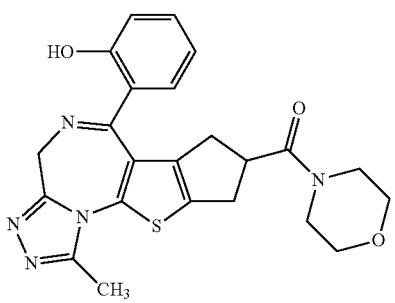 [SMILES: Cc1nnc2n1-c1sc3c(c1C(c1ccccc1O)=NC2)CC(C(=O)N1CCOCC1)C3]

The title compound is prepared from 3-methyl-9-(methylsulfanyl)-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene and (2-hydroxyphenyl)boronic acid following a procedure analogous to that described for Intermediate 19.

LC (Method 2): $t_R$=0.73 min; Mass spectrum (ESI$^+$): m/z=450 [M+H]$^+$.

Intermediate 22

9-(2-Chloro-5-methoxyphenyl)-3-methyl-13-(morpholine-4-carbonyl)-16-thia-2,4,5,8-tetraazatetracyclo-[8.6.0.0$^{2,6}$.0$^{11,15}$]hexadeca-1(10),3,5,8,11(15)-pentaene

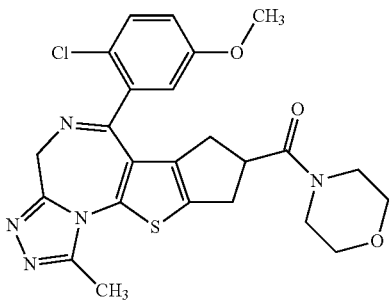 [SMILES: COc1ccc(Cl)c(C2=NCc3nnc(C)n3-c3sc4c(c32)CC(C(=O)N2CCOCC2)C4)c1]

The title compound is prepared from 3-methyl-9-(methylsulfanyl)-13-(morpholine-4-carbonyl)-16-thia-2,4,5,8-tetraazatetracyclo[8.6.0.0$^{2,6}$.0$^{11,15}$] hexadeca-1(10),3,5,8,11(15)-pentaene and (2-chloro-5-methoxyphenyl)boronic acid following a procedure analogous to that described for Intermediate 19.

LC (Method 2): $t_R$=0.84 min; Mass spectrum (ESI$^+$): m/z=498 [M+H]$^+$.

Intermediate 23

9-(2-Methylphenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

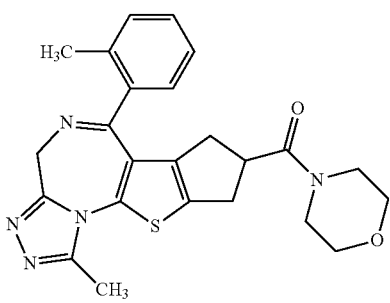 [SMILES: Cc1ccccc1C1=NCc2nnc(C)n2-c2sc3c(c21)CC(C(=O)N1CCOCC1)C3]

A vial charged with a stir bar, 9-(2-chlorophenyl)-3-methyl-13-(morpholine-4-carbonyl)-16-thia-2,4,5,8-tetraazatetracyclo[8.6.0.0$^{2,6}$.0$^{11,15}$]hexa-deca-1(10),3,5,8,11(15)-pentaene (50 mg), methylboronic acid (13 mg), K$_3$PO$_4$ (71 mg), Pd(OAc)$_2$ (1.2 mg), and dicyclohexyl(2',6'-dimethoxybiphenyl-2-yl)phosphine (4.4 mg) is purged with Ar for 5 min. Water (25 µL) and toluene (0.25 mL) are added, the vial is sealed, and the mixture is stirred in a microwave oven at 140° C. for 30 min. Another portion of methylboronic acid (13 mg), Pd(OAc)$_2$ (1.2 mg), and dicyclohexyl (2',6'-dimethoxybiphenyl-2-yl)phosphine (4.4 mg) are added at room temperature and the mixture is stirred in the microwave oven at 140° C. for 30 min. After cooling to room temperature, MeOH is added, the resulting mixture is filtered, and the filtrate is chromatographed on reversed phase (HPLC; ACN/water/TFA) to provide the title compound.

LC (Method 2): $t_R$=0.72 min; Mass spectrum (ESI+): m/z=448 [M+H]$^+$.

Intermediate 24

3-Methyl-13-(morpholine-4-carbonyl)-9-phenyl-16-thia-2,4,5,8-tetraazatetracyclo[8.6.0.0$^{2,6}$.0$^{11,15}$]hexadeca-1(10)3,5,8,11(15)-pentaene

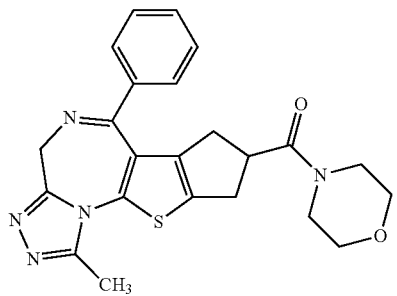 [SMILES: Cc1nnc2n1-c1sc3c(c1C(c1ccccc1)=NC2)CC(C(=O)N1CCOCC1)C3]

The title compound may be obtained from methyl 3-methyl-9-phenyl-16-thia-2,4,5,8-tetraazatetracyclo [8.6.0.0$^{2,6}$.0$^{11,15}$]hexadeca-1(10),3,5,8,11(15)-pentaene-13-carboxylate (for synthesis see EP0254245A1) applying a 2-step procedure that comprises hydrolysis of the methyl ester (analogous to that described for Intermediate 2) and amide coupling of the resulting carboxylic acid with morpholine (analogous to that described for Intermediate 5). LC (Method 2): $t_R$=0.69 min; Mass spectrum (ESI$^+$): m/z=434 [M+H]$^+$.

The Intermediates compiled in the following table are obtained by following a procedure analogous to that described for Intermediate 5 using (13S)-9-(2-chlorophenyl)-3-methyl-16-thia-2,4,5,8-tetraazatetracyclo[8.6.0. 0$^{2,6}$.0$^{11,15}$]-hexadeca-1(10),3,5,8,11(15)-pentaene-13-carboxylic acid or 9-(2-chlorophenyl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxylic acid and the respective amine.

| Intermediate | Structure/Name | Amine | LC Method | $t_R$ [min] | MS (ESI+): m/z [M + H]$^+$ |
|---|---|---|---|---|---|
| 25 | 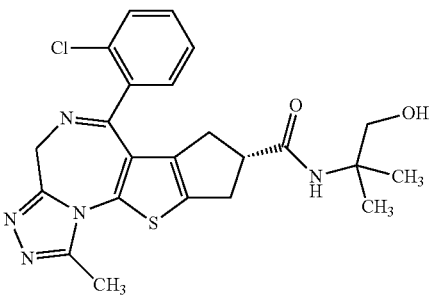<br>(13S)-9-(2-chlorophenyl)-N-(1-hydroxy-2-methylpropan-2-yl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxamide | 2-amino-2-methyl-1-propanol | 1 | 0.79 | 470 |
| 26 | 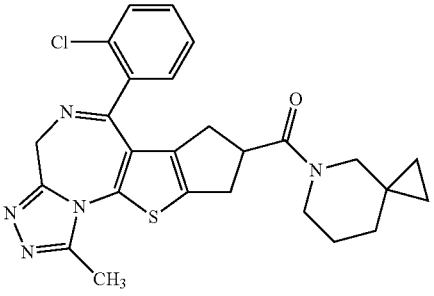<br>13-{5-azaspiro[2.5]octane-5-carbonyl}-9-(2-chlorophenyl)-3-methyl-16-thia-2,4,5,8-tetraazatetracyclo[8.6.0.0$^{2,6}$.0$^{11,15}$]hexadeca-1(10),3,5,11(15)-pentaene | 5-azaspiro[2.5]octane | 2 | 0.95 | 492 |
| 27 | 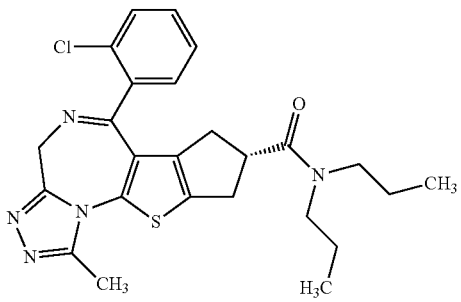<br>(13S)-9-(2-chlorophenyl)-3-methyl-N,N-dipropyl-16-thia-2,4,5,8-tetraazatetracyclo[8.6.0.0$^{2,6}$.0$^{11,15}$]hexadeca-1(10),3,5,8,11(15)-pentaene-13-carboxamide | dipropylamine | 2 | 0.97 | 482 |

Intermediate 28

9-(2-Chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene

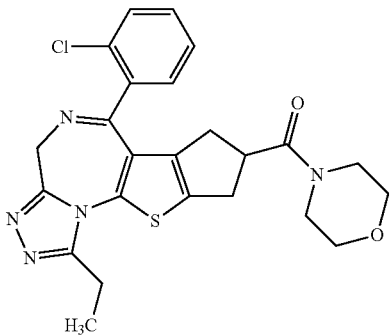 [SMILES: CCc1nnc2n1-c1sc3c(c1C(c1ccccc1Cl)=NC2)CC(C(=O)N1CCOCC1)C3]

The title compound may be obtained from methyl 13-(2-chlorophenyl)-10-oxo-7-thia-9,12-diazatricyclo[6.5.0.0$^{2,6}$]trideca-1(8),2(6),12-triene-4-carboxylate and propanohydrazide by following a procedure analogous to that described in Step 5 of Intermediate 1 providing methyl 9-(2-chlorophenyl)-3-ethyl-16-thia-2,4,5,8-tetraazatetracyclo[8.6.0.0$^{2,6}$.0$^{11,15}$]hexadeca-1(10),3,5,8,11(15)-pentaene-13-carboxylate. Subsequently, the ester is saponified by following a procedure analogous to that described for Intermediate 2 and the resulting carboxylic acid transformed into the title compound by following a procedure analogous to that described for Intermediate 5. Alternatively, methyl 9-(2-chlorophenyl)-3-ethyl-16-thia-2,4,5,8-tetraazatetracyclo[8.6.0.0$^{2,6}$.0$^{11,15}$]hexadeca-1(10),3,5,8,11(15)-pentaene-13-carboxylate may be obtained from methyl 13-(2-chlorophenyl)-10-sulfanylidene-7-thia-9,12-diazatricyclo[6.5.0.0$^{2,6}$]trideca-1(8),2(6),12-triene-4-carboxylate following a procedure analogous to that reported in Arzneimittelforschung 1978, 28, 1153-8 or U.S. Pat. No. 7,015,213B1.

LC (Method 2): $t_R$=0.82 min; Mass spectrum (ESI+): m/z=482 [M+H]$^+$.

Intermediate 29

9-(2-Chlorophenyl)-3-propyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

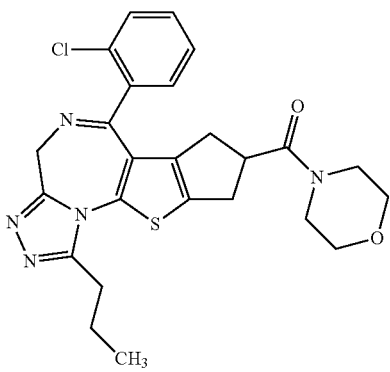 [SMILES: CCCc1nnc2n1-c1sc3c(c1C(c1ccccc1Cl)=NC2)CC(C(=O)N1CCOCC1)C3]

The title compound may be obtained from methyl 13-(2-chlorophenyl)-10-oxo-7-thia-9,12-diazatricyclo[6.5.0.0$^{2,6}$]trideca-1(8),2(6),12-triene-4-carboxylate and butyric acid hydrazide by following a procedure analogous to that described in Step 5 of Intermediate 1 providing methyl 9-(2-chlorophenyl)-3-propyl-16-thia-2,4,5,8-tetraazatetracyclo[8.6.0.0$^{2,6}$.0$^{11,15}$]hexadeca-1(10),3,5,8,11(15)-pentaene-13-carboxylate. Subsequently, the ester is saponified by following a procedure analogous to that described for Intermediate 2 and the resulting carboxylic acid transformed into the title compound by following a procedure analogous to that described for Intermediate 5. Alternatively, methyl 9-(2-chlorophenyl)-3-propyl-16-thia-2,4,5,8-tetraazatetracyclo[8.6.0.0$^{2,6}$.0$^{11,15}$]hexadeca-1(10),3,5,8,11(15)-pentaene-13-carboxylate may be obtained from methyl 13-(2-chlorophenyl)-10-sulfanylidene-7-thia-9,12-diazatricyclo[6.5.0.0$^{2,6}$]trideca-1(8),2(6),12-triene-4-carboxylate following a procedure analogous to that reported in Arzneimittelforschung 1978, 28, 1153-8 or U.S. Pat. No. 7,015,213B1.

LC (Method 2): $t_R$=0.87 min; Mass spectrum (ESI$^+$): m/z=496 [M+H]$^+$.

Intermediate 30

9-(2-Chlorophenyl)-3-cyclopropyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene

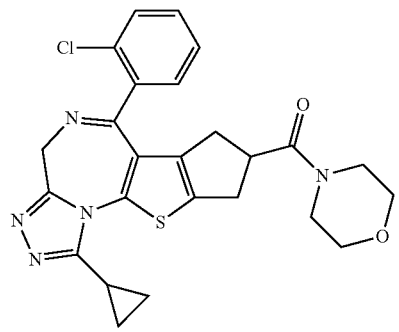 [SMILES: O=C(C1Cc2sc3c(c2C1)C(c1ccccc1Cl)=NCc1nnc(C2CC2)n1-3)N1CCOCC1]

The title compound may be obtained from methyl 13-(2-chlorophenyl)-10-oxo-7-thia-9,12-diazatricyclo[6.5.0.0$^{2,6}$]trideca-1(8),2(6),12-triene-4-carboxylate and cyclopropanecarbohydrazide by following a procedure analogous to that described in Step 5 of Intermediate 1 providing methyl 9-(2-chlorophenyl)-3-cyclopropyl-16-thia-2,4,5,8-tetraazatetracyclo[8.6.0.0$^{2,6}$.0$^{11,15}$]hexadeca-1(10),3,5,8,11(15)-pentaene-13-carboxylate.

Subsequently, the ester is saponified by a procedure analogous to that described for Intermediate 2 and the resulting carboxylic acid transformed into the title compound by following a procedure analogous to that described for Intermediate 5. Alternatively, methyl 9-(2-chlorophenyl)-3-cyclopropyl-16-thia-2,4,5,8-tetraazatetracyclo-[8.6.0.0$^{2,6}$.0$^{11,15}$]hexadeca-1(10),3,5,8,11(15)-pentaene-13-carboxylate may be obtained from methyl 13-(2-chlorophenyl)-10-sulfanylidene-7-thia-9,12-diazatricyclo[6.5.0.0$^{2,6}$]trideca-1(8),2(6),12-triene-4-carboxylate following a procedure analogous to that reported in Arzneimittelforschung 1978, 28, 1153-8 or U.S. Pat. No. 7,015,213B1.

LC (Method 2): $t_R$=0.83 min; Mass spectrum (ESI+): m/z=494 [M+H]$^+$.

Intermediate 31

(3-Methyl-9-[2-(methylsulfanyl)phenyl]-13-(morpholine-4-carbonyl)-16-thia-2,4,5,8-tetraazatetracyclo[8.6.0.0$^{2,6}$.0$^{11,15}$]-hexadeca-1(10)3,5,11(15)-pentaene

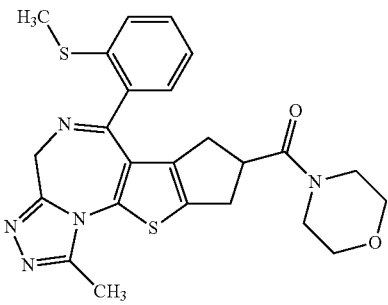

9-(2-Bromophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,8,11(15)-pentaene (135 mg), copper(I) iodide (50 mg) and DABCO (59 mg) are dissolved in anhydrous DMSO (2.0 mL). The reaction mixture is stirred for 16 h under argon at 130° C. The mixture is diluted with acetonitrile, filtered and purified by chromatography on reversed phase (HPLC; ACN/water/TFA) to give the title compound. LC (Method 2): $t_R$=0.74 min; Mass spectrum (ESI$^+$): m/z=480 [M+H]$^+$.

SYNTHESIS OF EXAMPLES

Example 1

9-(2-Chlorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene

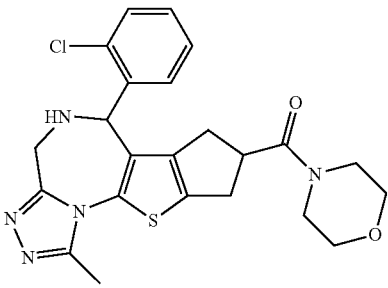 [SMILES: Cc1nnc2n1-c1sc3c(c1C(c1ccccc1Cl)NC2)CC(C(=O)N1CCOCC1)C3]

NaBH$_4$ (32 mg) and HCl (4 M in water; 0.26 mL) are added in turn to a solution of 9-(2-chlorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene (200 mg) in DCE (1 mL) at room temperature. The mixture is stirred for 2 h before another portion of NaBH$_4$ (16 mg) and HCl (4 mol/L in water; 0.26 mL) are added. The reaction is further stirred at room temperature until complete; if the reaction does not go to completion more NaBH$_4$ and HCl are added. Aqueous NaHCO$_3$ solution is added and the resulting mixture is extracted with DCM (3×). The combined organic extract is dried (Na$_2$SO$_4$) and concentrated. The residue is purified by chromatography on reversed phase (HPLC; ACN/water/aqueous ammonia) to give the title compound as a mixture of 2 racemic diastereomers (ca. 60/40).

LC (Method 2): $t_R$=0.72 min; Mass spectrum (ESI$^+$): m/z=470 [M+H]$^+$.

Examples 2 and Example 3

(9R,13S)-9-(2-Chlorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene (Example 2) and (9S,13S)-9-(2-chlorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene (Example 3)

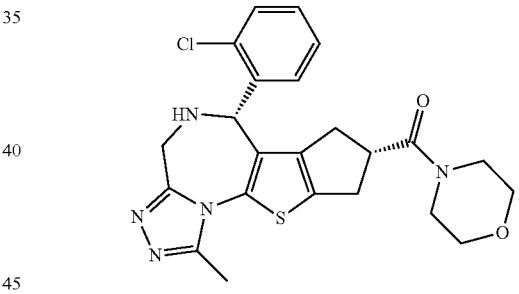

HCl (4 M in water, 1.07 mL) and NaBH$_4$ (323 mg) are added in turn to a solution of (13S)-9-(2-chlorophenyl)-3-methyl-13-(morpholine-4-carbonyl)-16-thia-2,4,5,8-tetraazatetra-cyclo[8.6.0.0$^{2,6}$.0$^{11,15}$]hexadeca-1(10),3,5,8,11(15)-pentaene (1.00 g) in DCM (25 mL) at room temperature. The mixture is stirred for 1 h until complete. The mixture is diluted with water and aqueous HCl (1 M) until a pH of 8-9 is achieved and is extracted with DCM (2×). The combined organic extract is dried (Na$_2$SO$_4$) and concentrated. The residue is purified repeatedly by chromatography on reversed phase (HPLC; ACN/water/aqueous TFA) to give the TFA salts of the diastereomers fully separated. The diastereomers can be liberated from their salt form by adding aqueous NaHCO$_3$ solution, extracting the resulting mixture with DCM, and concentrating the organic extract to give the title compounds.

Example 2: LC (Method 2): $t_R$=0.72 min; Mass spectrum (ESI$^+$): m/z=470 [M+H]$^+$;

Example 3: LC (Method 2): $t_R$=0.73 min; Mass spectrum (ESI$^+$): m/z=470 [M+H]$^+$.

Example 4

(9R,13S)-9-(2-Chlorophenyl)-3-methyl-13-[(2S)-2-methylmorpholine-4-carbonyl]-16-thia-2,4,5,8-tetraazatetracyclo-[8.6.0.0²,⁶.0¹¹,¹⁵]hexadeca-1(10)3,5,11(15)-tetraene

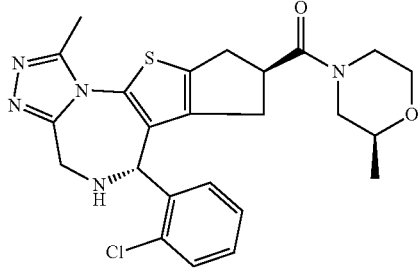 [SMILES: Cc1nnc2n1-c1sc3c(c1[C@H](c1ccccc1Cl)NC2)C[C@H](C(=O)N1CCO[C@@H](C)C1)C3]

The title compound is prepared from (9R,13S)-9-(2-chlorophenyl)-3-methyl-16-thia-2,4,5,8-tetraazatetracyclo[8.6.0.0²,⁶.0¹¹,¹⁵]hexadeca-1(10),3,5,11(15)-tetraene-13-carboxylic acid and (2S)-2-methylmorpholine hydrochloride following a procedure analogous to that described for Intermediate 5.

LC (Method 4): $t_R$=0.50 min; Mass spectrum (ESI⁺): m/z=484 [M+H]⁺.

The Examples (Ex.) compiled in the following table are obtained by following a procedure analogous to that described for Intermediate 5 using the respective stereoisomer or stereoisomeric mixture of 9-(2-chlorophenyl)-3-methyl-16-thia-2,4,5,8-tetraazatetracyclo[8.6.0.0²,⁶.0¹¹,¹⁵]hexadeca-1(10)3,5,11(15)-tetraene-13-carboxylic acid and the respective amine. SFC separation is used to obtain Example 11 and Example 12 [column: Chiral Art® Amylose-SA (10 mm×250 mm, 5 μm); column temperature: 40° C.; flow rate: 10 mL/min; BPR: 150 bar; injection volume: 250 μL (2.5 mg); isocratic conditions: 70:30 CO₂:MeOH (20 mM NH₃)], and Example 13 and Example 14 [column: Chiralpak® IA (10 mm×250 mm, 5 μm); column temperature: 40° C.; flow rate: 10 mL/min; BPR: 150 bar; injection volume: 200 μL (2 mg); isocratic conditions: 65:35 PO₂: EtOH (20 mM NH₃)].

| Ex. | Structure/Name | Amine employed | LC Method | MS (ESI+): m/z [M + H]⁺ | $t_R$ [min] | Comment |
|---|---|---|---|---|---|---|
| 5 | (9R,13S)-9-(2-chlorophenyl)-13-[(2R,6R)-2,6-dimethylmorpholine-4-carbonyl]-3-methyl-16-thia-2,4,5,8-tetraazatetracyclo-[8.6.0.0²,⁶.0¹¹,¹⁵]hexadeca-1(10),3,5,11(15)-tetraene | (2R,6R)-2,6-dimethylmorpholine | 4 | 498 | 0.52 | (9R,13S)-stereoisomer of carboxylic acid used |
| 6 | (9R,13S)-9-(2-chlorophenyl)-13-[(2S,6S)-2,6-dimethylmorpholine-4-carbonyl]-3-methyl-16-thia-2,4,5,8-tetraazatetracyclo-[8.6.0.0²,⁶.0¹¹,¹⁵]hexadeca-1(10),3,5,11(15)-tetraene | (2S,6S)-2,6-dimethylmorpholine | 4 | 498 | 0.52 | (9R,13S)-stereoisomer of carboxylic acid used |

-continued

| Ex. | Structure/Name | Amine employed | LC Method | MS (ESI+): m/z [M + H]+ | $t_R$ [min] | Comment |
| --- | --- | --- | --- | --- | --- | --- |
| 7 | (9R,13S)-9-(2-chlorophenyl)-3-methyl-N-{[6-(trifluoromethyl)pyridin-3-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[6-(trifluoromethyl)pyridin-3-yl]methanamine | 2 | 559 | 0.82 | (9R,13S)-stereoisomer of carboxylic acid used |
| 8 | (9S,13S)-9-(2-chlorophenyl)-3-methyl-N-[2-(trifluoromethoxy)ethyl]-16-thia-2,4,5,8-tetraazatetracyclo[8.6.0.0$^{2,6}$.0$^{11,15}$]-hexadeca-1(10),3,5,11(15)-tetraene-13-carboxamide | 2-(trifluoromethoxy)ethan-1-amine | 2 | 512 | 0.80 | (9S,13S)-stereoisomer of carboxylic acid used |
| 9 | (9S,13S)-9-(2-chlorophenyl)-N-cyclobutyl-3-methyl-16-thia-2,4,5,8-tetraazatetracyclo[8.6.0.0$^{2,6}$.0$^{11,15}$]-hexadeca-1(10),3,5,11(15)-tetraene-13-carboxamide | cyclobutanamine | 2 | 454 | 0.77 | (9S,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 10 | 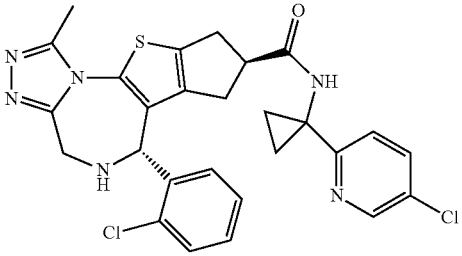<br>(9R,13S)-9-(2-chlorophenyl)-N-[1-(5-chloropyridin-2-yl)cyclopropyl]-3-methyl-16-thia-2,4,5,8-tetraazatetracyclo-[8.6.0.0$^{2,6}$.0$^{11,15}$]hexadeca-1(10),3,5,11(15)-tetraene-13-carboxamide | 1-(5-chloro-pyridin-2-yl)-cyclopropan-1-amine | 2 | 551 | 0.85 | (9R,13S)-stereoisomer of carboxylic acid used |
| 11 | 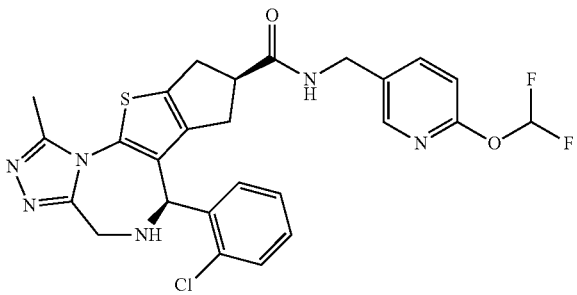<br>(9S,13S)-9-(2-chlorophenyl)-N-{[6-(difluoromethoxy)pyridin-3-yl]methyl}-3-methyl-16-thia-2,4,5,8-tetraazatetracyclo[8.6.0.0$^{2,6}$.0$^{11,15}$]hexadeca-1(10),3,5,11(15)-tetraene-13-carboxamide | 1-[6-(difluoro-methoxy)-pyridin-3-yl]-methanamine | 9 | 557 | 2.27 | (9S,13S)-stereoisomer of carboxylic acid used and SFC separation applied |
| 12 | 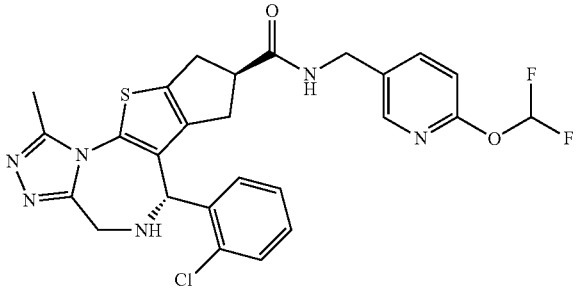<br>(9R,13S)-9-(2-chlorophenyl)-N-{[6-(difluoromethoxy)pyridin-3-yl]methyl}-3-methyl-16-thia-2,4,5,8-tetraazatetracyclo-[8.6.0.0$^{2,6}$.0$^{11,15}$]hexadeca-1(10),3,5,11(15)-tetraene-13-carboxamide | 1-[6-(difluoro-methoxy)-pyridin-3-yl]-methanamine | 9 | 557 | 6.18 | (9R,13S)-stereoisomer of carboxylic acid used and SFC separation applied |

| Ex. | Structure/Name | Amine employed | LC Method | MS (ESI+): m/z [M + H]+ | $t_R$ [min] | Comment |
|---|---|---|---|---|---|---|
| 13 | (9S,13S)-9-(2-chlorophenyl)-3-methyl-N-{[4-(trifluoromethyl)phenyl]methyl}-16-thia-2,4,5,8-tetraazatetracyclo[8.6.0.0²,⁶.0¹¹,¹⁵]-hexadeca-1(10),3,5,11(15)-tetraene-13-carboxamide | [4-(trifluoromethyl)phenyl]-methanamine | 5 | 558 | 2.59 | (9S,13S)-stereoisomer of carboxylic acid used, reaction run at 60° C., SFC separation applied |
| 14 | (9S,13S)-9-(2-chlorophenyl)-3-methyl-N-{[4-(trifluoromethyl)phenyl]methyl}-16-thia-2,4,5,8-tetraazatetracyclo[8.6.0.0²,⁶.0¹¹,¹⁵]-hexadeca-1(10),3,5,11(15)-tetraene-13-carboxamide | [4-(trifluoromethyl)phenyl]-methanamine | 5 | 558 | 4.62 | (9R,13S)-stereoisomer of carboxylic acid used, reaction run at 60° C., SFC separation applied |
| 15 | (9R,13S)-9-(2-chlorophenyl)-N-(cyclopropylmethyl)-3-methyl-16-thia-2,4,5,8-tetraazatetracyclo[8.6.0.0²,⁶.0¹¹,¹⁵]-hexadeca-1(10),3,5,11(15)-tetraene-13-carboxamide | 1-cyclopropyl-methanamine | 4 | 454 | 0.51 | (9R,13S)-stereoisomer of carboxylic acid used |

-continued

| Ex. | Structure/Name | Amine employed | LC Method | MS (ESI+): m/z [M + H]+ | $t_R$ [min] | Comment |
|---|---|---|---|---|---|---|
| 16 | (9R,13S)-9-(2-chlorophenyl)-N-[(1R)-3,3-difluorocyclopentyl]-3-methyl-16-thia-2,4,5,8-tetraazatetracyclo[8.6.0.0$^{2,6}$.0$^{11,15}$]-hexadeca-1(10),3,5,11(15)-tetraene-13-carboxamide | (1R)-3,3-difluorocyclopentan-1-amine | 4 | 504 | 0.54 | (9R,13S)-stereoisomer of carboxylic acid used |
| 17 | (9R,13S)-9-(2-chlorophenyl)-3-methyl-N-[2-(trifluoromethoxy)-ethyl]-16-thia-2,4,5,8-tetraazatetracyclo[8.6.0.0$^{2,6}$.0$^{11,15}$]-hexadeca-1(10),3,5,11(15)-tetraene-13-carboxamide | 2-(trifluoromethoxy)ethan-1-amine | 4 | 512 | 0.55 | (9R,13S)-stereoisomer of carboxylic acid used |
| 18 | (9R,13S)-9-(2-chlorophenyl)-13-(4,4-difluoropiperidine-1-carbonyl)-3-methyl-16-thia-2,4,5,8-tetraazatetracyclo-[8.6.0.0$^{2,6}$.0$^{11,15}$]hexadeca-1(10),3,5,11(15)-tetraene | 4,4-difluoropiperidine | 4 | 504 | 0.56 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 19 | (9R,13S)-9-(2-chlorophenyl)-3-methyl-N-propyl-16-thia-2,4,5,8-tetraazatetracyclo[8.6.0.0²,⁶.0¹¹,¹⁵]hexadeca-1(10),3,5,11(15)-tetraene-13-carboxamide | propan-1-amine | 4 | 442 | 0.49 | (9R,13S)-stereoisomer of carboxylic acid used |
| 20 | (9R,13S)-9-(2-chlorophenyl)-N-[(2S)-1-fluoropropan-2-yl]-3-methyl-16-thia-2,4,5,8-tetraazatetracyclo[8.6.0.0²,⁶.0¹¹,¹⁵]-hexadeca-1(10),3,5,11(15)-tetraene-13-carboxamide | (2S)-1-fluoro-propan-2-amine | 4 | 460 | 0.47 | (9R,13S)-stereoisomer of carboxylic acid used |
| 21 | (9S,13S)-13-{2-azabicyclo[2.1.1]hexane-2-carbonyl}-9-(2-chlorophenyl)-3-methyl-16-thia-2,4,5,8-tetraazatetracyclo-[8.6.0.0²,⁶.0¹¹,¹⁵]-hexadeca-1(10),3,5,11(15)-tetraene | 2-azabicyclo-[2.1.1]hexane | 4 | 466 | 0.50 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 22 | (9R,13S)-9-(2-chlorophenyl)-3-methyl-13-{5-oxa-2-azaspiro[3.4]octane-2-carbonyl}-16-thia-2,4,5,8-tetraazatetracyclo-[8.6.0.0²,⁶.0¹¹,¹⁵]-hexadeca-1(10),3,5,11(15)-tetraene | 5-oxa-2-aza-spiro[3.4]-octane | 4 | 496 | 0.49 | (9R,13S)-stereoisomer of carboxylic acid used |
| 23 | (9R,13S)-9-(2-chlorophenyl)-N-(4,4-difluorocyclohexyl)-3-methyl-16-thia-2,4,5,8-tetraazatetracyclo[8.6.0.0²,⁶.0¹¹,¹⁵]-hexadeca-1(10),3,5,11(15)-tetraene-13-carboxamide | 4,4-difluoro-cyclohexan-1-amine | 4 | 518 | 0.57 | (9R,13S)-stereoisomer of carboxylic acid used |
| 24 | (9R,13S)-9-(2-chlorophenyl)-13-(3,3-dimethylazetidine-1-carbonyl)-3-methyl-16-thia-2,4,5,8-tetraazatetracyclo-[8.6.0.0²,⁶.0¹¹,¹⁵]hexadeca-1(10),3,5,11(15)-tetraene | 3,3-dimethyl-azetidine | 4 | 468 | 0.55 | (9R,13S)-stereoisomer of carboxylic acid used |

-continued

| Ex. | Structure/Name | Amine employed | LC Method | MS (ESI+): m/z [M + H]+ | $t_R$ [min] | Comment |
|---|---|---|---|---|---|---|
| 25 | (9R,13S)-9-(2-chlorophenyl)-N-(3,5-dimethyl-1,2-oxazol-4-yl)-3-methyl-16-thia-2,4,5,8-tetraazatetracyclo-[8.6.0.0$^{2,6}$.0$^{11,15}$]hexadeca-1(10),3,5,11(15)-tetraene-13-carboxamide | dimethyl-1,2-oxazol-4-amine | 4 | 495 | 0.47 | (9R,13S)-stereoisomer of carboxylic acid used |
| 26 | (9R,13S)-9-(2-chlorophenyl)-13-(2,2-dimethylmorpholine-4-carbonyl)-3-methyl-16-thia-2,4,5,8-tetraazatetracyclo-[8.6.0.0$^{2,6}$.0$^{11,15}$]hexadeca-1(10),3,5,11(15)-tetraene | 2,2-dimethyl-morpholine | 4 | 498 | 0.51 | (9R,13S)-stereoisomer of carboxylic acid used and TBTU instead of HATU |
| 27 | (9R,13S)-9-(2-chlorophenyl)-13-[(2R,6S)-2,6-dimethylmorpholine-4-carbonyl]-3-methyl-16-thia-2,4,5,8-tetraazatetracyclo-[8.6.0.0$^{2,6}$.0$^{11,15}$]hexadeca-1(10),3,5,11(15)-tetraene | (2R,6S)-2,6-dimethyl-morpholine | 4 | 498 | 0.53 | (9R,13S)-stereoisomer of carboxylic acid used |

-continued

| Ex. | Structure/Name | Amine employed | LC Method | MS (ESI+): m/z [M + H]+ | $t_R$ [min] | Comment |
|---|---|---|---|---|---|---|
| 28 | (9R,13S)-9-(2-chlorophenyl)-N-cyclobutyl-3-methyl-16-thia-2,4,5,8-tetraazatetracyclo[8.6.0.0²,⁶.0¹¹,¹⁵]hexadeca-1(10),3,5,11(15)-tetraene-13-carboxamide | cyclobutan-amine | 4 | 454 | 0.51 | (9R,13S)-stereoisomer of carboxylic acid used |
| 29 | (9S,13S)-9-(2-chlorophenyl)-3-methyl-13-{3-methyl-5H,6H,7H,8H-imidazo[1,5-a]pyrazine-7-carbonyl}-16-thia-2,4,5,8-tetraazatetracyclo[8.6.0.0²,⁶.0¹¹,¹⁵]-hexadeca-1(10),3,5,11(15)-tetraene | 3-methyl-5H,6H,7H,8H-imidazo[1,5-a]-pyrazine | 4 | 520 | 0.35 | (9R,13S)-stereoisomer of carboxylic acid used |
| 30 | (9R,13S)-9-(2-chlorophenyl)-3-methyl-13-{7-oxa-2-azaspiro[3.5]nonane-2-carbonyl}-16-thia-2,4,5,8-tetraazatetracyclo-[8.6.0.0²,⁶.0¹¹,¹⁵]hexadeca-1(10),3,5,11(15)-tetraene | 7-oxa-2-azaspiro[3.5]-nonane | 4 | 510 | 0.49 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 31 | 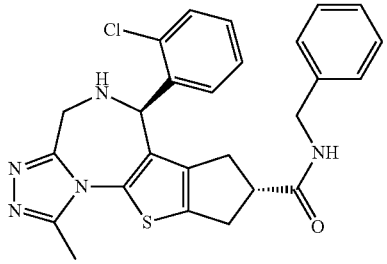<br>(9R,13S)-N-benzyl-9-(2-chlorophenyl)-3-methyl-16-thia-2,4,5,8-tetraazatetracyclo[8.6.0.0$^{2,6}$.0$^{11,15}$]hexadeca-1(10),3,5,11(15)-tetraene-13-carboxamide | 1-phenyl-methanamine | 2 | 490 | 0.8 | (9R,13S)-stereoisomer of carboxylic acid used and TBTU instead of HATU |
| 32 | 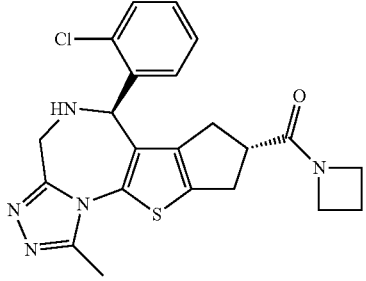<br>(9R,13S)-13-(azetidine-1-carbonyl)-9-(2-chlorophenyl)-3-methyl-16-thia-2,4,5,8-tetraazatetracyclo[8.6.0.0$^{2,6}$.0$^{11,15}$]hexadeca-1(10),3,5,11(15)-tetraene | azetidine | 2 | 440 | 0.71 | (9R,13S)-stereoisomer of carboxylic acid used and TBTU instead of HATU |
| 33 | 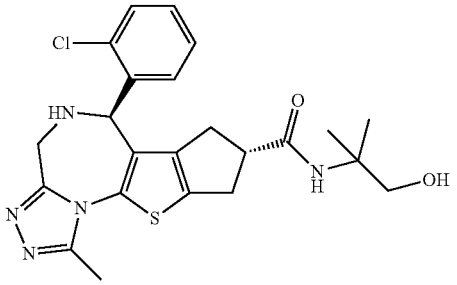<br>(9R,13S)-9-(2-chlorophenyl)-N-(1-hydroxy-2-methylpropan-2-yl)-3-methyl-16-thia-2,4,5,8-tetraazatetracyclo[8.6.0.0$^{2,6}$.0$^{11,15}$]-hexadeca-1(10),3,5,11(15)-tetraene-13-carboxamide | 2-amino-2-methylpropan-1-ol | 1 | 472 | 0.82 | (9R,13S)-stereoisomer of carboxylic acid used and TBTU instead of HATU |

-continued

| Ex. | Structure/Name | Amine employed | LC Method | MS (ESI+): m/z [M + H]⁺ | $t_R$ [min] | Comment |
|---|---|---|---|---|---|---|
| 34 | (9R,13S)-N-benzyl-9-(2-chlorophenyl)-N,3-dimethyl-16-thia-2,4,58-tetraazatetracyclo[8.6.0.0$^{2,6}$.0$^{11,15}$]hexadeca-1(10),3,5,11(15)-tetraene-13-carboxamide | benzyl(methyl)amine | 2 | 504 | 0.84 | (9R,13S)-stereoisomer of carboxylic acid used and TBTU instead of HATU |
| 35 | (9R,13S)-9-(2-chlorophenyl)-3-methyl-N-{[6-(trifluoromethyl)pyridin-2-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[6-(trifluoromethyl)pyridin-2-yl]methanamine | 4 | 559 | 0.59 | (9R,13S)-stereoisomer of carboxylic acid used |
| 36 | (9R,13S)-9-(2-chlorophenyl)-3-methyl-N-{[3-(trifluoromethyl)pyridin-2-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[3-(trifluoromethyl)pyridin-2-yl]methanamine | 4 | 559 | 0.57 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 37 | 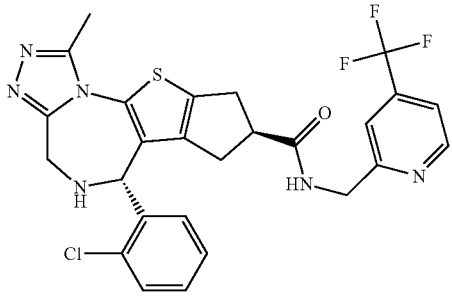<br>(9R,13S)-9-(2-chlorophenyl)-3-methyl-N-{[4-(trifluoromethyl)pyridin-2-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[4-(trifluoromethyl)pyridin-2-yl]methanamine | 4 | 559 | 0.57 | (9R,13S)-stereoisomer of carboxylic acid used |
| 38 | 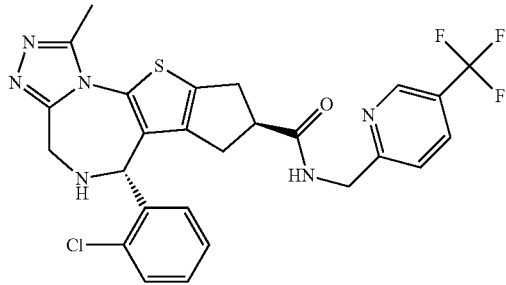<br>(9R,13S)-9-(2-chlorophenyl)-3-methyl-N-{[5-(trifluoromethyl)pyridin-2-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[5-(trifluoromethyl)pyridin-2-yl]methanamine | 4 | 559 | 0.57 | (9R,13S)-stereoisomer of carboxylic acid used |
| 39 | 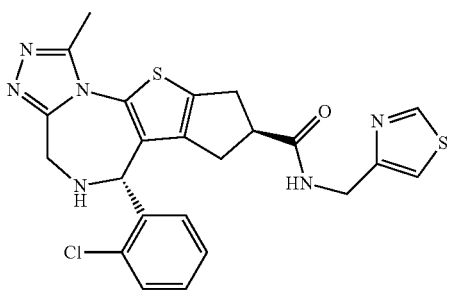<br>(9R,13S)-9-(2-chlorophenyl)-3-methyl-N-[(1,3-thiazol-4-yl)methyl]-16-thia-2,4,5,8-tetraazatetracyclo[8.6.0.0$^{2,6}$.0$^{11,15}$]hexadeca-1(10),3,5,11(15)-tetraene-13-carboxamide | 1-(1,3-thiazol-4-yl)methanamine | 4 | 497 | 0.43 | (9R,13S)-stereoisomer of carboxylic acid used |

| Ex. | Structure/Name | Amine employed | LC Method | MS (ESI+): m/z [M + H]+ | $t_R$ [min] | Comment |
| --- | --- | --- | --- | --- | --- | --- |
| 40 | (9R,13S)-9-(2-chlorophenyl)-3-methyl-N-[(1,3-thiazol-2-yl)methyl]-16-thia-2,4,5,8-tetraazatetracyclo[8.6.0.0²,⁶.0¹¹,¹⁵]hexadeca-1(10),3,5,11(15)-tetraene-13-carboxamide | 1-(1,3-thiazol-2-yl)methanamine | 4 | 497 | 0.44 | (9R,13S)-stereoisomer of carboxylic acid used |
| 41 | (9R,13S)-9-(2-chlorophenyl)-N-[(6-methoxypyridin-3-yl)methyl]-3-methyl-16-thia-2,4,5,8-tetraazatetracyclo-[8.6.0.0²,⁶.0¹¹,¹⁵]hexadeca-1(10),3,5,11(15)-tetraene-13-carboxamide | 1-(6-methoxy-pyridin-3-yl)-methanamine | 4 | 521 | 0.45 | (9R,13S)-stereoisomer of carboxylic acid used |
| 42 | (9R,13S)-9-(2-chlorophenyl)-3-methyl-N-[(pyrimidin-5-yl)methyl]-16-thia-2,4,5,8-tetraazatetracyclo[8.6.0.0²,⁶.0¹¹,¹⁵]hexadeca-1(10),3,5,11(15)-tetraene-13-carboxamide | 1-(pyrimidin-5-yl)methanamine | 4 | 492 | 0.39 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 43 | (9R,13S)-9-(2-chlorophenyl)-3-methyl-N-{[5-(trifluoromethyl)pyridin-3-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[5-(trifluoromethyl)pyridin-3-yl]methanamine | 4 | 559 | 0.55 | (9R,13S)-stereoisomer of carboxylic acid used |
| 44 | (9R,13S)-9-(2-chlorophenyl)-3-methyl-N-[(pyridazin-4-yl)methyl]-16-thia-2,4,5,8-tetraazatetracyclo[8.6.0.0$^{2,6}$.0$^{11,15}$]hexadeca-1(10),3,5,11(15)-tetraene-13-carboxamide | 1-(pyridazin-4-yl)methanamine | 4 | 492 | 0.36 | (9R,13S)-stereoisomer of carboxylic acid used |
| 45 | (9R,13S)-9-(2-chlorophenyl)-3-methyl-N-{[2-(trifluoromethyl)pyridin-4-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[2-(trifluoromethyl)pyridin-4-yl]methanamine | 4 | 559 | 0.56 | (9R,13S)-stereoisomer of carboxylic acid used |

| Ex. | Structure/Name | Amine employed | LC Method | MS (ESI+): m/z [M + H]+ | $t_R$ [min] | Comment |
|---|---|---|---|---|---|---|
| 46 | 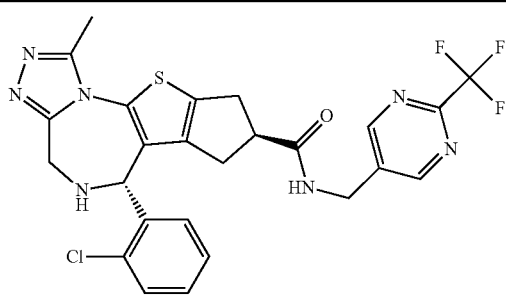<br>(9R,13S)-9-(2-chlorophenyl)-3-methyl-N-{[2-(trifluoromethyl)pyrimidin-5-yl]methyl}-16-thia-2,4,5,8-tetraazatetracyclo-[8.6.0.0$^{2,6}$.0$^{11,15}$]hexadeca-1(10),3,5,11(15)-tetraene-13-carboxamide | 1-[2-(trifluoromethyl)-pyrimidin-5-yl]-methanamine | 4 | 560 | 0.55 | (9R,13S)-stereoisomer of carboxylic acid used |
| 47 | 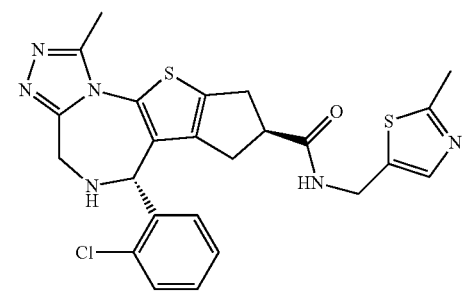<br>(9R,13S)-9-(2-chlorophenyl)-3-methyl-N-[(2-methyl-N-[(2-methyl-1,3-thiazol-5-yl)methyl]-16-thia-2,4,5,8-tetraazatetracyclo[8.6.0.0$^{2,6}$.0$^{11,15}$]-hexadeca-1(10),3,5,11(15)-tetraene-13-carboxamide | 1-(2-methyl-1,3-thiazol-5-yl)methan-amine | 4 | 511 | 0.40 | (9R,13S)-stereoisomer of carboxylic acid used |
| 48 | 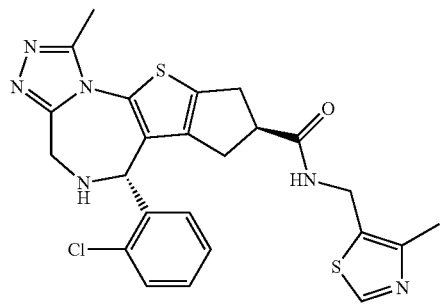<br>(9R,13S)-9-(2-chlorophenyl)-3-methyl-N-[(4-methyl-1,3-thiazol-5-yl)methyl]-16-thia-2,4,5,8-tetraazatetracyclo[8.6.0.0$^{2,6}$.0$^{11,15}$]-hexadeca-1(10),3,5,11(15)-tetraene-13-carboxamide | 1-(4-methyl-1,3-thiazol-5-yl)methan-amine | 4 | 511 | 0.41 | (9R,13S)-stereoisomer of carboxylic acid used |

| Ex. | Structure/Name | Amine employed | LC Method | MS (ESI+): m/z [M + H]⁺ | $t_R$ [min] | Comment |
|---|---|---|---|---|---|---|
| 49 | (9R,13S)-9-(2-chlorophenyl)-N-[(5-chloropyridin-2-yl)methyl]-3-methyl-16-thia-2,4,5,8-tetraazatetracyclo-[8.6.0.0²,⁶.0¹¹,¹⁵]hexadeca-1(10),3,5,11(15)-tetraene-13-carboxamide | 1-(5-chloro-pyridin-2-yl)-methanamine | 4 | 525 | 0.52 | (9R,13S)-stereoisomer of carboxylic acid used |
| 50 | (9R,13S)-9-(2-chlorophenyl)-N-{3-ethyl-bicyclo[1.1.1]pentan-1-yl}-3-methyl-16-thia-2,4,5,8-tetraazatetracyclo-[8.6.0.0²,⁶.0¹¹,¹⁵]hexadeca-1(10),3,5,11(15)-tetraene-13-carboxamide | 3-ethylbicyclo-[1.1.1]pentan-1-amine | 4 | 494 | 0.67 | (9R,13S)-stereoisomer of carboxylic acid used and TBTU instead of HATU |
| 51 | (9R,13S)-N-{bicyclo[1.1.1]pentan-1-yl}-9-(2-chlorophenyl)-3-methyl-16-thia-2,4,5,8-tetraazatetracyclo[8.6.0.0²,⁶.0¹¹,¹⁵]hexadeca-1(10),3,5,11(15)-tetraene-13-carboxamide | bicyclo[1.1.1]-pentan-1-amine | 4 | 466 | 0.56 | (9R,13S)-stereoisomer of carboxylic acid used and TBTU instead of HATU |

Example 52

9-(4-Chlorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

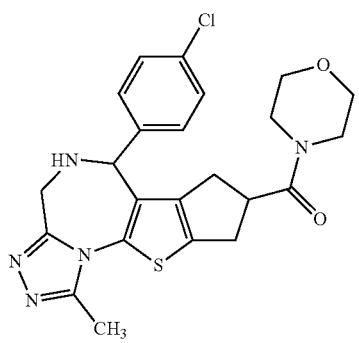 [SMILES: Cc1nnc2n1-c1sc3c(c1C(c1ccc(Cl)cc1)NC2)CC(C(=O)N1CCOCC1)C3]

The title compound is prepared from 9-(4-chlorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): $t_R$=0.72 min; Mass spectrum (ESI+): m/z=470 [M+H]$^+$.

Example 53

9-(2-Ethylphenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

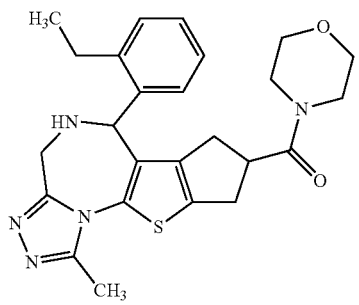 [SMILES: CCc1ccccc1C1NCc2nnc(C)n2-c2sc3c(c21)CC(C(=O)N1CCOCC1)C3]

The title compound is prepared from 9-(2-ethylphenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): $t_R$=0.72/0.74 min (diastereomers); Mass spectrum (ESI$^+$): m/z=464 [M+H]$^+$.

Example 54

9-(2-Methoxyphenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene

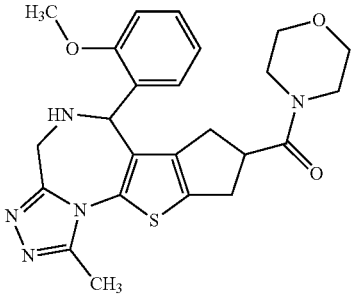 [SMILES: COc1ccccc1C1NCc2nnc(C)n2-c2sc3c(c21)CC(C(=O)N1CCOCC1)C3]

The title compound is prepared from 9-(2-methoxyphenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): $t_R$=0.68 min; Mass spectrum (ESI+): m/z=466 [M+H]$^+$.

Example 55

9-(2-Fluorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

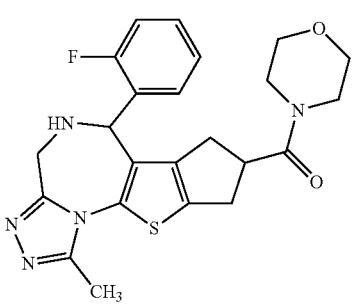 [SMILES: Cc1nnc2n1-c1sc3c(c1C(c1ccccc1F)NC2)CC(C(=O)N1CCOCC1)C3]

The title compound is prepared from 9-(2-fluorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): $t_R$=0.78/0.79 min (diastereomers); Mass spectrum (ESI$^+$): m/z=454 [M+H]$^+$.

Example 56

3-Methyl-13-(morpholine-4-carbonyl)-9-[2-(trifluoromethyl)phenyl]-16-thia-2,4,5,8-tetraazatetracyclo[8.6.0.0$^{2,6}$.0$^{11,15}$]-hexadeca-1(10),3,5,11(15)-tetraene

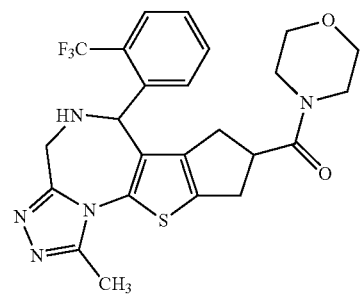 [SMILES: Cc1nnc2n1-c1sc3c(c1C(c1ccccc1C(F)(F)F)NC2)CC(C(=O)N1CCOCC1)C3]

The title compound is prepared from 3-methyl-13-(morpholine-4-carbonyl)-9-[2-(trifluoromethyl)phenyl]-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): t$_R$=0.76 min; Mass spectrum (ESI+): m/z=504 [M+H]$^+$.

Example 57

9-(2-Bromophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

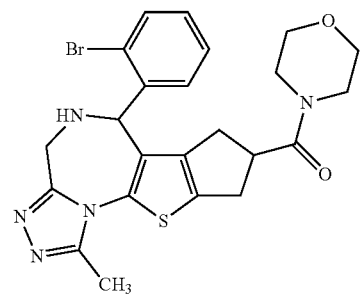 [SMILES: Cc1nnc2n1-c1sc3c(c1C(c1ccccc1Br)NC2)CC(C(=O)N1CCOCC1)C3]

The title compound is prepared from 9-(2-bromophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1.

LC (Method 2): t$_R$=0.71/0.72 min (diastereomers); Mass spectrum (ESI+): m/z=514/516 (Br) [M+H]$^+$.

Example 58

9-(3,5-Difluorophenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene

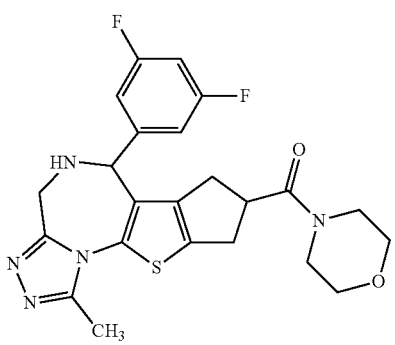 [SMILES: Cc1nnc2n1-c1sc3c(c1C(c1cc(F)cc(F)c1)NC2)CC(C(=O)N1CCOCC1)C3]

The title compound is prepared from 9-(3,5-difluorophenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): t$_R$=0.72 min; Mass spectrum (ESI+): m/z=472 [M+H]$^+$.

Example 59

9-(2-Cyclopropylphenyl)-3-methyl-13-(morpholine-4-carbonyl)-16-thia-2,4,5,8-tetraazatetracyclo[8.6.0.0$^{2,6}$.0$^{11,15}$]-hexadeca-1(10),3,5,11(15)-tetraene

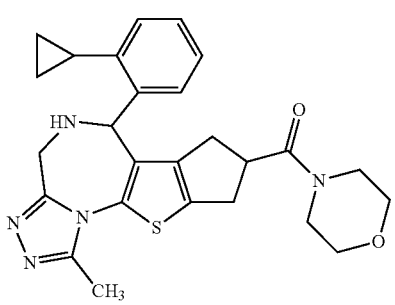 [SMILES: Cc1nnc2n1-c1sc3c(c1C(c1ccccc1C1CC1)NC2)CC(C(=O)N1CCOCC1)C3]

The title compound is prepared from 9-(2-cyclopropylphenyl)-3-methyl-13-(morpholine-4-carbonyl)-16-thia-2,4,5,8-tetraazatetracyclo[8.6.0.0$^{2,6}$.0$^{11,15}$]hexadeca-1(10),3,5,8,11(15)-pentaene following a procedure analogous to that described for Example 1. LC (Method 2): t$_R$=0.73/0.75 min (diastereomers); Mass spectrum (ESI+): m/z=476 [M+H]$^+$.

Example 60

{2-[3-Methyl-13-(morpholine-4-carbonyl)-16-thia-2,4,5,8-tetraazatetracyclo[8.6.0.0²,⁶.0¹¹,¹⁵]hexadeca-1(10),3,5,11(15)-tetraen-9-yl]phenyl}methanol

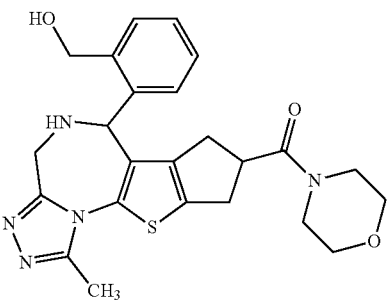 [SMILES: Cc1nnc2n1-c1sc3c(c1C(c1ccccc1CO)NC2)CC(C(=O)N1CCOCC1)C3]

The title compound is prepared from {2-[3-methyl-13-(morpholine-4-carbonyl)-16-thia-2,4,5,8-tetraazatetracyclo-[8.6.0.0²,⁶.0¹¹,¹⁵]hexadeca-1(10),3,5,8,11(15)-pentaen-9-yl]phenyl}methanol following a procedure analogous to that described for Example 1. LC (Method 2): $t_R$=0.64/0.65 min (diastereomers); Mass spectrum (ESI⁺): m/z=466 [M+H]⁺.

Example 61

2-[3-Methyl-13-(morpholine-4-carbonyl)-16-thia-2,4,5,8-tetraazatetracyclo[8.6.0.0²,⁶.0¹¹,¹⁵]hexadeca-1(10),3,5,11(15)-tetraen-9-yl]phenol

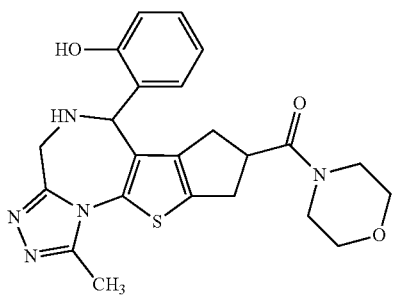 [SMILES: Cc1nnc2n1-c1sc3c(c1C(c1ccccc1O)NC2)CC(C(=O)N1CCOCC1)C3]

The title compound is prepared from 2-[3-methyl-13-(morpholine-4-carbonyl)-16-thia-2,4,5,8-tetraazatetracyclo-[8.6.0.0²,⁶.0¹¹,¹⁵]hexadeca-1(10),3,5,8,11(15)-pentaen-9-yl]phenol following a procedure analogous to that described for Example 1. LC (Method 1): $t_R$=0.74/0.75 min (diastereomers); Mass spectrum (ESI+): m/z=452 [M+H]⁺.

Example 62

9-(2-Chloro-5-methoxyphenyl)-3-methyl-13-(morpholine-4-carbonyl)-16-thia-2,4,5,8-tetraazatetracyclo-[8.6.0.0²,⁶.0¹¹,¹⁵]hexadeca-1(10),3,5,11(15)-tetraene

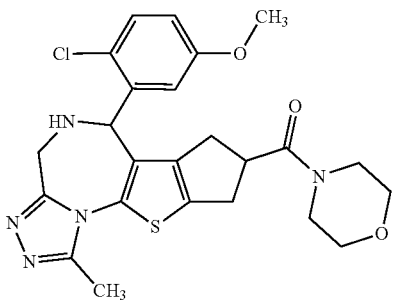 [SMILES: COc1ccc(Cl)c(C2NCc3nnc(C)n3-c3sc4c(c32)CC(C(=O)N2CCOCC2)C4)c1]

The title compound is prepared from 9-(2-chloro-5-methoxyphenyl)-3-methyl-13-(morpholine-4-carbonyl)-16-thia-2,4,5,8-tetraazatetracyclo[8.6.0.0²,⁶.0¹¹,¹⁵]hexadeca-1(10),3,5,8,11(15)-pentaene following a procedure analogous to that described for Example 1. LC (Method 2): $t_R$=0.73 min; Mass spectrum (ESI⁺): m/z=500 [M+H]⁺.

Example 63 and Example 64

(9R,13S)-3-Methyl-9-(2-methylphenyl)-13-(morpholine-4-carbonyl)-16-thia-2,4,5,8-tetraazatetracyclo[8.6.0.0²,⁶.0¹¹,¹⁵]-hexadeca-1(10),3,5,11(15)-tetraene (Example 63) and (9S,13S)-3-methyl-9-(2-methylphenyl)-13-(morpholine-4-carbonyl)-16-thia-2,4,5,8-tetraazatetracyclo[8.6.0.0²,⁶.0¹¹,¹⁵]-hexadeca-1(10),3,5,11(15)-tetraene (Example 64)

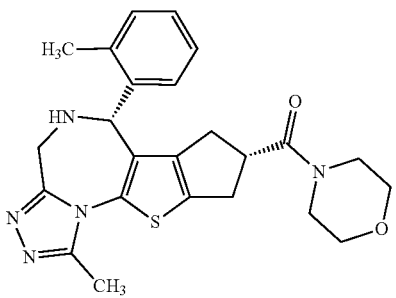

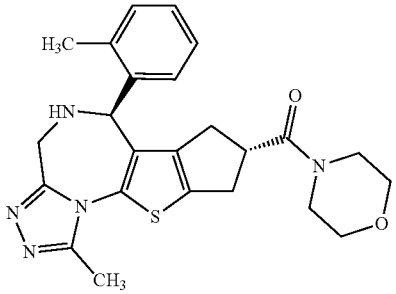

The title compounds are prepared from (13S)-3-methyl-9-(2-methylphenyl)-13-(morpholine-4-carbonyl)-16-thia-2,4,5,8-tetraazatetracyclo[8.6.0.0²,⁶.0¹¹,¹⁵]hexadeca-1(10),3, 5,8,11(15)-pentaene following a procedure analogous to that described for Example 1. The diastereomers are separated by reversed phase chromatography (HPLC; ACN/water/TFA) to obtain the title compounds.

Example 63: LC (Method 2): $t_R$=0.71 min; Mass spectrum (ESI+): m/z=450 [M+H]$^+$;

Example 64: LC (Method 2): $t_R$=0.69 min; Mass spectrum (ESI+): m/z=450 [M+H]$^+$.

Example 65

(13S)-9-(2-Chlorophenyl)-N-(1-hydroxy-2-methyl-propan-2-yl)-3-methyl-16-thia-2,4,5,8-tetraazatetra-cyclo-[8.6.0.0$^{2,6}$.0$^{11,15}$]hexadeca-1(10),3,5,11(15)-tetraene-13-carboxamide

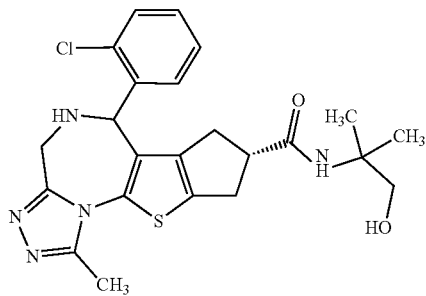 [SMILES: Cc1nnc2n1-c1sc3c(c1C(c1ccccc1Cl)NC2)C[C@H](C(=O)NC(C)(C)CO)C3]

The title compound is prepared from (13S)-9-(2-chlorophenyl)-N-(1-hydroxy-2-methylpropan-2-yl)-3-methyl-16-thia-2,4,5,8-tetraazatetracyclo[8.6.0.0$^{2,6}$.0$^{11,15}$]hexadeca-1(10),3,5,8,11(15)-pentaene-13-carboxamide following a procedure analogous to that described for Example 1.

LC (Method 2): $t_R$=0.72 min; Mass spectrum (ESI$^+$): m/z=472 [M+H]$^+$.

Example 66

13-{5-Azaspiro[2.5]octane-5-carbonyl}-9-(2-chlorophenyl)-3-methyl-16-thia-2,4,5,8-tetraazatetracyclo-[8.6.0.0$^{2,6}$.0$^{11,15}$]hexadeca-1(10),3,5,11(15)-tetraene

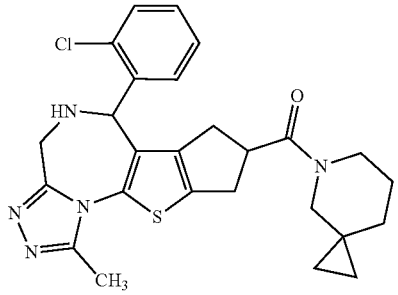 [SMILES: Cc1nnc2n1-c1sc3c(c1C(c1ccccc1Cl)NC2)CC(C(=O)N1CCCC2(CC2)C1)C3]

The title compound is prepared from 13-{5-azaspiro[2.5]octane-5-carbonyl}-9-(2-chlorophenyl)-3-methyl-16-thia-2,4,5,8-tetraazatetracyclo[8.6.0.0$^{2,6}$.0$^{11,15}$]hexadeca-1(10),3,5,11(15)-pentaene following a procedure analogous to that described for Example 1. LC (Method 1): $t_R$=0.99 min; Mass spectrum (ESI$^+$): m/z=494 [M+H]$^+$.

The Examples compiled in the following table are obtained from 9-(2-chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-pentaene by following a procedure analogous to that described for Example 1. Individual stereoisomers are obtained by chiral SFC: a first separation to obtain Example 68 and Example 69 [column: Chiralpak® IA (20 mm×250 mm, 5 μm); column temperature: 40° C.; flow rate: 60 mL/min; BPR: 150 bar; injection volume: 250 NL (2.5 mg); isocratic conditions: 70:30 CO$_2$: EtOH (20 mM NH$_3$)] followed by a second separation of the mixed fraction to obtain Reference Example 70 and Reference Example 71 [column: Chiral Art® Amylose-SA (10 mm×250 mm, 5 μm); column temperature: 40° C.; flow rate: 10 mL/min; BPR: 150 bar; injection volume: 200 NL (4 mg); isocratic conditions: 80:20 CO$_2$:MeOH (20 mM NH$_3$)].

| Example | Structure/Name | LC Method | $t_R$ [min] | MS (ESI+): m/z [M + H]$^+$ |
|---|---|---|---|---|
| 67 | 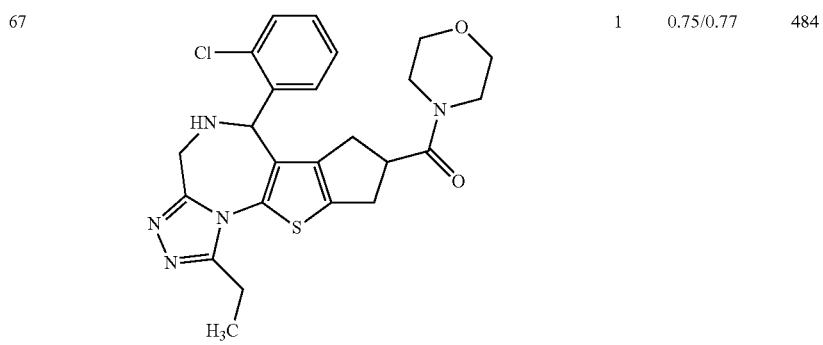<br>9-(2-Chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene | 1 | 0.75/0.77 | 484 |

| Example | Structure/Name | LC Method | $t_R$ [min] | MS (ESI+): m/z [M + H]$^+$ |
|---|---|---|---|---|
| 68 | 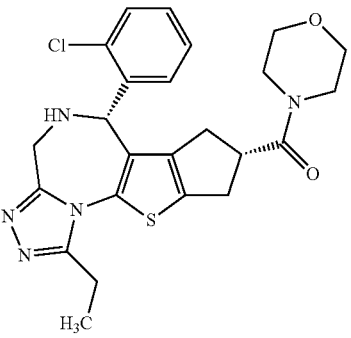<br>(9S,13S)-9-(2-chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene | 8 | 2.89 | 484 |
| 69 | 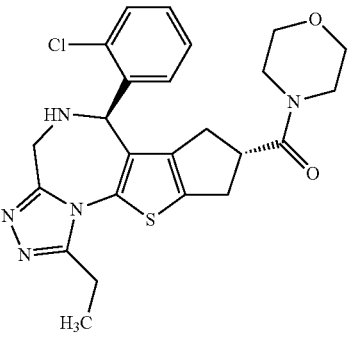<br>(9R,13S)-9-(2-chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene | 8 | 4.13 | 484 |
| 70* | 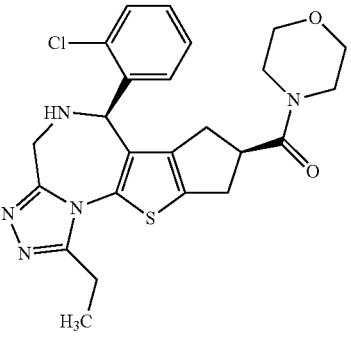<br>(9R,13R)-9-(2-chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene | 7 | 3.76 | 484 |

| Example | Structure/Name | LC Method | $t_R$ [min] | MS (ESI+): m/z [M + H]$^+$ |
|---|---|---|---|---|
| 71* | 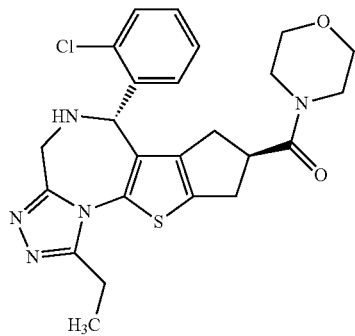<br>(9S,13R)-9-(2-chlorophenyl)-3-ethyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene | 7 | 4.72 | 484 |

*reference example outside the scope of the invention

Example 72 and Example 73

(9S,13S)-9-(2-Chlorophenyl)-3-methyl-N,N-dipropyl-16-thia-2,4,5,8-tetraazatetracyclo[8.6.0.0$^{2,6}$.0$^{11,15}$]hexadeca-1(10),3,5,11(15)-tetraene-13-carboxamide (Example 72) and (9R,13S)-9-(2-chlorophenyl)-3-methyl-N,N-dipropyl-16-thia-2,4,5,8-tetraazatetracyclo[8.6.0.0$^{2,6}$.0$^{11,15}$]hexadeca-1(10),3,5,11(15)-tetraene-13-carboxamide (Example 73)

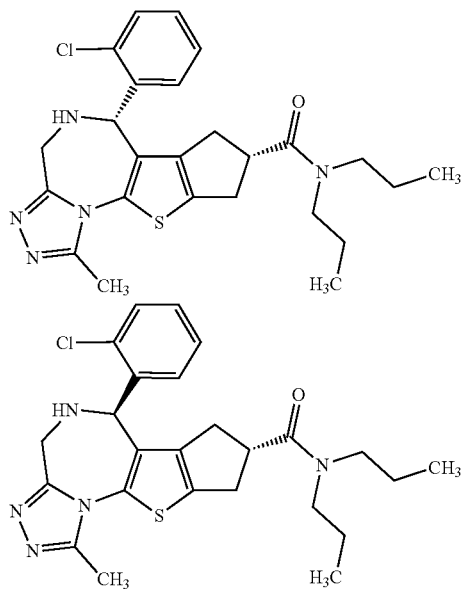

The title compounds are prepared from (13S)-9-(2-chlorophenyl)-3-methyl-N,N-dipropyl-16-thia-2,4,5,8-tetraazatetracyclo[8.6.0.0$^{2,6}$.0$^{11,15}$]hexadeca-1(10),3,5,11(15)-tetraene-13-carboxamide following a procedure analogous to that described for Example 1. The diastereomers are separated by chiral SFC [column: Chiral Art® Amylose-SA (10 mm×250 mm, 5 µm); column temperature: 40° C.; flow rate: 10 mL/min; BPR: 150 bar; injection volume: 100 µL (2 mg); isocratic conditions: 75:25 CO$_2$:MeOH (20 mM NH$_3$)].

Example 72: LL (Method 7): $t_R$=2.10 min; Mass spectrum (ESI+): m/z=484 [M+H]$^+$;

Example 73: LM (Method 7): $t_R$=3.02 min; Mass spectrum (ESI+): m/z=484 [M+H]$^+$.

The Examples compiled in the following table are obtained from 3-methyl-13-(morpholine-4-carbonyl)-9-phenyl-16-thia-2,4,5,8-tetraazatetracyclo[8.6.0.0$^{2,6}$.0$^{11,15}$]hexadeca-1(10),3,5,8,11(15)-pentaene by following a procedure analogous to that described for Example 1. The trans and cis diastereomers are separated by reversed phase chromatography (HPLC; ACN/water/TFA). The separated racemic diastereomers are further separated into individual enantiomers by chiral SFC to give Reference Example 75 and Example 76 [column: Chiralpak IA (20 mm×250 mm, 5 µm); column temperature: 40° C.; flow rate: 10 mL/min; BPR: 150 bar; injection volume: 200 µL (3 mg); isocratic conditions: 70:30 scCO$_2$:MeOH (20 mM NH$_3$)] and Reference Example 77 and Example 78 [column: CHIRAL ART® Cellulose-SB (10×250 mm, 5 µm); column temperature: 40° C.; flow rate: 10 mL/min; BPR: 150 bar; injection volume: 200 µL (2 mg); isocratic conditions: 70:30 CO$_2$:iPrOH (20 mM NH$_3$)].

| Example | Structure/Name | LC Method | $t_R$ [min] | MS (ESI+): m/z [M + H]$^+$ |
|---|---|---|---|---|
| 74 | 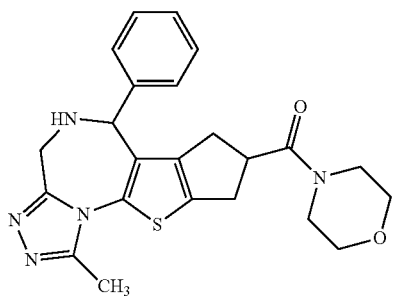<br>3-methyl-13-(morpholine-4-carbonyl)-9-phenyl-16-thia-2,4,5,8-tetraazatetracyclo[8.6.0.0$^{2,6}$.0$^{11,15}$]-hexadeca-1(10),3,5,11(15)-tetraene | 2 | 0.67/0.68 | 436 |
| 75* | 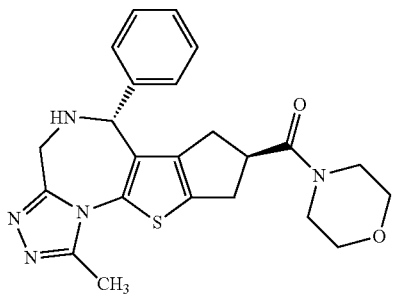<br>(9R,13R)-3-methyl-13-(morpholine-4-carbonyl)-9-phenyl-16-thia-2,4,5,8-tetraazatetracyclo-[8.6.0.0$^{2,6}$.0$^{11,15}$]hexadeca-1(10),3,5,11(15)-tetraene | 8 | 4.13 | 436 |
| 76 | 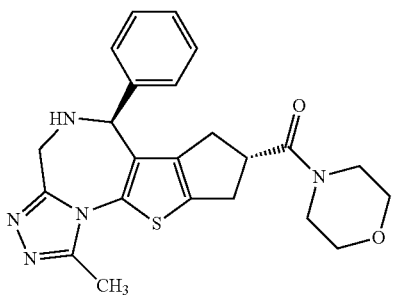<br>(9S,13S)-3-methyl-13-(morpholine-4-carbonyl)-9-phenyl-16-thia-2,4,5,8-tetraazatetracyclo-[8.6.0.0$^{2,6}$.0$^{11,15}$]hexadeca-1(10),3,5,11(15)-tetraene | 8 | 4.90 | 436 |

-continued

| Example | Structure/Name | LC Method | $t_R$ [min] | MS (ESI+): m/z [M + H]$^+$ |
|---|---|---|---|---|
| 77* | (9S,13R)-3-methyl-13-(morpholine-4-carbonyl)-9-phenyl-16-thia-2,4,5,8-tetraazatetracyclo-[8.6.0.0$^{2,6}$.0$^{11,15}$]hexadeca-1(10),3,5,11(15)-tetraene | 6 | 4.26 | 436 |
| 78 | (9R,13S)-3-methyl-13-(morpholine-4-carbonyl)-9-phenyl-16-thia-2,4,5,8-tetraazatetracyclo-[8.6.0.0$^{2,6}$.0$^{11,15}$]hexadeca-1(10),3,5,11(15)-tetraene | 6 | 5.82 | 436 |

*reference examples outside the scope of the invention

Example 79

3-Methyl-9-[2-(methylsulfanyl)phenyl]-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

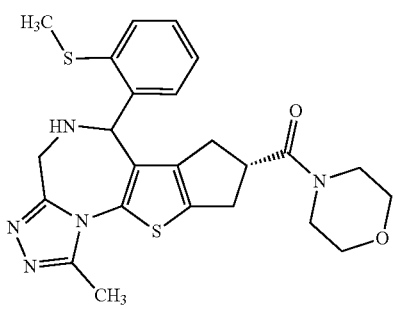 [SMILES: CSc1ccccc1C1NCc2nnc(C)n2-c2sc3c(c21)C[C@H](C(=O)N1CCOCC1)C3]

The title compound is prepared from (3-methyl-9-[2-(methylsulfanyl)phenyl]-13-(morpholine-4-carbonyl)-16-thia-2,4,5,8-tetraazatetracyclo[8.6.0.0$^{2,6}$.0$^{11,15}$]hexadeca-1(10),3,5,11(15)-pentaene following a procedure analogous to that described for Example 1.

LC (Method 2): $t_R$=0.70/0.71 min (diastereomers); Mass spectrum (ESI+): m/z=482 [M+H]$^+$.

Example 80

9-(2-Chlorophenyl)-13-(morpholine-4-carbonyl)-3-propyl-16-thia-2,4,5,8-tetraazatetracyclo[8.6.0.0$^{2,6}$.0$^{11,15}$]hexadeca-1(10),3,5,11(15)-tetraene

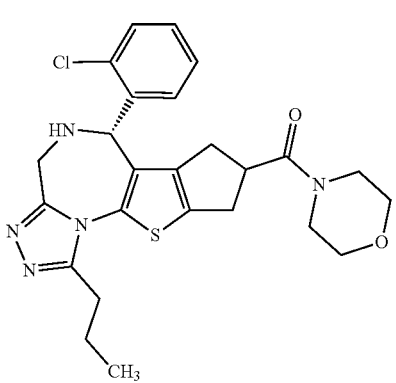 [SMILES: CCCc1nnc2n1-c1sc3c(c1[C@@H](c1ccccc1Cl)NC2)CC(C(=O)N1CCOCC1)C3]

The title compound is prepared from 9-(2-chlorophenyl)-13-(morpholine-4-carbonyl)-3-propyl-16-thia-2,4,5,8-tetraazatetracyclo[8.6.0.0$^{2,6}$.0$^{11,15}$]hexadeca-1(10),3,5,11(15)-pentaene following a procedure analogous to that described for Example 1. LC (Method 2): $t_R$=0.77/0.78 min (diastereomers); Mass spectrum (ESI+): m/z=498 [M+H]$^+$.

Example 81

9-(2-Chlorophenyl)-3-cyclopropyl-13-(morpholine-4-carbonyl)-16-thia-2,4,5,8-tetraazatetracyclo[8.6.0.0$^{2,6}$.0$^{11,15}$]hexadeca-1(10),3,5,11(15)-tetraene

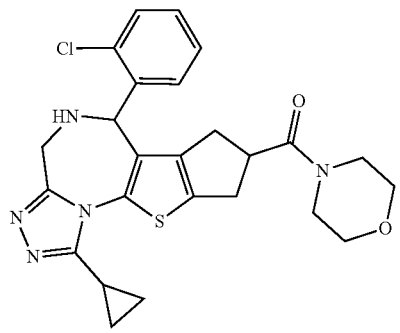 [SMILES: O=C(C1Cc2sc3c(c2C1)C(c1ccccc1Cl)NCc1nnc(C2CC2)n1-3)N1CCOCC1]

The title compound is prepared from 9-(2-chlorophenyl)-3-cyclopropyl-13-(morpholine-4-carbonyl)-16-thia-2,4,5,8-tetraazatetracyclo[8.6.0.0$^{2,6}$.0$^{11,15}$]hexadeca-1(10),3,5,11(15)-pentaene following a procedure analogous to that described for Example 1. LC (Method 2): $t_R$=0.75 min; Mass spectrum (ESI+): m/z=496 [M+H]$^+$.

The invention claimed is:

1. A compound of formula (I.1)

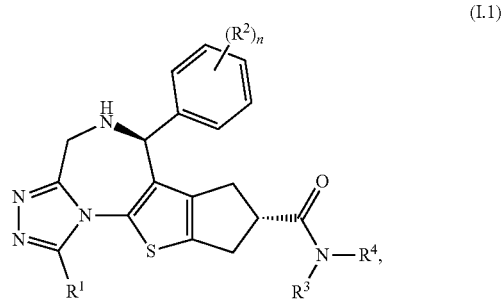

wherein
R$^1$ is selected from the group consisting of C$_{1-4}$-alkyl optionally substituted with 1 to 3 F and of C$_{3-4}$-cycloalkyl;
R$^2$ is selected from the group consisting of F, Cl, Br, I, C$_{1-4}$-alkyl, C$_{3-4}$-cycloalkyl, —CN, —CONH$_2$, —CONH(C$_{1-4}$-alkyl), —CON(C$_{1-4}$-alkyl)$_2$, —COOH, —COO—C$_{1-4}$-alkyl, OH, —O—C$_{1-4}$-alkyl, and S(O)$_r$—C$_{1-4}$-alkyl with r=0, 1, or 2; wherein
the C$_{1-4}$-alkyl R$^2$ group may be optionally substituted with 1 to 3 F or optionally substituted with 1 —CN, with 1 OH, or with 1 —O—C$_{1-4}$-alkyl, and
the —O—C$_{1-4}$-alkyl R$^2$ group may be optionally substituted with 1 to 3 F;
n is selected from the group consisting of 0, 1, 2, and 3;
R$^3$ and R$^4$, together with the amide N atom they are attached to, form a heterocyclyl selected from the group consisting of

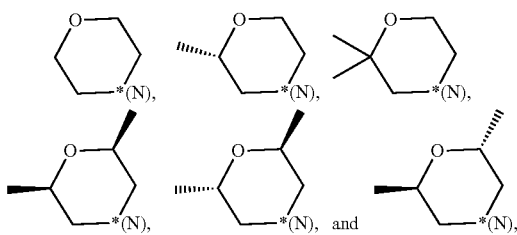

or a pharmaceutically acceptable salt thereof.

2. A pharmaceutically acceptable salt of the compound according to claim 1.

3. The compound according to claim 1, wherein
R$^1$ is selected from the group consisting of CH$_3$, CH$_2$CH$_3$, CH$_2$CH$_2$CH$_3$, CH$_F$2, C$_F$3, and cyclopropyl
or a pharmaceutically acceptable salt thereof.

4. The compound according to claim 1, wherein
R$^1$ is selected from the group consisting of CH$_3$, CH$_2$CH$_3$, CH$_2$CH$_2$CH$_3$, and cyclopropyl;
or a pharmaceutically acceptable salt thereof.

5. The compound according to claim 1, wherein
R$^1$ is CH$_3$;
or a pharmaceutically acceptable salt thereof.

6. The compound according to claim 1, wherein
R$^2$ is selected from the group consisting of
F, Cl, Br, C$_{1-3}$-alkyl, cyclopropyl, —CN, —C$_{1-3}$-alkylene-OH, —C$_{1-2}$-alkylene-O—C$_{1-2}$-alkyl, OH, —O—C$_{1-3}$-alkyl, and —S—C$_{1-3}$-alkyl; wherein
the C$_{1-3}$-alkyl R$^2$ group may be optionally substituted with 2 or 3 F, and
the —O—C$_{1-3}$-alkyl R$^2$ group may be optionally substituted with 2 or 3 F; and
n is selected from the group consisting of 0, 1, and 2;
or a pharmaceutically acceptable salt thereof.

7. The compound according to claim 1, wherein
R$^2$ is selected from the group consisting of
F, Cl, Br, CH$_3$, CH$_2$CH$_3$, cyclopropyl, CF$_3$, CH$_2$OH, OH, OCH$_3$, and S—CH$_3$; and
n is selected from the group consisting of 0, 1, and 2;
or a pharmaceutically acceptable salt thereof.

8. The compound according to claim 1, wherein
R$^2$ is selected from the group consisting of F, Cl, and Br; and
n is 1;
or a pharmaceutically acceptable salt thereof.

9. The compound according to claim 1, wherein
R$^2$ is Cl; and
n is 1;
or a pharmaceutically acceptable salt thereof.

10. The compound according to claim 1, wherein
R$^2$, n, and the phenyl substitution pattern are selected such that the resulting substituted phenyl ring shown in formula (I.1) is

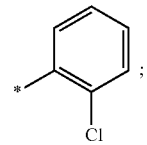

or a pharmaceutically acceptable salt thereof.

11. A pharmaceutical composition comprising one or more compounds according to claim 1, or pharmaceutically acceptable salt thereof, optionally together with one or more inert carriers and/or diluents.

12. A pharmaceutical composition comprising one or more compounds according to claim 1, or pharmaceutically acceptable salt thereof, and one or more additional therapeutic agents, optionally together with one or more inert carriers and/or diluents.

13. The pharmaceutical composition according to claim 12, wherein the one or more additional therapeutic agents are selected from the group consisting of antidiabetic agents, agents for the treatment of overweight and/or obesity, agents for the treatment of high blood pressure, heart failure and/or atherosclerosis, agents for the treatment of ocular diseases, and agents for the treatment of allergies and inflammation-related conditions and diseases.

14. A method for treating an ocular disease in a patient in need thereof, the method comprising administering to the patient one or more compounds according to claim 1, or pharmaceutically acceptable salt thereof.

15. The method according to claim 14, wherein the ocular disease is selected from the group consisting of diabetic macular edema, dry and wet age-related macular degeneration, geographic atrophy and non-exudative choroidal neovascularization.

16. A method for treating allergies and inflammation-related conditions and diseases, the method comprising administering to a patient in need thereof one or more compounds according to claim 1, or pharmaceutically acceptable salt thereof.

17. A method for treating urticaria or non alcoholic steatohepatitis) (NASH), the method comprising administering to a patient in need thereof one or more compounds according to claim 1, or pharmaceutically acceptable salts thereof.

18. A compound selected from the group consisting of:

2

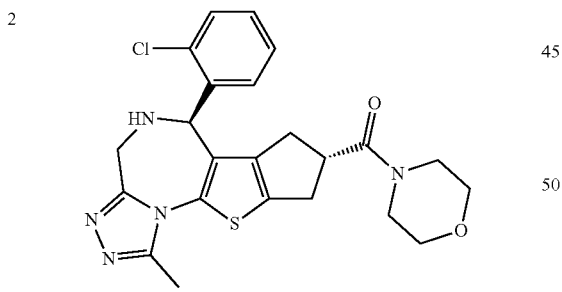

4

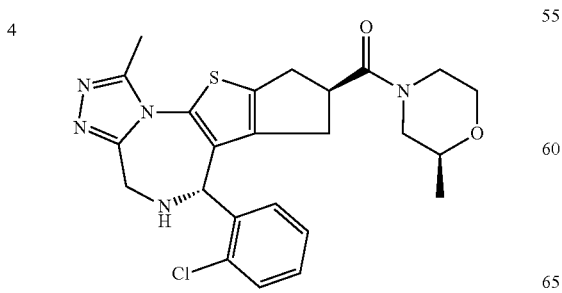

5

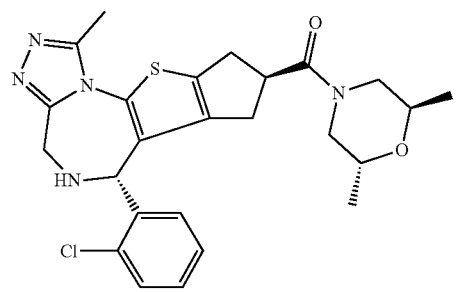 [SMILES: Cc1nnc2n1-c1sc3c(c1[C@H](c1ccccc1Cl)NC2)C[C@H](C(=O)N1C[C@@H](C)O[C@H](C)C1)C3]

6

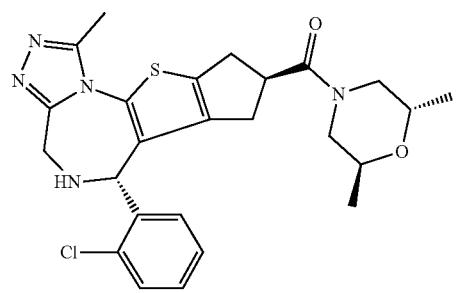 [SMILES: Cc1nnc2n1-c1sc3c(c1[C@H](c1ccccc1Cl)NC2)C[C@H](C(=O)N1C[C@H](C)O[C@@H](C)C1)C3]

26

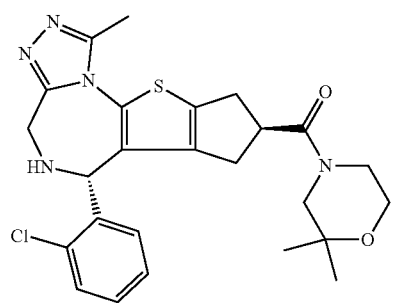 [SMILES: Cc1nnc2n1-c1sc3c(c1[C@H](c1ccccc1Cl)NC2)C[C@H](C(=O)N1CCOC(C)(C)C1)C3]

27

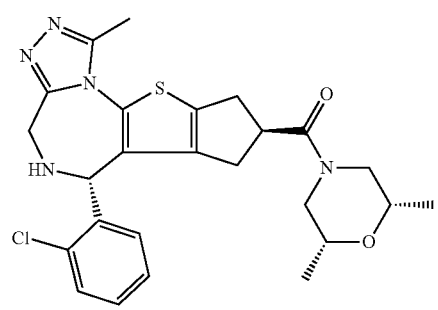 [SMILES: Cc1nnc2n1-c1sc3c(c1[C@H](c1ccccc1Cl)NC2)C[C@H](C(=O)N1C[C@@H](C)O[C@@H](C)C1)C3]

64

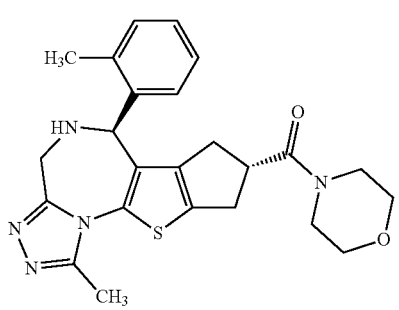 [SMILES: Cc1ccccc1[C@@H]1NCc2nnc(C)n2-c2sc3c(c21)C[C@H](C(=O)N1CCOCC1)C3]

69
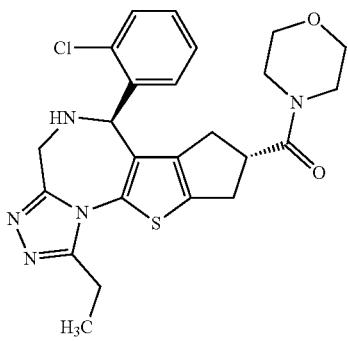
and
76
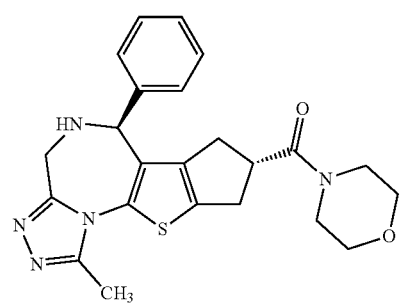 [SMILES: Cc1nnc2n1-c1sc3c(c1[C@H](c1ccccc1)NC2)C[C@H](C(=O)N1CCOCC1)C3]
or a pharmaceutically acceptable salt thereof.
19. Compound
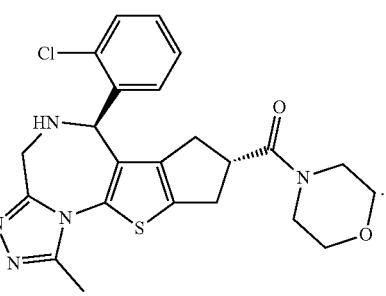
20. Compound
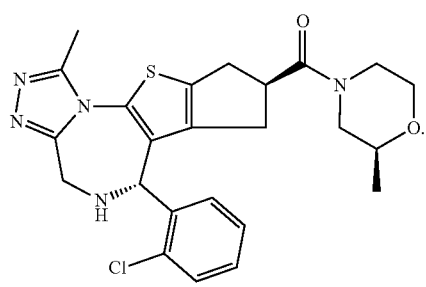 [SMILES: Cc1nnc2n1-c1sc3c(c1[C@H](c1ccccc1Cl)NC2)C[C@H](C(=O)N1CCO[C@@H](C)C1)C3]
21. Compound
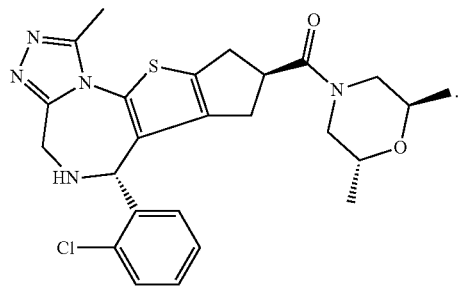 [SMILES: Cc1nnc2n1-c1sc3c(c1[C@H](c1ccccc1Cl)NC2)C[C@H](C(=O)N1C[C@@H](C)O[C@H](C)C1)C3]
22. Compound
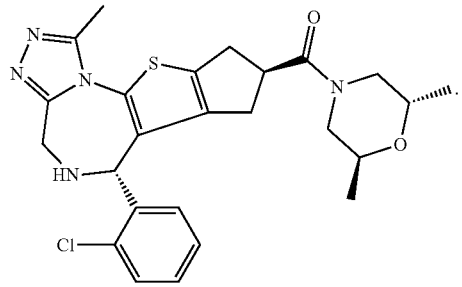 [SMILES: Cc1nnc2n1-c1sc3c(c1[C@H](c1ccccc1Cl)NC2)C[C@H](C(=O)N1C[C@H](C)O[C@@H](C)C1)C3]
23. Compound
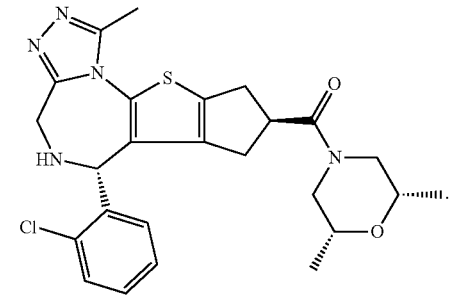 [SMILES: Cc1nnc2n1-c1sc3c(c1[C@H](c1ccccc1Cl)NC2)C[C@H](C(=O)N1C[C@@H](C)O[C@@H](C)C1)C3]
24. A pharmaceutically acceptable salt of compound
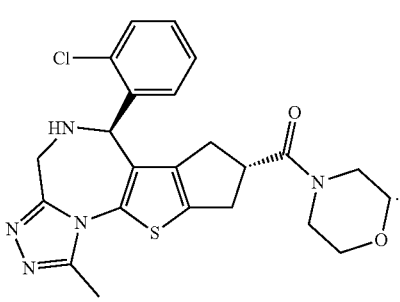 [SMILES: Cc1nnc2n1-c1sc3c(c1[C@H](c1ccccc1Cl)NC2)C[C@H](C(=O)N1CCOCC1)C3]

25. A pharmaceutically acceptable salt of compound

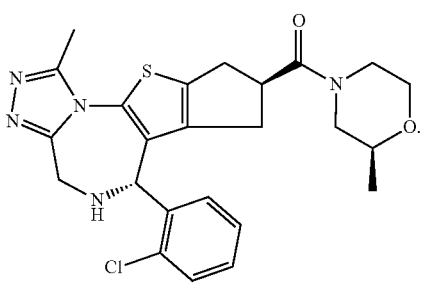 [SMILES: Cc1nnc2n1-c1sc3c(c1[C@H](c1ccccc1Cl)NC2)C[C@H](C(=O)N1CCO[C@@H](C)C1)C3]

26. A pharmaceutically acceptable salt of compound

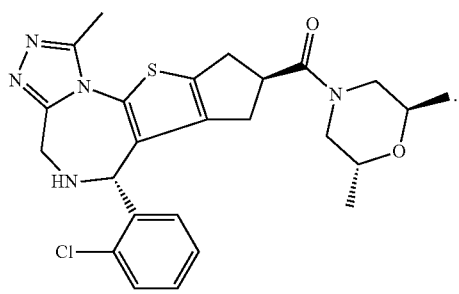 [SMILES: Cc1nnc2n1-c1sc3c(c1[C@H](c1ccccc1Cl)NC2)C[C@H](C(=O)N1C[C@@H](C)O[C@H](C)C1)C3]

27. A pharmaceutically acceptable salt of compound

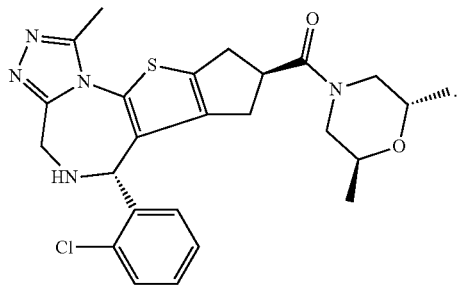 [SMILES: Cc1nnc2n1-c1sc3c(c1[C@H](c1ccccc1Cl)NC2)C[C@H](C(=O)N1C[C@H](C)O[C@@H](C)C1)C3]

28. A pharmaceutically acceptable salt of compound

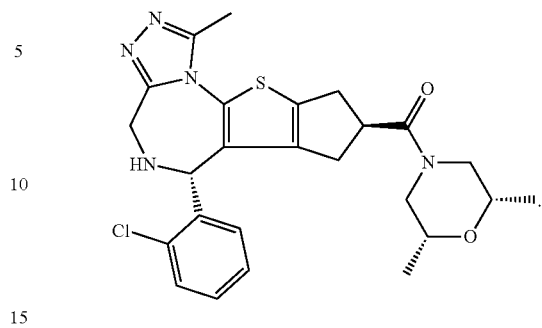

29. A pharmaceutical composition comprising one or more compounds according to claim 18, or pharmaceutically acceptable salt thereof, and one or more additional therapeutic agents, optionally together with one or more inert carriers and/or diluents.

30. The pharmaceutical composition according to claim 29, wherein the one or more additional therapeutic agents are selected from the group consisting of antidiabetic agents, agents for the treatment of overweight and/or obesity, agents for the treatment of high blood pressure, heart failure and/or atherosclerosis, agents for the treatment of ocular diseases, and agents for the treatment of allergies and inflammation-related conditions and diseases.

31. A method for treating an ocular disease in a patient in need thereof, the method comprising administering to the patient one or more compounds according to claim 18, or pharmaceutically acceptable salt thereof.

32. The method according to claim 31, wherein the ocular disease is selected from the group consisting of diabetic macular edema, dry and wet age-related macular degeneration, geographic atrophy and non-exudative choroidal neovascularization.

33. A method for treating allergies and inflammation-related conditions and diseases, the method comprising administering to a patient in need thereof one or more compounds according to claim 18, or pharmaceutically acceptable salt thereof.

34. A method for treating urticaria or non alcoholic steatohepatitis (NASH), the method comprising administering to a patient in need thereof one or more compounds according to claim 18, or pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 11,766,443 B2 | Page 1 of 1 |
| APPLICATION NO. | : 17/524759 | |
| DATED | : September 26, 2023 | |
| INVENTOR(S) | : Matthias Eckhardt et al. | |

It is certified that error appears in the above-identified patent and that said Letters Patent is hereby corrected as shown below:

On the Title Page

Item (30), insert:
-- (30) Foreign Application Priority Data
November 16, 2020 (EP) ......................... 20207719 --

Signed and Sealed this
Nineteenth Day of December, 2023

Katherine Kelly Vidal
*Director of the United States Patent and Trademark Office*